US012459950B2

(12) United States Patent
Luengo et al.

(10) Patent No.: US 12,459,950 B2
(45) Date of Patent: *Nov. 4, 2025

(54) SELECTIVE INHIBITORS OF PROTEIN ARGININE METHYLTRANSFERASE 5 (PRMT5)

(71) Applicant: Prelude Therapeutics, Incorporated, Wilmington, DE (US)

(72) Inventors: Juan Luengo, Phoenixville, PA (US); Hong Lin, Exton, PA (US); Michael Hawkins, Ambler, PA (US); Rupa Shetty, Blue Bell, PA (US); Philip Pitis, North Wales, PA (US); Gisela Saborit Villarroya, Barcelona (ES)

(73) Assignee: Prelude Therapeutics, Incorporated, Wilmington, DE (US)

( * ) Notice: Subject to any disclaimer, the term of this patent is extended or adjusted under 35 U.S.C. 154(b) by 823 days.

This patent is subject to a terminal disclaimer.

(21) Appl. No.: 17/674,010

(22) Filed: Feb. 17, 2022

(65) Prior Publication Data

US 2022/0177481 A1 Jun. 9, 2022

Related U.S. Application Data

(63) Continuation of application No. 16/985,611, filed on Aug. 5, 2020, now Pat. No. 11,254,683, which is a continuation of application No. 16/888,883, filed on Jun. 1, 2020, now Pat. No. 11,214,574, which is a continuation of application No. 16/376,100, filed on Apr. 5, 2019, now Pat. No. 10,711,007, which is a continuation of application No. PCT/US2019/022288, filed on Mar. 14, 2019.

(60) Provisional application No. 62/742,048, filed on Oct. 5, 2018, provisional application No. 62/666,726, filed on May 4, 2018, provisional application No. 62/642,727, filed on Mar. 14, 2018.

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01)

(58) Field of Classification Search
CPC ...... C07D 487/04; C07D 519/00; A61P 35/00
See application file for complete search history.

(56) References Cited

U.S. PATENT DOCUMENTS

| | | | |
|---|---|---|---|
| 3,657,744 | A | 4/1972 | Ersek et al. |
| 4,739,762 | A | 4/1988 | Palmaz |
| 4,992,445 | A | 2/1991 | Lawter et al. |
| 5,001,139 | A | 3/1991 | Lawter et al. |
| 5,023,252 | A | 6/1991 | Hseih |
| 5,040,548 | A | 8/1991 | Yock |
| 5,061,273 | A | 10/1991 | Yock |
| 5,195,984 | A | 3/1993 | Schatz |
| 5,292,331 | A | 3/1994 | Boneau |
| 5,451,233 | A | 9/1995 | Yock |
| 5,496,346 | A | 3/1996 | Horzewski et al. |
| 5,674,278 | A | 10/1997 | Boneau |
| 5,879,382 | A | 3/1999 | Boneau |
| 6,344,053 | B1 | 2/2002 | Boneau |
| 10,711,007 | B2 | 7/2020 | Luengo |
| 11,214,574 | B2 | 1/2022 | Luengo |
| 11,254,683 | B2 | 2/2022 | Luengo |
| 2016/0244475 | A1 | 8/2016 | Tatlock et al. |
| 2019/0048014 | A1 | 2/2019 | Lin et al. |

FOREIGN PATENT DOCUMENTS

| | | | | |
|---|---|---|---|---|
| WO | 2015200680 A2 | 12/2015 | | |
| WO | 2016135582 A1 | 9/2016 | | |
| WO | WO-2016178870 A1 * | 11/2016 | ............. | A61P 35/00 |
| WO | 2017032840 A1 | 3/2017 | | |

(Continued)

OTHER PUBLICATIONS

Beattie et al., "Synthesis and evaluation of two series of 42-aza-carbocyclic nucleosides as adenosine A"2" A receptor agonists", Bioorganic Medicinal Chemistry letters, 2010, 20, 1219-1224 [Cited in related U.S. Appl. No. 16/376,100].

(Continued)

*Primary Examiner* — James H Alstrum-Acevedo
*Assistant Examiner* — Justin Christopher Sanchez
(74) *Attorney, Agent, or Firm* — Polsinelli PC

(57) ABSTRACT

The disclosure is directed to compounds of Formula I

I

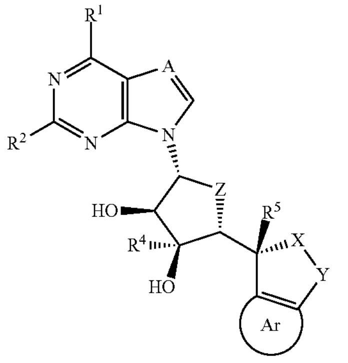

Pharmaceutical compositions comprising compounds of Formula I, as well as methods of their use and preparation, are also described.

20 Claims, No Drawings

(56) References Cited

FOREIGN PATENT DOCUMENTS

| | | | |
|---|---|---|---|
| WO | 2017153186 | A1 | 9/2017 |
| WO | 2017218802 | A1 | 12/2017 |
| WO | 2018065365 | A1 | 4/2018 |
| WO | 2018075601 | A1 | 4/2018 |
| WO | 2018085818 | A1 | 5/2018 |
| WO | 2018085833 | A2 | 5/2018 |
| WO | 2018152501 | A1 | 8/2018 |
| WO | 2018152548 | A1 | 8/2018 |
| WO | 2018160824 | A1 | 9/2018 |
| WO | 2018160855 | A1 | 9/2018 |
| WO | 2019032859 | A1 | 2/2019 |
| WO | 2019084470 | A1 | 5/2019 |

OTHER PUBLICATIONS

Chung et al., "Protein Arginine Methyltransferase 5 (PRMT5) Inhibition Induces Lymphoma Cell Death through Reactivation of the Retinoblastoma Tumor Suppressor Pathway and Polycomb Repressor Complex 2 (PRC2) Silencing", Journal of Biological Chemistry, Dec. 2013, vol. 288, No. 49, 35534-35547 [Cited in related U.S. Appl. No. 16/376,100].

Hsu et al., "The spliceosome is a therapeutic vulnerability in MYC-driven cancer", Nature, Sep. 2015, 525(7569), 384-388 [Cited in related U.S. Appl. No. 16/376,100].

Hulpia et al., "Synthesis of a 3-C-ethynyl—[beta]-d-ribofuranose purine nucleoside library: Discovery of C7-deazapurine analogs as potent antiproliferative nucleosides", European Journal of Medicinal Chemistry, Jul. 29, 2018, vol. 157, 248-267 [Cited in related U.S. Appl. No. 16/376,100].

Koh et al., "Myc regulates the core pre-mRNA splicing machinery as an essential step in lymphomagenesis", Nature, May 2015, 523(7558), 96-100 [Cited in related U.S. Appl. No. 16/376,100].

Pal et al., "Human SWI/SNF-Associated PRMT5 Methylates Histone H3 Arginine 8 and Negatively Regulates Expression of ST7 and NM23 Tumor Suppressor Genes", Molecular and Cellular Biology, 2004, vol. 24, No. 21, 9630-9645 [Cited in related U.S. Appl. No. 16/376,100].

Pal et al., "mSin3A/Histone Deacetylase 2- and PRMT5-Containing Brg1 Complex is Involved in Transcriptional Repression of the Myc Target Gene cad", Molecular and Cellular Biology, Nov. 2003, 7475-7487 [Cited in related U.S. Appl. No. 16/376,100].

Wang et al., "Protein Arginine Methyltransferase 5 Suppresses the Transcription of the RB Family of Tumor Suppressors in Leukemia and Lymphoma Cells", Molecular and Cellular Biology, Oct. 2008, 6262-6277 [Cited in related U.S. Appl. No. 16/376,100].

Zhao et al., "PRMT5-mediated methylation of histone H4R3 recruits DNMT3A, coupling histone and DNA methylation In gene silencing", Nature Structural Molecular Biology, Mar. 2009, 16(3), 304-311 [Cited in related U.S. Appl. No. 16/376,100].

International Search Report and Written Opinion issued in PCT/US2019/022288, dated May 2, 2019.

International Preliminary Report on Patentability and Written Opinion issued in PCT/US2019/022288, dated Sep. 24, 2020.

* cited by examiner

SELECTIVE INHIBITORS OF PROTEIN ARGININE METHYLTRANSFERASE 5 (PRMT5)

CROSS-REFERENCE TO RELATED APPLICATIONS

This application is a continuation of U.S. patent application Ser. No. 16/985,611, filed Aug. 5, 2020, which is a continuation of U.S. patent application Ser. No. 16/888,883, filed Jun. 1, 2020, now U.S. Pat. No. 11,214,574, which is a continuation of U.S. patent application Ser. No. 16/376,100, filed Apr. 5, 2019, now U.S. Pat. No. 10,711,007, which is a continuation of International Application No. PCT/US2019/022288, filed on Mar. 14, 2019, which designates the United States, and which claims the benefit of priority to U.S. Provisional Patent Application No. 62/742,048, filed Oct. 5, 2018; U.S. Provisional Patent Application No. 62/666,726 filed May 4, 2018; and U.S. Provisional Patent Application No. 62/642,727, filed Mar. 14, 2018. Each of the above-mentioned applications is incorporated by reference herein in its entirety.

TECHNICAL FIELD

The disclosure is directed to PRMT5 inhibitors and methods of their use.

BACKGROUND

Protein arginine methylation is a common post-translational modification that regulates numerous cellular processes, including gene transcription, mRNA splicing, DNA repair, protein cellular localization, cell fate determination, and signaling. Three types of methyl-arginine species exist: ω NG monomethylarginine (MMA), ω NG, NG asymmetric dimethylarginine (ADMA) and ω NG, N'G symmetric dimethylarginine (SDMA). The formation of methylated arginines is catalyzed by the protein arginine methyl transferases (PRMTs) family of methyltransferases. Currently, there are nine PRMTs annotated in the human genome. The majority of these enzymes are Type I enzymes (PRMT1, -2, -3, -4, -6, -8) that are capable of mono- and asymmetric dimethylation of arginine, with S-adenosylmethionine (SAM) as the methyl donor. PRMT-5, -7 and -9 are considered to be Type II enzymes that catalyze symmetric dimethylation of arginines. Each PRMT species harbors the characteristic motifs of seven beta strand methyltransferases (Katz et al., 2003), as well as additional "double E" and "THW" sequence motifs particular to the PRMT subfamily.

PRMT5 is as a general transcriptional repressor that functions with numerous transcription factors and repressor complexes, including BRG1 and hBRM, Blimp1, and Snail. This enzyme, once recruited to a promoter, symmetrically dimethylates H3R8 and H4R3. Importantly, the H4R3 site is a major target for PRMT1 methylation (ADMA) and is generally regarded as a transcriptional activating mark. Thus, both H4R3me2s (repressive; me2s indicates SDMA modification) and H4R3me2a (active; me2a indicates ADMA modification) marks are produced in vivo. The specificity of PRMT5 for H3R8 and H4R3 can be altered by its interaction with COPR5 and this could perhaps play an important role in determining PRMT5 corepressor status.

Role of PRMTs in Cancer

Aberrant expression of PRMTs has been identified in human cancers, and PRMTs are considered to be therapeutic targets. Global analysis of histone modifications in prostate cancer has shown that the dimethylation of histone H4R3 is positively correlated with increasing grade, and these changes are predictive of clinical outcome.

PRMT5 levels have been shown to be elevated in a panel of lymphoid cancer cell lines as well as mantle cell lymphoma clinical samples. PRMT5 interacts with a number of substrates that are involved in a variety of cellular processes, including RNA processing, signal transduction, and transcriptional regulation. PRMT5 can directly modify histone H3 and H4, resulting in the repression of gene expression. PRMT5 overexpression can stimulate cell growth and induce transformation by directly repressing tumor suppressor genes. Pal et al., Mol. Cell. Biol. 2003, 7475; Pal et al. Mol. Cell. Biol. 2004, 9630; Wang et al. Mol. Cell. Biol. 2008, 6262; Chung et al. J Biol Chem 2013, 5534. In addition to its well-documented oncogenic functions in transcription and translation, the transcription factor MYC also safeguards proper pre-messenger-RNA splicing as an essential step in lymphomagenesis. Koh et al. Nature 2015, 523 7558; Hsu et al. Nature 2015 525, 384.

The discovery of cancer dependencies has the potential to inform therapeutic strategies and to identify putative drug targets. Integrating data from comprehensive genomic profiling of cancer cell lines and from functional characterization of cancer cell dependencies, it has been recently discovered that loss of the enzyme methylthioadenosine phosphorylase (MTAP) confers a selective dependence on protein arginine methyltransferase 5 (PRMT5) and its binding partner WDR77. MTAP is frequently lost due to its proximity to the commonly deleted tumor suppressor gene, CDKN2A. Cells harboring MTAP deletions possess increased intracellular concentrations of methylthioadenosine (MTA, the metabolite cleaved by MTAP). Furthermore, MTA specifically inhibits PRMT5 enzymatic activity. Administration of either MTA or a small-molecule PRMT5 inhibitor shows a preferential impairment of cell viability for MTAP-null cancer cell lines compared to isogenic MTAP-expressing counterparts. Together, these findings reveal PRMT5 as a potential vulnerability across multiple cancer lineages augmented by a common "passenger" genomic alteration.

Role of PRMT5 in Hemoglobinopathies

The developmental switch in human globin gene subtype from fetal to adult that begins at birth heralds the onset of the hemoglobinopathies, b-thalassemia and sickle cell disease (SCD). The observation that increased adult globin gene expression (in the setting of hereditary persistence of fetal hemoglobin [HPFH] mutations) significantly ameliorates the clinical severity of thalassemia and SCD has prompted the search for therapeutic strategies to reverse gamma-globin gene silencing. Central to silencing of the gamma-genes is DNA methylation, which marks critical CpG dinucleotides flanking the gene transcriptional start site in adult bone marrow erythroid cells. It has been shown that these marks are established as a consequence of recruitment of the DNA methyltransferase, DNMT3A to the gamma-promoter by the protein arginine methyltransferase PRMT5. Zhao et al. Nat Struct Mol Biol. 2009 16, 304. PRMT5-mediated methylation of histone H4R3 recruits DNMT3A, coupling histone and DNA methylation in gene silencing.

PRMT5 induces the repressive histone mark, H4R3me2s, which serves as a template for direct binding of DNMT3A, and subsequent DNA methylation. Loss of PRMT5 binding or its enzymatic activity leads to demethylation of the CpG dinucleotides and gene activation. In addition to the H4R3me2s mark and DNA methylation, PRMT5 binding to the gamma-promoter, and its enzymatic activity are essential for assembly of a multiprotein complex on the gamma-promoter, which induces a range of coordinated repressive epigenetic marks. Disruption of this complex leads to reactivation of gamma gene expression. These studies provide the basis for developing PRMT5 inhibitors as targeted therapies for thalassemia and SCD.

SUMMARY

The disclosure is directed to compounds of Formula I.

I

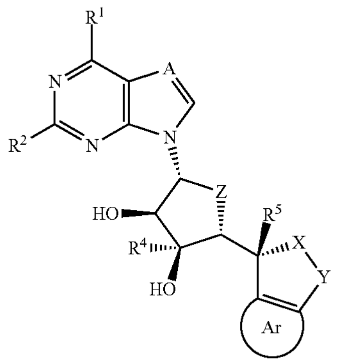

or a pharmaceutically acceptable salt or solvate thereof; wherein

A is N or C—$R^3$;

$R^1$ is H, halo, —$C_1$-$C_6$ alkyl, —$C_1$-$C_6$ alkoxy, —$C_1$-$C_4$ haloalkyl, —$C_3$-$C_6$ cycloalkyl, —$C_3$-$C_6$halocycloalkyl, —$C_1$-$C_6$ alk-O—$C_1$-$C_6$ alkyl, —$C_1$-$C_6$ alk-S(O)—$C_1$-$C_6$ alkyl, —$C_1$-$C_6$ alk-$S(O)_2$—$C_1$-$C_6$ alkyl, —$CR^6R^{6'}$CN, —$NR^6R^{6'}$, —$NHCR^6R^{6'}$CN, —$NHCONR^6R^{6'}$, —NHC(O)$OR^7$, NHC(O)—$C_1$-$C_6$ alkyl, NHC(O)—$C_1$-$C_6$ haloalkyl, —NH—$C_1$-$C_6$ alk-C(O)—$C_1$-$C_6$ alkyl, —NHC(S)$NR^6R^{6'}$, —NH—O—$R^6$, or —NH—$NR^6R^{6'}$;

$R^2$ is H, halo, —$C_1$-$C_6$ alkyl, or $NH_2$;

$R^3$ is H, halo, —$C_1$-$C_6$ alkyl, —$C_1$-$C_6$ alkoxy, —$C_2$-$C_6$ alkenyl, or —$C_2$-$C_6$ alkynyl;

$R^4$ is H, —$C_1$-$C_6$ alkyl, —$C_1$-$C_6$ haloalkyl, —$C_2$-$C_6$ alkenyl, or —$C_2$-$C_6$ alkynyl;

$R^5$ is H or —$C_1$-$C_6$ alkyl;

$R^6$ and $R^{6'}$ are each independently H, $C_1$-$C_6$ alkyl, or —$C_1$-$C_6$ alk-$OC_1$-$C_6$ alkyl;

or $R^6$ and $R^{6'}$, together with the atom to which they are attached, form a $C_2$-$C_6$ heterocycloalkyl ring or a $C_3$-$C_6$ cycloalkyl ring;

$R^7$ is —$C_1$-$C_6$ alkyl or —$C_0$-$C_6$ alk-$C_3$-$C_6$ cycloalkyl;

X is O, S, NH, or N($C_1$-$C_6$ alkyl), and Y is —$(CR^9R^{9'})_n$—, —$CR^9$═$CR^{9'}$—, C(═O), —C(═O)—$(CR^9R^{9'})_n$—, —C(═O)—O—$(CR^9R^{9'})_n$—, —$CR^9R^{9'}$—O—, —$(CR^9R^{9'})_n$—O—$(CR^9R^{9'})_m$—, —$(CR^9R^{9'})_n$—$NR^{10}$, C(═O)$NR^{10}$, or CH—$C_1$-$C_4$ alk-$NH_2$; or X is —$SO_2$— and Y is —$(CR^9R^{9'})_n$—, —$CR^9$═$CR^{9'}$—, —$CR^9R^{9'}$—O—, —$(CR^9R^{9'})_n$—O—$(CR^9R^{9'})_m$—, —$(CR^9R^{9'})_n$—$NR^{10}$, or CH—$C_1$-$C_4$ alk-$NH_2$;

wherein n=1, 2, or 3; m=1 or 2;

each instance of $R^9$ or $R^{9'}$ is independently H, D, $C_1$-$C_6$ alkyl, $C_1$-$C_6$ haloalkyl, halo, —$C_1$-$C_6$ alkoxy, or hydroxy; $R^{10}$ is H or $C_1$-$C_6$ alkyl;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Stereoisomers of the compounds of Formula I, and the pharmaceutical salts and solvates thereof, are also contemplated, described, and encompassed herein. Methods of using compounds of Formula I are described, as well as pharmaceutical compositions including the compounds of Formula I.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

The term "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$ alkyl), ethyl (Et, $C_2$ alkyl), n-propyl ($C_3$ alkyl), isopropyl ($C_3$ alkyl), butyl ($C_4$ alkyl), isobutyl ($C_4$ alkyl), sec-butyl ($C_4$ alkyl), tert-butyl ($C_4$ alkyl), pentyl ($C_5$ alkyl), isopentyl ($C_5$ alkyl), tert-pentyl ($C_5$ alkyl), hexyl ($C_6$ alkyl), isohexyl ($C_6$ alkyl), and the like.

The term "alkoxy," when used alone or as part of a substituent group, refers to an oxygen radical to which is attached an alkyl group (i.e., —O-alkyl) Examples of alkoxy groups include methoxy (—OMe, $C_1$ alkoxy), ethoxy (—OEt, $C_2$ alkoxy), n-propoxy ($C_3$ alkoxy), isopropoxy ($C_3$ alkoxy), and the like.

The term "halo" when used alone or as part of a substituent group refers to chloro, fluoro, bromo, or iodo.

The term "haloalkyl" when used alone or as part of a substituent group refers to refers to an alkyl group wherein one or more of the hydrogen atoms has been replaced with one or more halogen atoms. Halogen atoms include chlorine, fluorine, bromine, and iodine. Examples of haloalkyl groups of the disclosure include, for example, trifluoromethyl (—$CF_3$), chloromethyl (—$CH_2Cl$), and the like.

The term "haloalkoxy," when used alone or as part of a substituent group, refers to an oxygen radical to which is attached a haloalkyl group (i.e., —O-haloalkyl). Examples of haloalkoxy groups include trifluoromethoxy (—$OCF_3$, $C_1$ haloalkoxy), difluoromethoxy (—$OCHF_2$, $C_1$ haloalkoxy), fluoromethoxy (—$OCH_2F$, $C_1$ haloalkoxy), trifluoroethoxy (—$OCH_2CF_3$, $C_2$ haloalkoxy), and the like.

The term "cycloalkyl" when used alone or as part of a substituent group refers to cyclic-containing, non-aromatic hydrocarbon groups having from 3 to 10 carbon atoms ("$C_3$-$C_{10}$"), preferably from 3 to 6 carbon atoms ("$C_3$-$C_6$"). Examples of cycloalkyl groups include, for example, cyclopropyl ($C_3$), cyclobutyl ($C_4$), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like.

The term "halocycloalkyl" when used alone or as part of a substituent group refers to cyclic-containing, non-aromatic hydrocarbon groups having from 3 to 10 carbon atoms ("$C_3$-$C_{10}$"), preferably from 3 to 6 carbon atoms ("$C_3$-$C_6$"), wherein one or more of the hydrogen atoms has been replaced with one or more halogen atoms. Halogen atoms include chlorine, fluorine, bromine, and iodine. Examples of halocycloalkyl groups include, for example, halocyclopropyl ($C_3$), halocyclobutyl ($C_4$), halocyclopropylmethyl ($C_4$), halocyclopentyl ($C_5$), halocyclohexyl ($C_6$), and the like.

The term "heterocycloalkyl" when used alone or as part of a substituent group refers to any three to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

The term "alkenyl" when used alone or as part of a substituent group refers to a straight- or branched-chain group having from 2 to 12 carbon atoms ("$C_2$-$C_{12}$"), preferably 2 to 4 carbons atoms ("$C_2$-$C_4$"), in the group, wherein the group includes at least one carbon-carbon double bond. Examples of alkenyl groups include vinyl ($-CH{=}CH_2$; $C_2$ alkenyl) allyl ($-CH_2-CH{=}CH_2$; $C_3$ alkenyl), propenyl ($-CH{=}CHCH_3$; $C_3$ alkenyl); isopropenyl ($-C(CH_3){=}CH_2$; $C_3$ alkenyl), butenyl ($-CH{=}CHCH_2CH_3$; $C_4$ alkenyl), sec-butenyl ($-C(CH_3){=}CHCH_3$; $C_4$ alkenyl), iso-butenyl ($-CH{=}C(CH_3)_2$; $C_4$ alkenyl), 2-butenyl ($-CH_2CH{=}CHCH_3$; $C_4$ alkyl), pentenyl ($CH{=}CHCH_2CH_2CH_3$; $C_5$ alkenyl), and the like.

The term "alkynyl" when used alone or as part of a substituent group refers to a straight- or branched-chain group having from 1 to 12 carbon atoms ("$C_1$-$C_{12}$"), preferably 1 to 4 carbons atoms ("$C_2$-$C_4$"), in the group, and wherein the group includes at least one carbon-carbon triple bond. Examples of alkynyl groups include ethynyl ($-C{\equiv}CH$; $C_2$ alkynyl); propargyl ($-CH_2-C{\equiv}CH$; $C_3$ alkynyl), propynyl ($-C{\equiv}CCH_3$; $C_3$ alkynyl); butynyl ($-C{\equiv}CCH_2CH_3$; $C_4$ alkynyl), pentynyl ($C{\equiv}CCH_2CH_2CH_3$; $C_5$ alkynyl), and the like.

The term "aryl" when used alone or as part of a substituent group refers to a mono- or bicyclic-aromatic hydrocarbon ring structure having 6 or 10 carbon atoms in the ring, wherein one or more of the carbon atoms in the ring is optionally substituted. Exemplary substituents include halogen atoms, $-C_1$-$C_3$ alkyl groups, and $C_1$-$C_3$ haloalkyl groups. Halogen atoms include chlorine, fluorine, bromine, and iodine. $C_1$-$C_3$ haloalkyl groups include, for example, $-CF_3$, $-CH_2CF_3$, and the like.

The term "heteroaryl" when used alone or as part of a substituent group refers to a mono- or bicyclic-aromatic ring structure including carbon atoms as well as up to four heteroatoms selected from nitrogen, oxygen, and sulfur. Heteroaryl rings can include a total of 5, 6, 9, or 10 ring atoms. The heteroaryl moiety can be optionally substituted. Exemplary substituents include halogen atoms; $-C_1$-$C_3$ alkyl groups, and $C_1$-$C_3$ haloalkyl groups. Halogen atoms include chlorine, fluorine, bromine, and iodine.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "$C_1$-$C_6$alk" when used alone or as part of a substituent group refers to an aliphatic linker having 1, 2, 3, 4, 5, or 6 carbon atoms and includes, for example, $-CH_2-$, $-CH(CH_3)-$, $-CH(CH_3)-CH_2-$, and $-C(CH_3)_2-$. The term "$-C_0$ alk-" refers to a bond. In some aspects, the $C_1$-$C_6$alk can be substituted with one or more $-OH$, $-NH_2$, or halo (e.g., $-F$, $-Cl$, $-Br$, with $-F$ being preferred) substituents.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder. In some embodiments, "treating" or "treatment" refers to prophylactic treatment, i.e., preventing the onset of the disease or disorder.

"Compounds of the present disclosure," and equivalent expressions, are meant to embrace compounds of Formula I as described herein, as well as their subgenera, which expression includes the stereoisomers (e.g., enantiomers, diastereomers) and constitutional isomers (e.g., tautomers) of compounds of Formula I as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

In some aspects, the disclosure is directed to compounds of Formula I.

I

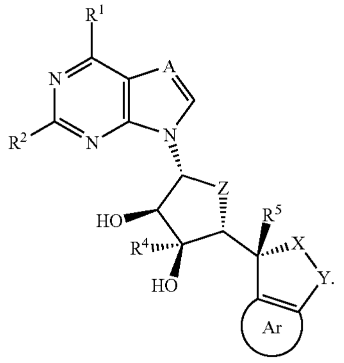

According to the disclosure, $R^1$ in Formula I is H, halo, —$C_1$-$C_6$ alkyl, —$C_1$-$C_6$ alkoxy, —$C_1$-$C_4$ haloalkyl, —$C_3$-$C_6$ cycloalkyl, —$C_3$-$C_6$halocycloalkyl, —$C_1$-$C_6$ alk-O—$C_1$-$C_6$ alkyl, —$C_1$-$C_6$ alk-S(O)—$C_1$-$C_6$ alkyl, —$C_1$-$C_6$ alk-S(O)$_2$—$C_1$-$C_6$ alkyl, —$CR^6R^{6'}$CN, —$NR^6R^{6'}$, —NHC$R^6R^{6'}$CN, —NHCON$R^6R^{6'}$, —NHC(O)O$R^7$, NHC(O)—$C_1$-$C_6$ alkyl, NHC(O)—$C_1$-$C_6$ haloalkyl, —NH—$C_1$-$C_6$ alk-C(O)—$C_1$-$C_6$ alkyl, —NHC(S)N$R^6R^{6'}$, —NH—O—$R^6$, or —NH—N$R^6R^{6'}$ In some embodiments, $R^1$ in Formula I is H.

In some embodiments, $R^1$ is halo (e.g., —F, —Cl, —Br, or —I), preferably —F.

In other embodiments, $R^1$ is —$C_1$-$C_6$ alkyl, for example, —$C_1$ alkyl, —$C_2$ alkyl, —$C_3$ alkyl, —$C_4$ alkyl, —$C_5$ alkyl, —$C_6$ alkyl, methyl, ethyl, propyl, isopropyl, butyl, isobutyl, s-butyl, t-butyl, pentyl, and the like. In some embodiments, $R^1$ is methyl.

In some embodiments, when $R^1$ is —$C_1$ alkyl, $R^1$ is —$CD_3$.

In yet other embodiments $R^1$ is —$C_1$-$C_6$ alkoxy, for example, —$C_1$ alkoxy, —$C_2$ alkoxy, —$C_3$ alkoxy, —$C_4$ alkoxy, —$C_5$ alkoxy, —$C_6$ alkoxy, methoxy, ethoxy, propoxy, isopropoxy, butoxy, isobutoxy, s-butoxy, t-butox, pentoxy, and the like.

In other embodiments, $R^1$ is —$C_1$-$C_4$ haloalkyl, for example, —$CF_3$ or —$CHF_2$, —$CH_2CH_2Cl$, —$CH_2CH_2F$, or —$CH_2CHF_2$. In some embodiments, $R^1$ is —$CH_2CH_2Cl$. In other embodiments, $R^1$ is —$CH_2CH_2F$. In yet other embodiments, $R^1$ is —$CH_2CHF_2$.

In other embodiments, $R^1$ is —$C_3$-$C_6$ cycloalkyl, for example, for example, cyclopropyl, cyclobutyl, cyclopentyl, or cyclohexyl. In some embodiments, $R^1$ is cyclopropyl.

In other embodiments, $R^1$ is —$C_3$-$C_6$halocycloalkyl, for example chlorocyclopropyl, fluorocyclobutyl, bromocyclopentyl, iodocyclohexyl, and the like.

In other embodiments, $R^1$ is —$C_1$-$C_6$ alk-O—$C_1$-$C_6$ alkyl, for example, —$C_1$ alk-O—$C_1$ alkyl, —$C_2$ alk-O—$C_1$ alkyl, —$C_3$ alk-O—$C_1$ alkyl, —$C_4$ alk-O—$C_1$ alkyl, —$C_5$ alk-O—$C_1$ alkyl, —$C_6$ alk-O—$C_1$ alkyl, —$C_1$ alk-O—$C_2$ alkyl, —$C_2$ alk-O—$C_2$ alkyl, —$C_3$ alk-O—$C_2$ alkyl, —$C_4$ alk-O—$C_2$ alkyl, —$C_5$ alk-O—$C_2$ alkyl, —$C_6$ alk-O—$C_2$ alkyl, —$C_1$ alk-O—$C_3$ alkyl, —$C_2$ alk-O—$C_3$ alkyl, —$C_3$ alk-O—$C_3$ alkyl, —$C_4$ alk-O—$C_3$ alkyl, —$C_5$ alk-O—$C_3$ alkyl, —$C_6$ alk-O—$C_3$ alkyl, —$C_1$ alk-O—$C_4$ alkyl, —$C_2$ alk-O—$C_4$ alkyl, —$C_3$ alk-O—$C_4$ alkyl, —$C_4$ alk-O—$C_4$ alkyl, —$C_5$ alk-O—$C_4$ alkyl, —$C_6$ alk-O—$C_4$ alkyl, —$C_1$ alk-O—$C_5$ alkyl, —$C_2$ alk-O—$C_5$ alkyl, —$C_3$ alk-O—$C_5$ alkyl, —$C_4$ alk-O—$C_5$ alkyl, —$C_5$ alk-O—$C_5$ alkyl, —$C_6$ alk-O—$C_5$ alkyl, —$C_1$ alk-O—$C_6$ alkyl, —$C_2$ alk-O—$C_6$ alkyl, —$C_3$ alk-O—$C_6$ alkyl, —$C_4$ alk-O—$C_6$ alkyl, —$C_5$ alk-O—$C_6$ alkyl, —$C_6$ alk-O—$C_6$ alkyl, —$CH_2CH_2OMe$, —$CH_2OMe$, —$CH_2CH_2OCH_2CH_3$, —$CH_2OCH_2CH_3$, —$CH_2CH_2CH_2OCH_3$, and the like.

In other embodiments, $R^1$ is —$C_1$-$C_6$ alk-S(O)—$C_1$-$C_6$ alkyl, for example, —$C_1$ alk-S(O)—$C_1$ alkyl, —$C_2$ alk-S(O)—$C_1$ alkyl, —$C_3$ alk-S(O)—$C_1$ alkyl, —$C_4$ alk-S(O)—$C_1$ alkyl, —$C_5$ alk-S(O)—$C_1$ alkyl, —$C_6$ alk-S(O)—$C_1$ alkyl, —$C_1$ alk-S(O)—$C_2$ alkyl, —$C_2$ alk-S(O)—$C_2$ alkyl, —$C_3$ alk-S(O)—$C_2$ alkyl, —$C_4$ alk-S(O)—$C_2$ alkyl, —$C_5$ alk-S(O)—$C_2$ alkyl, —$C_6$ alk-S(O)—$C_2$ alkyl, —$C_1$ alk-S(O)—$C_3$ alkyl, —$C_2$ alk-S(O)—$C_3$ alkyl, —$C_3$ alk-S(O)—$C_3$ alkyl, —$C_4$ alk-S(O)—$C_3$ alkyl, —$C_5$ alk-S(O)—$C_3$ alkyl, —$C_6$ alk-S(O)—$C_3$ alkyl, —$C_1$ alk-S(O)—$C_4$ alkyl, —$C_2$ alk-S(O)—$C_4$ alkyl, —$C_3$ alk-S(O)—$C_4$ alkyl, —$C_4$ alk-S(O)—$C_4$ alkyl, —$C_5$ alk-S(O)—$C_4$ alkyl, —$C_6$ alk-S(O)—$C_4$ alkyl, —$C_1$ alk-S(O)—$C_5$ alkyl, —$C_2$ alk-S(O)—$C_5$ alkyl, —$C_3$ alk-S(O)—$C_5$ alkyl, —$C_4$ alk-S(O)—$C_5$ alkyl, —$C_5$ alk-S(O)—$C_5$ alkyl, —$C_6$ alk-S(O)—$C_5$ alkyl, —$C_1$ alk-S(O)—$C_6$ alkyl, —$C_2$ alk-S(O)—$C_6$ alkyl, —$C_3$ alk-S(O)—$C_6$ alkyl, —$C_4$ alk-S(O)—$C_6$ alkyl, —$C_5$ alk-S(O)—$C_6$ alkyl, —$C_6$ alk-S(O)—$C_6$ alkyl, —$CH_2CH_2S(O)Me$, and the like.

In other embodiments, $R^1$ is —$C_1$-$C_6$ alk-$S(O)_2$—$C_1$-$C_6$ alkyl, for example, —$C_1$ alk-$S(O)_2$—$C_1$ alkyl, —$C_2$ alk-$S(O)_2$—$C_1$ alkyl, —$C_3$ alk-$S(O)_2$—$C_1$ alkyl, —$C_4$ alk-$S(O)_2$—$C_1$ alkyl, —$C_5$ alk-$S(O)_2$—$C_1$ alkyl, —$C_6$ alk-$S(O)_2$—$C_1$ alkyl, —$C_1$ alk-$S(O)_2$—$C_2$ alkyl, —$C_2$ alk-$S(O)_2$—$C_2$ alkyl, —$C_3$ alk-$S(O)_2$—$C_2$ alkyl, —$C_4$ alk-$S(O)_2$—$C_2$ alkyl, —$C_5$ alk-$S(O)_2$—$C_2$ alkyl, —$C_6$ alk-$S(O)_2$—$C_2$ alkyl, —$C_1$ alk-$S(O)_2$—$C_3$ alkyl, —$C_2$ alk-$S(O)_2$—$C_3$ alkyl, —$C_3$ alk-$S(O)_2$—$C_3$ alkyl, —$C_4$ alk-$S(O)_2$—$C_3$ alkyl, —$C_5$ alk-$S(O)_2$—$C_3$ alkyl, —$C_6$ alk-$S(O)_2$—$C_3$ alkyl, —$C_1$ alk-$S(O)_2$—$C_4$ alkyl, —$C_2$ alk-$S(O)_2$—$C_4$ alkyl, —$C_3$ alk-$S(O)_2$—$C_4$ alkyl, —$C_4$ alk-$S(O)_2$—$C_4$ alkyl, —$C_5$ alk-$S(O)_2$—$C_4$ alkyl, —$C_6$ alk-$S(O)_2$—$C_4$ alkyl, —$C_1$ alk-$S(O)_2$—$C_5$ alkyl, —$C_2$ alk-$S(O)_2$—$C_5$ alkyl, —$C_3$ alk-$S(O)_2$—$C_5$ alkyl, —$C_4$ alk-$S(O)_2$—$C_5$ alkyl, —$C_5$ alk-$S(O)_2$—$C_5$ alkyl, —$C_6$ alk-$S(O)_2$—$C_5$ alkyl, —$C_1$ alk-$S(O)_2$—$C_6$ alkyl, —$C_2$ alk-$S(O)_2$—$C_6$ alkyl, —$C_3$ alk-$S(O)_2$—$C_6$ alkyl, —$C_4$ alk-$S(O)_2$—$C_6$ alkyl, —$C_5$ alk-$S(O)_2$—$C_6$ alkyl, —$C_6$ alk-$S(O)_2$—$C_6$ alkyl, —$CH_2CH_2SO_2Me$, and the like.

In some embodiments, $R^1$ is —$CR^6R^{6'}CN$. Thus, in some embodiments wherein $R^6$ and $R^{6'}$ are both H, $R^1$ is cyanomethyl (i.e., —$CH_2CN$).

In some embodiments, $R^1$ is —$NR^6R^{6'}$. Thus, in some embodiments wherein $R^6$ and $R^{6'}$ are both H, $R^1$ is —$NH_2$. In some embodiments wherein $R^6$ and $R^{6'}$ are both methyl, $R^1$ is —$N(CH_3)_2$. In embodiments wherein $R^6$ is H and $R^{6'}$ is methyl, $R^1$ is —$NH(CH_3)$.

In some embodiments, $R^1$ is —$NHCR^6R^{6'}CN$. Thus, in some embodiments wherein $R^6$ and $R^{6'}$ are both H, $R^1$ is —$NHCH_2CN$.

In some embodiments, $R^1$ is —$NHCONR^6R^{6'}$. Thus, in some embodiments wherein $R^6$ and $R^{6'}$ are both H, $R^1$ is —$NHCONH_2$. In embodiments wherein $R^6$ and $R^{6'}$ are both methyl, $R^1$ is —$NHCON(CH_3)_2$. In embodiments wherein $R^6$ is H and $R^{6'}$ is methyl, $R^1$ is —$NHCONHCH_3$.

In some embodiments, $R^1$ is or —$NHC(O)OR^7$. Thus, in some embodiments wherein $R^7$ is methyl, $R^1$ is or —$NHC(O)OCH_3$.

In some aspects, $R^1$ is —NHC(O)—$C_1$-$C_6$ alkyl, for example, —NHC(O)—$C_1$ alkyl, NHC(O)—$C_2$ alkyl, NHC(O)—$C_3$ alkyl, NHC(O)—$C_4$ alkyl, NHC(O)—$C_5$ alkyl, NHC(O)—$C_6$ alkyl, NHC(O)-methyl, NHC(O)-ethyl, and the like.

In other aspects, $R^1$ is NHC(O)—$C_1$-$C_6$ haloalkyl, for example, —NHC(O)—$C_1$ haloalkyl, NHC(O)—$C_2$ haloalkyl, NHC(O)—$C_3$ haloalkyl, NHC(O)—$C_4$ haloalkyl, NHC(O)—$C_5$ haloalkyl, —NHC(O)—$C_6$ haloalkyl, —NHC(O)-chloromethyl, —NHC(O)-chloroethyl, —NHC(O)-fluoromethyl, —NHC(O)— fluoroethyl and the like.

In other aspects, $R^1$ is —NH—$C_1$-$C_6$ alk-C(O)—$C_1$-$C_6$ alkyl, for example, —NH—$C_1$ alk-C(O)—$C_1$-$C_6$ alkyl, —NH—$C_2$ alk-C(O)—$C_1$-$C_6$ alkyl, —NH—$C_3$ alk-C(O)—$C_1$-$C_6$ alkyl, —NH—$C_4$ alk-C(O)—$C_1$-$C_6$ alkyl, —NH—$C_5$ alk-C(O)—$C_1$-$C_6$ alkyl, —NH—$C_6$ alk-C(O)—$C_1$-$C_6$ alkyl, —NH—$C_1$-$C_6$ alk-C(O)—$C_1$ alkyl, —NH—$C_1$-$C_6$ alk-C(O)—$C_2$ alkyl, —NH—$C_1$-$C_6$ alk-C(O)—$C_3$ alkyl, —NH—$C_1$-$C_6$ alk-C(O)—$C_4$ alkyl, —NH—$C_1$-$C_6$ alk-C(O)—$C_5$ alkyl, —NH—$C_1$-$C_6$ alk-C(O)—$C_6$ alkyl and the like. In some aspects, $R^1$ is —NH—$CH_2$—C(O)—$CH_3$.

In some aspects, $R^1$ is $NHC(S)NR^6R^{6'}$. Thus, in some embodiments wherein $R^6$ and $R^{6'}$ are both H, $R^1$ is —$NHC(S)NH_2$. In embodiments wherein $R^6$ and $R^{6'}$ are both methyl, $R^1$ is —$NHC(S)N(CH_3)_2$. In embodiments wherein $R^6$ is H and $R^{6'}$ is methyl, $R^1$ is —$NHC(S)NHCH_3$.

In some aspects, $R^1$ is —NH—O—$R^6$. In some embodiments wherein $R^6$ is $C_1$-$C_6$ alkyl, for example, methyl, $R^1$ is —NH—$OCH_3$. In some embodiments wherein $R^6$ is H, $R^1$ is —NH—OH.

In some aspects, $R^1$ is —NH—$NR^6R^{6'}$. In some embodiments wherein $R^6$ and $R^{6'}$ are both H, $R^1$ is —NH—$NH_2$. In embodiments wherein $R^6$ and $R^{6'}$ are both $C_1$-$C_6$ alkyl, for example, methyl, $R^1$ is —NH—$N(CH_3)_2$. In embodiments wherein $R^6$ is H and $R^{6'}$ is $C_1$-$C_6$ alkyl, for example, methyl, $R^1$ is —NH—$NHCH_3$.

It will be apparent that when $R^1$ is —NH—O—$R^6$ or —NH—$NR^6R^{6'}$, the compounds of Formula I may exist as tautomers having (E)- or (Z)-geometry at the exocyclic carbon-nitrogen double bond. The compounds of Formula I described and claimed herein are meant to encompass all such tautomers and geometric isomers. The depiction of a particular tautomer or geometric isomer is not intended to be limiting.

In embodiments of the disclosure, $R^6$ and $R^{6'}$ in Formula I are each independently H, $C_1$-$C_6$ alkyl (e.g., methyl, ethyl, propyl, isopropyl, butyl, isobutyl, s-butyl, t-butyl, pentyl, and the like), or —$C_0$-$C_6$ alk-$OC_1$-$C_6$ alkyl (e.g., —$C_0$ alk-$OC_1$-$C_6$ alkyl, —$C_1$-$C_6$ alk-$OC_1$-$C_6$ alkyl, —$C_1$-$C_5$ alk-$OC_1$-$C_6$ alkyl, —$C_1$-$C_4$ alk-$OC_1$-$C_6$ alkyl, —$C_1$-$C_3$ alk-$OC_1$-$C_6$ alkyl, —$C_1$-$C_2$ alk-$OC_1$-$C_6$ alkyl, —$C_1$ alk-$OC_1$-$C_6$ alkyl, —$C_0$-$C_6$ alk-$OC_1$-$C_5$ alkyl, —$C_0$-$C_6$ alk-$OC_1$-$C_4$ alkyl, —$C_0$-$C_6$ alk-$OC_1$-$C_3$ alkyl, —$C_0$-$C_6$ alk-$OC_1$-$C_2$ alkyl, or —$C_0$-$C_6$ alk-$OC_1$ alkyl).

In some embodiments, $R^6$ is H or $C_1$-$C_6$ alkyl. In some embodiments, $R^{6'}$ is H or $C_1$-$C_6$ alkyl.

In some embodiments, $R^6$ and $R^{6'}$ are each H.

In other embodiments, $R^6$ and $R^{6'}$ are each independently $C_1$-$C_6$ alkyl. Thus, in some embodiments $R^6$ is methyl and $R^{6'}$ is methyl.

In some aspects, $R^6$ is $C_1$-$C_6$ alkyl and $R^{6'}$ is H. Thus, in some embodiments, $R^6$ is methyl and $R^{6'}$ is H.

In other aspects, $R^6$ and $R^{6'}$ are each independently —$C_0$-$C_6$ alk-$OC_1$-$C_6$ alkyl.

In other aspects, $R^6$ is —$C_0$-$C_6$ alk-$OC_1$-$C_6$ alkyl and $R^{6'}$ is H.

In embodiments of the disclosure, $R^6$ and $R^{6'}$, together with the atom to which they are attached, may form a $C_3$-$C_6$ cycloalkyl ring, for example, cyclopropyl, cyclobutyl, cyclopentyl, or cyclohexyl. In other embodiments of the disclosure, $R^6$ and $R^{6'}$, together with the atom to which they are attached, form a $C_2$-$C_6$ heterocycloalkyl, for example, azepanyl, aziridinyl, azetidinyl, pyrrolidinyl, imidazolidinyl, pyrazolidinyl, piperazinyl, piperidinyl, morpholinyl, thiomorpholinyl, oxazepanyl, piperazinyl, and the like.

In embodiments of the disclosure, $R^7$ is —$C_1$-$C_6$ alkyl, or —$C_0$-$C_6$ alk-$C_3$-$C_6$ cycloalkyl.

In some embodiments, $R^7$ is $C_1$-$C_6$ alkyl, for example, methyl, ethyl, propyl, isopropyl, butyl, isobutyl, s-butyl, t-butyl, pentyl, and the like. Thus, in some embodiments, $R^7$ is methyl.

In other aspects, $R^7$ is —$C_0$-$C_6$ alk-$C_3$-$C_6$ cycloalkyl, for example, —$C_0$ alk-$C_3$ cycloalkyl, —$C_1$ alk-$C_3$ cycloalkyl, —$C_2$ alk-$C_3$ cycloalkyl, —$C_3$ alk-$C_3$ cycloalkyl, —$C_4$ alk-$C_3$ cycloalkyl, —$C_5$ alk-$C_3$ cycloalkyl, —$C_6$ alk-$C_3$ cycloalkyl, —$C_0$ alk-$C_4$ cycloalkyl, —$C_1$ alk-$C_4$ cycloalkyl, —$C_2$ alk-$C_4$ cycloalkyl, —$C_3$ alk-$C_4$ cycloalkyl, —$C_4$ alk-$C_4$ cycloalkyl, —$C_5$ alk-$C_4$ cycloalkyl, —$C_6$ alk-$C_4$ cycloalkyl, —$C_0$ alk-$C_5$ cycloalkyl, —$C_1$ alk-$C_5$ cycloalkyl, —$C_2$ alk-$C_5$ cycloalkyl, —$C_3$ alk-$C_5$ cycloalkyl, —$C_4$ alk-$C_5$ cycloalkyl, —$C_5$ alk-$C_5$ cycloalkyl, —$C_6$ alk-$C_5$ cycloalkyl, —$C_0$ alk-$C_6$ cycloalkyl, —$C_1$ alk-$C_6$ cycloalkyl, —$C_2$ alk-$C_6$ cycloalkyl, —$C_3$ alk-$C_6$ cycloalkyl, —$C_4$ alk-$C_6$ cycloalkyl, —$C_5$ alk-$C_6$ cycloalkyl, —$C_6$ alk-$C_6$ cycloalkyl.

According to the disclosure, $R^2$ in Formula I is H, halo, —$C_1$-$C_6$ alkyl, or $NH_2$. Thus in some embodiments, $R^2$ is H. In other embodiments, $R^2$ is halo, for example F, Cl, Br, or I. In other embodiments, $R^2$ is —$C_1$-$C_6$ alkyl, for example, methyl, ethyl, propyl, isopropyl, butyl, isobutyl, s-butyl, t-butyl, pentyl, and the like. Thus, in some embodiments, $R^2$ is methyl (Me). In yet other embodiments, $R^2$ is $NH_2$. In the most preferred embodiments, $R^2$ is H.

According to the disclosure, $R^4$ in Formula I is H, —$C_1$-$C_6$ alkyl, —$C_1$-$C_6$ haloalkyl, —$C_2$-$C_6$ alkenyl, or —$C_2$-$C_6$ alkynyl. Thus in some embodiments, $R^4$ is H.

In other embodiments, $R^4$ is —$C_1$-$C_6$ alkyl, for example, methyl, ethyl, propyl, isopropyl, butyl, isobutyl, s-butyl, t-butyl, pentyl, and the like. Thus, in some embodiments, $R^4$ is methyl (Me).

In other aspects, $R^4$ is —$C_1$-$C_6$ haloalkyl, for example, —$CF_3$ or —$CHF_2$. In some embodiments, $R^4$ is —$CF_3$.

In some aspects, $R^4$ is —$C_2$-$C_6$ alkenyl, preferably —$C_2$-$C_4$ alkenyl, for example, vinyl, allyl, and the like.

In other aspects, $R^4$ is —$C_2$-$C_6$ alkynyl, preferably —$C_2$-$C_4$ alkynyl, for example, ethynyl, propargyl, and the like.

According to the disclosure, $R^5$ in Formula I is H or —$C_1$-$C_6$ alkyl. Thus in some embodiments, $R^5$ is H. In other embodiments, $R^5$ is —$C_1$-$C_6$ alkyl, for example, methyl, ethyl, propyl, isopropyl, butyl, isobutyl, s-butyl, t-butyl, pentyl, and the like. Thus, in some embodiments, $R^5$ is methyl (Me).

In some aspects of the disclosure, X in Formula I is O, S, NH, or N($C_1$-$C_6$ alkyl); and Y in Formula I is —$(CR^9R^{9'})_n$—, —$CR^9$═$CR^{9'}$—, C(═O), —C(═O)—$(CR^9R^{9'})_n$—, —C(═O)—O—$(CR^9R^{9'})_n$—, —$CR^9R^{9'}$—O—, —$(CR^9R^{9'})_n$—O—$(CR^9R^{9'})_m$—, —$(CR^9R^{9'})_n$—$NR^{10}$, C(═O)$NR^{10}$, or CH—$C_1$-$C_4$ alk-$NH_2$, wherein n=1 or 2, m=1 or 2, and wherein each instance of $R^9$ or $R^{9'}$ is independently H, D (i.e., deuterium), $C_1$-$C_6$ alkyl, $C_1$-$C_6$ haloalkyl, halo, —$C_1$-$C_6$ alkoxy, or hydroxy, and wherein $R^{10}$ is H or $C_1$-$C_6$ alkyl.

In other aspects of the disclosure, X in Formula I is —$SO_2$— and Y in Formula I is —$(CR^9R^{9'})_n$—, —$CR^9$═$CR^{9'}$—, —$CR^9R^{9'}$—O—, —$(CR^9R^{9'})_n$—O—$(CR^9R^{9'})_m$—, —$(CR^9R^{9'})_n$—$NR^{10}$, or CH—$C_1$-$C_4$ alk-$NH_2$, wherein n=1 or 2, m=1 or 2, and wherein each instance of $R^9$ or $R^{9'}$ is independently H, D (i.e., deuterium), $C_1$-$C_6$ alkyl, $C_1$-$C_6$ haloalkyl, halo, —$C_1$-$C_6$ alkoxy, or hydroxy, and wherein $R^{10}$ is H or $C_1$-$C_6$ alkyl.

In some embodiments, X is O. In other embodiments, X is S. In other embodiments, X is $SO_2$. In yet other embodiments, X is NH. In some embodiments, X is N($C_1$-$C_6$ alkyl), for example, N($C_1$ alkyl), N($C_2$ alkyl), N($C_3$ alkyl), N($C_4$ alkyl), N($C_5$ alkyl), N($C_6$ alkyl), N($CH_3$), N($CH_2CH_3$), and the like.

In some aspects, Y is —$(CR^9R^{9'})_n$—. In some embodiments n=1, and Y is —$CR^9R^{9'}$—.

In some embodiments n=1, $R^9$ and $R^{9'}$ are each H, and Y is —$CH_2$—.

In other embodiments wherein Y is —$(CR^9R^{9'})_n$—, n=1, $R^9$ and $R^{9'}$ are each F, and Y is —$CF_2$—.

In some embodiments wherein Y is —$(CR^9R^{9'})_n$—, n=1, $R^9$ and $R^{9'}$ are each $C_1$-$C_6$ alkyl, and Y is —C($C_1$-$C_6$ alkyl)$_2$-. In some embodiments, $C_1$-$C_6$ alkyl is —$CH_3$, and Y is —C$(CH_3)_2$—.

In some embodiments wherein Y is —$(CR^9R^{9'})_n$—, n=2, and Y is —$CR^9R^{9'}$—$CR^9R^{9'}$—.

In some embodiments wherein Y is —$(CR^9R^{9'})_n$— and n=2, each $R^9$ and each $R^{9'}$ is H, and Y is —$CH_2CH_2$—.

In some embodiments wherein Y is —$(CR^9R^{9'})_n$— and n=2, one $R^9$ is —$C_1$-$C_6$ alkoxy, the other $R^9$ is H, and each $R^{9'}$ is H, and Y is —$CH_2$CH($C_1$-$C_6$ alkoxy)—. In some embodiments, $C_1$-$C_6$ alkoxy is —$OCH_3$, and Y is —$CH_2$CH($OCH_3$)—.

In some embodiments wherein Y is —$(CR^9R^{9'})_n$— and n=2, one $R^9$ is -hydroxy, the other $R^9$ is H, and each $R^{9'}$ is H, and Y is —$CH_2$CH(OH)—.

In some embodiments wherein Y is —$(CR^9R^{9'})_n$— and n=2, one $R^9$ is —$C_1$-$C_6$ alkyl, the other $R^9$ is H, and each $R^{9'}$ is H, and Y is —$CH_2$CH($C_1$-$C_6$ alkyl). In some embodiments, $C_1$-$C_6$ alkyl is —$CH_3$, and Y is —$CH_2CH(CH_3)$—.

In some embodiments wherein Y is —$(CR^9R^{9'})_n$— and n=2, one $R^9$ is —$C_1$-$C_6$ alkyl, one $R^9$ is H, one $R^{9'}$ is —$C_1$-$C_6$ alkyl, one $R^{9'}$ is H, and Y is —$CH_2$C($C_1$-$C_6$ alkyl)$_2$-. In some embodiments, $C_1$-$C_6$ alkyl is —$CH_3$, and Y is —$CH_2C(CH_3)_2$—.

In some embodiments wherein Y is —$(CR^9R^{9'})_n$— and n=2, one $R^9$ is —$C_1$-$C_6$ haloalkyl, the other $R^9$ is H, and each $R^{9'}$ is H, and Y is —$CH_2$CH($C_1$-$C_6$ haloalkyl)-. In some embodiments, $C_1$-$C_6$ haloalkyl is —$CF_3$, and Y is —$CH_2$CH($CF_3$)—.

In some embodiments wherein Y is —$(CR^9R^{9'})_n$— and n=2, one $R^9$ is —F, the other $R^9$ is H, and each $R^{9'}$ is H, and Y is —$CH_2$CHF—.

In some embodiments wherein Y is —$(CR^9R^{9'})_n$— and n=2, one $R^9$ is F, the other $R^9$ is H, one $R^{9'}$ is F, and the other $R^{9'}$ is H, and Y is —$CH_2CF_2$—.

In some embodiments wherein Y is —$(CR^9R^{9'})_n$— and n=2, one $R^9$ is D, the other $R^9$ is H, one $R^{9'}$ is D, and the other $R^{9'}$ is H, and Y is —$CH_2CD_2$-.

In some embodiments wherein Y is —$(CR^9R^{9'})_n$— and n=1, $R^9$ and $R^{9'}$ are each $C_1$-$C_6$ alkyl, and Y is —C($C_1$-$C_6$ alkyl)$_2$-. In some embodiments, $C_1$-$C_6$ alkyl is —$CH_3$, and Y is —C$(CH_3)_2$—.

In some embodiments, Y is —$(CR^9R^{9'})_n$— and n=3. In some embodiments n=3, $R^9$ and $R^{9'}$ are each H, and Y is —$CH_2CH_2CH_2$—.

In some aspects, Y is —$CR^9$═$CR^{9'}$—. In some embodiments wherein Y is —$CR^9$═$CR^{9'}$—, $R^9$ and $R^{9'}$ are each H, and Y is —CH═CH—.

In other aspects, Y is C(═O).

In some aspects, Y is —C(═O)—$(CR^9R^{9'})_n$—. In some embodiments, n=1, $R^9$ and $R^{9'}$ are both H, and Y is —C(═O)—$CH_2$—.

In some aspects, Y is —C(═O)—O—$(CR^9R^{9'})_n$—. In some embodiments, n=1, $R^9$ and $R^{9'}$ are both H, and Y is —C(═O)—O—$CH_2$—. In other embodiments, n=2, $R^9$ and $R^{9'}$ are both H, and Y is —C(═O)—O—$CH_2CH_2$—.

In some aspects, Y is —$CR^9R^{9'}$—O—. In some embodiments, $R^9$ and $R^{9'}$ are both H, and Y is —$CH_2$—O—. In other embodiments, $R^9$ and $R^{9'}$ are both F, and Y is —$CF_2$—O—.

In some aspects, Y is —$(CR^9R^{9'})_n$—O—$(CR^9R^{9'})_m$—. In some embodiments, n=m=1, and each $R^9$ and each $R^{9'}$ is H, and Y is —$CH_2$—O—$CH_2$—. In other embodiments, n=m=1, and one $R^9$ is H and one $R^9$ is F, and one $R^{9'}$ is H and one $R^{9'}$ is F, and Y is —$CF_2$—O—$CH_2$—. In other embodiments, n=1, m=2, each $R^9$ and each $R^{9'}$ is H, and Y is —$CH_2$—O—$CH_2CH_2$—. In other embodiments, n=1, m=2, one $R^9$ is F and the other $R^9$ are H, and one $R^{9'}$ is F and the other $R^{9'}$ are H, and Y is —$CF_2$—O—$CH_2CH_2$—.

In some aspects, Y is —$(CR^9R^{9'})_n$—$NR^{10}$—. In some embodiments, n=1, $R^9$, $R^{9'}$, and $R^{10}$ is H, and Y is —$CH_2$—NH—. In other embodiments, n=1, $R^9$ are $R^{9'}$ are both H, $R^{10}$ is $C_1$-$C_6$ alkyl, and Y is —$CH_2$—N($C_1$-$C_6$ alkyl)-.

In some aspects, Y is —C(═O)$NR^{10}$. In some embodiments, $R^{10}$ is H, and Y is —C(═O)NH—. In other embodiments, $R^{10}$ is $C_1$-$C_6$ alkyl, and Y is —C(═O)N($C_1$-$C_6$ alkyl)-.

It will be apparent to those skilled in the art that some embodiments of the element Y attach to the element X of Formula I through one atom, and to the Ar group of Formula I through a different atom (i.e., when Y is —$(CR^9R^{9'})_n$— with n=2, —$CR^9$═$CR^{9'}$—, —C(═O)—$(CR^9R^{9'})_n$—, —C(═O)—O—$(CR^9R^{9'})_n$—, —$CR^9R^{9'}$—O—, —$(CR^9R^{9'})_n$—O—$(CR^9R^{9'})_m$—, —$(CR^9R^{9'})_n$—$NR^{10}$, and —C(═O)$NR^{10}$). When such embodiments of Y attach to X and Ar through only non-carbonyl carbon atoms (i.e., when Y is —$(CR^9R^{9'})_n$— with n=2, —$CR^9$═$CR^{9'}$—, or —$(CR^9R^{9'})_n$—O—$(CR^9R^{9'})_m$—, then Y may attach to X or to Ar through either carbon atom. For example, when Y is —$CR^9$═$CR^{9'}$—, Y may attach as either Ar—$CR^9$═$CR^{9'}$—X or as X—$CR^9$═$CR^{9'}$—Ar. Similarly, when Y is —$(CR^9R^{9'})_n$—O—$(CR^9R^{9'})_m$—, Y may attach as either Ar—$(CR^9R^{9'})_n$—O—$(CR^9R^{9'})_m$—X or as X—$(CR^9R^{9'})_n$—O—$(CR^9R^{9'})_m$—Ar.

When such embodiments of Y attach through a non-carbonyl carbon atom and a carbonyl carbon atom (i.e., when Y is —C(═O)—$(CR^9R^{9'})_n$— or —C(═O)—O—$(CR^9R^{9'})_n$—), then the carbonyl carbon atom of Y attaches to X, and the non-carbonyl carbon atom of Y attaches to Ar. The following examples illustrate this point. When Y is —C(═O)—$(CR^9R^{9'})_n$—, then Y attaches as:

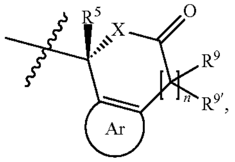

but NOT as:

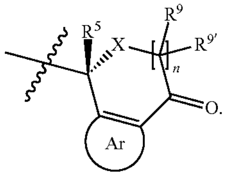

Similarly, when Y is —C(═O)—O—$(CR^9R^{9'})_n$—, then Y attaches as:

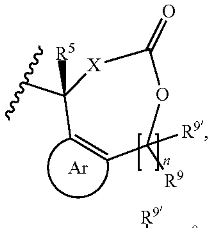

but NOT as:

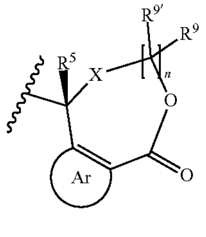

When embodiments of Y attach to X and Ar through a carbon atom of Y and an oxygen or nitrogen atom of Y (i.e., when Y is —$CR^9R^{9'}$—O—, —$(CR^9R^{9'})_n$—$NR^{10}$—, or —C(═O)$NR^{10}$—), then Y attaches to Ar through only the oxygen or nitrogen atom, and Y attaches to X through only the carbon atom. That is, Y attaches as X—$CR^9R^{9'}$—O—Ar, X—$(CR^9R^{9'})_n$—$NR^{10}$—Ar, or X—C(═O)$NR^{10}$—Ar. The following examples illustrate this point. When Y is —$CR^9R^{9'}$—O—, or —$(CR^9R^{9'})_n$—$NR^{10}$—, then Y attaches as:

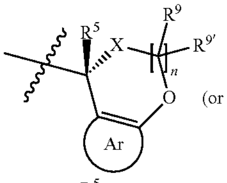

(or $NR^{10}$), but NOT as:

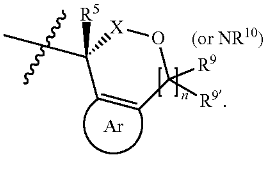

(or $NR^{10}$)

When Y is —C(═O)$NR^{10}$—, then Y attaches as:

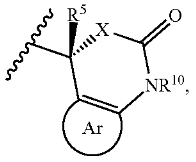

but NOT as

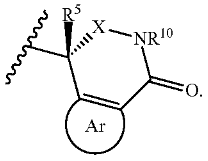

In other embodiments, Y is CH—$C_1$-$C_4$ alk-$NH_2$, for example, CH—$C_1$ alk-$NH_2$, CH—$C_2$ alk-$NH_2$, CH—$C_3$ alk-$NH_2$, CH—$C_4$ alk-$NH_2$, CH—$CH_2$—$NH_2$, CH—$CH_2CH_2$—$NH_2$, and the like.

According to the disclosure, Ar in Formula I is an optionally substituted 6-membered aryl ring, an optionally substituted 6-membered heteroaryl ring, or an optionally substituted 5-membered heteroaryl ring. In some embodiments, Ar is an optionally substituted 6-membered aryl ring. In some embodiments, the 6-membered aryl ring is unsubstituted. In other embodiments, the 6-membered aryl ring is substituted with one or more substituents, independently selected from halo, $C_1$-$C_6$ alkyl, $C_1$-$C_6$ haloalkyl, $C_1$-$C_6$ alkoxy, and $C_1$-$C_6$ haloalkoxy. In some preferred embodiments, the 6-membered aryl ring is substituted with one or more —F, —Cl, —$CH_3$, —$CF_3$, or —$OCF_3$ substituents.

In some embodiments, Ar is an optionally substituted 6-membered heteroaryl ring. In some embodiments, the 6-membered heteroaryl ring is unsubstituted. In other embodiments, the 6-membered heteroaryl ring is substituted with one or more substituents, independently selected from halo, $C_1$-$C_6$ alkyl, $C_1$-$C_6$ haloalkyl, $C_1$-$C_6$ alkoxy, and $C_1$-$C_6$ haloalkoxy. In some preferred embodiments, the 6-membered heteroaryl ring is substituted with one or more —F, —Cl, —$CH_3$, —$CF_3$, or —$OCF_3$ substituents.

In some embodiments, Ar is an optionally substituted 5-membered heteroaryl ring. In some embodiments, the 5-membered heteroaryl ring is unsubstituted. In other embodiments, the 5-membered heteroaryl ring is substituted with one or more substituents, independently selected from halo, $C_1$-$C_6$ alkyl, $C_1$-$C_6$ haloalkyl, $C_1$-$C_6$ alkoxy, and $C_1$-$C_6$ haloalkoxy. In some preferred embodiments, the 5-membered heteroaryl ring is substituted with one or more —F, —Cl, —$CH_3$, —$CF_3$, or —$OCF_3$ substituents.

According to the disclosure, A in Formula I is N or C—$R^3$. In some embodiments, A is N and the compounds of Formula I are of the Formula I-B:

I-B

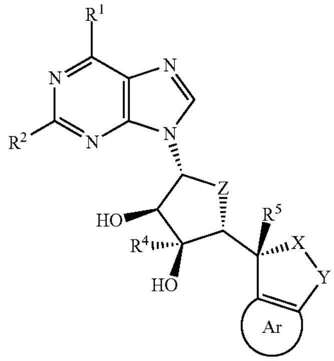

In other embodiments, A is C—$R^3$ and the compounds of Formula I are of the Formula I-C:

I-C

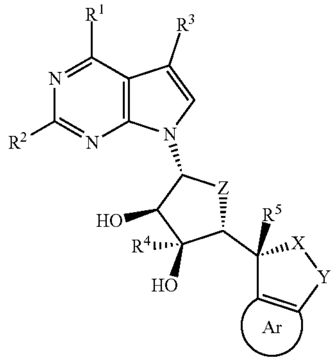

In embodiments of the disclosure that are compounds of Formula I-C, $R^3$ is H, halo, —$C_1$-$C_6$ alkyl, —$C_1$-$C_6$ alkoxy, —$C_2$-$C_6$ alkenyl, or —$C_2$-$C_6$ alkynyl.

In some embodiments of the compound of Formula I-C, $R^3$ is H. In other embodiments of the compound of Formula I-C, $R^3$ is halo (i.e., —F, —Cl, —Br, or —I), preferably F. In other embodiments of the compounds of Formula I-C, $R^3$ is —$C_1$-$C_6$ alkyl, for example, —$C_1$ alkyl, —$C_2$ alkyl, —$C_3$ alkyl, —$C_4$ alkyl, —$C_5$ alkyl, —$C_6$ alkyl, methyl, ethyl, propyl, isopropyl, butyl, isobutyl, s-butyl, t-butyl, pentyl, and the like. In yet other embodiments of the compounds of Formula I-C, $R^3$ is —$C_1$-$C_6$ alkoxy, for example, —$C_1$ alkoxy, —$C_2$ alkoxy, —$C_3$ alkoxy, —$C_4$ alkoxy, —$C_5$ alkoxy, —$C_6$ alkoxy, methoxy, ethoxy, propoxy, isopropoxy, butoxy, isobutoxy, s-butoxy, t-butox, pentoxy, and the like. In some other embodiments, $R^3$ is —$C_2$-$C_6$ alkenyl, preferably —$C_2$-$C_4$ alkenyl, for example, vinyl, allyl, and the like. In yet other embodiments, $R^3$ is —$C_2$-$C_6$ alkynyl, preferably —$C_2$-$C_4$ alkynyl, for example, ethynyl, propargyl, and the like.

According to the disclosure, Z in Formula I is O, $CH_2$, or $CF_2$. In some embodiments, Z is O, and the compounds of Formula I are of the Formula I-D:

I-D

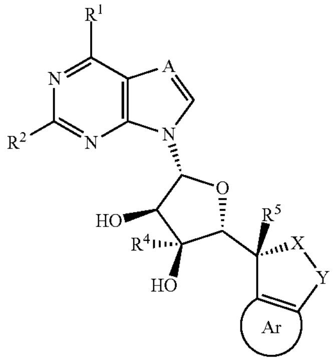

In other embodiments, Z is $CH_2$, and the compounds of Formula I are of the Formula I-E:

I-E

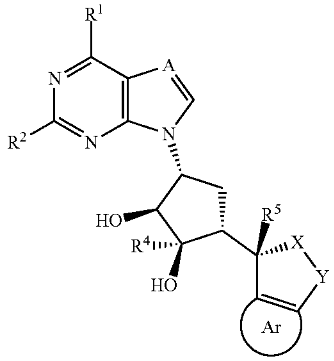

In yet other embodiments, Z is $CF_2$, and the compounds of Formula I are of the Formula I-F:

I-F

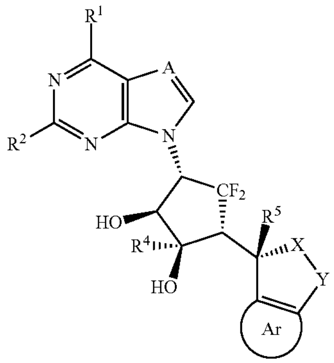

In some embodiments, Ar in the compounds of Formula I is an optionally substituted 6-membered aryl ring, or an optionally substituted 6-membered heteroaryl ring, and the compounds of Formula I are of the Formula I-G:

I-G

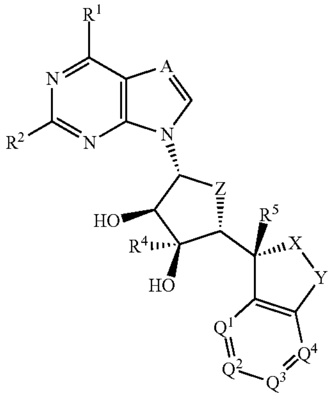

wherein $Q^1$, $Q^2$, $Q^3$, and $Q^4$ are each independently selected from CH, C—$R^8$, or N; and $R^8$ is halo, $C_1$-$C_6$ alkyl, $C_1$-$C_6$ haloalkyl, $C_1$-$C_6$ alkoxy, or $C_1$-$C_6$ haloalkoxy.

Thus, in some embodiments of compounds of Formula I-G, $R^8$ is halo (e.g., —F, —Cl, —Br, —I), preferably —F or —Cl. In other embodiments of compounds of Formula I-G, $R^8$ is $C_1$-$C_6$ alkyl, for example, —$C_1$ alkyl, —$C_2$ alkyl, —$C_3$ alkyl, —$C_4$ alkyl, —$C_5$ alkyl, —$C_6$ alkyl, methyl, ethyl, propyl, isopropyl, butyl, isobutyl, s-butyl, t-butyl, pentyl, and the like.

In other embodiments of compounds of Formula I-G, $R^8$ is $C_1$-$C_6$ haloalkyl, for example, —$C_1$ haloalkyl, —$C_2$ haloalkyl, —$C_3$ haloalkyl, —$C_4$ haloalkyl, —$C_5$ haloalkyl, —$C_6$ haloalkyl, fluoromethyl, fluoroethyl, fluoropropyl, fluorobutyl, fluoropentyl, chloromethyl, chloroethyl, chloropropyl, chlorobutyl, chloropentyl, bromomethyl, bromoethyl, bromopropyl, bromobutyl, bromopentyl, iodomethyl, iodoethyl, iodopropyl, iodobutyl, iodopentyl, and the like.

In other embodiments of compounds of Formula I-G, $R^8$ is —$C_1$-$C_6$ alkoxy, for example, —$C_1$ alkoxy, —$C_2$ alkoxy, —$C_3$ alkoxy, —$C_4$ alkoxy, —$C_5$ alkoxy, —$C_6$ alkoxy, methoxy, ethoxy, propoxy, isopropoxy, butoxy, isobutoxy, s-butoxy, t-butox, pentoxy, and the like.

In other embodiments of compounds of Formula I-G, $R^8$ is —$C_1$-$C_6$ haloalkoxy, for example, —$C_1$ haloalkoxy, —$C_2$ haloalkoxy, —$C_3$ haloalkoxy, —$C_4$ haloalkoxy, —$C_5$ haloalkoxy, —$C_6$ haloalkoxy, halomethoxy, haloethoxy, halopropoxy, haloisopropoxy, halobutoxy, haloisobutoxy, halo-s-butoxy, halo-t-butoxy, halopentoxy, and the like.

In other embodiments, Ar is a 5-membered heteroaryl group, and the compounds of Formula I are of the Formula I-H:

I-H

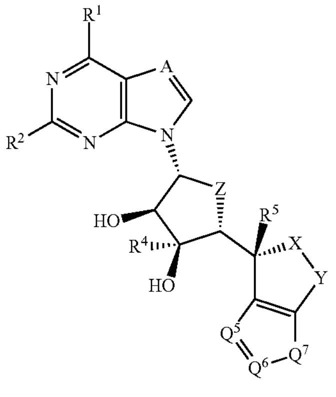

wherein $Q^5$ and $Q^6$ are CH, C—$R^8$, or N, and $Q^7$ is NH, N($C_1$-$C_6$ alkyl), S, O, or, when at least one of $Q^5$ and $Q^6$ is N, $Q^7$ may be $CH_2$ or CH—$R^8$; and wherein and $R^8$ is halo, $C_1$-$C_6$ alkyl, $C_1$-$C_6$ haloalkyl, $C_1$-$C_6$ alkoxy, or $C_1$-$C_6$ haloalkoxy.

It will be apparent that when $Q^7$ is NH, $CH_2$, or CH—$R^8$, then the 5-membered heteroaryl group in compounds of Formula I-H may exist in tautomeric forms. All such tautomeric forms are encompassed by the present disclosure.

Thus, in some embodiments of compounds of Formula I-H, $R^8$ is halo (e.g., —F, —Cl, —Br, —I), preferably —F or —Cl. In other embodiments of compounds of Formula I-H, $R^8$ is $C_1$-$C_6$ alkyl, for example, —$C_1$ alkyl, —$C_2$ alkyl, —$C_3$ alkyl, —$C_4$ alkyl, —$C_5$ alkyl, —$C_6$ alkyl, methyl, ethyl, propyl, isopropyl, butyl, isobutyl, s-butyl, t-butyl, pentyl, and the like.

In other embodiments of compounds of Formula I-H, $R^8$ is $C_1$-$C_6$ haloalkyl, for example, —$C_1$ haloalkyl, —$C_2$ haloalkyl, —$C_3$ haloalkyl, —$C_4$ haloalkyl, —$C_5$ haloalkyl, —$C_6$ haloalkyl, fluoromethyl, fluoroethyl, fluoropropyl, fluorobutyl, fluoropentyl, chloromethyl, chloroethyl, chloropropyl, chlorobutyl, chloropentyl, bromomethyl, bromoethyl, bromopropyl, bromobutyl, bromopentyl, iodomethyl, iodoethyl, iodopropyl, iodobutyl, iodopentyl, and the like.

In other embodiments of compounds of Formula I-H, $R^8$ is —$C_1$-$C_6$ alkoxy, for example, —$C_1$ alkoxy, —$C_2$ alkoxy, —$C_3$ alkoxy, —$C_4$ alkoxy, —$C_5$ alkoxy, —$C_6$ alkoxy, methoxy, ethoxy, propoxy, isopropoxy, butoxy, isobutoxy, s-butoxy, t-butox, pentoxy, and the like.

In other embodiments of compounds of Formula I-H, $R^8$ is —$C_1$-$C_6$ haloalkoxy, for example, —$C_1$ haloalkoxy, —$C_2$ haloalkoxy, —$C_3$ haloalkoxy, —$C_4$ haloalkoxy, —$C_5$ haloalkoxy, —$C_6$ haloalkoxy, halomethoxy, haloethoxy, halopropoxy, haloisopropoxy, halobutoxy, haloisobutoxy, halo-s-butoxy, halo-t-butoxy, halopentoxy, and the like.

In other embodiments, Ar is a 5-membered heteroaryl group, and the compounds of Formula I are of the Formula I-I.

I-I

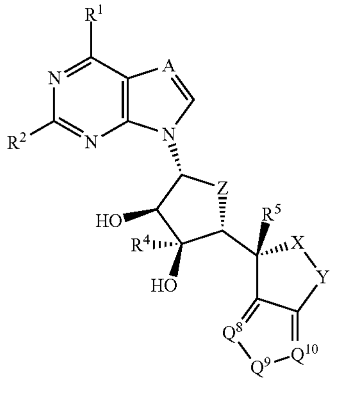

wherein $Q^8$ and $Q^{10}$ are CH, C—$R^8$, or N, and $Q^9$ is NH, N($C_1$-$C_6$ alkyl), S, O, or, when at least one of $Q^8$ and $Q^{10}$ is N, $Q^9$ may be $CH_2$ or CH—$R^8$; and wherein $R^8$ is halo, $C_1$-$C_6$ alkyl, $C_1$-$C_6$ haloalkyl, $C_1$-$C_6$ alkoxy, or $C_1$-$C_6$ haloalkoxy.

It will be apparent that when $Q^9$ is NH, $CH_2$, or CH—$R^8$, then the 5-membered heteroaryl group in compounds of Formula I-I may exist in tautomeric forms. All such tautomeric forms are encompassed by the present disclosure.

Thus, in some embodiments of compounds of Formula I-I, $R^8$ is halo (e.g., —F, —Cl, —Br, —I), preferably —F or —Cl. In other embodiments of compounds of Formula I-I, $R^8$ is $C_1$-$C_6$ alkyl, for example, —$C_1$ alkyl, —$C_2$ alkyl, —$C_3$ alkyl, —$C_4$ alkyl, —$C_5$ alkyl, —$C_6$ alkyl, methyl, ethyl, propyl, isopropyl, butyl, isobutyl, s-butyl, t-butyl, pentyl, and the like.

In other embodiments of compounds of Formula I-I, $R^8$ is $C_1$-$C_6$ haloalkyl, for example, —$C_1$ haloalkyl, —$C_2$ haloalkyl, —$C_3$ haloalkyl, —$C_4$ haloalkyl, —$C_5$ haloalkyl, —$C_6$ haloalkyl, fluoromethyl, fluoroethyl, fluoropropyl, fluorobutyl, fluoropentyl, chloromethyl, chloroethyl, chloropropyl, chlorobutyl, chloropentyl, bromomethyl, bromoethyl, bromopropyl, bromobutyl, bromopentyl, iodomethyl, iodoethyl, iodopropyl, iodobutyl, iodopentyl, and the like.

In other embodiments of compounds of Formula I-I, $R^8$ is —$C_1$-$C_6$ alkoxy, for example, —$C_1$ alkoxy, —$C_2$ alkoxy, —$C_3$ alkoxy, —$C_4$ alkoxy, —$C_5$ alkoxy, —$C_6$ alkoxy, methoxy, ethoxy, propoxy, isopropoxy, butoxy, isobutoxy, s-butoxy, t-butox, pentoxy, and the like.

In other embodiments of compounds of Formula I-I, $R^8$ is —$C_1$-$C_6$ haloalkoxy, for example, —$C_1$ haloalkoxy, —$C_2$ haloalkoxy, —$C_3$ haloalkoxy, —$C_4$ haloalkoxy, —$C_5$ haloalkoxy, —$C_6$ haloalkoxy, halomethoxy, haloethoxy, halopropoxy, haloisopropoxy, halobutoxy, haloisobutoxy, halo-s-butoxy, halo-t-butoxy, halopentoxy, and the like.

In yet other embodiments, Ar is a 5-membered heteroaryl group, and the compounds of Formula I are of the Formula I-J:

I-J

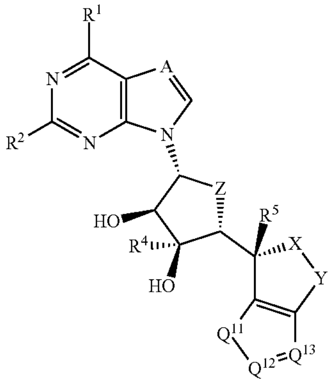

wherein $Q^{12}$ and $Q^{13}$ are CH, C—$R^8$, or N, and $Q^{11}$ is NH, N($C_1$-$C_6$ alkyl), S, O, or, when at least one of $Q^{12}$ and $Q^{13}$ is N, $Q^{11}$ may be $CH_2$ or CH—$R^8$; and wherein $R^8$ is halo, $C_1$-$C_6$ alkyl, $C_1$-$C_6$ haloalkyl, $C_1$-$C_6$ alkoxy, or $C_1$-$C_6$ haloalkoxy.

It will be apparent that when $Q^{11}$ is NH, $CH_2$, or CH—$R^8$, then the 5-membered heteroaryl group in compounds of Formula I-J may exist in tautomeric forms. All such tautomeric forms are encompassed by the present disclosure.

Thus, in some embodiments of compounds of Formula I-J, $R^8$ is halo (e.g., —F, —Cl, —Br, —I), preferably —F or —Cl. In other embodiments of compounds of Formula I-J, $R^8$ is $C_1$-$C_6$ alkyl, for example, —$C_1$ alkyl, —$C_2$ alkyl, —$C_3$ alkyl, —$C_4$ alkyl, —$C_5$ alkyl, —$C_6$ alkyl, methyl, ethyl, propyl, isopropyl, butyl, isobutyl, s-butyl, t-butyl, pentyl, and the like.

In other embodiments of compounds of Formula I-J, $R^8$ is $C_1$-$C_6$ haloalkyl, for example, —$C_1$ haloalkyl, —$C_2$ haloalkyl, —$C_3$ haloalkyl, —$C_4$ haloalkyl, —$C_5$ haloalkyl, —$C_6$ haloalkyl, fluoromethyl, fluoroethyl, fluoropropyl, fluorobutyl, fluoropentyl, chloromethyl, chloroethyl, chloropropyl, chlorobutyl, chloropentyl, bromomethyl, bromoethyl, bromopropyl, bromobutyl, bromopentyl, iodomethyl, iodoethyl, iodopropyl, iodobutyl, iodopentyl, and the like.

In other embodiments of compounds of Formula I-J, $R^8$ is —$C_1$-$C_6$ alkoxy, for example, —$C_1$ alkoxy, —$C_2$ alkoxy, —$C_3$ alkoxy, —$C_4$ alkoxy, —$C_5$ alkoxy, —$C_6$ alkoxy, methoxy, ethoxy, propoxy, isopropoxy, butoxy, isobutoxy, s-butoxy, t-butox, pentoxy, and the like.

In other embodiments of compounds of Formula I-J, $R^8$ is —$C_1$-$C_6$ haloalkoxy, for example, —$C_1$ haloalkoxy, —$C_2$ haloalkoxy, —$C_3$ haloalkoxy, —$C_4$ haloalkoxy, —$C_5$ haloalkoxy, —$C_6$ haloalkoxy, halomethoxy, haloethoxy, halopropoxy, haloisopropoxy, halobutoxy, haloisobutoxy, halo-s-butoxy, halo-t-butoxy, halopentoxy, and the like.

In some embodiments, compounds of formula I-J are those wherein A is C—H; $R^2$ is H, $R^3$ is —$NH_2$ or —$CH_3$; $R^4$=$R^5$=H; X=Z=O; Y=—$CH_2CH_2$—; $Q^{11}$ is S, $Q^{13}$ is CH, and $Q^{12}$ is C—$R^8$, wherein $R^8$ is halogen.

Some preferred embodiments of the compounds of Formula I are compounds of Formula I-A:

I-A

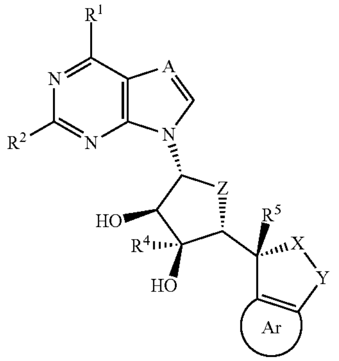

or a pharmaceutically acceptable salt, or solvate thereof; wherein

A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, NH, or N($C_1$-$C_6$ alkyl); and Y is $CH_2$, —$CH_2CH_2$—, $C(CH_3)_2$, $CF_2$, C(=O), or CH—$C_1$-$C_4$ alk-$NH_2$; or X is $SO_2$; and Y is $CH_2$, —$CH_2CH_2$—, $C(CH_3)_2$, $CF_2$, or CH—$C_1$-$C_4$ alk-$NH_2$;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Other preferred embodiments of the compounds of Formula I are compounds of Formula I-A, or a pharmaceutically acceptable salt, or solvate thereof, wherein A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, NH, or N($C_1$-$C_6$ alkyl);

Y is —C(=O)—$(CR^9R^{9'})_n$—, wherein n=1 or 2, each $R^9$ and $R^{9'}$ is H;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Other preferred embodiments of the compounds of Formula I are compounds of Formula I-A, or a pharmaceutically acceptable salt, or solvate thereof, wherein A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, $SO_2$, NH, or N($C_1$-$C_6$ alkyl);

Y is —$CR^9$=$CR^{9'}$—, each $R^9$ and $R^{9'}$ is H;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Other preferred embodiments of the compounds of Formula I are compounds of Formula I-A, or a pharmaceutically acceptable salt, or solvate thereof, wherein A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, NH, or N($C_1$-$C_6$ alkyl);

Y is —C(=O)—O—$(CR^9R^{9'})_n$— wherein n=1 or 2 and each $R^9$ and $R^{9'}$ is H;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Other preferred embodiments of the compounds of Formula I are compounds of Formula I-A-1:

I-A-1

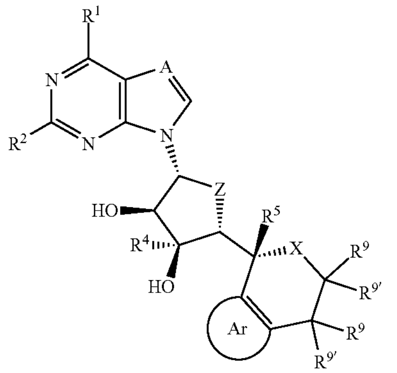

or a pharmaceutically acceptable salt, or solvate thereof; wherein

A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, $SO_2$, NH, or N($C_1$-$C_6$ alkyl);

each $R^9$ is independently selected from H, D, F, OH, $OCH_3$, $CH_3$, or $CF_3$; each $R^{9'}$ is independently selected from H, D, F, OH, $OCH_3$, $CH_3$, or $CF_3$;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Other preferred embodiments of the compounds of Formula I are compounds of Formula I-A-2:

I-A-2

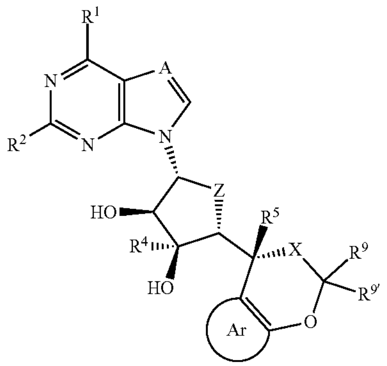

or a pharmaceutically acceptable salt, or solvate thereof; wherein

A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, $SO_2$, NH, or N($C_1$-$C_6$ alkyl);

each $R^9$ is independently selected from H, D, or F; each $R^{9'}$ is independently selected from H, D, or F;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

In some preferred embodiments, the compounds of Formula I-A-2 are those wherein A is C—$R^3$; $R^1$ is —$NH_2$ or —$CH_3$; $R^2$=$R^3$=$R^4$=$R^5$=$R^9$=$R^{9'}$=H; Z is O; X is O; and Ar is a phenyl ring substituted with 1-2 halogen atoms.

Other preferred embodiments of the compounds of Formula I are compounds of Formula I-A-3:

I-A-3

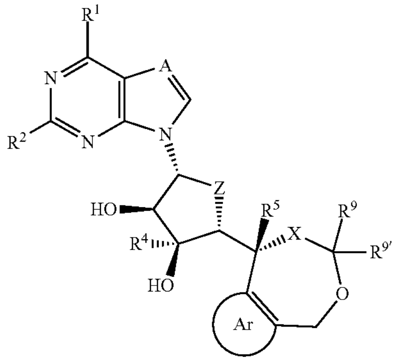

or a pharmaceutically acceptable salt, or solvate thereof;

wherein

A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, $SO_2$, NH, or N($C_1$-$C_6$ alkyl);

$R^9$ is selected from H, D, or F; $R^{9'}$ is selected from H, D, or F;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

In some preferred embodiments, the compounds of Formula I-A-3 are those wherein A is C—$R^3$; $R^1$ is —$NH_2$ or —$CH_3$; $R^2$═$R^3$═$R^4$═$R^5$═$R^9$═$R^{9'}$═H; Z is O; X is O; and Ar is a phenyl ring substituted with 1-2 halogen atoms.

Other preferred embodiments of the compounds of Formula I are compounds of Formula I-A-4:

I-A-4

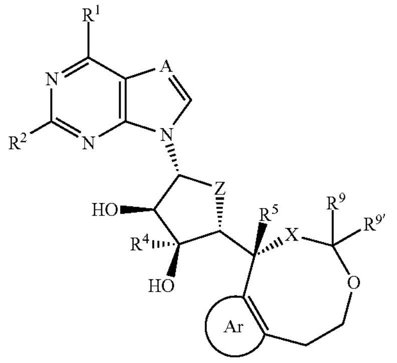

or a pharmaceutically acceptable salt, or solvate thereof; wherein

A is N or C—$R^3$;

$R^1$ is halo, $NH_2$, —$C_1$-$C_6$ alkyl, —$C_1$-$C_6$ alkoxy, or —$C_1$-$C_6$ alk-O—$C_1$-$C_6$ alkyl;

$R^2$ is H, halo, —$C_1$-$C_6$ alkyl, or $NH_2$;

$R^3$ is H, halo, —$C_1$-$C_6$ alkyl, or —$C_1$-$C_6$ alkoxy;

$R^4$ is H or —$C_1$-$C_6$ alkyl;

$R^5$ is H or —$C_1$-$C_6$ alkyl;

X is O, S, $SO_2$, NH, or N($C_1$-$C_6$ alkyl);

$R^9$ is selected from H, D, or F; $R^{9'}$ is selected from H, D, or F;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

In other preferred embodiments, the compounds of the disclosure are compounds of Formula I-G-1

I-G-1

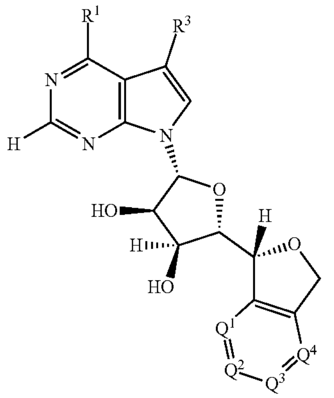

wherein $R^1$ is $NH_2$, —$C_1$-$C_6$ alkyl, or —$C_1$-$C_6$ alk-O—$C_1$-$C_6$ alkyl; $R^3$ is H or halo; and $Q^1$, $Q^2$, $Q^3$, and $Q^4$ are each independently selected from N, CH, or C—$R^8$, wherein $R^8$ is halo, —$C_1$ haloalkyl, or $C_1$ haloalkoxy.

In some preferred embodiments, the compounds of Formula I-G-1 are those wherein $R^1$ is $NH_2$, —$CH_3$, or —$CH_2$—O—$CH_2CH_3$; $R^3$ is H or F; and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-1 are those wherein $R^1$ is $NH_2$; $R^3$ is H; and $Q^1$, $Q^2$, $Q^3$, and $Q^4$ are each independently selected from N, CH, or C—$R^8$, wherein $R^8$ is —F, —Cl, —$CF_3$, or —$OCF_3$. In some preferred embodiments, the compounds of Formula I-G-1 are those wherein $R^1$ is $NH_2$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F, —Cl, —$CF_3$, or —$OCF_3$.

In other preferred embodiments, the compounds of Formula I-G-1 are those wherein $R^1$ is —$CH_3$; $R^3$ is H; and $Q^1$, $Q^2$, $Q^3$, and $Q^4$ are each independently selected from N, CH, or C—$R^8$, wherein $R^8$ is —F, —Cl, —$CF_3$, or —$OCF_3$. In some preferred embodiments, the compounds of Formula I-G-1 are those wherein $R^1$ is —$CH_3$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F, —Cl, —$CF_3$, or —$OCF_3$.

In other preferred embodiments, the compounds of Formula I-G-1 are those wherein $R^1$ is $NH_2$; $R^3$ is H; and $Q^1$, $Q^2$, $Q^3$, and $Q^4$ are each independently selected from CH, or C—$R^8$, wherein $R^8$ is —F, —Cl, —$CF_3$, or —$OCF_3$. In other preferred embodiments, the compounds of Formula I-G-1 are those wherein $R^1$ is —$CH_3$; $R^3$ is H; and $Q^1$, $Q^2$, $Q^3$, and $Q^4$ are each independently selected from CH, or C—$R^8$, wherein $R^8$ is —F, —Cl, —$CF_3$, or —$OCF_3$.

In other preferred embodiments, the compounds of Formula I-G-1 are those wherein $R^1$ is $NH_2$; $R^3$ is H; and $Q^1$, $Q^2$, $Q^3$, and $Q^4$ are each independently selected from N, CH, or C—$R^8$, wherein $R^8$ is —F or —Cl. In some preferred embodiments, the compounds of Formula I-G-1 are those wherein $R^1$ is $NH_2$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F or —Cl.

In other preferred embodiments, the compounds of Formula I-G-1 are those wherein $R^1$ is —$CH_3$; $R^3$ is H; and $Q^1$, $Q^2$, $Q^3$, and $Q^4$ are each independently selected from N, CH, or C—$R^8$, wherein $R^8$ is —F or —Cl. In some preferred embodiments, the compounds of Formula I-G-1 are those wherein $R^1$ is —$CH_3$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F or —Cl.

In other preferred embodiments, the compounds of Formula I-G-1 are those wherein $R^1$ is $NH_2$; $R^3$ is H; and $Q^1$, $Q^2$, $Q^3$, and $Q^4$ are each independently selected from CH, or C—$R^8$, wherein $R^8$ is —F or —Cl. In other preferred embodiments, the compounds of Formula I-G-1 are those wherein $R^1$ is —$CH_3$; $R^3$ is H; and $Q^1$, $Q^2$, $Q^3$, and $Q^4$ are each independently selected from CH, or C—$R^8$, wherein $R^8$ is —F or —Cl.

In other preferred embodiments, the compounds of the disclosure are compounds of Formula I-G-2:

I-G-2

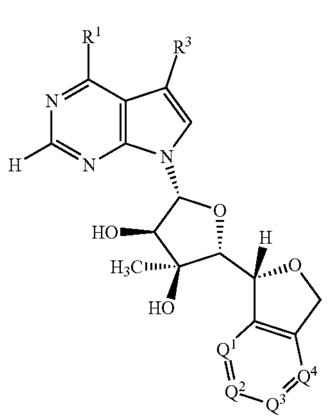

wherein $R^1$ is $NH_2$ or —$C_1$-$C_6$ alkyl; $R^3$ is H or halo; and $Q^1$, $Q^2$, $Q^3$, and $Q^4$ are each independently selected from CH, or C—$R^8$, wherein $R^8$ is halo, —$C_1$ haloalkyl, or $C_1$ haloalkoxy.

In some preferred embodiments, the compounds of Formula I-G-2 are those wherein $R^1$ is $NH_2$ or —$CH_3$; $R^3$ is H or F; and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-2 are those wherein $R^1$ is $NH_2$; $R^3$ is H; and $Q^1$, $Q^2$, $Q^3$, and $Q^4$ are each independently selected from N, CH, or C—$R^8$, wherein $R^8$ is —F, —Cl, —$CF_3$, or —$OCF_3$. In some preferred embodiments, the compounds of Formula I-G-2 are those wherein $R^1$ is $NH_2$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F, —Cl, —$CF_3$, or —$OCF_3$.

In other preferred embodiments, the compounds of Formula I-G-2 are those wherein $R^1$ is —$CH_3$; $R^3$ is H; and $Q^1$, $Q^2$, $Q^3$, and $Q^4$ are each independently selected from N, CH, or C—$R^8$, wherein $R^8$ is —F, —Cl, —$CF_3$, or —$OCF_3$. In some preferred embodiments, the compounds of Formula I-G-2 are those wherein $R^1$ is —$CH_3$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F, —Cl, —$CF_3$, or —$OCF_3$.

In other preferred embodiments, the compounds of Formula I-G-2 are those wherein $R^1$ is $NH_2$; $R^3$ is H; and $Q^1$, $Q^2$, $Q^3$, and $Q^4$ are each independently selected from CH, or C—$R^8$, wherein $R^8$ is —F or —Cl. In other preferred embodiments, the compounds of Formula I-G-2 are those wherein $R^1$ is —$CH_3$; $R^3$ is H; and $Q^1$, $Q^2$, $Q^3$, and $Q^4$ are each independently selected from CH, or C—$R^8$, wherein $R^8$ is —F or —Cl.

In other preferred embodiments, the compounds of Formula I-G-2 are those wherein $R^1$ is $NH_2$; $R^3$ is H; and $Q^1$, $Q^2$, $Q^3$, and $Q^4$ are each independently selected from N, CH, or C—$R^8$, wherein $R^8$ is —F or —Cl. In some preferred embodiments, the compounds of Formula I-G-2 are those wherein $R^1$ is $NH_2$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F or —Cl.

In other preferred embodiments, the compounds of Formula I-G-2 are those wherein $R^1$ is —$CH_3$; $R^3$ is H; and $Q^1$, $Q^2$, $Q^3$, and $Q^4$ are each independently selected from N, CH, or C—$R^8$, wherein $R^8$ is —F or —Cl. In some preferred embodiments, the compounds of Formula I-G-2 are those wherein $R^1$ is —$CH_3$; $R^3$ is H; and $Q^1$, $Q^2$, $Q^3$, and $Q^4$ are each independently selected from N, CH, or C—$R^8$, wherein at least one of $Q^1$, $Q^2$, $Q^3$, and $Q^4$ is C—$R^8$, and wherein $R^8$ is —F or —Cl.

In other preferred embodiments, the compounds of Formula I-G-2 are those wherein $R^1$ is $NH_2$; $R^3$ is H; and $Q^1$, $Q^2$, $Q^3$, and $Q^4$ are each independently selected from CH, or C—$R^8$, wherein $R^8$ is —F or —Cl. In other preferred embodiments, the compounds of Formula I-G-2 are those wherein $R^1$ is —$CH_3$; $R^3$ is H; and $Q^1$, $Q^2$, $Q^3$, and $Q^4$ are each independently selected from CH, or C—$R^8$, wherein $R^8$ is —F or —Cl.

In other preferred embodiments, the compounds of formula I-G-2 are those wherein wherein $R^1$ is $NH_2$, —$C_1$-$C_6$ alkyl, or —$C_1$-$C_6$ alk-O—$C_1$-$C_6$ alkyl; $R^3$ is H or halo; Y is —$(CR^9R^{9'})_n$—, —$CR^9$=$CR^{9'}$—, C(=O), —C(=O)—$(CR^9R^{9'})_n$—, —C(=O)—O—$(CR^9R^{9'})_n$—, —$CR^9R^{9'}$—O, —$(CR^9R^{9'})_n$—O—$(CR^9R^{9'})_m$—, —$(CR^9R^{9'})_n$—$NR^{10}$—, —C(=O)$NR^{10}$—; n=1 or 2; m=1 or 2; $R^9$ and $R^{9'}$ are each independently H, D, $CH_3$, $CF_3$, OH, $OCH_3$, or F; $R^{10}$ is H or $C_1$-$C_6$ alkyl; each and $Q^1$, $Q^2$, $Q^3$, and $Q^4$ are each independently selected from N, CH, or C—$R^8$, wherein $R^8$ is halo, —$C_1$ haloalkyl, or $C_1$ haloalkoxy.

In some preferred embodiments, the compounds of Formula I-G-2 are those wherein $R^1$ is $NH_2$ or —$CH_3$; $R^3$ is H or F; Y is —$CH_2CH_2$—, —$CH_2CH$($C_1$-$C_6$ alkoxy)-, —$CH_2CH(OCH_3)$—, —$CH(OH)CH_2$—, —CH($C_1$-$C_6$ alkyl)$CH_2$—, —$CH(CH_3)CH_2$—, —$CH_2C$($C_1$-$C_6$ alkyl$)_2$-, —$CH_2C(CH_3)_2$—, —CH($C_1$-$C_6$ haloalkyl)$CH_2$—, —$CH_2CH(CF_3)$—, —$CH_2CHF$—, —$CH_2CF_2$—, —$CH_2CD_2$, —CH=CH—, —C(=O)—$CH_2$—, —C(=O)—O—$CH_2$—, —C(=O)—O—$CH_2CH_2$—, —$CH_2$—O—, —$CF_2$—O—, —$CH_2$—O—$CH_2$—, —$CF_2$—O—$CH_2$—, —$CH_2$—O—$CH_2CH_2$—, —$CF_2$—O—$CH_2CH_2$—; and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-2 are those wherein $R^1$ is $NH_2$ or —$CH_3$; $R^3$ is H; Y is —$CH_2CH_2$—, —$CH(OCH_3)CH_2$—, —CH(OH)$CH_2$—, —$CH_2CH(CH_3)$—, —$CH_2C$($C_1$-$C_6$ alkyl$)_2$-, —$CH_2C(CH_3)_2$—, —$CH_2CH(CF_3)$—, —$CH_2CHF$—, —$CH_2CF_2$—, —$CH_2CD_2$-, —CH=CH—, —C(=O)$CH_2$—, —C(=O)—O—$CH_2$—, —C(=O)—O—$CH_2CH_2$—, —$CH_2$—O—, —$CF_2$—O—, —$CH_2$—O—$CH_2$—, —$CF_2$—O—$CH_2$—, —$CH_2$—O—$CH_2CH_2$—, —$CF_2$—O—$CH_2CH_2$—; and $Q^1$, $Q^2$, $Q^3$, and $Q^4$ are each independently selected from N, CH, or C—$R^8$, wherein $R^8$ is —F or —Cl.

In some preferred embodiments, the compounds of the disclosure are compounds of Formula I-G-3

I-G-3

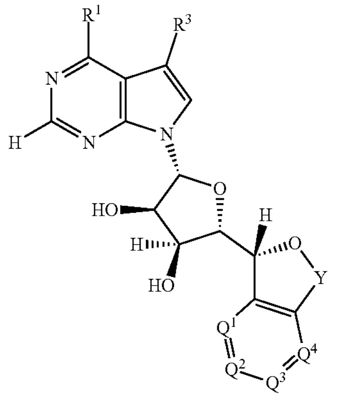

wherein $R^1$ is $NH_2$, —$C_1$-$C_6$ alkyl, or —$C_1$-$C_6$ alk-O—$C_1$-$C_6$ alkyl; $R^3$ is H or halo; Y is —$CH_2CH_2$—, $C(CH_3)_2$, $CF_2$, or C(═O); and $Q^1$, $Q^2$, $Q^3$, and $Q^4$ are each independently selected from N, CH, or C—$R^8$, wherein $R^8$ is halo, —$C_1$ haloalkyl, or $C_1$ haloalkoxy.

In some preferred embodiments, the compounds of Formula I-G-3 are those wherein $R^1$ is $NH_2$, —$CH_3$, or —$CH_2$—O—$CH_2CH_3$; $R^3$ is H or F; Y is —$CH_2CH_2$—, $C(CH_3)_2$, $CF_2$, or C(═O); and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-3 are those wherein $R^1$ is $NH_2$; $R^3$ is H; Y is —$CH_2CH_2$—, $C(CH_3)_2$, $CF_2$, or C(═O); and $Q^1$, $Q^2$, $Q^3$, and $Q^4$ are each independently selected from N, CH, or C—$R^8$, wherein $R^8$ is —F, —Cl, —$CF_3$, or —$OCF_3$. In other preferred embodiments, the compounds of Formula I-G-3 are those wherein $R^1$ is —$CH_3$; $R^3$ is H; Y is —$CH_2CH_2$—, $C(CH_3)_2$, $CF_2$, or C(═O); and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-3 are those wherein $R^1$ is $NH_2$; $R^3$ is H; Y is —$CH_2CH_2$—, $C(CH_3)_2$, $CF_2$, or C(═O); and $Q^1$, $Q^2$, $Q^3$, and $Q^4$ are each independently selected from CH, or C—$R^8$, wherein $R^8$ is —F, —Cl, —$CF_3$, or —$OCF_3$. In other preferred embodiments, the compounds of Formula I-G-3 are those wherein $R^1$ is —$CH_3$; $R^3$ is H; Y is —$CH_2CH_2$—, $C(CH_3)_2$, $CF_2$, or C(═O); and $Q^1$, $Q^2$, $Q^3$, and $Q^4$ are each independently selected from CH, or C—$R^8$, wherein $R^8$ is —F, —Cl, —$CF_3$, or —$OCF_3$.

In other preferred embodiments, the compounds of Formula I-G-3 are those wherein $R^1$ is $NH_2$; $R^3$ is H; Y is —$CH_2CH_2$—, $C(CH_3)_2$, $CF_2$, or C(═O); and $Q^1$, $Q^2$, $Q^3$, and $Q^4$ are each independently selected from N, CH, or C—$R^8$, wherein $R^8$ is —F or —Cl. In other preferred embodiments, the compounds of Formula I-G-3 are those wherein $R^1$ is —$CH_3$; $R^3$ is H; Y is —$CH_2CH_2$—, $C(CH_3)_2$, $CF_2$, or C(═O); and $Q^1$, $Q^2$, $Q^3$, and $Q^4$ are each independently selected from N, CH, or C—$R^8$, wherein $R^8$ is —F or —Cl.

In other preferred embodiments, the compounds of Formula I-G-3 are those wherein $R^1$ is $NH_2$; $R^3$ is H; Y is —$CH_2CH_2$—, $C(CH_3)_2$, $CF_2$, or C(═O); and $Q^1$, $Q^2$, $Q^3$, and $Q^4$ are each independently selected from CH, or C—$R^8$, wherein $R^8$ is —F or —Cl. In other preferred embodiments, the compounds of Formula I-G-3 are those wherein $R^1$ is —$CH_3$; $R^3$ is H; Y is —$CH_2CH_2$—, $C(CH_3)_2$, $CF_2$, or C(═O); and $Q^1$, $Q^2$, $Q^3$, and $Q^4$ are each independently selected from CH, or C—$R^8$, wherein $R^8$ is —F or —Cl.

In other preferred embodiments, the compounds of Formula I-G-3 are those wherein wherein $R^1$ is $NH_2$, —$C_1$-$C_6$ alkyl, or —$C_1$-$C_6$ alk-O—$C_1$-$C_6$ alkyl; $R^3$ is H or halo; Y is —$(CR^9R^{9'})_n$—, —$CR^9$═$CR^{9'}$—, —C(═O)—$(CR^9R^{9'})_n$—, —C(═O)—O—$(CR^9R^{9'})_n$—, —$CR^9R^{9'}$—O, —$(CR^9R^{9'})_n$—O—$(CR^9R^{9'})_m$—, n=1 or 2, $R^9$ and $R^{9'}$ are each independently H, D, $CH_3$, $CF_3$, OH, $OCH_3$, of F; each and $Q^1$, $Q^2$, $Q^3$, and $Q^4$ are each independently selected from N, CH, or C—$R^8$, wherein $R^8$ is halo, —$C_1$ haloalkyl, or $C_1$ haloalkoxy.

In some preferred embodiments, the compounds of Formula I-G-3 are those wherein $R^1$ is $NH_2$ or —$CH_3$; $R^3$ is H or F; Y is —$CH_2CH_2$—, —$CH_2CH$($C_1$-$C_6$ alkoxy)-, —$CH_2CH(OCH_3)$—, —$CH(OH)CH_2$—, —CH($C_1$-$C_6$ alkyl)$CH_2$—, —$CH(CH_3)CH_2$—, —$CH_2C$($C_1$-$C_6$ alkyl)$_2$-, —$CH_2C(CH_3)_2$—, —CH($C_1$-$C_6$ haloalkyl)$CH_2$—, —$CH_2CH(CF_3)$—, —$CH_2CHF$—, —$CH_2CF_2$—, —$CH_2CD_2$, —CH═CH—, —C(═O)—$CH_2$—, —C(═O)—O—$CH_2$—, —C(═O)—O—$CH_2CH_2$—, —$CH_2$—O—, —$CF_2$—O—, —$CH_2$—O—$CH_2$—, —$CF_2$—O—$CH_2$—, —$CH_2$—O—$CH_2CH_2$—, —$CF_2$—O—$CH_2CH_2$—, and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-3 are those wherein $R^1$ is NIH2 or —$CH_3$; $R^3$ is H; Y is —$CH_2CH_2$—, —$CH(OCH_3)CH_2$—, —CH(OH) $CH_2$—, —$CH_2CH(CH_3)$—, —$CH_2C$($C_1$-$C_6$ alkyl)$_2$-, —$CH_2C(CH_3)_2$—, —$CH_2CH(CF_3)$—, —$CH_2CHF$—, —$CH_2CF_2$—, —$CH_2CD_2$-, —CH═CH—, —C(═O) $CH_2$—, —C(═O)—O—$CH_2$—, —C(═O)—O—$CH_2CH_2$—, —$CH_2$—O—, —$CF_2$—O—, —$CH_2$—O—$CH_2$—, —$CF_2$—O—$CH_2$—, —$CH_2$—O—$CH_2CH_2$—, —$CF_2$—O—$CH_2CH_2$—; and $Q^1$, $Q^2$, $Q^3$, and $Q^4$ are each independently selected from N, CH, or C—$R^8$, wherein $R^8$ is —F or —Cl.

In other preferred embodiments, the compounds of Formula I-G-3 are those wherein $R^1$ is $NH_2$, —$CH_3$, or —$CD_3$; $R^3$ is H or F; Y is —$CH_2CH_2$—, —$CH_2CH_2CH_2$—, —C(═O)$CH_2$—, or —$CH_2CHF$—; and $Q^1$, $Q^2$, $Q^3$, and $Q^4$ are each independently selected from N, CH, or C—$R^8$, wherein $R^8$ is —F, —Cl, or —$CH_3$.

In other preferred embodiments, the compounds of Formula I-G-3 are those wherein $R^1$ is $NH_2$, —$CH_3$, or —$CD_3$; $R^3$ is H or F; Y is —$CH_2CH_2$—, —$CH_2CH_2CH_2$—, —C(═O)$CH_2$—, or —$CH_2CHF$—; and $Q^1$, $Q^2$, and $Q^4$ are each independently selected from CH or C—$R^8$, wherein $R^8$ is —F, —$C_1$, or —$CH_3$; and $Q^3$ is C—$R^8$, wherein $R^8$ is —$C_1$.

In other preferred embodiments, the compounds of Formula I-G-3 are those wherein $R^1$ is $NH_2$, or —$CH_3$; $R^3$ is H; Y is —$CH_2CH_2$—, —$CH_2CH_2CH_2$—, —C(═O)$CH_2$—, or —$CH_2CHF$—; and $Q^1$, $Q^2$, and $Q^4$ are each independently selected from CH or C—$R^8$, wherein $R^8$ is —F, —Cl, or —$CH_3$; and $Q^3$ is C—$R^8$, wherein $R^8$ is —$C_1$.

In other preferred embodiments, the compounds of Formula I-G-3 are those wherein $R^1$ is $NH_2$, —$CH_3$, or —$CD_3$; $R^3$ is H or F; Y is —$CH_2CH_2$—, —$CH_2CH_2CH_2$—, —C(═O)$CH_2$—, or —$CH_2CHF$—; and $Q^1$ is CH; $Q^2$ and $Q^4$ are each independently selected from CH or C—$R^8$, wherein $R^8$ is —F, —Cl, or —$CH_3$; and $Q^3$ is C—$R^8$, wherein $R^8$ is —$C_1$.

In other preferred embodiments, the compounds of Formula I-G-3 are those wherein $R^1$ is $NH_2$, or —$CH_3$; $R^3$ is H; Y is —$CH_2CH_2$—, —$CH_2CH_2CH_2$—, —C(═O)$CH_2$—, or —$CH_2CHF$—; and $Q^1$ is CH; $Q^2$, and $Q^4$ are each independently selected from CH or C—$R^8$, wherein $R^8$ is —F, —Cl, or —$CH_3$; and $Q^3$ is C—$R^8$, wherein $R^8$ is —$C_1$.

In some preferred embodiments, the compounds of the disclosure are compounds of Formula I-G-4

I-G-4

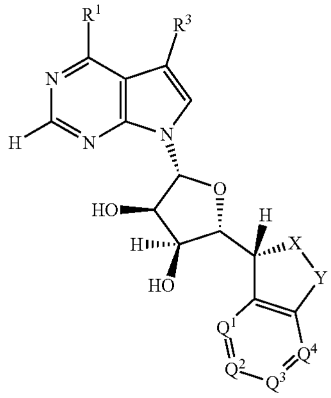

wherein $R^1$ is $NH_2$, —$C_1$-$C_6$ alkyl, or —$C_1$-$C_6$ alk-O—$C_1$-$C_6$ alkyl; $R^3$ is H or halo; X is S, NH, or N($C_1$-$C_6$ alkyl); Y is $CH_2$, or C(═O); and $Q^1$, $Q^2$, $Q^3$, and $Q^4$ are each independently selected from N, CH, or C—$R^8$, wherein $R^8$ is halo, —$C_1$ haloalkyl, or $C_1$ haloalkoxy.

In some preferred embodiments, the compounds of Formula I-G-4 are those wherein $R^1$ is $NH_2$, —$CH_3$, or —$CH_2$—O—$CH_2CH_3$; $R^3$ is H or F; X is S, NH, or N($C_1$-$C_6$ alkyl); Y is $CH_2$, or C(═O); and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-4 are those wherein $R^1$ is $NH_2$; $R^3$ is H; X is S, $SO_2$, NH, or N($C_1$-$C_6$ alkyl); Y is $CH_2$, or C(═O); and $Q^1$, $Q^2$, $Q^3$ and $Q^4$ are each independently selected from N, CH, or C—$R^8$, wherein $R^8$ is —F, —Cl, —$CF_3$, or —$OCF_3$.

In other preferred embodiments, the compounds of Formula I-G-4 are those wherein $R^1$ is —$CH_3$; $R^3$ is H; X is S, NH, or N($C_1$-$C_6$ alkyl); Y is $CH_2$, or C(═O); and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-4 are those wherein $R^1$ is $NH_2$; $R^3$ is H; X is S, NH, or N($C_1$-$C_6$ alkyl); Y is $CH_2$, or C(═O); and $Q^1$, $Q^2$, $Q^3$, and $Q^4$ are each independently selected from CH, or C—$R^8$, wherein $R^8$ is —F, —Cl, —$CF_3$, or —$OCF_3$. In other preferred embodiments, the compounds of Formula I-G-4 are those wherein $R^1$ is —$CH_3$; $R^3$ is H; X is S, NH, or N($C_1$-$C_6$ alkyl); Y is $CH_2$, or C(═O); and $Q^1$, $Q^2$, $Q^3$, and $Q^4$ are each independently selected from CH, or C—$R^8$, wherein $R^8$ is —F, —Cl, —$CF_3$, or —$OCF_3$.

In other preferred embodiments, the compounds of Formula I-G-4 are those wherein $R^1$ is $NH_2$; $R^3$ is H; X is S, NH, or N($C_1$-$C_6$ alkyl); Y is $CH_2$, or C(═O); and $Q^1$, $Q^2$, $Q^3$, and $Q^4$ are each independently selected from N, CH, or C—$R^8$, wherein $R^8$ is —F or —Cl. In other preferred embodiments, the compounds of Formula I-G-4 are those wherein $R^1$ is —$CH_3$; $R^3$ is H; X is S, NH, or N($C_1$-$C_6$ alkyl); Y is $CH_2$, or C(═O); and $Q^1$, $Q^2$, $Q^3$, and $Q^4$ are each independently selected from N, CH, or C—$R^8$, wherein $R^8$ is —F or —Cl.

In other preferred embodiments, the compounds of Formula I-G-4 are those wherein $R^1$ is $NH_2$; $R^3$ is H; X is S, NH, or N($C_1$-$C_6$ alkyl); Y is $CH_2$, or C(═O); and $Q^1$, $Q^2$, $Q^3$, and $Q^4$ are each independently selected from CH, or C—$R^8$, wherein $R^8$ is —F or —Cl. In other preferred embodiments, the compounds of Formula I-G-4 are those wherein $R^1$ is —$CH_3$; $R^3$ is H; X is S, NH, or N($C_1$-$C_6$ alkyl); Y is $CH_2$, or C(═O); and $Q^1$, $Q^2$, $Q^3$, and $Q^4$ are each independently selected from CH, or C—$R^8$, wherein $R^8$ is —F or —Cl.

In some preferred embodiments, the compounds of Formula I-G-4 are those wherein $R^1$ is $NH_2$ or $CH_3$; $R^3$ is H; X is NH; Y is —$CH_2CH_2$—; and $Q^1$, $Q^2$, $Q^3$, and $Q^4$ are each independently selected from CH, or C—$R^8$, wherein $R^8$ is —F or —Cl.

In some preferred embodiments, the compounds of the disclosure are compounds of Formula I-G-5

I-G-5

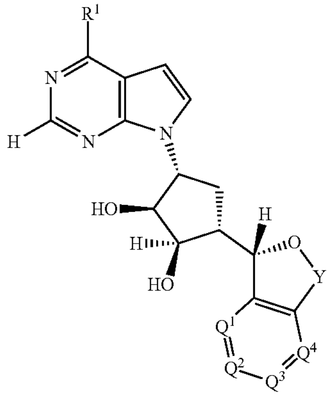

wherein $R^1$ is $NH_2$, or —$C_1$-$C_6$ alkyl, Y is —$CH_2$— or C(═O); and $Q^1$, $Q^2$, $Q^3$, and $Q^4$ are each independently N, CH, or C—$R^8$, wherein $R^8$ is halo.

In some preferred embodiments, the compounds of Formula I-G-5 are those wherein $R^1$ is $NH_2$, Y is —$CH_2$—; and $Q^1$, $Q^2$, $Q^3$, and $Q^4$ are each independently CH, or C—$R^8$, wherein $R^8$ is —F or —Cl. In other preferred embodiments, the compounds of Formula I-G-5 are those wherein $R^1$ is —$CH_3$, Y is —$CH_2$—; and $Q^1$, $Q^2$, $Q^3$, and $Q^4$ are each independently CH, or C—$R^8$, wherein $R^8$ is —F or —Cl.

In some preferred embodiments, the compounds of Formula I-G-5 are those wherein $R^1$ is $NH_2$, Y is C(═O); and $Q^1$, $Q^2$, $Q^3$, and $Q^4$ are each independently CH, or C—$R^8$, wherein $R^8$ is —F or —Cl. In other preferred embodiments, the compounds of Formula I-G-5 are those wherein $R^1$ is —$CH_3$, Y is C(═O); and $Q^1$, $Q^2$, $Q^3$, and $Q^4$ are each independently CH, or C—$R^8$, wherein $R^8$ is —F or —Cl.

In some preferred embodiments, the compounds of the disclosure are compounds of Formula I-G-6

I-G-6

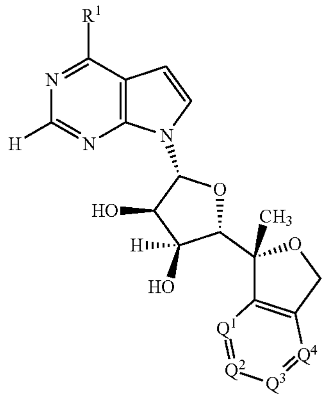

wherein $R^1$ is $NH_2$, or —$C_1$-$C_6$ alkyl; and $Q^1$, $Q^2$, $Q^3$, and $Q^4$ are each independently selected from N, CH, or C—$R^8$, wherein $R^8$ is halo, —$C_1$ haloalkyl, or $C_1$ haloalkoxy.

In some preferred embodiments, the compounds of Formula I-G-6 are those wherein $R^1$ is $NH_2$, or —$CH_3$, and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-6 are those wherein $R^1$ is $NH_2$; and $Q^1$, $Q^2$, $Q^3$, and $Q^4$ are each independently selected from N, CH, or C—$R^8$, wherein $R^8$ is —F, —Cl, —$CF_3$, or —$OCF_3$. In other preferred embodiments, the compounds of Formula I-G-6 are those wherein $R^1$ is —$CH_3$; and $Q^1$, $Q^2$, $Q^3$, and $Q^4$ are each independently selected from N, CH, or C—$R^8$, wherein $R^8$ is —F, —Cl, —$CF_3$, or —$OCF_3$.

In other preferred embodiments, the compounds of Formula I-G-6 are those wherein $R^1$ is $NH_2$; and $Q^1$, $Q^2$, $Q^3$, and $Q^4$ are each independently selected from CH, or C—$R^8$, wherein $R^8$ is —F, —Cl, —$CF_3$, or —$OCF_3$. In other preferred embodiments, the compounds of Formula I-G-6 are those wherein $R^1$ is —$CH_3$; and $Q^1$, $Q^2$, $Q^3$, and $Q^4$ are each independently selected from CH, or C—$R^8$, wherein $R^8$ is —F, —Cl, —$CF_3$, or —$OCF_3$.

In other preferred embodiments, the compounds of Formula I-G-6 are those wherein $R^1$ is $NH_2$; and $Q^1$, $Q^2$, $Q^3$, and $Q^4$ are each independently selected from N, CH, or C—$R^8$, wherein $R^8$ is —F or —Cl. In other preferred embodiments, the compounds of Formula I-G-6 are those wherein $R^1$ is —$CH_3$; and $Q^1$, $Q^2$, $Q^3$, and $Q^4$ are each independently selected from N, CH, or C—$R^8$, wherein $R^8$ is —F or —Cl.

In other preferred embodiments, the compounds of Formula I-G-6 are those wherein $R^1$ is $NH_2$; and $Q^1$, $Q^2$, $Q^3$, and $Q^4$ are each independently selected from CH, or C—$R^8$, wherein $R^8$ is —F or —Cl. In other preferred embodiments, the compounds of Formula I-G-6 are those wherein $R^1$ is —$CH_3$; $R^3$ is H; and $Q^1$, $Q^2$, $Q^3$, and $Q^4$ are each independently selected from CH, or C—$R^8$, wherein $R^8$ is —F or —Cl.

In other aspects, the disclosure is directed to compounds of Formula I-H-1:

I-H-1

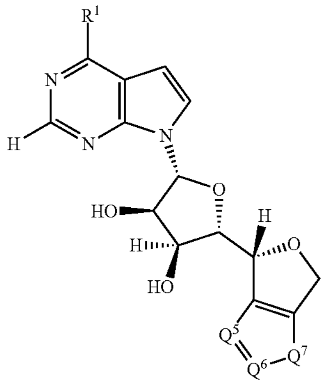

wherein $R^1$ is $NH_2$ or $C_1$-$C_6$ alkyl; $Q^5$ and $Q^6$ are independently CH, C—$R^8$, or N, and $Q^7$ is NH, or S, and $R^8$ is halo, $C_1$-$C_6$ alkyl, $C_1$-$C_6$ haloalkyl, $C_1$-$C_6$ alkoxy, or $C_1$-$C_6$ haloalkoxy. In preferred embodiments, compounds of Formula I-H-1 are those wherein $R^1$ is $NH_2$; $Q^5$ and $Q^6$ are independently CH, C—$R^8$, or N, $Q^7$ is NH, or S; and $R^8$ is —F or —Cl. In other preferred embodiments, compounds of Formula I-H-1 are those wherein $R^1$ is —$CH_3$; $Q^5$ and $Q^6$ are independently CH, C—$R^8$, or N, $Q^7$ is NH, or S; and $R^8$ is —F or —Cl.

In other aspects, the disclosure is directed to compounds Formula I-I-1:

I-I-1

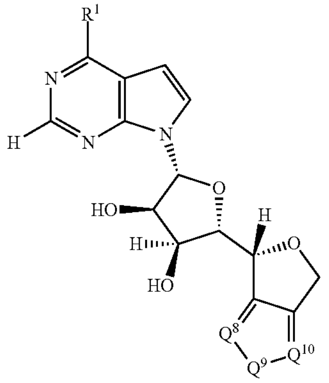

wherein $R^1$ is $NH_2$ or $C_1$-$C_6$ alkyl; $Q^8$ and $Q^{10}$ are independently CH, C—$R^8$, or N, and $Q^9$ is N($C_1$-$C_6$ alkyl), and $R^8$ is halo, $C_1$-$C_6$ alkyl, $C_1$-$C_6$ haloalkyl, $C_1$-$C_6$ alkoxy, or $C_1$-$C_6$ haloalkoxy. In preferred embodiments, compounds of Formula I-I-1 are those wherein $R^1$ is $NH_2$; $Q^8$ and $Q^{10}$ are independently CH, C—$R^8$, or N, and $Q^9$ is N($CH_3$), and $R^8$ is —F, or —Cl. In other preferred embodiments, compounds of Formula I-I-1 are those wherein $R^1$ is —$CH_3$; $Q^8$ and $Q^{10}$ are independently CH, C—$R^8$, or N; $Q^9$ is N($CH_3$), and $R^8$ is —F, or —Cl.

References to compounds of Formula I herein also refer to all subgenera described herein, including, for example, compounds of Formula I-A, I-A-1, I-A-2, I-A-3, I-A-4, I-B, I-C, I-D, I-E, I-F, I-G, I-G-1, I-G-2, I-G-3, I-G-4, I-G-5, I-G-6, I-H, I-H-1, I-I, I-I-1, and I-J.

It will be apparent that the compounds of Formula I, including all subgenera described herein, have multiple stereogenic centers. As a result, there exist multiple stereoisomers (enantiomers and diastereomers) of the compounds of Formula I (subgenera described herein). The present disclosure contemplates and encompasses each stereoisomer of any compound of Formula I (and subgenera described herein), as well as mixtures of said stereoisomers.

Pharmaceutically acceptable salts and solvates of the compounds of Formula I (including all subgenera described herein) are also within the scope of the disclosure.

Isotopic variants of the compounds of Formula I (including all subgenera described herein) are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range.

For example, in the treatment of adult humans, dosages from 0.01 to 100 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof, carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%), 100%, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a PRMT5 inhibitor with an IC50 value of about or less than a predetermined value, as ascertained in an in vitro assay. In some embodiments, the PRMT5 inhibitor inhibits PRMT5 a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 μM or less, 1.1 μM or less, 1.2 μM or less, 1.3 μM or less, 1.4 μM or less, 1.5 μM or less, 1.6 μM or less, 1.7 μM or less, 1.8 μM or less, 1.9 μM or less, 2 μM or less, 5 μM or less, 10 μM or less, 15 μM or less, 20 μM or less, 25 μM or less, 30 μM or less, 40 μM or less, 50 μM, 60 μM, 70 μM, 80 μM, 90 μM, 100 μM, 200 μM, 300 μM, 400 μM, or 500 μM, or less, (or a number in the range defined by and including any two numbers above).

In some embodiments, the PRMT5 inhibitor selectively inhibits PRMT5 a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other PRMTs.

In some embodiments, the PRMT5 inhibitor selectively inhibits PRMT5 a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 μM, 1.1 μM, 1.2 μM, 1.3 μM, 1.4 μM, 1.5 μM, 1.6 μM, 1.7 μM, 1.8 μM, 1.9 μM, 2 μM, 5 μM, 10 μM, 15 μM, 20 μM, 25 μM, 30 μM, 40 μM, 50 μM, 60 μM, 70 μM, 80 μM, 90 μM, 100 μM, 200 μM, 300 μM, 400 μM, or 500 μM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other PRMTs.

The subject methods are useful for treating a disease condition associated with PRMT5. Any disease condition that results directly or indirectly from an abnormal activity or expression level of PRMT5 can be an intended disease condition.

Different disease conditions associated with PRMT5 have been reported. PRMT5 has been implicated, for example, in a variety of human cancers as well as a number of hemoglobinopathies.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuromas, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, *Lentigo maligna* melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In yet other embodiments, said method is for treating a disease selected from CDKN2A deleted cancers; 9P deleted cancers; MTAP deleted cancers; glioblastoma, NSCLC, head and neck cancer, bladder cancer, or hepatocellular carcinoma.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

In other aspects, compounds of the disclosure, as well as pharmaceutical compositions comprising them, can be administered to treat any of the described diseases, alone or in combination with one or more other chemotherapeutic agents. Examples of other chemotherapeutic agents include, for example, abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate, as well as any combination thereof.

In other aspects, the other agent is a therapeutic agent that targets an epigenetic regulator. Examples of epigenetic regulator agents include, for example, bromodomain inhibitors, the histone lysine methyltransferases, histone arginine methyl transferases, histone demethylases, histone deacetylases, histone acetylases, and DNA methyltransferases, as well as any combination thereof. Histone deacetylase inhibitors are preferred in some aspects, and include, for example, vorinostat.

In other methods wherein the disease to be treated is cancer or another proliferative disease, the compounds of the disclosure, as well as pharmaceutical compositions comprising them, can be administered in combination with targeted therapy agents. Targeted therapies include, for example, JAK kinase inhibitors (e.g. Ruxolitinib), PI3 kinase inhibitors (including PI3K-delta selective and broad spectrum PI3K inhibitors), MEK inhibitors, Cyclin Dependent kinase inhibitors (e.g., CDK4/6 inhibitors), BRAF inhibitors, mTOR inhibitors, proteasome inhibitors (e.g., Bortezomib, Carfilzomib), HDAC-inhibitors (e.g., panobinostat, vorinostat), DNA methyl transferase inhibitors, dexamethasone, bromo and extra terminal family members, BTK inhibitors (e.g., ibrutinib, acalabrutinib), BCL2 inhibitors (e.g., venetoclax), MCL1 inhibitors, PARP inhibitors, FLT3 inhibitors, and LSD1 inhibitors, as well as any combination thereof.

In other methods wherein the disease to be treated is cancer or another proliferative disease, the compounds of the disclosure, as well as pharmaceutical compositions comprising them, can be administered in combination with an immune checkpoint inhibitor agents. Immune checkpoint inhibitors include, for example, inhibitors of PD-1, for example, an anti-PD-1 monoclonal antibody. Examples of anti-PD-1 monoclonal antibodies include, for example, nivolumab, pembrolizumab (also known as MK-3475), pidilizumab, SHR-1210, PDR001, and AMP-224, as well as combinations thereof. In some aspects, the anti-PD1 antibody is nivolumab. In some aspects, the anti-PD1 antibody is pembrolizumab. In some aspects, the immune checkpoint inhibitor is an inhibitor of PD-L1, for example, an anti-PD-L1 monoclonal antibody. In some aspects, the anti-PD-L1 monoclonal antibody is BMS-935559, MEDI4736, MPDL3280A (also known as RG7446), or MSB0010718C, or any combination thereof. In some aspects, the anti-PD-L1 monoclonal antibody is MPDL3280A or MEDI4736. In other aspects, the immune checkpoint inhibitor is an inhibitor of CTLA-4, for example, and anti-CTLA-4 antibody. In some aspects, the anti-CTLA-4 antibody is ipilimumab.

In other methods wherein the disease to be treated is cancer or another proliferative disease, the compounds of the disclosure, as well as pharmaceutical compositions comprising them, can be administered in combination with an alkylating agent (e.g., cyclophosphamide (CY), melphalan (MEL), and bendamustine), a proteasome inhibitor agent (e.g., carfilzomib), a corticosteroid agent (e.g., dexamethasone (DEX)), or an immunomodulatory agent (e.g., lenalidomide (LEN) or pomalidomide (POM)), or any combination thereof.

In some embodiments, the disease to be treated is an autoimmune condition or an inflammatory condition. In these aspects, the compounds of the disclosure, as well as pharmaceutical compositions comprising them, can be administered in combination with a corticosteroid agent such as, for example, triamcinolone, dexamethasone, fluocinolone, cortisone, prednisolone, or flumetholone, or any combination thereof.

In other methods wherein the disease to be treated is an autoimmune condition or an inflammatory condition, the compounds of the disclosure, as well as pharmaceutical compositions comprising them, can be administered in combination with an immune suppressant agent such as, for example, fluocinolone acetonide (RETISERT™), rimexolone (AL-2178, VEXOL™, ALCO™), or cyclosporine (RESTASIS™), or any combination thereof.

In some embodiments, the disease to be treated is beta-thalassemia or sickle cell disease. In these aspects, the compounds of the disclosure, as well as pharmaceutical compositions comprising them, can be administered in combination with one or more agents such as, for example, HYDREA™ (hydroxyurea).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Compounds of the disclosure include, for example, the compounds identified in Table A.

TABLE A

| Ex. | Structures | MW | Chemical Names |
|---|---|---|---|
| 1A | 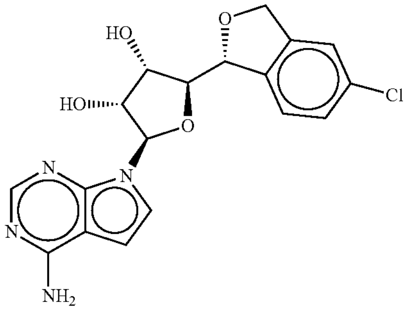 | 388.81 | (2R,3R,4S,5S)-2-(4-amino-7H-pyrrolo[2,3-d]pyrimidin-7-yl)-5-((R)-5-chloro-1,3-dihydroisobenzofuran-1-yl)tetrahydrofuran-3,4-diol |
| 2A | 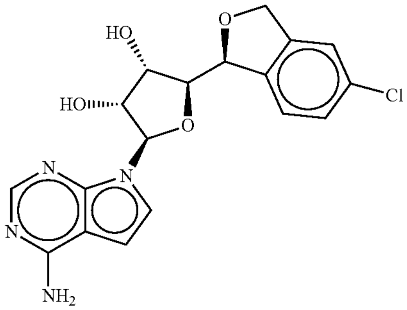 | 386.83 | (1R,2S,3R,5S)-3-(4-amino-7H-pyrrolo[2,3-d]pyrimidin-7-yl)-5-((R)-5-chloro-1,3-dihydroisobenzofuran-1-yl)cyclopentane-1,2-diol |
| 3A | 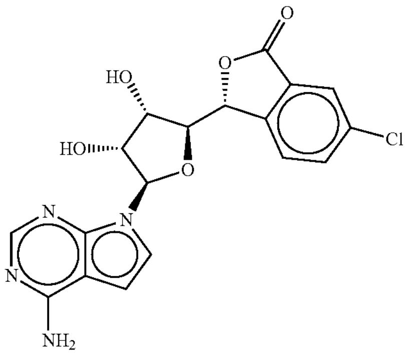 | 400.82 | (S)-3-((1S,2R,3S,4R)-4-(4-amino-7H-pyrrolo[2,3-d]pyrimidin-7-yl)-2,3-dihydroxycyclopentyl)-6-chloroisobenzofuran-1(3H)-one |
| 3B | 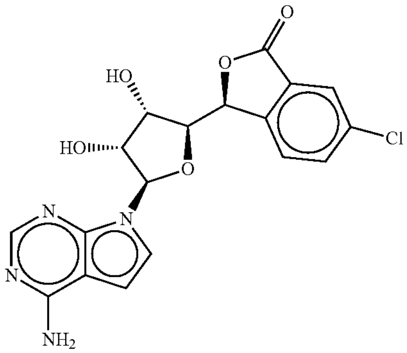 | 400.82 | (R)-3-((1S,2R,3S,4R)-4-(4-amino-6H-7I4-pyrrolo[2,3-d]pyrimidin-7-yl)-2,3-dihydroxycyclopentyl)-6-chloroisobenzofuran-1(3H)-one |

TABLE A-continued

| Ex. | Structures | MW | Chemical Names |
|---|---|---|---|
| 1B | 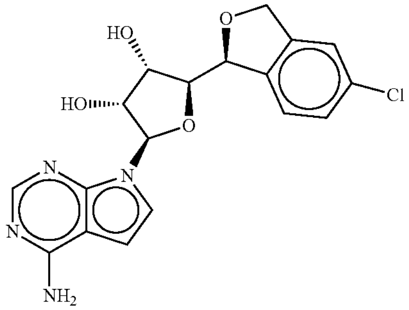 | 388.81 | (2R,3R,4S,5S)-2-(4-amino-7H-pyrrolo[2,3-d]pyrimidin-7-yl)-5-((S)-5-chloro-1,3-dihydroisobenzofuran-1-yl)tetrahydrofuran-3,4-diol |
| 2B | 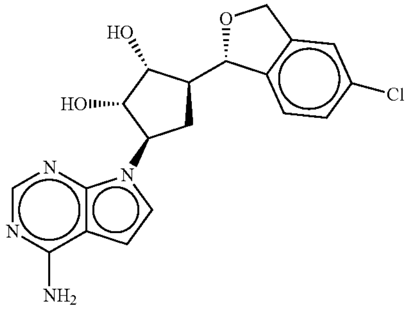 | 386.83 | (1R,2S,3R,5S)-3-(4-amino-7H-pyrrolo[2,3-d]pyrimidin-7-yl)-5-((S)-5-chloro-1,3-dihydroisobenzofuran-1-yl)cyclopentane-1,2-diol |
| 4 | 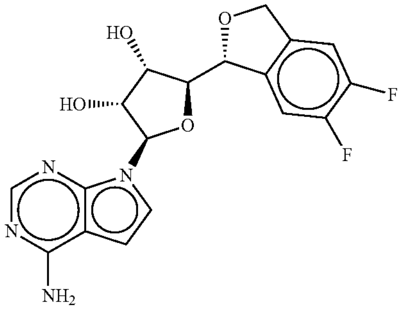 | 390.34 | (2R,3R,4S,5S)-2-(4-amino-7H-pyrrolo[2,3-d]pyrimidin-7-yl)-5-((R)-5,6-difluoro-1,3-dihydroisobenzofuran-1-yl)tetrahydrofuran-3,4-diol |
| 5 | 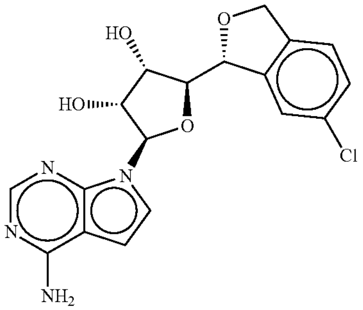 | 388.8 | (2R,3R,4S,5S)-2-(4-amino-7H-pyrrolo[2,3-d]pyrimidin-7-yl)-5-((R)-6-chloro-1,3-dihydroisobenzofuran-1-yl)tetrahydrofuran-3,4-diol |
| 6 | 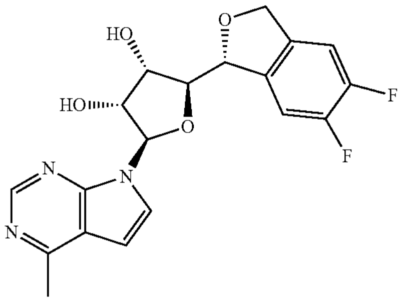 [SMILES: Cc1ncnc2c1ccn2[C@@H]1O[C@H]([C@@H]2OCc3cc(F)c(F)cc32)[C@@H](O)[C@H]1O] | 389.3588 | (2S,3S,4R,5R)-2-((R)-5,6-difluoro-1,3-dihydroisobenzofuran-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 7 | 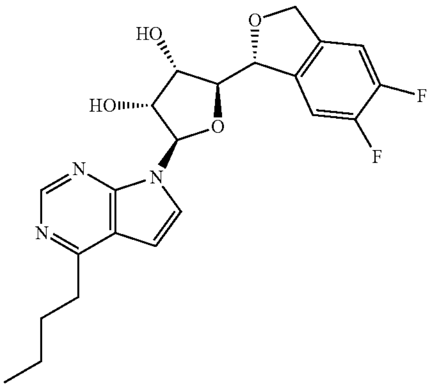 [SMILES: CCCCc1ncnc2c1ccn2[C@@H]1O[C@H]([C@@H]2OCc3cc(F)c(F)cc32)[C@@H](O)[C@H]1O] | 431.4398 | (2R,3R,4S,5S)-2-(4-butyl-7H-pyrrolo[2,3-d]pyrimidin-7-yl)-5-((R)-5,6-difluoro-1,3-dihydroisobenzofuran-1-yl)tetrahydrofuran-3,4-diol |
| 8 | 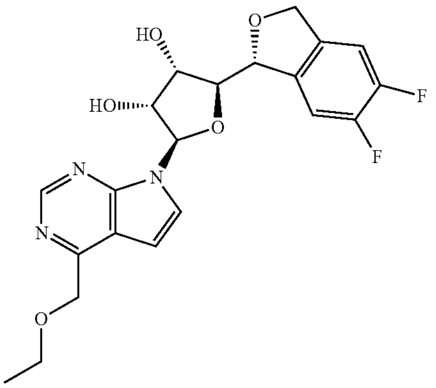 [SMILES: CCOCc1ncnc2c1ccn2[C@@H]1O[C@H]([C@@H]2OCc3cc(F)c(F)cc32)[C@@H](O)[C@H]1O] | 433.4118 | (2S,3S,4R,5R)-2-((R)-5,6-difluoro-1,3-dihydroisobenzofuran-1-yl)-5-(4-(ethoxymethyl)-7H-pyrrolo[2,3-d]pyrimidin-7-yl)tetrahydrofuran-3,4-diol |
| 9 | 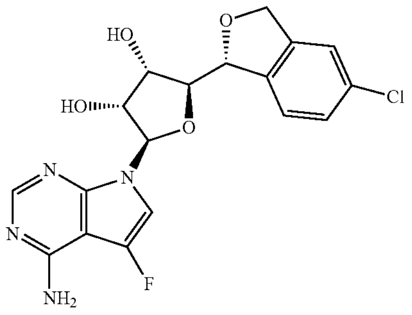 [SMILES: Nc1ncnc2c1c(F)cn2[C@@H]1O[C@H]([C@@H]2OCc3cc(Cl)ccc32)[C@@H](O)[C@H]1O] | 406.7984 | (2R,3R,4S,5S)-2-(4-amino-5-fluoro-7H-pyrrolo[2,3-d]pyrimidin-7-yl)-5-((R)-5-chloro-1,3-dihydroisobenzofuran-1-yl)tetrahydrofuran-3,4-diol |
| 10 | 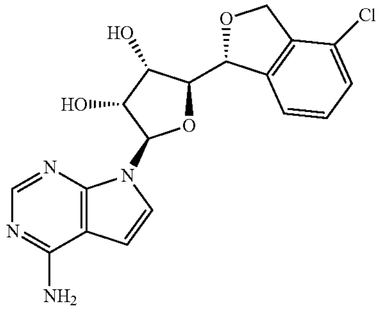 [SMILES: Nc1ncnc2c1ccn2[C@@H]1O[C@H]([C@@H]2OCc3c(Cl)cccc32)[C@@H](O)[C@H]1O] | 388.808 | (2R,3R,4S,5S)-2-(4-amino-7H-pyrrolo[2,3-d]pyrimidin-7-yl)-5-((R)-4-chloro-1,3-dihydroisobenzofuran-1-yl)tetrahydrofuran-3,4-diol |

TABLE A-continued

| Ex. | Structures | MW | Chemical Names |
| --- | --- | --- | --- |
| 11 | 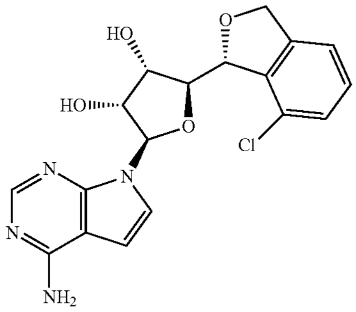 [SMILES: Nc1ncnc2c1ccn2[C@@H]1O[C@H]([C@@H]2OCc3cccc(Cl)c32)[C@@H](O)[C@H]1O] | 388.808 | (2R,3R,4S,5S)-2-(4-amino-7H-pyrrolo[2,3-d]pyrimidin-7-yl)-5-((R)-7-chloro-1,3-dihydroisobenzofuran-1-yl)tetrahydrofuran-3,4-diol |
| 12 | 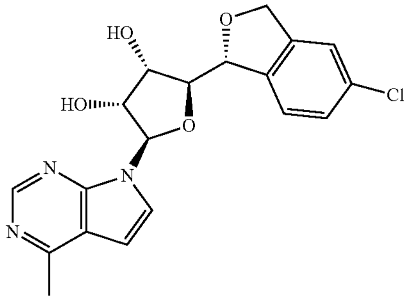 [SMILES: Cc1ncnc2c1ccn2[C@@H]1O[C@H]([C@@H]2OCc3cc(Cl)ccc32)[C@@H](O)[C@H]1O] | 387.82 | (2S,3S,4R,5R)-2-((R)-5-chloro-1,3-dihydroisobenzofuran-1-yl)-5-(4-methyl-7H-pyrrolo[2,3-d]pyrimidin-7-yl)tetrahydrofuran-3,4-diol |
| 13 | 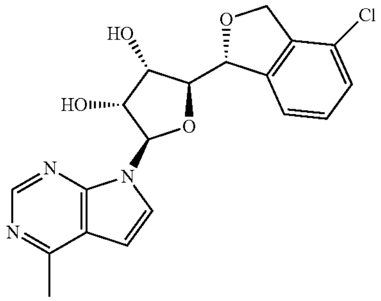 [SMILES: Cc1ncnc2c1ccn2[C@@H]1O[C@H]([C@@H]2OCc3c(Cl)cccc32)[C@@H](O)[C@H]1O] | 387.82 | (2S,3S,4R,5R)-2-((R)-4-chloro-1,3-dihydroisobenzofuran-1-yl)-5-(4-methyl-7H-pyrrolo[2,3-d]pyrimidin-7-yl)tetrahydrofuran-2,3-diol |
| 14 | 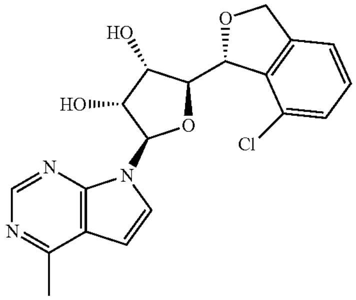 [SMILES: Cc1ncnc2c1ccn2[C@@H]1O[C@H]([C@@H]2OCc3cccc(Cl)c32)[C@@H](O)[C@H]1O] | 387.82 | (2S,3S,4R,5R)-2-((R)-7-chloro-1,3-dihydroisobenzofuran-1-yl)-5-(4-methyl-7H-pyrrolo[2,3-d]pyrimidin-7-yl)tetrahydrofuran-3,4-diol |
| 15 | 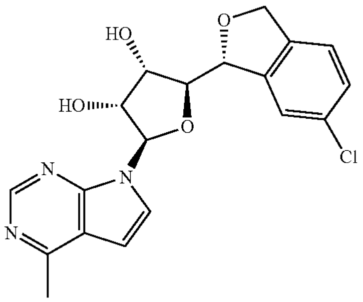 [SMILES: Cc1ncnc2c1ccn2[C@@H]1O[C@H]([C@@H]2OCc3ccc(Cl)cc32)[C@@H](O)[C@H]1O] | 387.82 | (2S,3S,4R,5R)-2-((R)-6-chloro-1,3-dihydroisobenzofuran-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 16 | 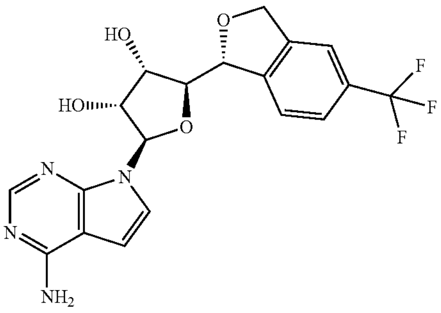 [SMILES: Nc1ncnc2c1ccn2[C@@H]1O[C@H]([C@@H]2OCc3cc(C(F)(F)F)ccc32)[C@@H](O)[C@H]1O] | 422.3642 | (2R,3R,4S,5S)-2-(4-amino-7H-pyrrolo[2,3-d]pyrimidin-7-yl)-5-((R)-5-(trifluoromethyl)-1,3-dihydroisobenzofuran-1-yl)tetrahydrofuran-3,4-diol |
| 17 | 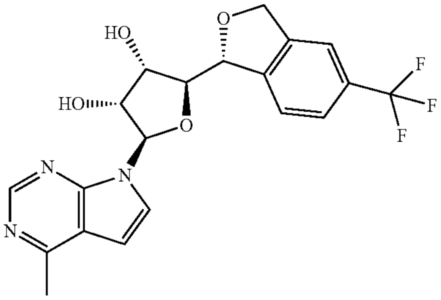 [SMILES: Cc1ncnc2c1ccn2[C@@H]1O[C@H]([C@@H]2OCc3cc(C(F)(F)F)ccc32)[C@@H](O)[C@H]1O] | 421.3762 | (2R,3R,4S,5S)-2-(4-methyl-7H-pyrrolo[2,3-d]pyrimidin-7-yl)-5-((R)-5-(trifluoromethyl)-1,3-dihydroisobenzofuran-1-yl)tetrahydrofuran-3,4-diol |
| 18 | 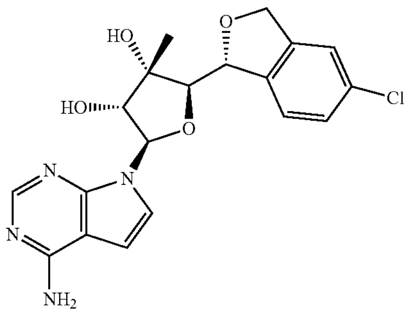 [SMILES: C[C@@]1(O)[C@@H]([C@@H]2OCc3cc(Cl)ccc32)O[C@@H](n2ccc3c(N)ncnc32)[C@@H]1O] | 402.835 | (2R,3S,4R,5R)-5-(4-amino-7H-pyrrolo[2,3-d]pyrimidin-7-yl)-2-((R)-5-chloro-1,3-dihydroisobenzofuran-1-yl)-3-methyltetrahydrofuran-3,4-diol |
| 19 | 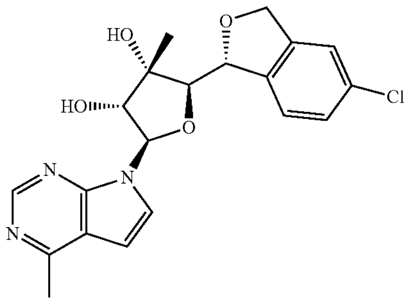 [SMILES: Cc1ncnc2c1ccn2[C@@H]1O[C@H]([C@@H]2OCc3cc(Cl)ccc32)[C@@](C)(O)[C@H]1O] | 401.847 | (2R,3S,4R,5R)-2-((R)-5-chloro-1,3-dihydroisobenzofuran-1-yl)-3-methyl-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 20 | 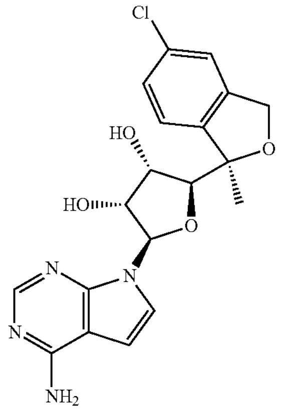 [SMILES: C[C@@]1([C@H]2O[C@@H](n3ccc4c(N)ncnc43)[C@H](O)[C@@H]2O)OCc2cc(Cl)ccc21] | 402.835 | (2R,3R,4S,5S)-2-(4-amino-7H-pyrrolo[2,3-d]pyrimidin-7-yl)-5-((R)-5-chloro-1-methyl-1,3-dihydroisobenzofuran-1-yl)tetrahydrofuran-3,4-diol |
| 21 | 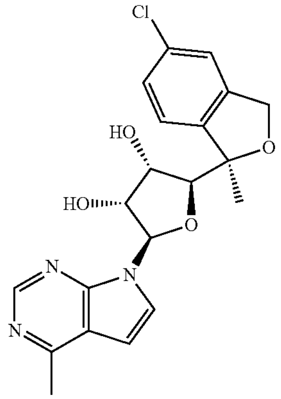 [SMILES: Cc1ncnc2c1ccn2[C@@H]1O[C@H]([C@]2(C)OCc3cc(Cl)ccc32)[C@@H](O)[C@H]1O] | 401.847 | (2S,3S,4R,5R)-2-((R)-5-chloro-1-methyl-1,3-dihydroisobenzofuran-1-yl)-5-(4-methyl-7H-pyrrolo[2,3-d]pyrimidin-7-yl)tetrahydrofuran-3,4-diol |
| 22 | 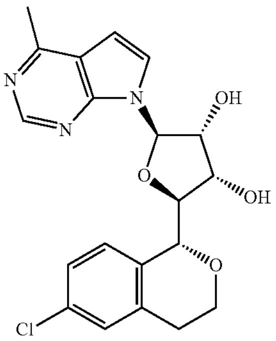 [SMILES: Cc1ncnc2c1ccn2[C@@H]1O[C@H]([C@@H]2OCCc3cc(Cl)ccc32)[C@@H](O)[C@H]1O] | 401.847 | (2S,3S,4R,5R)-2-((R)-6-chloroisochroman-1-yl)-5-(4-methyl-7H-pyrrolo[2,3-d]pyrimidin-7-yl)tetrahydrofuran-3,4-diol |
| 23 | 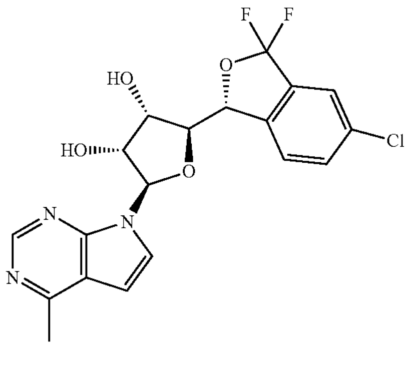 [SMILES: Cc1ncnc2c1ccn2[C@@H]1O[C@H]([C@@H]2OC(F)(F)c3cc(Cl)ccc32)[C@@H](O)[C@H]1O] | 423.8008 | (2S,3S,4R,5R)-2-((R)-5-chloro-3,3-difluoro-1,3-dihydroisobenzofuran-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 24 | 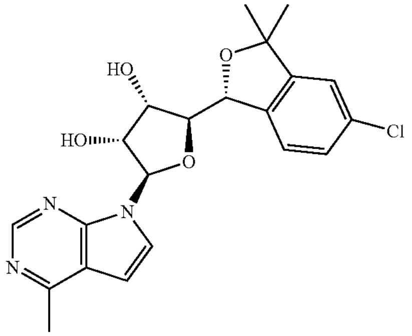 [SMILES: Cc1ncnc2c1ccn2[C@@H]1O[C@H]([C@@H]2OC(C)(C)c3cc(Cl)ccc32)[C@@H](O)[C@H]1O] | 415.874 | (2S,3S,4R,5R)-2-((R)-5-chloro-3,3-dimethyl-1,3-dihydroisobenzofuran-1-yl)-5-(4-methyl-7H-pyrrolo[2,3-d]pyrimidin-7-yl)tetrahydrofuran-3,4-diol |
| 25 | 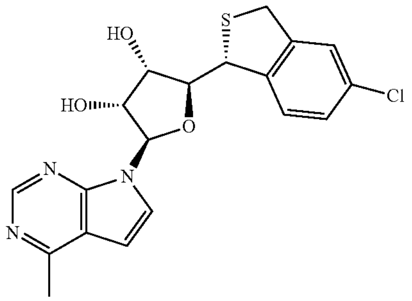 [SMILES: Cc1ncnc2c1ccn2[C@@H]1O[C@H]([C@@H]2SCc3cc(Cl)ccc32)[C@@H](O)[C@H]1O] | 403.881 | (2S,3S,4R,5R)-2-((R)-5-chloro-1,3-dihydrobenzo[c]thiophen-1-yl)-5-(4-methyl-7H-pyrrolo[2,3-d]pyrimidin-7-yl)tetrahydrofuran-3,4-diol |
| 26 | 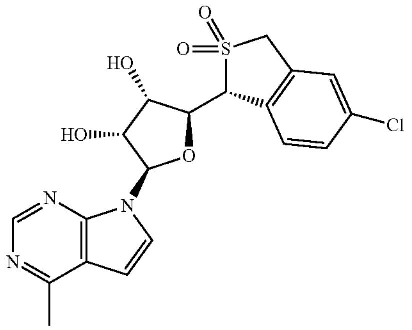 [SMILES: Cc1ncnc2c1ccn2[C@@H]1O[C@H]([C@H]2c3ccc(Cl)cc3CS2(=O)=O)[C@@H](O)[C@H]1O] | 435.879 | (R)-5-chloro-1-((2S,3S,4R,5R)-3,4-dihydroxy-5-(4-methyl-7H-pyrrolo[2,3-d]pyrimidin-7-yl)tetrahydrofuran-2-yl)-1,3-dihydrobenzo[c]thiophene 2,2-dioxide |
| 27 | 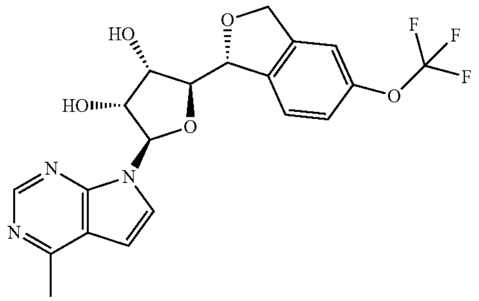 [SMILES: Cc1ncnc2c1ccn2[C@@H]1O[C@H]([C@@H]2OCc3cc(OC(F)(F)F)ccc32)[C@@H](O)[C@H]1O] | 437.3752 | (2R,3R,4S,5S)-2-(4-methyl-7H-pyrrolo[2,3-d]pyrimidin-7-yl)-5-((R)-5-(trifluoromethoxy)-1,3-dihydroisobenzofuran-1-yl)tetrahydrofuran-3,4-diol |
| 28 | 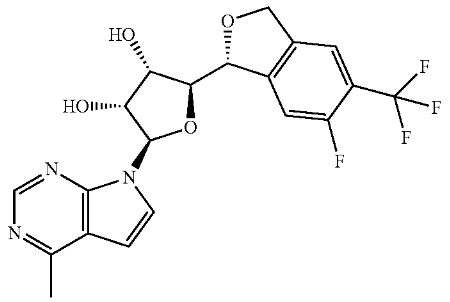 [SMILES: Cc1ncnc2c1ccn2[C@@H]1O[C@H]([C@@H]2OCc3cc(C(F)(F)F)c(F)cc32)[C@@H](O)[C@H]1O] | 439.3666 | (2S,3S,4R,5R)-2-((R)-6-fluoro-5-(trifluoromethyl)-1,3-dihydroisobenzofuran-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
| --- | --- | --- | --- |
| 29 | 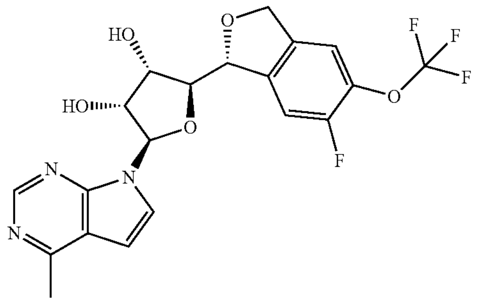 [SMILES: Cc1ncnc2c1ccn2[C@@H]1O[C@H]([C@@H]2OCc3cc(OC(F)(F)F)c(F)cc32)[C@@H](O)[C@H]1O] | 455.3656 | (2S,3S,4R,5R)-2-((R)-6-fluoro-5-(trifluoromethoxy)-1,3-dihydroisobenzofuran-1-yl)-5-(4-methyl-7H-pyrrolo[2,3-d]pyrimidin-7-yl)tetrahydrofuran-3,4-diol |
| 30 | 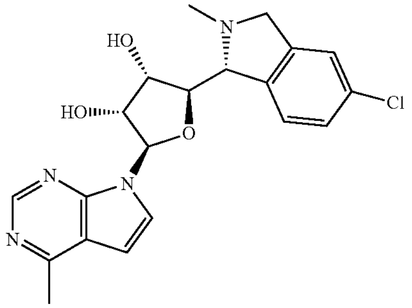 [SMILES: Cc1ncnc2c1ccn2[C@@H]1O[C@H]([C@H]2c3ccc(Cl)cc3CN2C)[C@@H](O)[C@H]1O] | 400.863 | (2R,3S,4R,5R)-2-((R)-5-chloro-2-methylisoindolin-1-yl)-5-(4-methyl-7H-pyrrolo[2,3-d]pyrimidin-7-yl)tetrahydrofuran-3,4-diol |
| 31 | 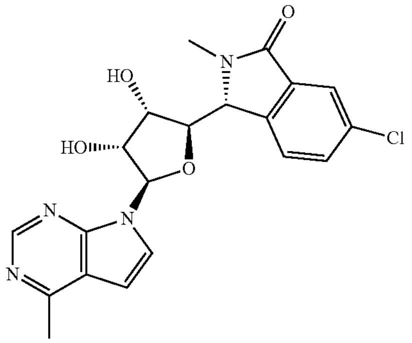 [SMILES: Cc1ncnc2c1ccn2[C@@H]1O[C@H]([C@H]2c3ccc(Cl)cc3C(=O)N2C)[C@@H](O)[C@H]1O] | 414.846 | (R)-6-chloro-3-((2R,3S,4R,5R)-3,4-dihydroxy-5-(4-methyl-7H-pyrrolo[2,3-d]pyrimidin-7-yl)tetrahydrofuran-2-yl)-2-methylisoindolin-1-one |
| 32 | 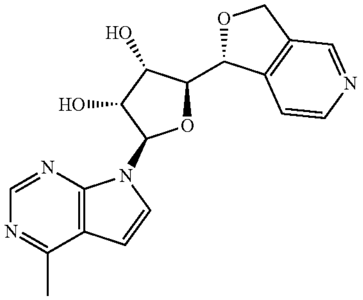 [SMILES: Cc1ncnc2c1ccn2[C@@H]1O[C@H]([C@@H]2OCc3cnccc32)[C@@H](O)[C@H]1O] | 354.366 | (2S,3S,4R,5R)-2-((R)-1,3-dihydrofuro[3,4-c]pyridin-1-yl)-5-(4-methyl-7H-pyrrolo[2,3-d]pyrimidin-7-yl)tetrahydrofuran-3,4-diol |
| 33 | 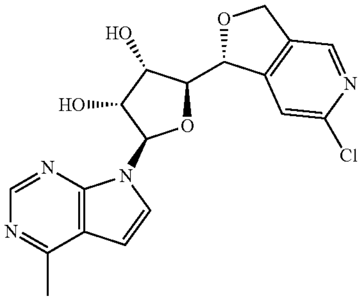 [SMILES: Cc1ncnc2c1ccn2[C@@H]1O[C@H]([C@@H]2OCc3cnc(Cl)cc32)[C@@H](O)[C@H]1O] | 388.808 | (2S,3S,4R,5R)-2-((R)-6-chloro-1,3-dihydrofuro[3,4-c]pyridin-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
| --- | --- | --- | --- |
| 34 | 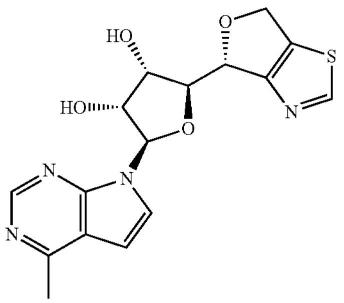 [SMILES: Cc1ncnc2c1ccn2[C@@H]1O[C@H]([C@@H]2OCc3scnc32)[C@@H](O)[C@H]1O] | 360.388 | (2S,3S,4R,5R)-2-((R)-2,6-dihydrofuro[3,4-d]thiazol-4-yl)-5-(4-methyl-7H-pyrrolo[2,3-d]pyrimidin-7-yl)tetrahydrofuran-3,4-diol |
| 35 | 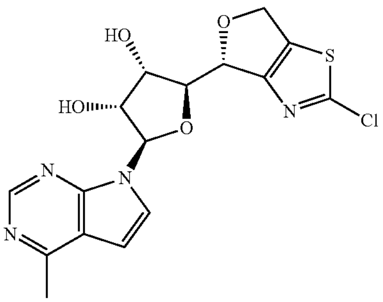 [SMILES: Cc1ncnc2c1ccn2[C@@H]1O[C@H]([C@@H]2OCc3sc(Cl)nc32)[C@@H](O)[C@H]1O] | 394.83 | (2S,3S,4R,5R)-2-((R)-2-chloro-4,6-dihydrofuro[3,4-d]thiazol-4-yl)-5-(4-methyl-7H-pyrrolo[2,3-d]pyrimidin-7-yl)tetrahydrofuran-3,4-diol |
| 36 | 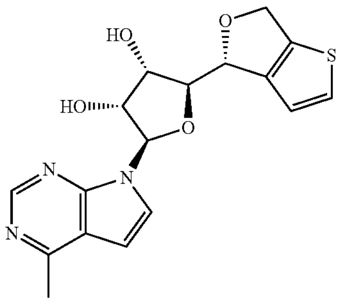 [SMILES: Cc1ncnc2c1ccn2[C@@H]1O[C@H]([C@@H]2OCc3sccc32)[C@@H](O)[C@H]1O] | 359.4 | (2S,3S,4R,5R)-2-((R)-4,6-dihydrothieno[2,3-c]furan-4-yl)-5-(4-methyl-7H-pyrrolo[2,3-d]pyrimidin-7-yl)tetrahydrofuran-3,4-diol |
| 37 | 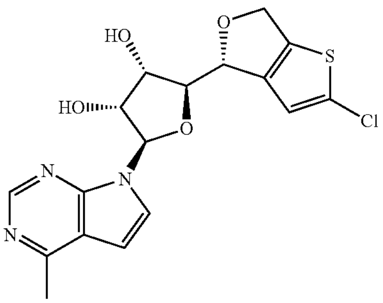 [SMILES: Cc1ncnc2c1ccn2[C@@H]1O[C@H]([C@@H]2OCc3sc(Cl)cc32)[C@@H](O)[C@H]1O] | 393.842 | (2S,3S,4R,5R)-2-((R)-2-chloro-4,6-dihydrothieno[2,3-c]furan-4-yl)-5-(4-methyl-7H-pyrrolo[2,3-d]pyrimidin-7-yl)tetrahydrofuran-3,4-diol |
| 38 | 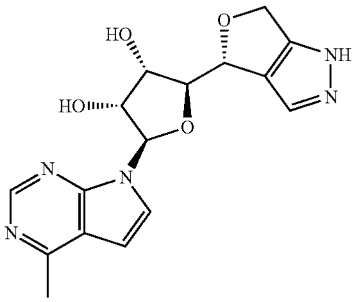 [SMILES: Cc1ncnc2c1ccn2[C@@H]1O[C@H]([C@@H]2OCc3[nH]ncc32)[C@@H](O)[C@H]1O] | 343.343 | (2S,3S,4R,5R)-2-((R)-4,6-dihydro-1H-furo[3,4-c]pyrazol-4-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
| --- | --- | --- | --- |
| 39 | 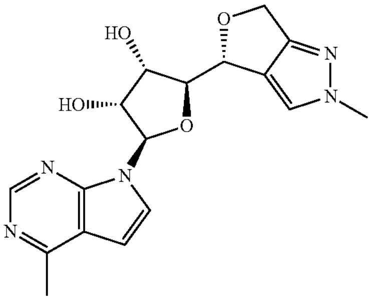 [SMILES: Cc1ncnc2c1ccn2[C@@H]1O[C@H]([C@@H]2OCc3nn(C)cc32)[C@@H](O)[C@H]1O] | 357.37 | (2S,3S,4R,5R)-2-((R)-2-methyl-2,6-dihydro-4H-furo[3,4-c]pyrazol-4-yl)-5-(4-methyl-7H-pyrrolo[2,3-d]pyrimidin-7-yl)tetrahydrofuran-3,4-diol |
| 40 | 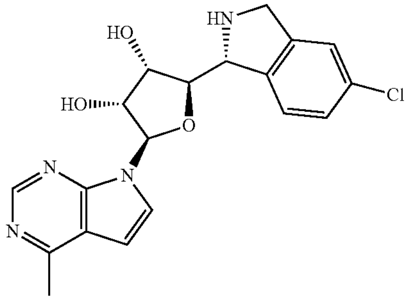 [SMILES: Cc1ncnc2c1ccn2[C@@H]1O[C@H]([C@@H]2NCc3cc(Cl)ccc32)[C@@H](O)[C@H]1O] | 386.84 | (2R,3S,4R,5R)-2-((R)-5-chloroisoindolin-1-yl)-5-(4-methyl-7H-pyrrolo[2,3-d]pyrimidin-7-yl)tetrahydrofuran-3,4-diol |
| 41 | 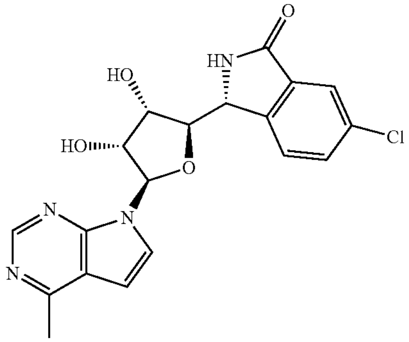 [SMILES: Cc1ncnc2c1ccn2[C@@H]1O[C@H]([C@@H]2NC(=O)c3cc(Cl)ccc32)[C@@H](O)[C@H]1O] | 400.82 | (R)-6-chloro-3-((2R,3S,4R,5R)-3,4-dihydroxy-5-(4-methyl-7H-pyrrolo[2,3-d]pyrimidin-7-yl)tetrahydrofuran-2-yl)isoindolin-1-one |
| 42 | 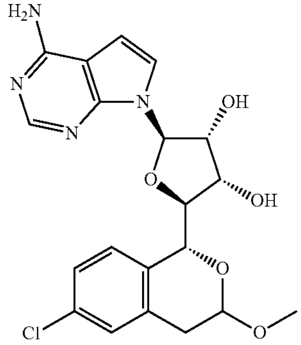 | 432.86 | (2R,3R,4S,5S)-2-(4-amino-7H-pyrrolo[2,3-d]pyrimidin-7-yl)-5-((1R)-6-chloro-3-methoxyisochroman-1-yl)tetrahydrofuran-3,4-diol |

TABLE A-continued

| Ex. | Structures | MW | Chemical Names |
| --- | --- | --- | --- |
| 43 | 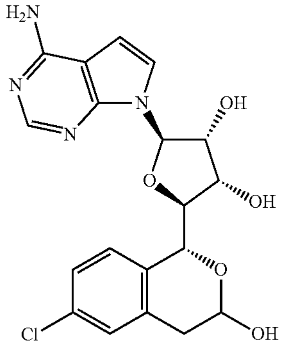 | 418.83 | (2R,3R,4S,5S)-2-(4-amino-7H-pyrrolo[2,3-d]pyrimidin-7-yl)-5-((1R)-6-chloro-3-hydroxyisochroman-1-yl)tetrahydrofuran-3,4-diol |
| 44 | 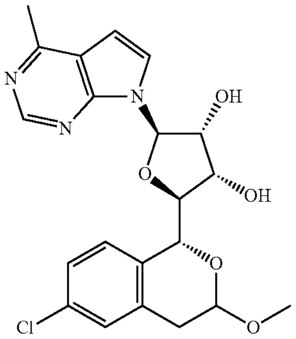 | 431.87 | (2S,3S,4R,5R)-2-((1R)-6-chloro-3-methoxyisochroman-1-yl)-5-(4-methyl-7H-pyrrolo[2,3-d]pyrimidin-7-yl)tetrahydrofuran-3,4-diol |
| 45 | 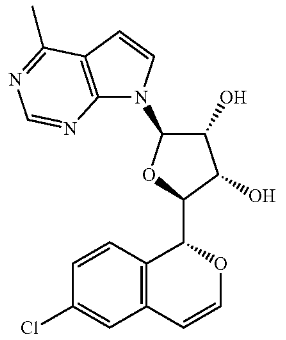 [SMILES: Cc1ncnc2c1ccn2[C@@H]1O[C@H]([C@@H]2OC=Cc3cc(Cl)ccc32)[C@@H](O)[C@H]1O] | 399.83 | (2S,3S,4R,5R)-2-((R)-6-chloro-1H-isochromen-1-yl)-5-(4-methyl-7H-pyrrolo[2,3-d]pyrimidin-7-yl)tetrahydrofuran-3,4-diol |
| 46 | 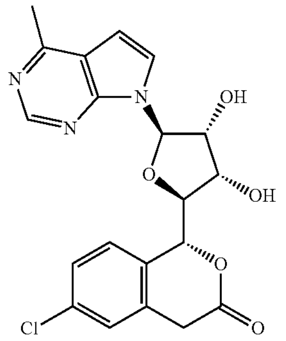 [SMILES: Cc1ncnc2c1ccn2[C@@H]1O[C@H]([C@@H]2OC(=O)Cc3cc(Cl)ccc32)[C@@H](O)[C@H]1O] | 415.83 | (R)-6-chloro-1-((2S,3S,4R,5R)-3,4-dihydroxy-5-(4-methyl-7H-pyrrolo[2,3-d]pyrimidin-7-yl)tetrahydrofuran-2-yl)isochroman-3-one |

TABLE A-continued

| Ex. | Structures | MW | Chemical Names |
|---|---|---|---|
| 47 | 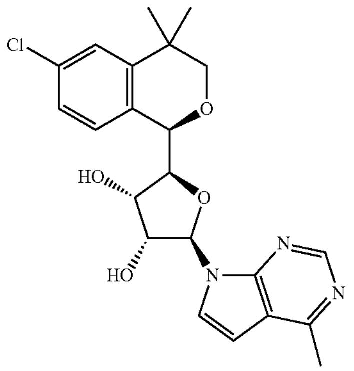 [SMILES: Cc1ncnc2c1ccn2[C@@H]1O[C@H]([C@@H]2OCC(C)(C)c3cc(Cl)ccc32)[C@@H](O)[C@H]1O] | 429.90 | (2S,3S,4R,5R)-2-((R)-6-chloro-4,4-dimethylisochroman-1-yl)-5-(4-methyl-7H-pyrrolo[2,3-d]pyrimidin-7-yl)tetrahydrofuran-3,4-diol |
| 48 | 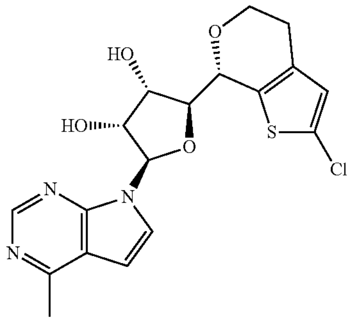 [SMILES: Cc1ncnc2c1ccn2[C@@H]1O[C@H]([C@@H]2OCCc3cc(Cl)sc32)[C@@H](O)[C@H]1O] | 407.87 | (2S,3S,4R,5R)-2-((S)-2-chloro-4,7-dihydro-5H-thieno[2,3-c]pyran-7-yl)-5-(4-methyl-7H-pyrrolo[2,3-d]pyrimidin-7-yl)tetrahydrofuran-3,4-diol |
| 49 | 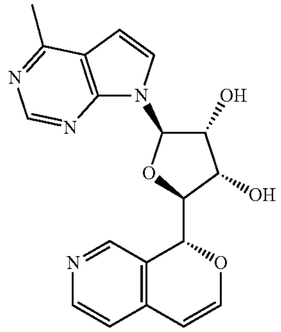 [SMILES: Cc1ncnc2c1ccn2[C@@H]1O[C@H]([C@@H]2OC=Cc3ccncc32)[C@@H](O)[C@H]1O] | 366.38 | (2R,3R,4S,5S)-2-(4-methyl-7H-pyrrolo[2,3-d]pyrimidin-7-yl)-5-((R)-1H-pyrano[3,4-c]pyridin-1-yl)tetrahydrofuran-3,4-diol |
| 50 | 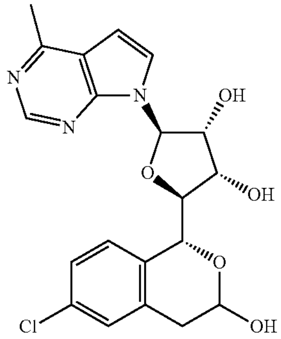 | 417.85 | (2S,3S,4R,5R)-2-((1R)-6-chloro-3-hydroxyisochroman-1-yl)-5-(4-methyl-7H-pyrrolo[2,3-c]pyrimidin-7-yl)tetrahydrofuran-3,4-diol |

TABLE A-continued

| Ex. | Structures | MW | Chemical Names |
|---|---|---|---|
| 51 | 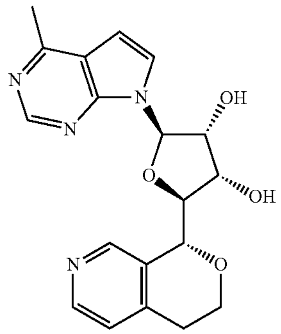 [SMILES: Cc1ncnc2c1ccn2[C@@H]1O[C@H]([C@@H]2OCCc3ccncc32)[C@@H](O)[C@H]1O] | 368.39 | (2S,3S,4R,5R)-2-((R)-3,4-dihydro-1H-pyrano[3,4-c]pyridin-1-yl)-5-(4-methyl-7H-pyrrolo[2,3-d]pyrimidin-7-yl)tetrahydrofuran-3,4-diol |
| 52 | 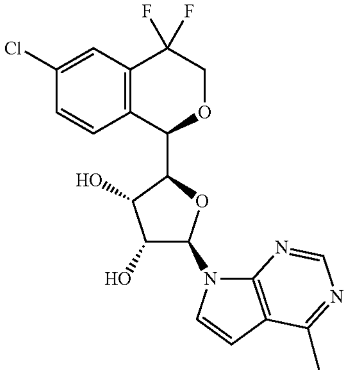 [SMILES: Cc1ncnc2c1ccn2[C@@H]1O[C@H]([C@@H]2OCC(F)(F)c3cc(Cl)ccc32)[C@@H](O)[C@H]1O] | 437.83 | (2S,3S,4R,5R)-2-((R)-6-chloro-4,4-difluoroisochroman-1-yl)-5-(4-methyl-7H-pyrrolo[2,3-d]pyrimidin-7-yl)tetrahydrofuran-3,4-diol |
| 53 | 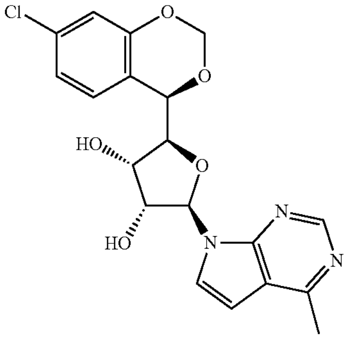 [SMILES: Cc1ncnc2c1ccn2[C@@H]1O[C@H]([C@@H]2OCOc3cc(Cl)ccc32)[C@@H](O)[C@H]1O] | 403.82 | (2S,3S,4R,5R)-2-((R)-7-chloro-4H-benzo[d][1,3]dioxin-4-yl)-5-(4-methyl-7H-pyrrolo[2,3-d]pyrimidin-7-yl)tetrahydrofuran-3,4-diol |
| 54 | 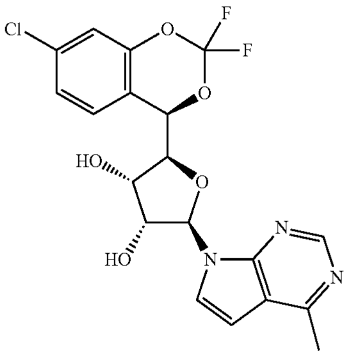 [SMILES: Cc1ncnc2c1ccn2[C@@H]1O[C@H]([C@@H]2OC(F)(F)Oc3cc(Cl)ccc32)[C@@H](O)[C@H]1O] | 439.80 | (2S,3S,4R,5R)-2-((R)-7-chloro-2,2-difluoro-4H-benzo[d][1,3]dioxin-4-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 55 | 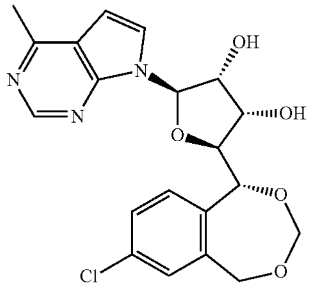 [SMILES: Cc1ncnc2c1ccn2[C@@H]1O[C@H]([C@@H]2OCOCc3cc(Cl)ccc32)[C@@H](O)[C@H]1O] | 417.85 | (2S,3S,4R,5R)-2-((R)-7-chloro-1,5-dihydrobenzo[e][1,3]dioxepin-1-yl)-5-(4-methyl-7H-pyrrolo[2,3-d]pyrimidin-7-yl)tetrahydrofuran-3,4-diol |
| 56 | 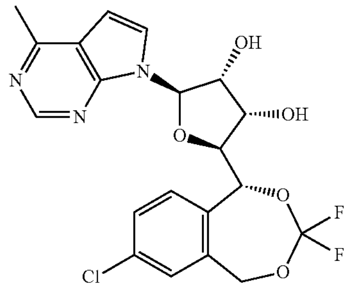 [SMILES: Cc1ncnc2c1ccn2[C@@H]1O[C@H]([C@@H]2OC(F)(F)OCc3cc(Cl)ccc32)[C@@H](O)[C@H]1O] | 453.83 | (2S,3S,4R,5R)-2-((R)-7-chloro-3,3-difluoro-1,5-dihydrobenzo[e][1,3]dioxepin-1-yl)-5-(4-methyl-7H-pyrrolo[2,3-d]pyrimidin-7-yl)tetrahydrofuran-3,4-diol |
| 57 | 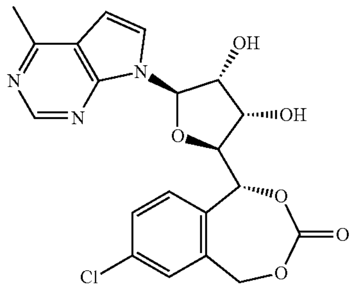 [SMILES: Cc1ncnc2c1ccn2[C@@H]1O[C@H]([C@@H]2OC(=O)OCc3cc(Cl)ccc32)[C@@H](O)[C@H]1O] | 431.83 | (R)-7-chloro-1-((2S,3S,4R,5R)-3,4-dihydroxy-5-(4-methyl-7H-pyrrolo[2,3-d]pyrimidin-7-yl)tetrahydrofuran-2-yl)-1,5-dihydrobenzo[e][1,3]dioxepin-3-one |
| 58 | 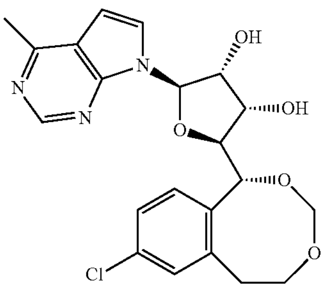 [SMILES: Cc1ncnc2c1ccn2[C@@H]1O[C@H]([C@@H]2OCOCCc3cc(Cl)ccc32)[C@@H](O)[C@H]1O] | 431.87 | (2S,3S,4R,5R)-2-((R)-8-chloro-5,6-dihydro-1H-benzo[e][1,3]dioxocin-1-yl)-5-(4-methyl-7H-pyrrolo[2,3-d]pyrimidin-7-yl)tetrahydrofuran-3,4-diol |
| 59 | 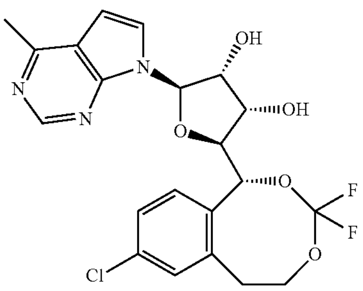 [SMILES: Cc1ncnc2c1ccn2[C@@H]1O[C@H]([C@@H]2OC(F)(F)OCCc3cc(Cl)ccc32)[C@@H](O)[C@H]1O] | 467.85 | (2S,3S,4R,5R)-2-((R)-8-chloro-3,3-difluoro-5,6-dihydro-1H-benzo[e][1,3]dioxocin-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 60 | 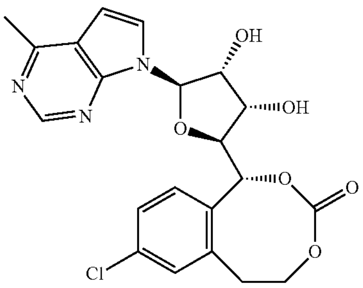 [SMILES: Cc1ncnc2c1ccn2[C@@H]1O[C@H]([C@@H]2OC(=O)OCCc3cc(Cl)ccc32)[C@@H](O)[C@H]1O] | 445.86 | (R)-8-chloro-1-((2S,3S,4R,5R)-3,4-dihydroxy-5-(4-methyl-7H-pyrrolo[2,3-d]pyrimidin-7-yl)tetrahydrofuran-2-yl)-5,6-dihydro-1H-benzo[e][1,3]dioxocin-3-one |
| 61 | 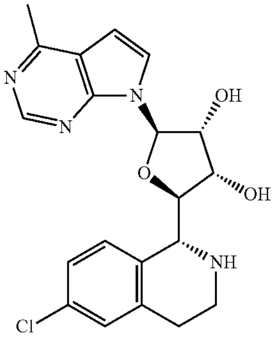 [SMILES: Cc1ncnc2c1ccn2[C@@H]1O[C@H]([C@@H]2NCCc3cc(Cl)ccc32)[C@@H](O)[C@H]1O] | 400.86 | (2R,3S,4R,5R)-2-((R)-6-chloro-1,2,3,4-tetrahydroisoquinolin-1-yl)-5-(4-methyl-7H-pyrrolo[2,3-d]pyrimidin-7-yl)tetrahydrofuran-3,4-diol |
| 62 | 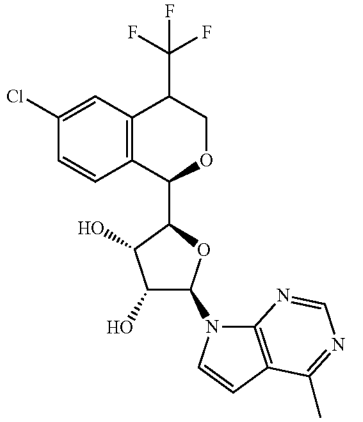 | 469.85 | (2S,3S,4R,5R)-2-((1R)-6-chloro-4-(trifluoromethyl)isochroman-1-yl)-5-(4-methyl-7H-pyrrolo[2,3-d]pyrimidin-7-yl)tetrahydrofuran-3,4-diol |
| 63 | 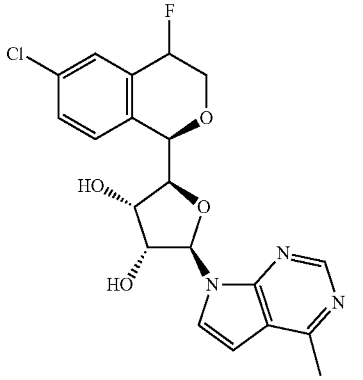 | 419.84 | (2S,3S,4R,5R)-2-((1R)-6-chloro-4-fluoroisochroman-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
| --- | --- | --- | --- |
| 64 | 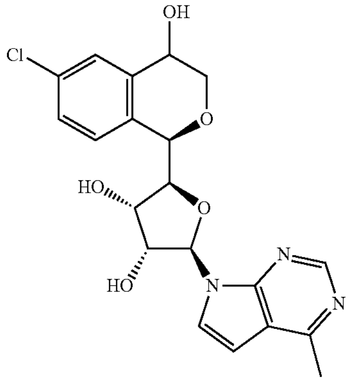 | 417.85 | (2S,3S,4R,5R)-2-((1R)-6-chloro-4-hydroxyisochroman-1-yl)-5-(4-methyl-7H-pyrrolo[2,3-d]pyrimidin-7-yl)tetrahydrofuran-3,4-diol |
| 65 | 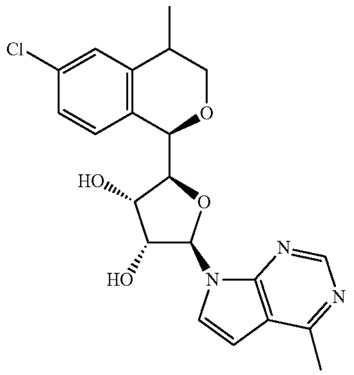 | 415.87 | (2S,3S,4R,5R)-2-((1R)-6-chloro-4-methylisochroman-1-yl)-5-(4-methyl-7H-pyrrolo[2,3-d]pyrimidin-7-yl)tetrahydrofuran-3,4-diol |
| 66 | 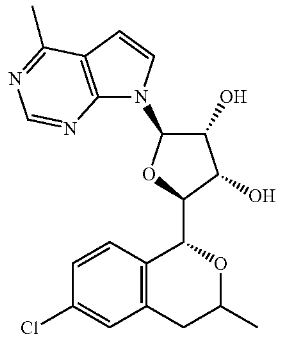 | 415.87 | (2S,3S,4R,5R)-2-((1R)-6-chloro-3-methylisochroman-1-yl)-5-(4-methyl-7H-pyrrolo[2,3-d]pyrimidin-7-yl)tetrahydrofuran-3,4-diol |
| 67 | 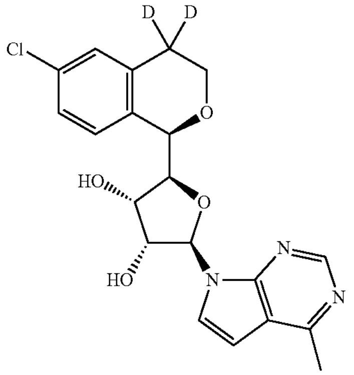 [SMILES: [2H]C1([2H])CO[C@@H]([C@H]2O[C@@H](n3ccc4c(C)ncnc43)[C@H](O)[C@@H]2O)c2ccc(Cl)cc21] | 403.86 | (2S,3S,4R,5R)-2-((R)-6 chloroisochroman-1-yl)-4,4-d2)-5-(4-methyl-7H-pyrrolo[2,3-d]pyrimidin-7-yl)tetrahydrofuran-3,4-diol |

TABLE A-continued

| Ex. | Structures | MW | Chemical Names |
| --- | --- | --- | --- |
| 68 | 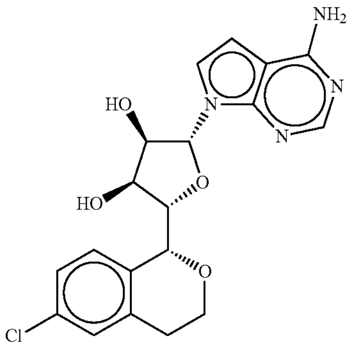 | 402.84 | (2R,3R,4S,5S)-2-(4-amino-7H-pyrrolo[2,3-d]pyrimidin-7-yl)-5-((R)-6-chloroisochroman-1-yl)tetrahydrofuran-3,4-diol |
| 69 | 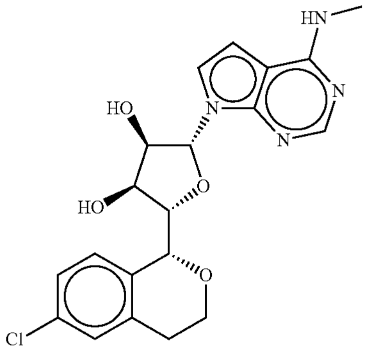 | 416.86 | (2S,3S,4R,5R)-2-((R)-6-chloroisochroman-1-yl)-5-(4-(methylamino)-7H-pyrrolo[2,3-d]pyrimidin-7-yl)tetrahydrofuran-3,4-diol |
| 70 | 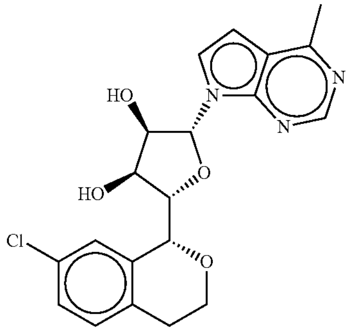 | 401.85 | (2S,3S,4R,5R)-2-((R)-7-chloroisochroman-1-yl)-5-(4-methyl-7H-pyrrolo[2,3-d]pyrimidin-7-yl)tetrahydrofuran-3,4-diol |
| 71 | 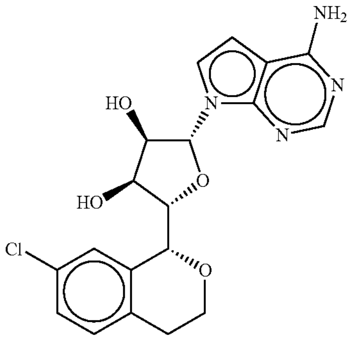 | 402.84 | (2R,3R,4S,5S)-2-(4-amino-7H-pyrrolo[2,3-d]pyrimidin-7-yl)-5-((R)-7-chloroisochroman-1-yl)tetrahydrofuran-3,4-diol |

TABLE A-continued

| Ex. | Structures | MW | Chemical Names |
|---|---|---|---|
| 72 | 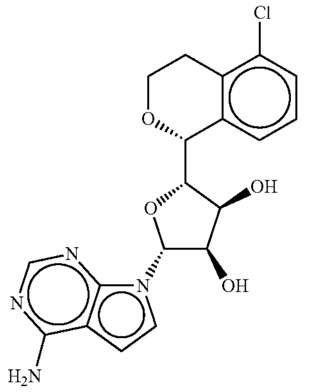 | 402.84 | (2R,3R,4S,5S)-2-(4-amino-7H-pyrrolo[2,3-d]pyrimidin-7-yl)-5-((R)-5-chloroisochroman-1-yl)tetrahydrofuran-3,4-diol |
| 73 | 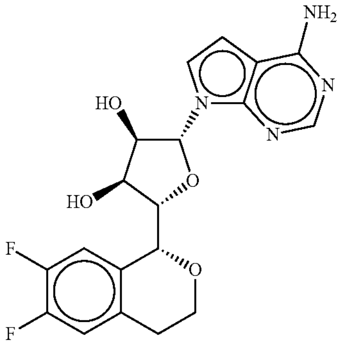 | 404.37 | (2R,3R,4S,5S)-2-(4-amino-7H-pyrrolo[2,3-d]pyrimidin-7-yl)-5-((R)-6,7-difluoroisochroman-1-yl)tetrahydrofuran-3,4-diol |
| 74 | 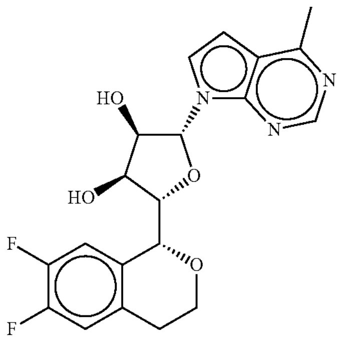 | 403.39 | (2S,3S,4R,5R)-2-((R)-6,7-difluoroisochroman-1-yl)-5-(4-methyl-7H-pyrrolo[2,3-d]pyrimidin-7-yl)tetrahydrofuran-3,4-diol |
| 75 | 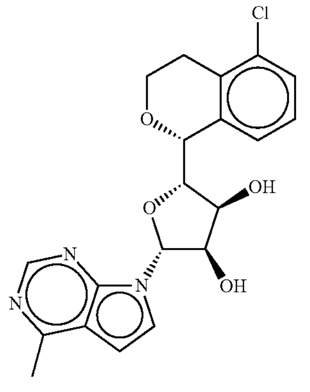 | 401.85 | (2S,3S,4R,5R)-2-((R)-5-chloroisochroman-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 76 | 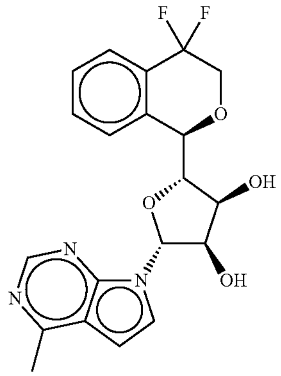 | 403.39 | (2S,3S,4R,5R)-2-((R)-4,4-difluoroisochroman-1-yl)-5-(4-methyl-7H-pyrrolo[2,3-d]pyrimidin-7-yl)tetrahydrofuran-3,4-diol |
| 77 | 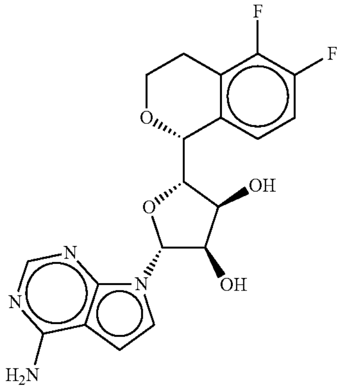 | 404.37 | (2R,3R,4S,5S)-2-(4-amino-7H-pyrrolo[2,3-d]pyrimidin-7-yl)-5-((R)-5,6-difluoroisochroman-1-yl)tetrahydrofuran-3,4-diol |
| 78 | 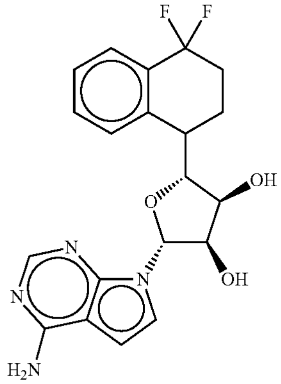 | 404.37 | (2R,3R,4S,5S)-2-(4-amino-7H-pyrrolo[2,3-d]pyrimidin-7-yl)-5-((R)-4,4-difluoroisochroman-1-yl)tetrahydrofuran-3,4-diol |
| 79 | 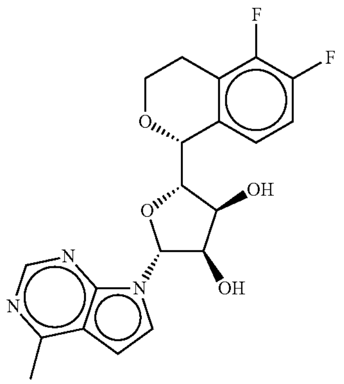 | 403.39 | (2S,3S,4R,5R)-2-((R)-5,6-difluoroisochroman-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 80 | 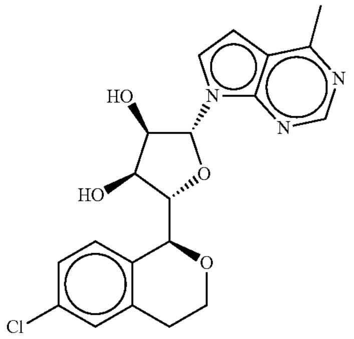 | 401.85 | (2S,3S,4R,5R)-2-((S)-6-chloroisochroman-1-yl)-5-(4-methyl-7H-pyrrolo[2,3-d]pyrimidin-7-yl)tetrahydrofuran-3,4-diol |
| 81 | 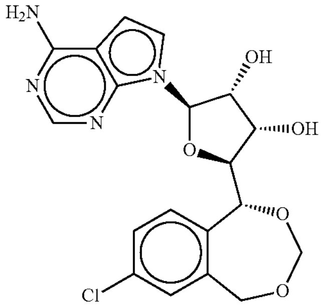 | 418.83 | (2R,3R,4S,5S)-2-(4-amino-7H-pyrrolo[2,3-d]pyrimidin-7-yl)-5-((R)-7-chloro-1,5-dihydrobenzo[e][1,3]dioxepin-1-yl)tetrahydrofuran-3,4-diol |
| 82 | 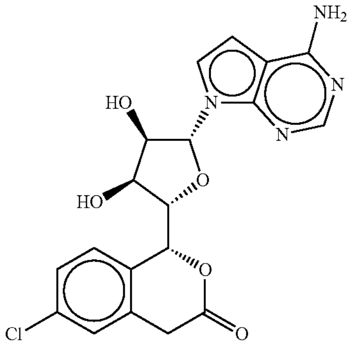 | 416.82 | (R)-1-((2S,3S,4R,5R)-5-(4-amino-7H-pyrrolo[2,3-d]pyrimidin-7-yl)-3,4-dihydroxytetrahydrofuran-2-yl)-6-chloroisochroman-3-one |
| 83 | 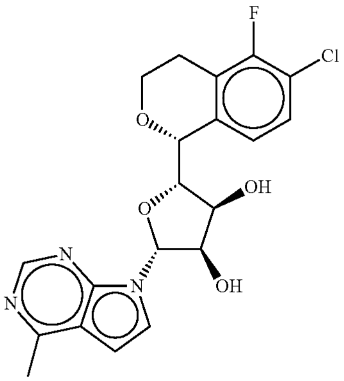 | 419.84 | (2S,3S,4R,5R)-2-((R)-6-chloro-5-fluoroisochroman-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
|---|---|---|---|
| 84 | 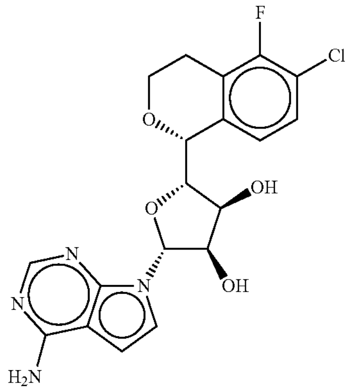 | 420.83 | (2R,3R,4S,5S)-2-(4-amino-7H-pyrrolo[2,3-d]pyrimidin-7-yl)-5-((R)-6-chloro-5-fluoroisochroman-1-yl)tetrahydrofuran-3,4-diol |
| 85 | 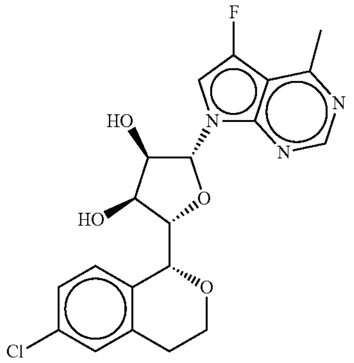 | 419.84 | (2S,3S,4R,5R)-2-((R)-6-chloroisochroman-1-yl)-5-(5-fluoro-4-methyl-7H-pyrrolo[2,3-d]pyrimidin-7-yl)tetrahydrofuran-3,4-diol |
| 86 | 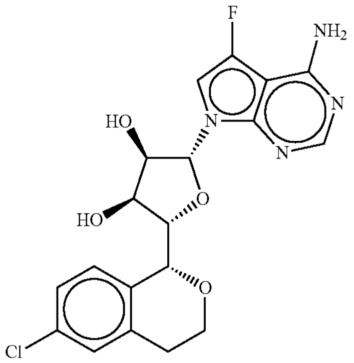 | 420.83 | (2R,3R,4S,5S)-2-(4-amino-5-fluoro-7H-pyrrolo[2,3-d]pyrimidin-7-yl)-5-((R)-6-chloroisochroman-1-yl)tetrahydrofuran-3,4-diol |
| 87 | 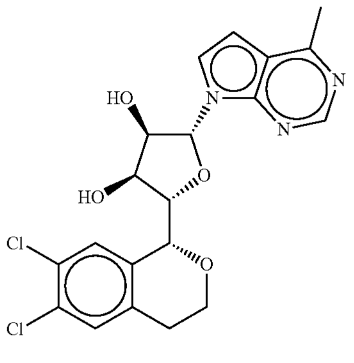 | 436.29 | (2S,3S,4R,5R)-2-((R)-6,7-dichloroisochroman-1-yl)-5-(4-methyl-7H-pyrrolo[2,3-d]pyrimidin-7-yl)tetrahydrofuran-3,4-diol |

TABLE A-continued

| Ex. | Structures | MW | Chemical Names |
| --- | --- | --- | --- |
| 88 | 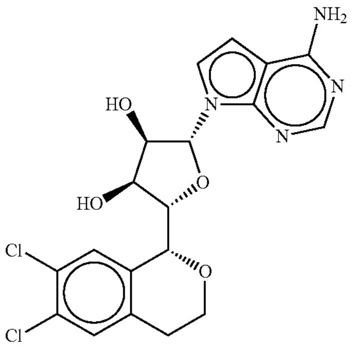 | 437.28 | (2R,3R,4S,5S)-2-(4-amino-7H-pyrrolo[2,3-d]pyrimidin-7-yl)-5-((R)-6,7-dichloroisochroman-1-yl)tetrahydrofuran-3,4-diol |
| 89 | 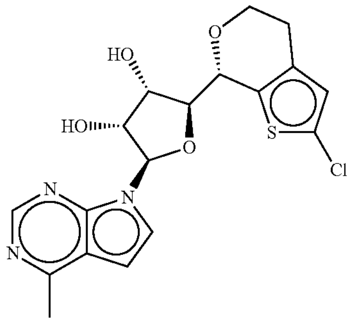 | 408.88 | (2S,3S,4R,5R)-2-((S)-2-chloro-4,7-dihydro-5H-thieno[2,3-c]pyran-7-yl)-5-(4-methyl-7H-pyrrolo[2,3-d]pyrimidin-7-yl)tetrahydrofuran-3,4-diol |
| 90 | 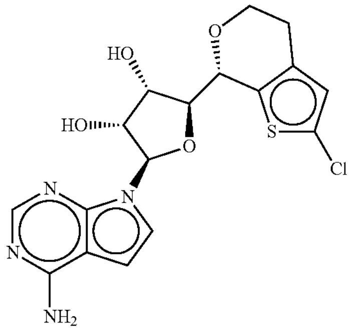 | 409.87 | (2R,3R,4S,5S)-2-(4-amino-7H-pyrrolo[2,3-d]pyrimidin-7-yl)-5-((S)-2-chloro-4,7-dihydro-5H-thieno[2,3-c]pyran-7-yl)tetrahydrofuran-3,4-diol |
| 91 | 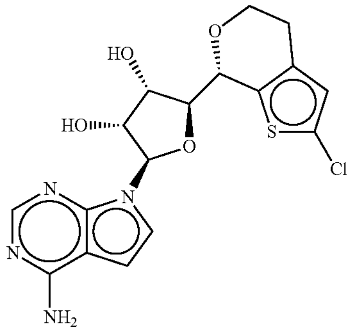 | 409.87 | (2R,3R,4S,5S)-2-(4-amino-7H-pyrrolo[2,3-d]pyrimidin-7-yl)-5-((R)-2-chloro-4,7-dihydro-5H-thieno[2,3-c]pyran-7-yl)tetrahydrofuran-3,4-diol |

TABLE A-continued

| Ex. | Structures | MW | Chemical Names |
|---|---|---|---|
| 92 | 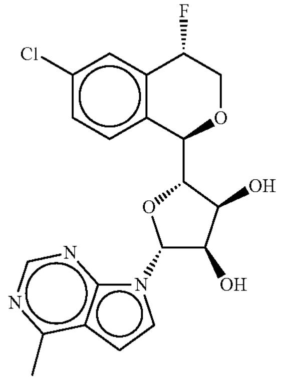 | 419.84 | (2S,3S,4R,5R)-2-((1R,4S)-6-chloro-4-fluoroisochroman-1-yl)-5-(4-methyl-7H-pyrrolo[2,3-d]pyrimidin-7-yl)tetrahydrofuran-3,4-diol |
| 93 | 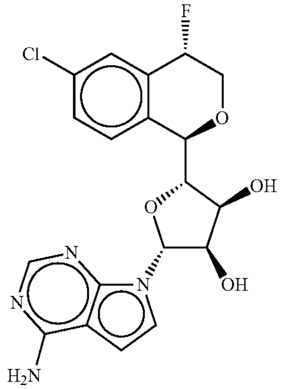 | 420.83 | (2R,3R,4S,5S)-2-(4-aminopyrrolo[2,3-d]pyrimidin-7-yl)-5-[(1R,4S)-6-chloro-4-fluoro-isochroman-1-yl]tetrahydrofuran-3,4-diol |
| 94 | 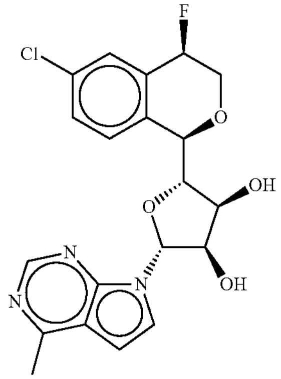 | 419.84 | (2R,3R,4S,5S)-2-(4-methylpyrrolo[2,3-d]pyrimidin-7-yl)-5-[(1R,4R)-6-chloro-4-fluoro-isochroman-1-yl]tetrahydrofuran-3,4-diol |
| 95 | 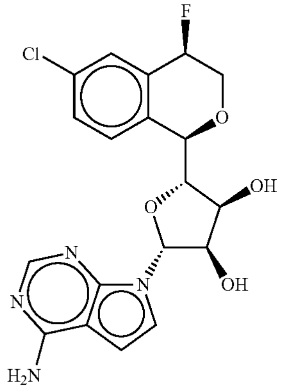 | 420.83 | (2R,3R,4S,5S)-2-(4-amino-7H-pyrrolo[2,3-d]pyrimidin-7-yl)-5-((1R,4R)-6-chloro-4-fluoroisochroman-1-yl)tetrahydrofuran-3,4-diol |

TABLE A-continued

| Ex. | Structures | MW | Chemical Names |
|---|---|---|---|
| 97 | 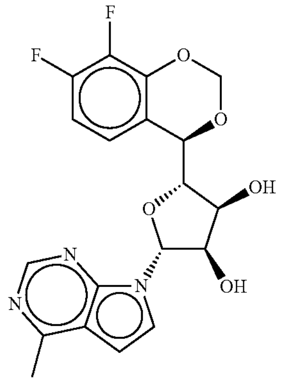 | 405.36 | (2S,3S,4R,5R)-2-((R)-7,8-difluoro-4H-benzo[d][1,3]dioxin-4-yl)-5-(4-methyl-7H-pyrrolo[2,3-d]pyrimidin-7-yl)tetrahydrofuran-3,4-diol |
| 98 | 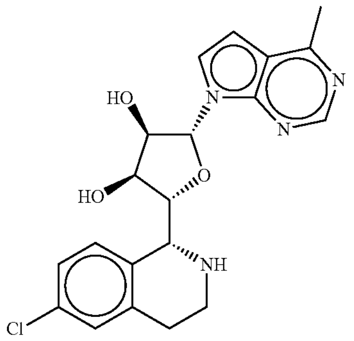 | 400.86 | (2R,3S,4R,5R)-2-[(1R)-6-chloro-1,2,3,4-tetrahydroisoquinolin-1-yl]-5-(4-methylpyrrolo[2,3-d]pyrimidin-7-yl)tetrahydrofuran-3,4-diol |
| 99 | 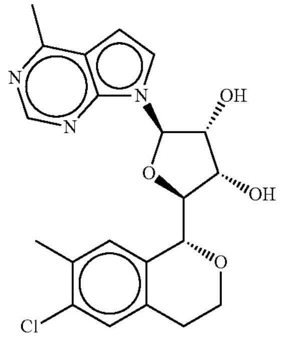 | 415.87 | (2S,3S,4R,5R)-2-((R)-6-chloro-7-methylisochroman-1-yl)-5-(4-methyl-7H-pyrrolo[2,3-d]pyrimidin-7-yl)tetrahydrofuran-3,4-diol |
| 100 | 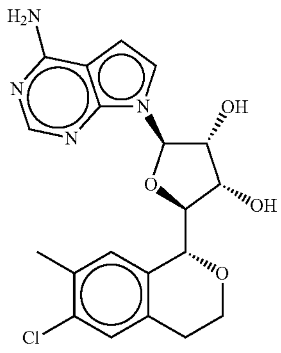 | 416.86 | (2R,3R,4S,5S)-2-(4-amino-7H-pyrrolo[2,3-d]pyrimidin-7-yl)-5-((R)-6-chloro-7-methylisochroman-1-yl)tetrahydrofuran-3,4-diol |

TABLE A-continued

| Ex. | Structures | MW | Chemical Names |
|---|---|---|---|
| 101 | 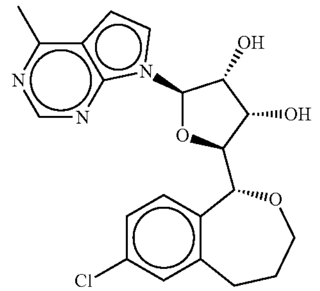 | 415.87 | (2S,3S,4R,5R)-2-((R)-7-chloro-1,3,4,5-tetrahydrobenzo[c]oxepin-1-yl)-5-(4-methyl-7H-pyrrolo[2,3-d]pyrimidin-7-yl)tetrahydrofuran-3,4-diol |
| 102 | 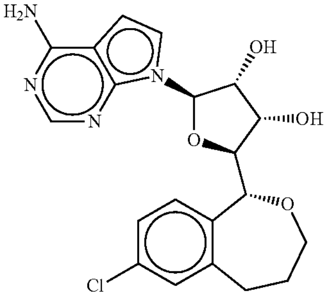 | 416.86 | (2R,3R,4S,5S)-2-(4-amino-6H-7I4-pyrrolo[2,3-d]pyrimidin-7-yl)-5-((R)-7-chloro-1,3,4,5-tetrahydrobenzo[c]oxepin-1-yl)tetrahydrofuran-3,4-diol |
| 103 | 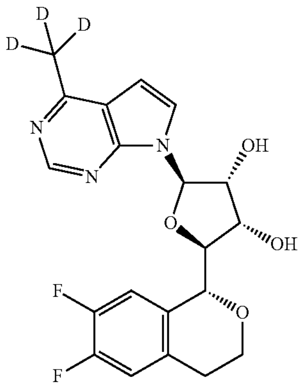 [SMILES: [2H]C([2H])([2H])c1ncnc2c1ccn2[C@@H]1O[C@H]([C@@H]2OCCc3cc(F)c(F)cc32)[C@@H](O)[C@H]1O] | 406.4 | (2S,3S,4R,5R)-2-((R)-6,7-difluoroisochroman-1-yl)-5-(4-(methyl-d3)-7H-pyrrolo[2,3-d]pyrimidin-7-yl)tetrahydrofuran-3,4-diol |

EXPERIMENTAL PROCEDURES

Example 1A. Synthesis of (2R,3R,4S,5S)-2-(4-amino-7H-pyrrolo[2,3-d]pyrimidin-7-yl)-5-((R)-5-chloro-1,3-dihydroisobenzofuran-1-yl)tetrahydrofuran-3,4-diol (Ex. 1A

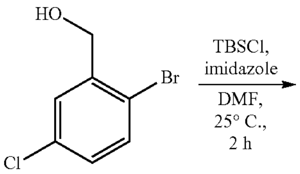

1Aa

-continued

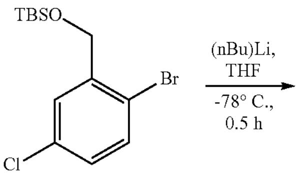

1Ab

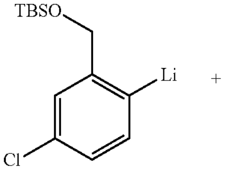

1Ac

-continued

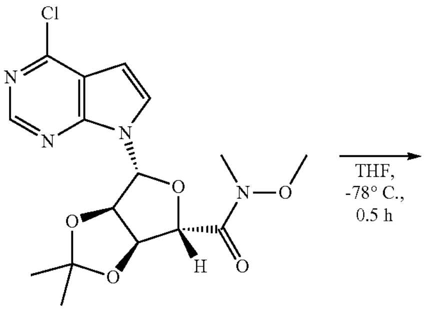

1Ad

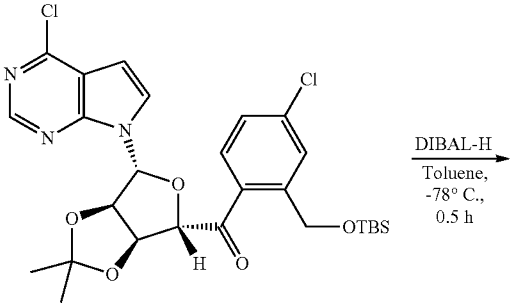

1Ae

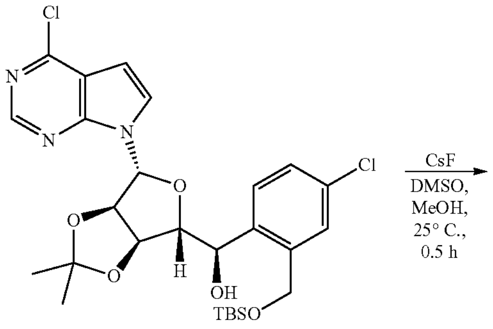

1Af

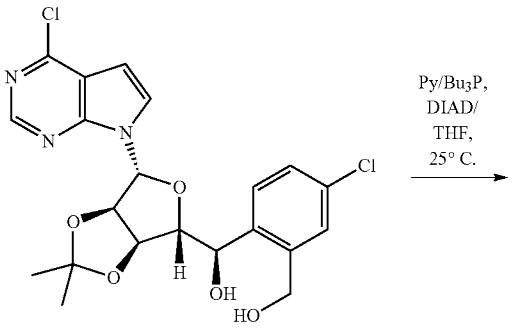

1Ag

-continued

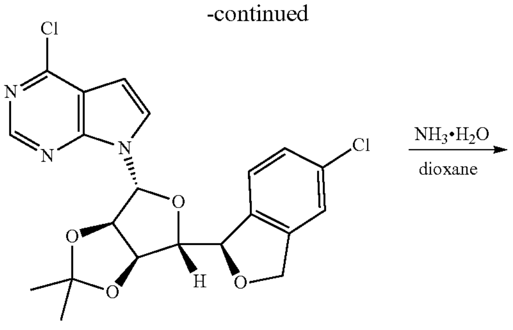

1Ah

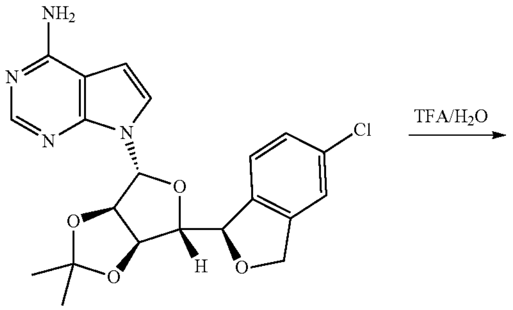

1Ai

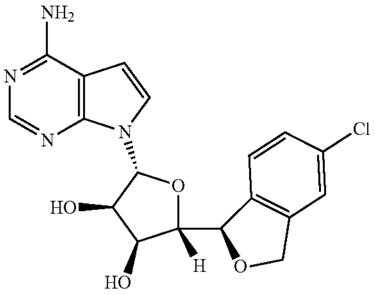

Ex. 1A

Step 1. Synthesis of (2-bromo-5-chloro-phenyl) methoxy-tert-butyl-dimethyl-silane (1Ab)

To a solution of (2-bromo-5-chloro-phenyl)methanol (1Aa, 5.0 g, 22.58 mmol) in DMF (10 mL) was added TBSCl (10.21 g, 67.73 mmol) and imidazole (3073.9 mg, 45.15 mmol). The reaction mixture was stirred at 25° C. for 16 h. TLC (PE:EA=10:1, $R_f$=0.8) showed the reaction was completed. The reaction mixture was diluted with water (100 mL) and the mixture was extracted with EA (50 mL×3), then the organic layers were washed with brine (100 mL×3), dried over $Na_2SO_4$ and concentrated in vacuum to give the crude product which was purified by silica chromatography column (100-200 mesh size, PE:EA=200:1 to 100:1) to give (2-bromo-5-chloro-phenyl)methoxy-tert-butyl-dimethyl-silane (5.0 g, 14.9 mmol, 66% yield) as a colorless oil.

Step 2. Synthesis of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl] methanone (1Ae)

To a solution of (2-bromo-5-chloro-phenyl)methoxy-tert-butyl-dimethyl-silane (1Ab, 4.3 g, 12.80 mmol) in THF (50 mL) was added butyllithium (0.6 g, 9.10 mmol) at −78° C. under $N_2$. The mixture was stirred at −78° C. for 10 min to yield 1Ac. A solution of the (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1Ad, 1.4 g, 3.70 mmol) in THF (50 mL) was added. The mixture was stirred at −78° C. for 30 min. LCMS showed the reaction was complete. The reaction mixture was quenched with saturated $NH_4Cl$ solution (50 mL). The mixture was extracted with ethyl acetate (100 mL×3). The combined organic layers were washed with brine (40 mL×3), dried over $Na_2SO_4$ and concentrated in vacuum to give the crude product which was purified by silica chromatography column (100-200 mesh size, PE:EA=20:1 to 10:1) to give [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanone (1Ae, 1.3 g, 2.20 mmol, 61.4% yield) as a pale yellow oil. LCMS [M+H]: 578.2.

Step 3. Synthesis of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanol (1Af)

To a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanone (1Ae, 50 mg, 0.11 mmol) in toluene (5 mL) was added diisobutylaluminum hydride (24.6 mg, 0.20 mmol). The reaction mixture was stirred at −78° C. for 0.5 h under $N_2$. TLC (PE:EA=3:1, $R_f$=0.3) showed the reaction was complete. The reaction mixture was washed with water (10 mL×3) brine (10 mL×3). The organic layer was dried over $Na_2SO_4$, filtered and concentrated to afford the crude product which was purified silica chromatography column (100-200 mesh size, PE:EA=10:1 to 5:1) to give (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanol (1Af, 50 mg, 0.10 mmol, 99.7% yield) as a pale yellow solid.

Step 4. Synthesis of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-chloro-2-(hydroxymethyl)phenyl]methanol (1Ag)

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanol (1Af, 50 mg, 0.10 mmol) in DMSO (12 mL) and methanol (0.2 mL) was added CsF (39.3 mg, 0.3 mmol) and the reaction mixture was stirred at 25° C. for 0.5 h. LCMS showed the reaction was completed. The reaction mixture was filtered and purified by reversed-phase combi-flash, eluted with $CH_3CN$ in $H_2O$ (neutral condition) from 10% to 55% to give (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-chloro-2-(hydroxymethyl)phenyl]methanol (1Ag, 30 mg, 0.1 mmol, 71.7% yield) as a pale yellow oil. LCMS [M+H]: 466.1.

Step 5. Synthesis of 7-[(3aR,4R,6R,6aR)-6-[(1R)-5-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (1Ah)

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-chloro-2-(hydroxymethyl)phenyl]methanol (100.0 mg, 0.21 mmol) in THF (20 mL) was added Pyridine (0.02 mL, 0.21 mmol) at 25° C., Tributylphosphine (0.1 mL, 0.42 mmol) was added followed by DIAD (0.1 mL, 0.52 mmol) at 25° C. The reaction was stirred at 25° C. under $N_2$ for 4 h. TLC (PE:EA=1:1, $R_f$=0.4) showed the reaction was completed. The mixture was concentrated in vacuum to give crude product which was purified by silica chromatography column (100-200 mesh size, PE:EA=10:1 to 1:1) to give to give 7-[(3aR,4R,6R,6aR)-6-[(1R)-5-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (1Ah, 80.0 mg, 0.2 mmol, 83.2% yield) as a pale yellow oil.

Step 6. Synthesis of 7-[(3aR,4R,6R,6aR)-6-[(1R)-5-chloro-1,3-dihydroisobenzofuran-1-yl]-2,2-dimethyl-3a,4,6,6a-tetrahydrofuro[3,4-d][1,3]dioxol-4-yl]pyrrolo[2,3-d]pyrimidin-4-amine (1Ag)

A solution of 7-[(3aR,4R,6R,6aR)-6-[(1R)-5-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (1Ah, 80.0 mg, 0.2 mmol) in 1,4-dioxane (3 mL) and $NH_3 \cdot H_2O$ (3 mL, 77.9 mmol) was stirred at 120° C. for 16 h in an autoclave. LCMS showed the reaction was complete. The mixture was concentrated in vacuum to give the crude product which was purified by reversed-phase combi-flash, eluted with $CH_3CN$ in $H_2O$ (neutral condition) from 10% to 95% to give 7-[(3aR,4R,6R,6aR)-6-[(1R)-5-chloro-1,3-dihydroisobenzofuran-1-yl]-2,2-dimethyl-3a,4,6,6a-tetrahydrofuro[3,4-d][1,3]dioxol-4-yl]pyrrolo[2,3-d]pyrimidin-4-amine (1Ai, 45.0 mg, 0.11 mmol, 58.8% yield) as a pale yellow solid. LCMS [M+H]: 429.1.

Step 7. Synthesis of (Ex. 1A)

A solution of 7-[(3aR,4R,6R,6aR)-6-[(1R)-5-chloro-1,3-dihydroisobenzofuran-1-yl]-2,2-dimethyl-3a,4,6,6a-tetrahydrofuro[3,4-d][1,3]dioxol-4-yl]pyrrolo[2,3-d]pyrimidin-4-amine (1Ai, 45.0 mg, 0.10 mmol) in water (3 mL) and TFA (3 mL, 33.30 mmol) was stirred at 25° C. for 1 h. LCMS showed the reaction was completed. The reaction mixture was concentrated and purified by prep-HPLC, (0.1% $NH_3 \cdot H_2O$), eluted with $CH_3CN$ in $H_2O$ from 10% to 95% to give (2R,3R,4S,5S)-2-(4-aminopyrrolo[2,3-d]pyrimidin-7-yl)-5-[(1R)-5-chloro-1,3-dihydroisobenzofuran-1-yl]tetrahydrofuran-3,4-diol (Ex. 1A, 6.0 mg, 0.02 mmol, 14.5% yield) as a white solid. LCMS [M+H]: 389.1. $^1$H NMR (400 M Hz, DMSO-$d_6$): δ 8.06 (s, 1H), 7.42 (s, 1H), 7.34-7.35 (d, J=4.0 Hz, 1H), 7.29-7.32 (m, 1H), 7.22-7.24 (m, 1H), 7.03 (s, 2H), 6.64 (d, J=3.6 Hz, 1H), 6.14-6.16 (d, J=7.6 Hz, 1H), 5.34-5.36 (m, 1H), 5.27-5.28 (d, J=6.4 Hz, 1H), 5.19-5.20 (d, J=4.0 Hz, 1H), 5.04-5.12 (m, 2H), 4.51-4.56 (m, 1H), 4.05-4.06 (m, 1H), 3.93-3.95 (m, 1H). $^1$H NMR (400 M Hz, DMSO-d6+D2O): δ 8.07 (s, 1H), 7.43 (s, 1H), 7.34-7.35 (d, J=3.6 Hz, 1H), 7.30-7.33 (m, 1H), 7.23-7.25 (m, 1H), 6.65-6.66 (d, J=3.6 Hz, 1H), 6.14-6.16 (d, J=7.6 Hz, 1H), 5.35-5.36 (m, 1H), 5.08-5.10 (m, 2H), 4.51-4.54 (m, 1H), 4.07-4.09 (m, 1H), 3.93-3.94 (m, 1H).

Example 1B. Synthesis of (2R,3R,4S,5S)-2-(4-amino-7H-pyrrolo[2,3-d]pyrimidin-7-yl)-5-((S)-5-chloro-1,3-dihydroisobenzofuran-1-yl)tetrahydrofuran-3,4-diol (Ex. 1B)

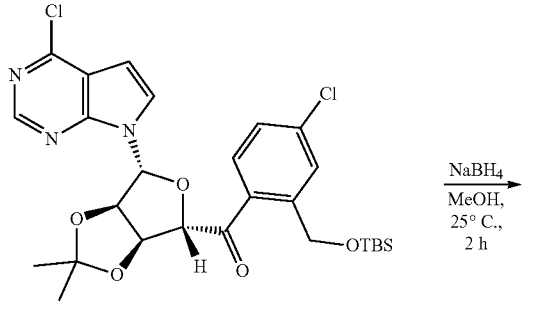

1Ae

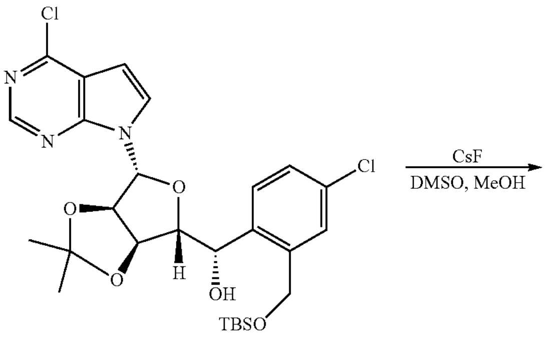

1Ba

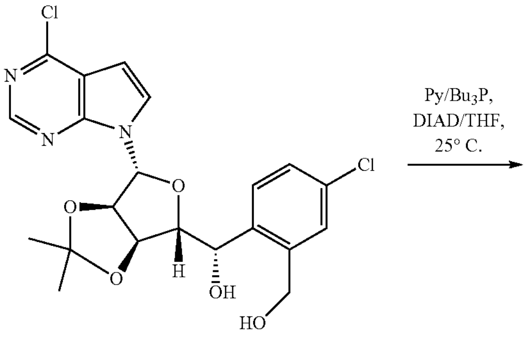

1Bb

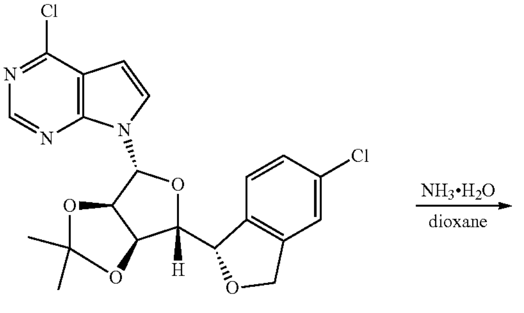

1Bc

-continued

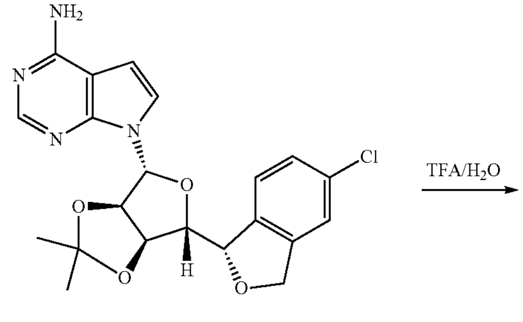

1Bd

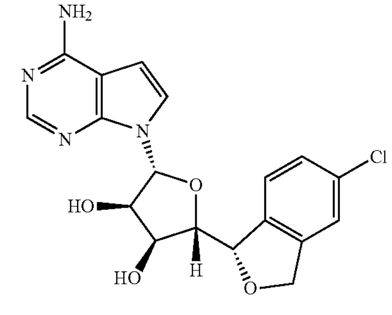

Ex. 1B

Step 1. Synthesis of (1Ba)

To a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanone (1Ae, 630 mg, 1.10 mmol) in methanol (5 mL) was added $NaBH_4$ (82.4 mg, 2.20 mmol), and the mixture was stirred at 25° C. for 1 h. TLC (PE:EA=1:1, $R_f$=0.4) showed the starting material was consumed. LCMS showed the reaction was complete. The reaction mixture was quenched with saturated $NH_4Cl$ solution (50 mL). The mixture was extracted with ethyl acetate (100 mL×3). The combined organic layers were washed with brine (40 mL×3), dried over $Na_2SO_4$ and concentrated in vacuum to give the crude product which was purified by silica chromatography column (100-200 mesh size, PE:EA=10:1 to 5:1) to give (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanol (1Af, 10.0 mg, 0.02 mmol, 1.6% yield) and (S)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanol (1Ba), 520 mg, 0.9 mmol, 82.3% yield) as a pale yellow oil.

Step 2. Synthesis of (S)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-chloro-2-(hydroxymethyl)phenyl]methanol (1Bb)

To a solution of (S)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-4-chloro-phenyl]methanol (1Ba, 520 mg, 0.90 mmol) in DMSO (5 mL) and methanol (0.1 mL) was added CsF (408.2 mg, 2.70 mmol) and the reaction mixture was stirred at 25° C. for 1 h. LCMS showed the reaction was complete. The reaction mixture was filtered and purified by reversed-phase combi-flash, eluted with $CH_3CN$ in $H_2O$ (neutral condition) from 10% to 95% to give (S)-[(3aR,4R, 6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-chloro-2-(hydroxymethyl)phenyl]methanol (1Bb, 300 mg, 0.64 mmol, 71.8% yield) as a white solid. LCMS [M+H]: 466.1.

Step 3. Synthesis of 7-[(3aR,4R,6R,6aR)-6-[(1S)-5-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (1Bc)

To a solution of (S)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[4-chloro-2-(hydroxymethyl)phenyl]methanol (1Bb, 250 mg, 0.5 mmol) in THF (5 mL) and was added pyridine (0.04 mL, 0.50 mmol), tributylphosphine (0.3 mL, 1.10 mmol) and DIAD (0.2 mL, 1.10 mmol). The reaction mixture was stirred at 25° C. for 16 h. TLC (PE:EA=3:1, $R_f$=0.4) showed the reaction was complete. The mixture was concentrated in vacuum to give the crude product which was purified by silica chromatography column (100-200 mesh size, PE:EA=50:1 to 20:1) to give 7-[(3aR,4R,6R,6aR)-6-[(1S)-5-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (1Bc, 180.0 mg, 0.4 mmol, 74.9% yield) as a white solid.

Step 4. Synthesis of 7-[(3aR,4R,6R,6aR)-6-[(1S)-5-chloro-1,3-dihydroisobenzofuran-1-yl]-2,2-dimethyl-3a,4,6,6a-tetrahydrofuro[3,4-d][1,3]dioxol-4-yl]pyrrolo[2,3-d]pyrimidin-4-amine (1Bd)

To a solution of 7-[(3aR,4R,6R,6aR)-6-[(1S)-5-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (1Bc, 180 mg, 0.40 mmol) in 1,4-dioxane (5 mL) and was added $NH_3 \cdot H_2O$ (5 mL, 129.81 mmol) and the reaction mixture was stirred at 25° C. for 16 h in a autoclave. LCMS showed the reaction was complete. The mixture was concentrated in vacuum to give the crude product which was purified by reversed-phase combi-flash, eluted with $CH_3CN$ in $H_2O$ (neutral condition) from 10% to 90% to give 7-[(3aR,4R,6R,6aR)-6-[(1S)-5-chloro-1,3-dihydroisobenzofuran-1-yl]-2,2-dimethyl-3a,4,6,6a-tetrahydrofuro[3,4-d][1,3]dioxol-4-yl]pyrrolo[2,3-d]pyrimidin-4-amine (1Bd, 140 mg, 0.32 mmol, 81.3% yield) as a white solid. LCMS [M+H]: 429.1.

Step 5. Synthesis of (2R,3R,4S,5S)-2-(4-aminopyrrolo[2,3-d]pyrimidin-7-yl)-5-[(1S)-5-chloro-1,3-dihydroisobenzofuran-1-yl]tetrahydrofuran-3,4-diol Hydrochloride (Ex. 1B)

A solution of 7-[(3aR,4R,6R,6aR)-6-[(1S)-5-chloro-1,3-dihydroisobenzofuran-1-yl]-2,2-dimethyl-3a,4,6,6a-tetrahydrofuro[3,4-d][1,3]dioxol-4-yl]pyrrolo[2,3-d]pyrimidin-4-amine (1Bd, 180 mg, 0.40 mmol) in water (5 mL) and TFA (5 mL, 67.31 mmol) was stirred at 25° C. for 1 h. LCMS showed the reaction was complete. The reaction mixture was concentrated and purified by prep-HPLC, (0.1% $NH_3 \cdot H_2O$), eluted with $CH_3CN$ in $H_2O$ from 10% to 95% and added 1 mL of HCl (1 M) and lyophilized to obtain (2R,3R,4S,5S)-2-(4-aminopyrrolo[2,3-d]pyrimidin-7-yl)-5-[(1S)-5-chloro-1,3-dihydroisobenzofuran-1-yl]tetrahydrofuran-3,4-diol hydrochloride (Ex. 1B, 45.1 mg, 0.10 mmol, 25.1% yield) as pale yellow solid. LCMS [M+H]: 389.1. $^1H$ NMR (400 M Hz, DMSO-$d_6$): δ 13.89 (s, 1H), 9.45 (s, 1H), 8.50 (s, 1H), 8.36 (s, 1H), 7.54-7.55 (d, J=3.6 Hz, 1H), 7.30-7.39 (m, 3H), 7.01-7.02 (d, J=3.6 Hz, 1H), 6.08-6.09 (d, J=4.8 Hz, 1H), 5.39 (s, 1H), 4.97-5.05 (m, 2H), 4.32-4.38 (m, 3H). $^1H$ NMR (400 M Hz, DMSO-$d_6$+D2O): δ 8.37 (s, 1H), 7.55-7.56 (d, J=3.6 Hz, 1H), 7.37-7.39 (m, 1H), 7.30-7.33 (m, 2H), 7.01-7.02 (d, J=3.6 Hz, 1H), 6.08-6.10 (d, J=7.2 Hz, 1H), 5.39 (s, 1H), 5.00-5.05 (m, 2H), 4.32-4.39 (m, 3H).

Example 2A. Synthesis of (1R,2S,3R,5S)-3-(4-amino-7H-pyrrolo[2,3-d]pyrimidin-7-yl)-5-((R)-5-chloro-1,3-dihydroisobenzofuran-1-yl)cyclopentane-1,2-diol (Ex. 2A)

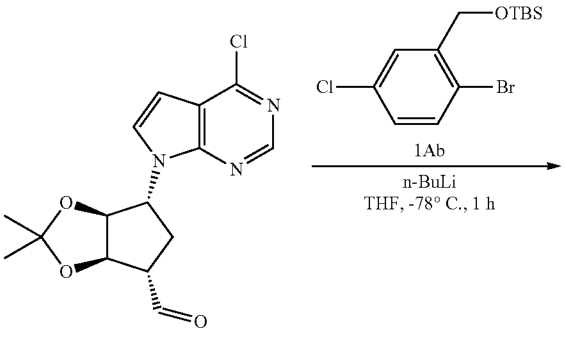

2Aa

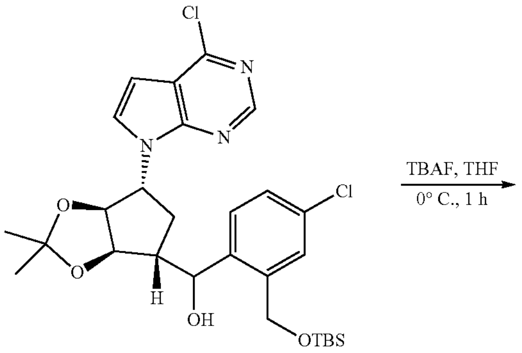

2Ab

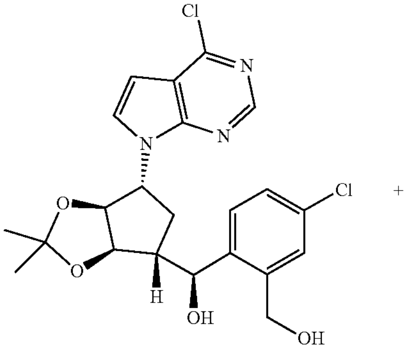

2Ac

-continued

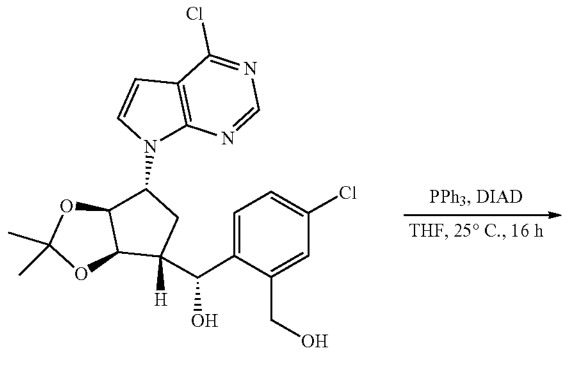

2Ad

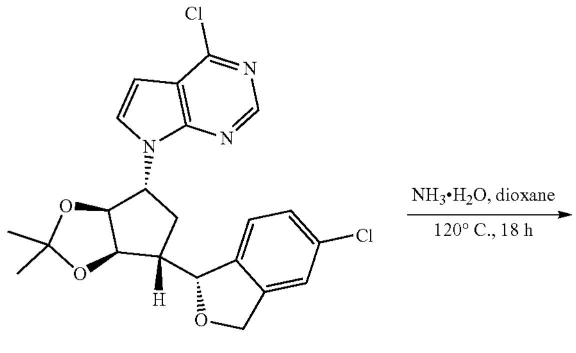

2Ae

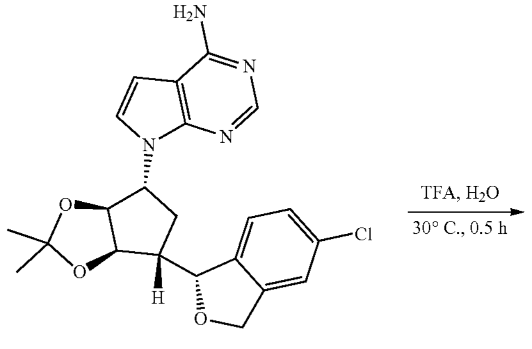

2Af

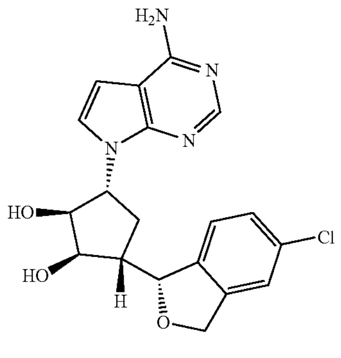

Ex. 2A

Step 1. Synthesis of [(3aS,4R,6R,6aR)-4-(4-chloro-pyrrolo[2,3-d]pyrimidin-7-yl)-2,2-dimethyl-4,5,6,6a-tetrahydro-3aH-cyclopenta[d][1,3]dioxol-6-yl]-[2-[[tert-butyl(dimethyl)silyl]oxymethyl]-4-chloro-phenyl]methanol (2Ab)

To a solution of (2-bromo-5-chloro-phenyl)methoxy-tert-butyl-dimethyl-silane (1Ab, 1826.0 mg, 5.44 mmol) in THF (20 mL) was added butyllithium (2.8 mL, 5.44 mmol) at −78° C. The reaction mixture was stirred at −78° C. for 0.5 h. Then, (3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxole-6-carbaldehyde (2Aa, 1750 mg, 5.44 mmol) was added to the mixture. The reaction mixture was stirred at −78° C. for 1 h. LCMS showed the reaction was complete. The reaction was quenched with $H_2O$ (30 mL) and extracted with ethyl acetate (60 mL). The organic layer was dried over $Na_2SO_4$, filtered, and concentrated in vacuum to give the crude product which was purified by silica chromatography column (PE:EA=3:1) to give [(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-[2-[[tert-butyl(dimethyl)silyl]oxymethyl]-4-chloro-phenyl]methanol (2Ab, 360.0 mg, 0.62 mmol, 11.4% yield). LCMS [M+H]: 578.2.

Step 2. Synthesis of (2Ac) and (2Ad)

To a solution of [(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-[2-[[tert-butyl(dimethyl)silyl]oxymethyl]-4-chloro-phenyl]methanol (2Ab, 360 mg, 0.62 mmol) in THF (5 mL) was added TBAF (0.62 mL, 1N in THF, 0.62 mmol) at 0° C. The mixture was stirred at 0° C. for 1 h. LCMS showed the reaction was complete. To the mixture was added ethyl acetate (50 mL) which was washed with $H_2O$ (20 mL×3) and brine (30 mL). The organic layer was dried over $Na_2SO_4$, concentrated in vacuum to give the crude product which was purified by prep-TLC (PE:EA=3:1) to give (S)-[(3aS,4R,6R,6aR)-4-(4-chloropyrrolo-[2,3-d]pyrimidin-7-yl)-2,2-dimethyl-4,5,6,6a-tetrahydro-3aH-cyclopenta[d][1,3]dioxol-6-yl]-[4-chloro-2-(hydroxymethyl)phenyl]methanol (2Ac, 42.0 mg, 0.09 mmol, 14.5% yield) and (R)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-[4-chloro-2-(hydroxymethyl)phenyl]methanol (2Ad, 55.0 mg, 0.12 mmol, 19.0% yield). LCMS [M+H]: 464.1.

Step 3. Synthesis of 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]-4-chloro-pyrrolo[2,3-d]pyrimidine (2Ae)

To a solution of (R)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-[4-chloro-2-(hydroxymethyl)phenyl]methanol (2Ad, 100 mg, 0.22 mmol) in THF (5 mL) was added $PPh_3$ (56.5 mg, 0.22 mmol), then added DIAD (0.04 mL, 0.22 mmol), the mixture was stirred at 25° C. for 16 h. The reaction mixture was concentrated in vacuum to give crude product which was purified by prep-TLC (PE:EA=3:1) to give 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]-4-chloro-pyrrolo[2,3-d]pyrimidine (2Ae, 70 mg, 0.16 mmol, 72.8% yield). LCMS [M+H]: 446.2.

Step 4. Synthesis of 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]pyrrolo[2,3-d]pyrimidin-4-amine (2Af)

To a solution of 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]-4-chloro-pyrrolo[2,3-d]pyrimidine (2Ae, 90 mg, 0.20 mmol) in 1,4-dioxane (3 mL) was added ammonia hydrate (3 mL, 0.60 mmol), then the mixture was sealed and stirred at 120° C. for 16 h. LCMS showed the mixture was complete. The reaction mixture was concentrated in vacuum, added ethyl acetate (100 mL), and washed with brine (60 mL). The organic layer was dried over $Na_2SO_4$, concentrated in vacuum to give 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]pyrrolo[2,3-d]pyrimidin-4-amine (2Af, 90 mg, 0.18 mmol, 92.0% yield). LCMS [M+H]: 427.1.

Step 5. Synthesis of (1R,2S,3R,5S)-3-(4-aminopyrrolo[2,3-d]pyrimidin-7-yl)-5-[(1R)-5-chloro-1,3-dihydroisobenzofuran-1-yl]cyclopentane-1,2-diol (Ex. 2A)

To a solution of 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]pyrrolo[2,3-d]pyrimidin-4-amine (2Af, 70 mg, 0.16 mmol) in water (2 mL) was added TFA (0.9 mL, 11.45 mmol) and the reaction mixture was stirred at 30° C. for 0.5 h. LCMS showed the reaction was complete. The mixture was purified by prep-HPLC, eluted with $CH_3CN$ in $H_2O$ (0.1% $NH_4OH$) from 5% to 95% to give (1R,2S,3R,5S)-3-(4-aminopyrrolo[2,3-d]pyrimidin-7-yl)-5-[(1R)-5-chloro-1,3-dihydroisobenzofuran-1-yl]cyclopentane-1,2-diol (Ex. 2A, 30 mg, 0.08 mmol, 47% yield) as a white solid. LCMS [M+H]: 387.3. $^1H$ NMR (400 MHz, DMSO-$d_6$+D2O): δ 8.00 (s, 1H), 7.31-7.37 (m, 3H), 7.15-7.16 (m, 1H), 6.52-6.53 (m, 1H), 5.41-5.42 (m, 1H), 5.10-5.14 (m, 1H), 4.99-5.03 (m, 1H), 4.78-4.85 (m, 1H), 4.18-4.21 (m, 1H), 4.04-4.06 (m, 1H), 2.47-2.50 (m, 1H), 1.71-1.79 (m, 1H), 1.33-1.40 (m, 1H).

Example 2B. Synthesis of (1R,2S,3R,5S)-3-(4-amino-7H-pyrrolo[2,3-d]pyrimidin-7-yl)-5-((S)-5-chloro-1,3-dihydroisobenzofuran-1-yl)cyclopentane-1,2-diol (Ex. 2B)

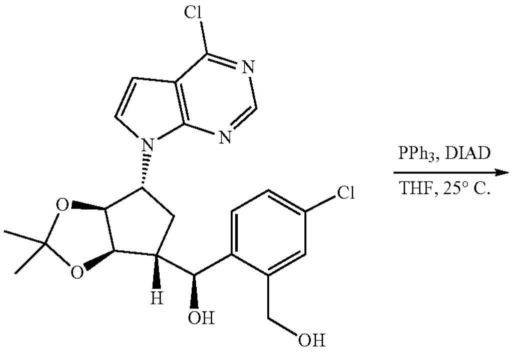

2Ac

-continued

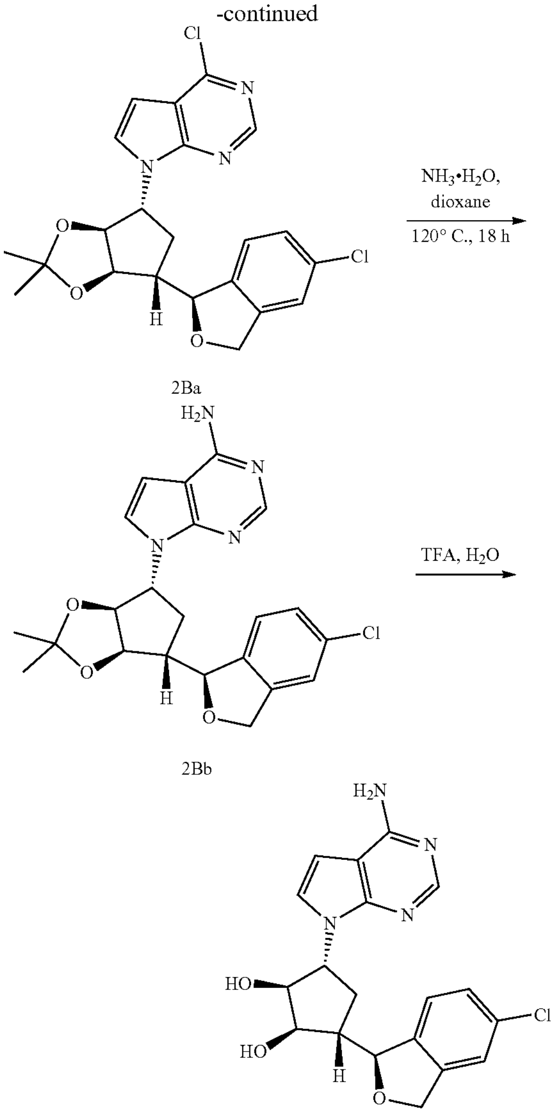

2Ba

2Bb

Ex. 2B

Step 1. Synthesis of 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]-4-chloro-pyrrolo[2,3-d]pyrimidine (2Ba)

To a solution of (S)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-[4-chloro-2-(hydroxymethyl)phenyl]methanol (2Ac, 90 mg, 0.19 mmol) in THF (4 mL) was added $PPh_3$ (101.7 mg, 0.39 mmol) and DIAD (0.11 mL, 0.39 mmol). The mixture was stirred at 25° C. for 16 h under $N_2$. TLC (PE:EA=3:1, $R_f$=0.4) showed the reaction was complete. The mixture was concentrated in vacuum to give the crude product which was purified by pre-TLC (PE:EA=3:1) to give 7-[(3aS,4R,6R,6aR)-6-[(1R)-5-chloro-1,3-dihydroisobenzofuran-1-yl]-2,2-dimethyl-4,5,6,6a-tetrahydro-3aH-cyclopenta[d][1,3]dioxol-4-yl]-4-chloro-pyrrolo[2,3-d]pyrimidine (2Ba, 70 mg, 0.16 mmol, 80.9% yield). LCMS [M+H]: 446.2.

Step 2. Synthesis of 7-[(3aS,4R,6R,6aR)-6-[(1S)-5-chloro-1,3-dihydroisobenzofuran-1-yl]-2,2-dimethyl-4,5,6,6a-tetrahydro-3aH-cyclopenta[d][1,3]dioxol-4-yl]pyrrolo[2,3-d]pyrimidin-4-amine (2Bb)

To a solution of 7-[(3aS,4R,6R,6aR)-6-[(1S)-5-chloro-1,3-dihydroisobenzofuran-1-yl]-2,2-dimethyl-4,5,6,6a-tetrahydro-3aH-cyclopenta[d][1,3]dioxol-4-yl]-4-chloro-pyrrolo[2,3-d]pyrimidine (2Ba, 70 mg, 0.16 mmol) in 1,4-dioxane (3.5 mL) was added ammonia hydrate (3.5 mL, 0.47 mmol). The mixture was sealed and stirred at 120° C. for 16 h. LCMS showed the reaction was complete. The mixture was concentrated in vacuum to give 7-[(3aS,4R,6R,6aR)-6-[(1S)-5-chloro-1,3-dihydroisobenzofuran-1-yl]-2,2-dimethyl-4,5,6,6a-tetrahydro-3aH-cyclopenta[d][1,3]dioxol-4-yl]pyrrolo[2,3-d]pyrimidin-4-amine (2Bb, 60 mg, 0.09 mmol, 59.2% yield). LCMS [M+H]: 427.1.

Step 3. Synthesis of (1R,2S,3R,5S)-3-(4-aminopyrrolo[2,3-d]pyrimidin-7-yl)-5-[(1S)-5-chloro-1,3-dihydroisobenzofuran-1-yl]cyclopentane-1,2-diol (Ex. 2B)

To a solution of 7-[(3aS,4R,6R,6aR)-6-[(1S)-5-chloro-1,3-dihydroisobenzofuran-1-yl]-2,2-dimethyl-4,5,6,6a-tetrahydro-3aH-cyclopenta[d][1,3]dioxol-4-yl]pyrrolo[2,3-d]pyrimidin-4-amine (2Bb, 60 mg, 0.09 mmol) in water (2 mL) was added TFA (1 mL, 13.0 mmol). The reaction mixture was stirred at 30° C. for 0.5 h. LCMS showed the reaction was complete. The reaction mixture was purified by prep-HPLC (0.1% $NH_3 \cdot H_2O$), eluted with $CH_3CN$ in $H_2O$ from 10% to 95% to give (1R,2S,3R,5S)-3-(4-aminopyrrolo[2,3-d]pyrimidin-7-yl)-5-[(1S)-5-chloro-1,3-dihydroisobenzofuran-1-yl]cyclopentane-1,2-diol (Ex. 2B, 27 mg, 0.07 mmol, 76.1% yield) as a white solid. LCMS [M+H]: 387.1. $^1$H NMR (400 MHz, DMSO-$d_6$+D2O): δ 8.03 (s, 1H), 7.41-7.42 (m, 1H), 7.34-7.36 (m, 2H), 7.21-7.22 (m, 1H), 6.57-6.58 (m, 1H), 5.21-5.22 (m, 1H), 4.97-5.07 (m, 2H), 4.86-4.91 (m, 1H), 4.16-4.191 (m, 1H), 3.65-3.66 (m, 1H), 2.38-2.43 (m, 1H), 2.25-2.32 (m, 1H), 1.75-1.83 (m, 1H).

Example 3A. Synthesis of (S)-3-((1S,2R,3S,4R)-4-(4-amino-7H-pyrrolo[2,3-d]pyrimidin-7-yl)-2,3-dihydroxycyclopentyl)-6-chloroisobenzofuran-1(3H)-one (Ex. 3A)

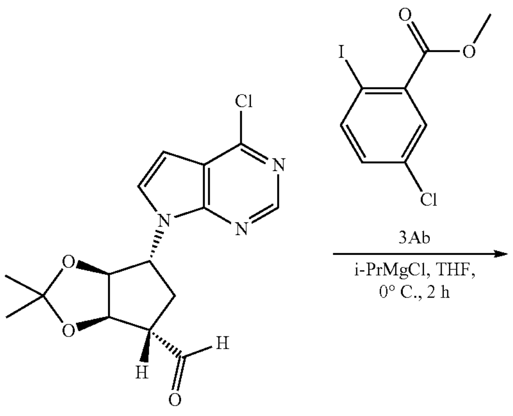

3Aa

-continued

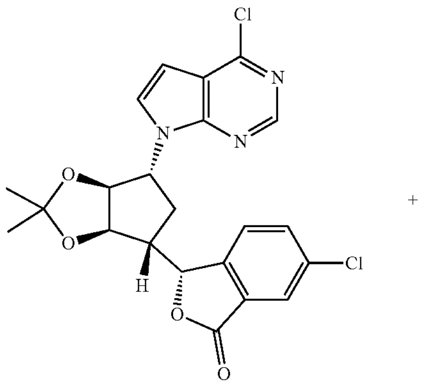

3Ac

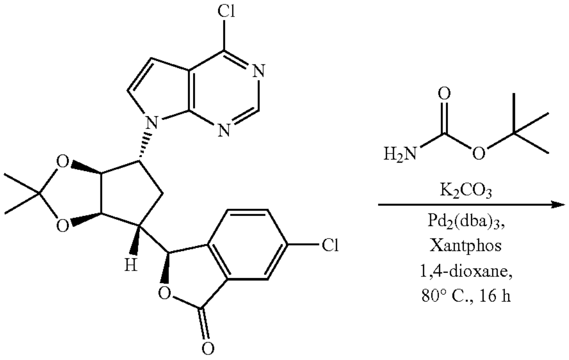

3Ad

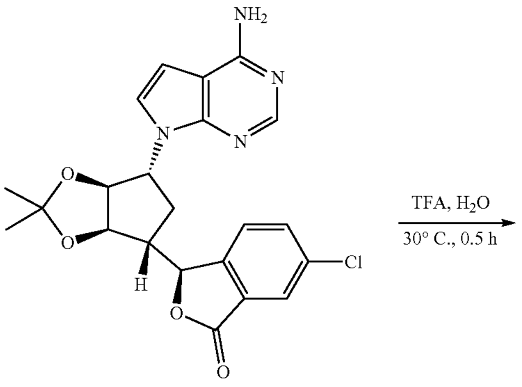

3Ae

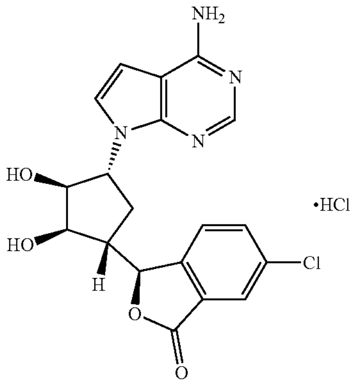

Ex. 3A

Step 1. Synthesis of (3R)-3-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ac) and (3S)-3-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ad)

To a solution of methyl 5-chloro-2-iodo-benzoate (3Ab, 829.3 mg, 2.80 mmol) in THF (15 mL) was added isopropyl magnesium chloride (2.2 mL, 2.80 mmol) at −20° C., and the solution was stirred at −20° C. for 2 h. (3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxole-6-carbaldehyde (3Aa, 900 mg, 2.80 mmol) in THF (10 mL) was added to the mixture and stirred at 0° C. for 2 h. LCMS showed the reaction was complete. The reaction mixture was added $H_2O$ (30 mL) and ethyl acetate (60 mL). The organic layer was washed with $H_2O$ (30 mL) and brine (30 mL), dried over $Na_2SO_4$, filtered and concentrated in vacuum to give the crude product which was purified by silica chromatography column (PE:EA=6:1) to give (3R)-3-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ac, 330 mg, 0.72 mmol, 25.6% yield) and (3S)-3-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ad, 270.0 mg, 0.59 mmol, 21.0% yield). LCMS [M+H]: 460.0.

Step 2. Synthesis of (3S)-3-[(3aS,4R,6R,6aR)-4-(4-aminopyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ae)

To a solution of (3S)-3-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ad, 170 mg, 0.37 mmol) in 1,4-dioxane (5 mL) was added tert-butyl carbamate (86.5 mg, 0.74 mmol), Xantphos (32.1 mg, 0.06 mmol) and $Pd_2(dba)_3$ (13.5 mg, 0.01 mmol). The mixture was stirred at 80° C. 16 h under $N_2$. LCMS showed the reaction was complete. The reaction mixture was filtered and concentrated in vacuum to give the crude product which was purified by silica chromatography column ($DCM:CH_3OH$=30:1) to give (3S)-3-[(3aS,4R,6R,6aR)-4-(4-aminopyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ae, 100 mg, 0.23 mmol, 61.4% yield). LCMS [M+H]: 441.2.

Step 3. Synthesis of (3S)-3-[(1S,2R,3S,4R)-4-(4-aminopyrrolo[2,3-d]pyrimidin-7-yl)-2,3-dihydroxy-cyclopentyl]-6-chloro-3H-isobenzofuran-1-one hydrochloride (Ex. 3A)

To a solution of (3S)-3-[(3aS,4R,6R,6aR)-4-(4-aminopyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ae, 100 mg, 0.23 mmol) in water (3 mL) was added TFA (1.5 mL, 19.47 mmol). The reaction mixture was stirred at 30° C. for 0.5 h. LCMS showed the reaction was complete. The mixture was purified by prep-HPLC, eluted with $CH_3CN$ in $H_2O$ (0.1% TFA) from 5% to 9%, added HCl (1 mL, 2N), and lyophilized to give (3S)-3-[(1S,2R,3 S,4R)-4-(4-aminopyrrolo[2,3-d]pyrimidin-7-yl)-2,3-dihydroxy-cyclopentyl]-6-chloro-3H-isobenzofuran-1-one hydrochloride (Ex. 3A, 15 mg, 0.03 mmol, 15.1% yield) as a white solid. LCMS [M+H]: 401.1. $^1$H NMR (400 MHz, DMSO-$d_6$+D2O): δ 8.35 (s, 1H), 7.94-7.95 (m, 1H), 7.86-7.88 (m, 1H), 7.74-7.76 (m, 1H), 7.65-7.66 (m, 1H), 6.98-6.99 (m, 1H), 5.78-5.79 (m, 1H), 4.93-5.00 (m, 1H), 4.14-4.18 (m, 1H), 3.54-3.56 (m, 1H), 2.68-2.69 (m, 1H), 2.38-2.46 (m, 1H), 1.95-2.03 (m, 1H).

Example 3B. Synthesis of (R)-3-((1S,2R,3S,4R)-4-(4-amino-6H-714-pyrrolo[2,3-d]pyrimidin-7-yl)-2,3-dihydroxycyclopentyl)-6-chloroisobenzofuran-1(3H)-one (Ex. 3B)

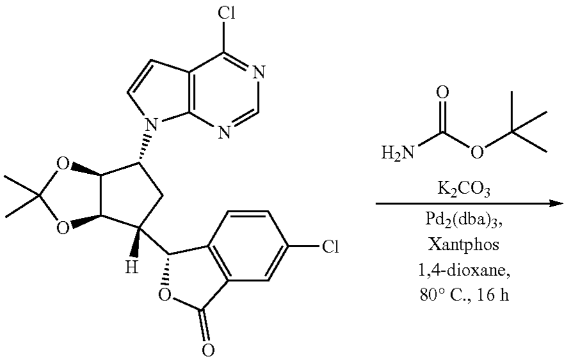

3Ac

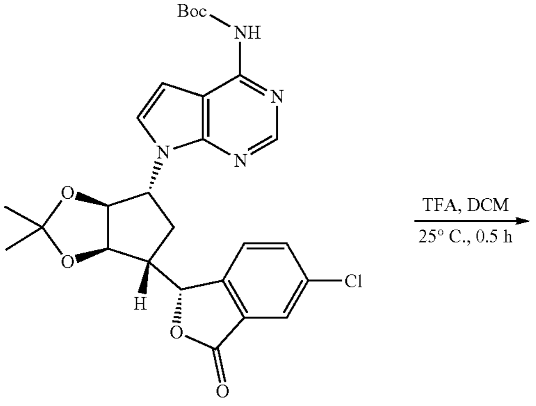

3Ba

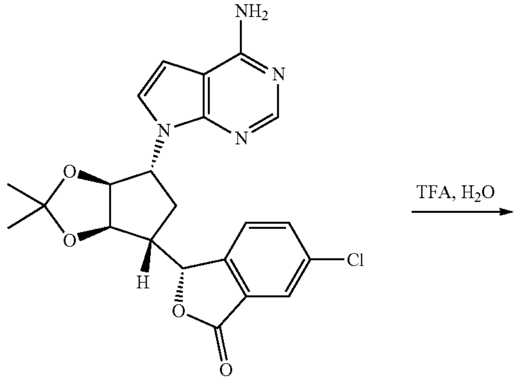

3Bb

-continued

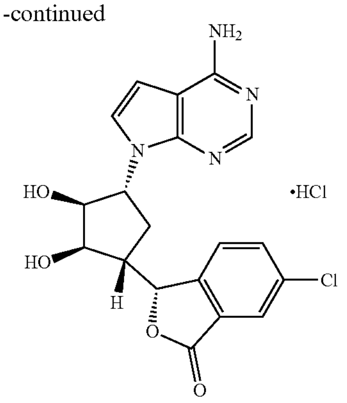

Ex. 3B

Step 1. Synthesis of tert-butyl N-[7-[(3aS,4R,6R,6aR)-6-[(1R)-5-chloro-3-oxo-1H-isobenzofuran-1-yl]-2,2-dimethyl-4,5,6,6a-tetrahydro-3aH-cyclopenta[d][1,3]dioxol-4-yl]pyrrolo[2,3-d]pyrimidin-4-yl]carbamate (3Ba)

To a solution of (3R)-3-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Ac, 230 mg, 0.50 mmol) in 1,4-dioxane (6 mL) was added tert-butyl carbamate (117.1 mg, 1.00 mmol), Xantphos (43.4 mg, 0.07 mmol) and $Pd_2(dba)_3$ (18.3 mg, 0.02 mmol). The mixture was stirred at 80° C. for 16 h under $N_2$. LCMS showed the reaction was complete. The reaction mixture was filtered and concentrated in vacuum to give the crude product which was purified by silica chromatography column (DCM:$CH_3OH$=30:1) to give tert-butyl N-[7-[(3aS,4R,6R,6aR)-6-[(1R)-5-chloro-3-oxo-1H-isobenzofuran-1-yl]-2,2-dimethyl-4,5,6,6a-tetrahydro-3aH-cyclopenta[d][1,3]dioxol-4-yl]pyrrolo[2,3-d]pyrimidin-4-yl]carbamate (3Ba, 100 mg, 0.18 mmol, 37% yield). LCMS [M+H]: 541.2.

Step 2. Synthesis of (3R)-3-[(3aS,4R,6R,6aR)-4-(4-aminopyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Bb)

To a solution of tert-butyl N-[7-[(3aS,4R,6R,6aR)-6-[(1R)-5-chloro-3-oxo-1H-isobenzofuran-1-yl]-2,2-dimethyl-4,5,6,6a-tetrahydro-3aH-cyclopenta[d][1,3]dioxol-4-yl]pyrrolo[2,3-d]pyrimidin-4-yl]carbamate (3Ba, 100 mg, 0.18 mmol) in DCM (3 mL) and was added TFA (3 mL, 38.94 mmol). The reaction mixture was stirred at 25° C. 0.5 h. LCMS showed the reaction was complete. The reaction mixture was concentrated in vacuum to give crude (3R)-3-[(3aS,4R,6R,6aR)-4-(4-aminopyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Bb) which was used in the next step directly. LCMS [M+H]: 441.1.

Step 3. Synthesis of (3R)-3-[(1S,2R,3S,4R)-4-(4-aminopyrrolo[2,3-d]pyrimidin-7-yl)-2,3-dihydroxy-cyclopentyl]-6-chloro-3H-isobenzofuran-1-one Hydrochloride (Ex. 3B)

To a solution of (3R)-3-[(3aS,4R,6R,6aR)-4-(4-aminopyrrolo[2,3-d]pyrimidin-7-yl)-2,2-dimethyl-4,5,6,6a-tetrahydro-3aH-cyclopenta[d][1,3]dioxol-6-yl]-6-chloro-3H-isobenzofuran-1-one (3Bb, 70 mg, 0.16 mmol) in water (3 mL) was added TFA (1.4 mL, 18.2 mmol). The reaction mixture was stirred at 30° C. for 0.5 h. LCMS showed the reaction was complete. The mixture was purified by prep-HPLC, eluted with $CH_3CN$ in $H_2O$ (0.1% TFA) from 5% to 95%, added HCl (1 mL, 2N), and lyophilized to give (3R)-3-[(1S,2R,3S,4R)-4-(4-aminopyrrolo[2,3-d]pyrimidin-7-yl)-2,3-dihydroxy-cyclopentyl]-6-chloro-3H-isobenzofuran-1-one hydrochloride (Ex. 3B, 14.0 mg, 0.03 mmol, 19.0% yield) as a white solid. LCMS [M+H]: 401.3. $^1$H NMR (400 MHz, DMSO-$d_6$+D2O): δ 8.30 (s, 1H), 7.80-7.90 (m, 3H), 7.48-7.49 (m, 1H), 6.93-6.94 (m, 1H), 5.94-5.95 (m, 1H), 4.83-4.89 (m, 1H), 4.24-4.27 (m, 1H), 4.15-4.18 (m, 1H), 2.68-2.76 (m, 1H), 1.73-1.80 (m, 1H), 1.18-1.26 (m, 1H).

Example 5. Synthesis of (2R,3R,4S,5S)-2-(4-amino-7H-pyrrolo[2,3-d]pyrimidin-7-yl)-5-((R)-6-chloro-1,3-dihydroisobenzofuran-1-yl)tetrahydrofuran-3,4-diol (Ex. 5)

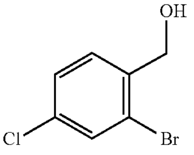

TBSCl, imidazole
DMF, 25° C., 2 h

5a

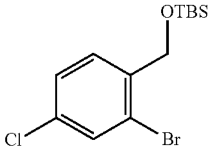

n-BuLi
THF, -78° C., 0.5 h

5b

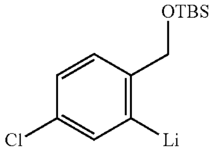

5c

+

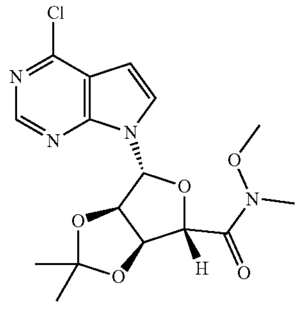

THF, -78° C., 0.5 h

1Ad

-continued

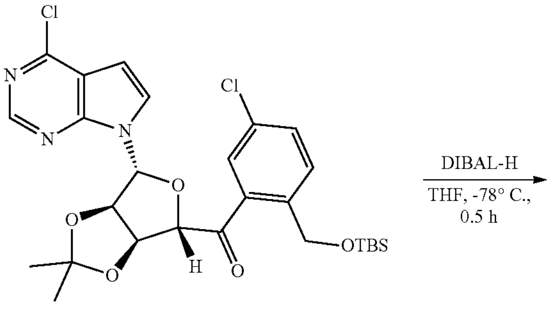

5d

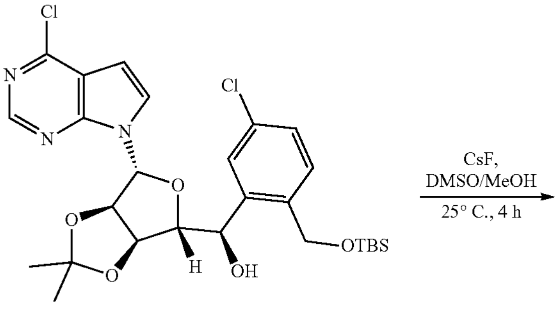

5e

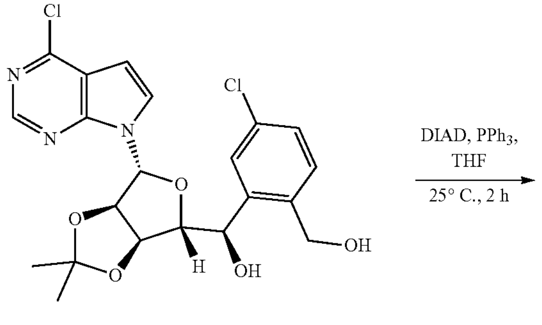

5f

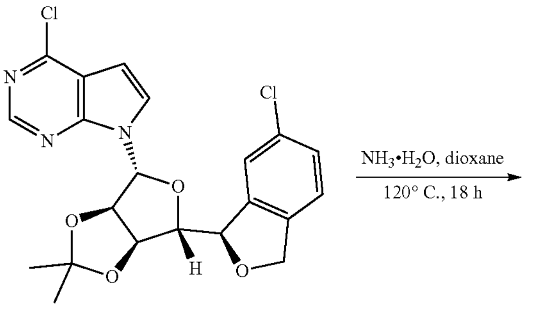

5g

-continued

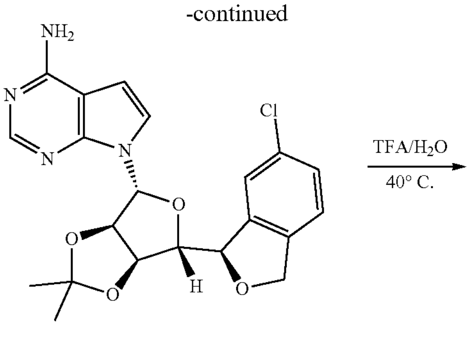

5h

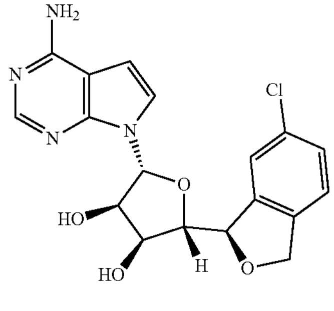

Ex. 5

Step 1. Synthesis of (2-bromo-4-chloro-phenyl) methoxy-tert-butyl-dimethyl-silane (5b)

To a mixture of (2-bromo-4-chloro-phenyl)methanol (5a, 5.0 g, 22.58 mmol) and imidazole (3.07 g, 45.15 mmol) in DMF (10 mL) was added TBSCl (5.10 g, 33.86 mmol) at 0° C. The mixture stirred at rt for 2 h. TCL (PE:EA=10:1, $R_f$=0.7) showed the reaction was complete. The reaction mixture was diluted with water (100 mL) and the mixture was extracted with ethyl acetate (50 mL×3), then the organic layers were washed with brine (100 mL×3), dried over $Na_2SO_4$ and concentrated in vacuum to give crude product which was purified on a silica chromatography column (100-200 mesh size, PE:EA=200:1 to 100:1) to give (2-bromo-4-chloro-phenyl)methoxy-tert-butyl-dimethyl-silane (5b, 6.80 g, 18.23 mmol, 80.7% yield) as a colorless oil. $^1H$ NMR (400 M Hz, DMSO-d6): δ 7.70 (s, 1H), 7.49 (s, 2H), 4.66 (s, 2H), 0.91 (s, 9H), 0.10 (s, 6H).

Step 2. Synthesis of [(3aR,4R,6S,6aS)-4-(4-chloro-pyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-5-chloro-phenyl] methanone (5d)

To a solution of (2-bromo-4-chloro-phenyl)methoxy-tert-butyl-dimethyl-silane (5b, 6.74 g, 20.06 mmol) in THF (50 mL) was added butyllithium (8.6 mL, 13.79 mmol) at −78° C. under $N_2$. The resulting solution of 5c was stirred at −78° C. for 10 min under $N_2$. A solution of the (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1Ad, 2.4 g, 6.27 mmol) in THF (50 mL) was added and the mixture was stirred at −78° C. for 30 min under $N_2$. LCMS showed the reaction was complete. The reaction mixture was quenched with saturated $NH_4Cl$ solution (50 mL). The mixture was extracted with ethyl acetate (100 mL×3). The combined organic layers were washed with brine (40 mL×3), dried over $Na_2SO_4$, concentrated in vacuum to give the crude product which was purified by silica chromatography column (100-200 mesh size, PE:EA=20:1 to 10:1) to give [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-5-chloro-phenyl]methanone (5d, 3.36 g, 5.81 mmol, 92.6% yield) as a pale yellow oil. LCMS [M+H]: 578.1.

Step 3. Synthesis of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-5-chloro-phenyl]methanol (5e)

To a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-5-chloro-phenyl]methanone (5d, 3.3 g, 5.71 mmol) in toluene (100 mL) was added diisobutylaluminum hydride (9.5 mL, 14.26 mmol) at −78° C. under $N_2$. The reaction mixture was stirred at −78° C. for 0.5 h under $N_2$. TLC (PE:EA=3:1, $R_f$=0.3) showed the reaction was complete. The reaction mixture was washed with water (10 mL×3) and brine (10 mL×3). The organic layer was dried over $Na_2SO_4$, filtered and concentrated to afford crude product which was purified silica chromatography column (100-200 mesh size, PE:EA=10:1 to 8:1) to give (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-5-chloro-phenyl]methanol (5e, 1.8 g, 2.67 mmol, 46.7% yield) as a white solid. LCMS [M+H]: 580.2.

Step 4. Synthesis of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[5-chloro-2-(hydroxymethyl)phenyl]methanol (5f)

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-5-chloro-phenyl]methanol (5e, 1.8 g, 3.10 mmol) in DMSO (12 mL) and methanol (0.2 mL) was added CsF (1.2 g, 9.3 mmol). The reaction mixture was stirred at 25° C. for 4 h. LCMS showed the reaction was complete. The reaction mixture was filtered and purified by reversed-phase combi-flash, eluted with $CH_3CN$ in $H_2O$ (neutral condition) from 10% to 95% to give (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[5-chloro-2-(hydroxymethyl)phenyl]methanol (5f, 560 mg, 1.19 mmol, 38.3% yield) as a white solid. LCMS [M+H]: 466.1.

Step 5. Synthesis of 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (5g)

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[5-chloro-2-(hydroxymethyl)phenyl]methanol (5f, 510 mg, 1.09 mmol) in THF (15.0 mL) was added pyridine (0.1 mL, 1.09 mmol), tributylphosphine (0.6 mL, 2.19 mmol) and DIAD (0.2 mL, 2.3 mmol). The reaction mixture was stirred at 25° C. for 2 h. TLC (PE:EA=3:1, $R_f$=0.4) showed the reaction was complete. The mixture was concentrated in vacuum to give the crude product which was purified by silica chromatography column (100-200 mesh size, PE:EA=20:1 to 10:1) to give 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (5g, 350 mg, 0.78 mmol, 71.4% yield) as a white solid. LCMS [M+H]: 448.1.

Step 6. Synthesis of 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (5h)

A mixture of 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (5g, 48.1 mg, 0.11 mmol), 1,4-dioxane (0.5 mL) and $NH_3 \cdot H_2O$ (0.5 mL, 12.98 mmol) was stirred at 120° C. for 16 h in a autoclave. LCMS showed the reaction was complete. The mixture was concentrated in vacuum to give 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (5h, 50 mg, 0.10 mmol, 94.6% yield) as a white solid. LCMS [M+H]: 429.1.

Step 7. Synthesis of (2R,3R,4S,5S)-2-(4-aminopyrrolo[2,3-d]pyrimidin-7-yl)-5-[(1R)-6-chloro-1,3-dihydroisobenzofuran-1-yl]tetrahydrofuran-3,4-diol (Ex. 5)

A mixture of 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]pyrrolo[2,3-d]pyrimidin-4-amine (5h, 50 mg, 0.12 mmol), water (0.5 mL) and TFA (0.8 mL, 9.06 mmol) was stirred at 40° C. for 16 h. LCMS showed the reaction was complete. The reaction mixture was concentrated and purified by prep-HPLC, (0.1% $NH_3 \cdot H_2O$), eluted with $CH_3CN$ in $H_2O$ from 10% to 95% to give (2R,3R,4S,5S)-2-(4-aminopyrrolo[2,3-d]pyrimidin-7-yl)-5-[(1R)-6-chloro-1,3-dihydroisobenzofuran-1-yl]tetrahydrofuran-3,4-diol (Ex. 5, 19.5 mg, 0.05 mmol, 42.9% yield) as a white solid. LCMS [M+H]: 389.1. $^1$H NMR (400 M Hz, DMSO-$d_6$): δ 8.07 (s, 1H), 7.37 (s, 3H), 7.30 (s, 1H), 7.03 (br, 2H), 6.65 (d, J=3.6 Hz, 1H), 6.16 (d, J=7.6 Hz, 1H), 5.36 (d, J=2.0 Hz, 1H), 5.26 (d, J=7.2 Hz, 1H), 5.19 (d, J=4.0 Hz, 1H), 5.04-5.13 (m, 2H), 4.52 (dd, $J_1$=7.2 Hz, $J_2$=5.2 Hz, 1H), 4.11 (d, J=4.8 Hz, 1H), 3.93 (t, J=4.4 Hz, 1H). $^1$H NMR (400 M Hz, DMSO-$d_6$+D2O): δ 8.07 (s, 1H), 7.37 (s, 3H), 7.29 (s, 1H), 6.66 (d, J=3.6 Hz, 1H), 6.15 (d, J=3.6 Hz, 1H), 5.37 (br, 1H), 5.04-5.13 (m, 2H), 4.52 (dd, $J_1$=2.0 Hz, $J_2$=5.2 Hz, 1H), 4.11 (d, J=5.2 Hz, 1H), 3.93 (d, J=4.8 Hz, 1H).

Example 15. Synthesis of (2S,3S,4R,5R)-2-((R)-6-chloro-1,3-dihydroisobenzofuran-1-yl)-5-(4-methyl-7H-pyrrolo[2,3-d]pyrimidin-7-yl)tetrahydrofuran-3,4-diol (Ex. 15)

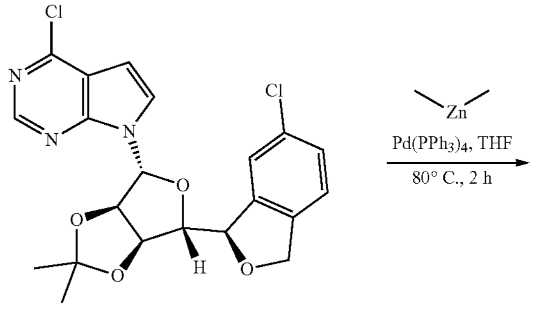

5g

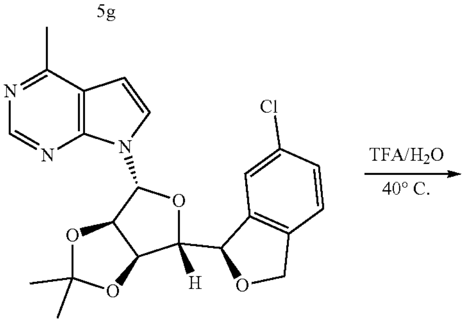

15a

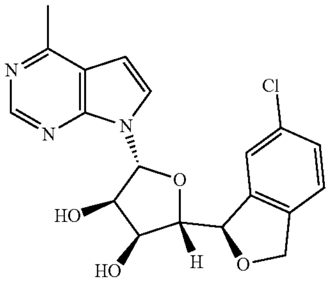

Ex. 15

Step 1. Synthesis of 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-methyl-pyrrolo[2,3-d]pyrimidine (15a)

To a solution of 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-chloro-pyrrolo[2,3-d]pyrimidine (5g, 200.0 mg, 0.45 mmol) in THF (5 mL) was added dimethylzinc (4.5 mL, 4.46 mmol) at 25° C. The reaction mixture was stirred at 80° C. for 2 h. LCMS showed the reaction was complete. The mixture was cooled to room temperature and quenched with saturated $NaHCO_3$ (aq) and extracted with ethyl acetate (100 mL×3). The organic layer was washed with brine (50 mL×3), dried over anhydrous $Na_2SO_4$, filtered and concentrated in vacuum to give 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-methyl-pyrrolo[2,3-d]pyrimidine (15a, 206 mg, 0.40 mmol, 90.6% yield) as a brown solid. LCMS [M+H]: 428.1.

Step 2. Synthesis of (2S,3S,4R,5R)-2-[(1R)-6-chloro-1,3-dihydroisobenzofuran-1-yl]-5-(4-methylpyrrolo[2,3-d]pyrimidin-7-yl)tetrahydrofuran-3,4-diol (Ex. 15)

A mixture of 7-[(3aR,4R,6R,6aR)-6-[(1R)-6-chloro-1,3-dihydroisobenzofuran-1-yl]-2,2-dimethyl-3a,4,6,6a-tetrahydrofuro[3,4-d][1,3]dioxol-4-yl]-4-methyl-pyrrolo[2,3-d]pyrimidine (15a, 106 mg, 0.25 mmol), water (0.5 mL) and TFA (0.8 mL, 8.33 mmol), was stirred at 40° C. for 2 h. LCMS showed the reaction was complete. The reaction mixture was filtered and purified by prep-HPLC (0.1% $NH_3{\cdot}H_2O$), eluted with $CH_3CN$ in $H_2O$ from 10% to 95% to give (2S,3S,4R,5R)-2-[(1R)-6-chloro-1,3-dihydroisobenzofuran-1-yl]-5-(4-methylpyrrolo[2,3-d]pyrimidin-7-yl)tetrahydrofuran-3,4-diol (Ex. 15, 36.6 mg, 0.09 mmol, 37.1% yield) as a white solid. LCMS [M+H]: 388.1. $^1$H NMR (400 M Hz, DMSO-$d_6$): δ 8.67 (s, 1H), 7.78 (d, J=3.6 Hz, 1H), 7.38 (s, 2H), 7.31 (s, 1H), 6.83 (d, J=3.6 Hz, 1H), 6.29 (d, J=7.2 Hz, 1H), 5.33-5.40 (m, 3H), 5.06-5.15 (m, 2H), 4.55-4.58 (m, 1H), 4.18 (d, J=4.8 Hz, 1H), 3.93 (d, J=4.8 Hz, 1H), 2.68 (s, 3H). $^1$H NMR (400 M Hz, DMSO-$d_6$+D2O): δ 8.67 (s, 1H), 7.77 (d, J=4.0 Hz, 1H), 7.38 (s, 2H), 7.31 (s, 1H), 6.84 (d, J=4.0 Hz, 1H), 6.29 (d, J=3.2 Hz, 1H), 5.39 (br, 1H), 5.06-5.16 (m, 2H), 4.55-4.58 (m, 1H), 4.18 (d, J=4.0 Hz, 1H), 3.93 (d, J=3.2 Hz, 1H), 2.68 (s, 3H).

Example 22. Synthesis of (2S,3S,4R,5R)-2-((R)-6-chloroisochroman-1-yl)-5-(4-methyl-7H-pyrrolo[2,3-d]pyrimidin-7-yl)tetrahydrofuran-3,4-diol (Ex. 22)

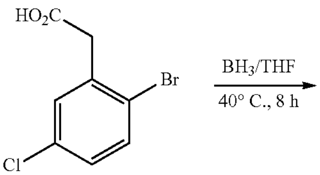

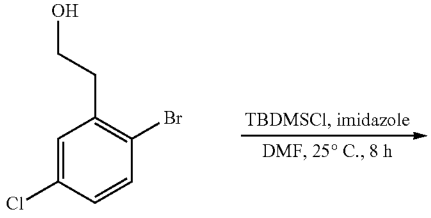

22a

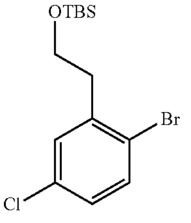

+

22b

-continued

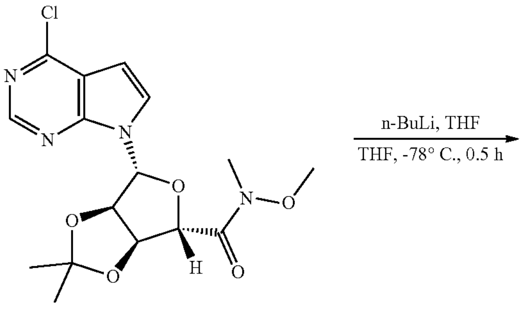

1Ad

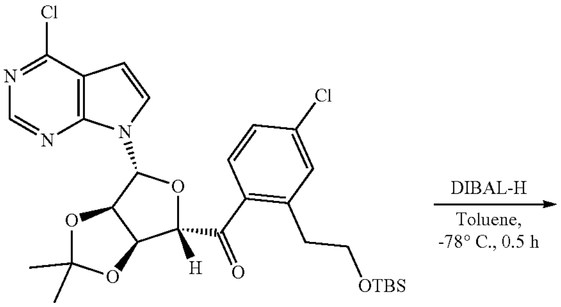

22c

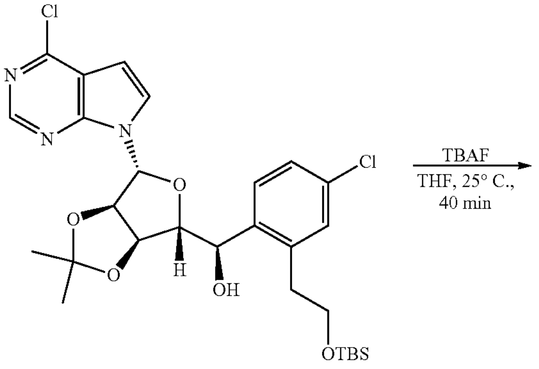

22d

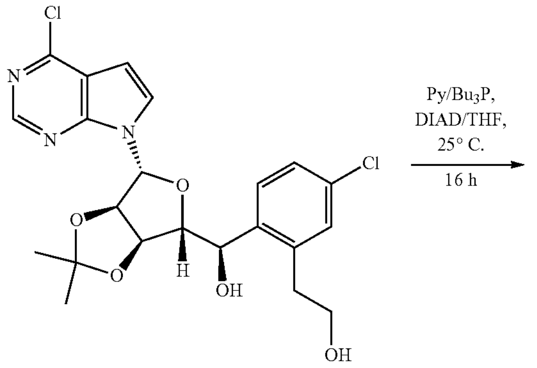

22e

-continued

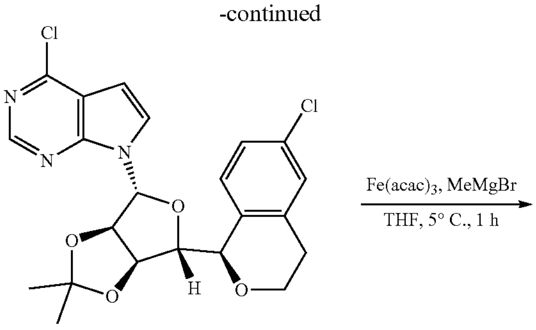

22f

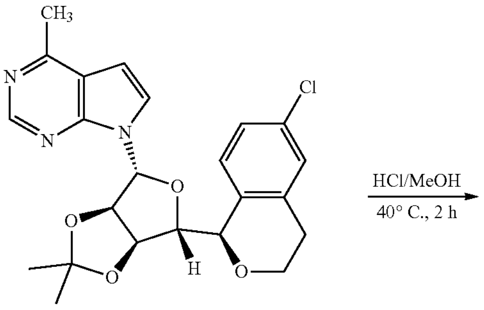

22g

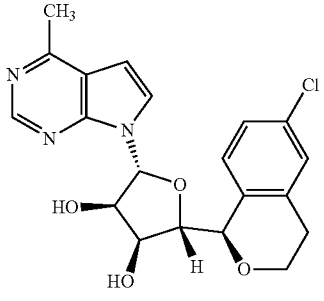

Ex. 22

Step 1. Synthesis of 2-(2-bromo-5-chloro-phenyl)ethanol (22a)

To a solution of 2-(2-bromo-5-chloro-phenyl)acetic acid (20.0 g, 80.16 mmol) in THF (200 mL), borane in THF (240.49 mL, 240.49 mmol) was added, and the mixture was stirred at 40° C. for 8 h. The mixture was quenched with MeOH at 0° C., concentrated, and extracted with EA (400 mLx2). The combined organic layers were dried, concentrated and purified by combi flash eluting with $CH_3CN/H_2O$ (neutral) from 5/95 to 95/5 to give 22b (18.1 g, 76.854 mmol, 95.9% yield) as a colorless oil. LCMS [M−18]: 217.0/219.0.

Step 2. Synthesis of 2-(2-bromo-5-chloro-phenyl) ethoxy-tert-butyl-dimethyl-silane (22b)

To a solution of 22a (18.1 g, 76.85 mmol) in DMF (200 mL), imidazole (7.85 g, 115.28 mmol) and TBDMSCl (13.9 g, 92.23 mmol) were added and the mixture was stirred at 25° C. for 8 h. EA (800 mL) was added and the mixture was washed with brine (400 mLx2). The organic layer was concentrated and purified by flash column (PE) to give 22b (26.7 g, 76.34 mmol, 99.3% yield) as a colorless oil.

Step 3. Synthesis of [2-[2-[tert-butyl(dimethyl)silyl]oxyethyl]-4-chloro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (22c)

To a solution of 22b (8.91 g, 25.6 mmol) in dry THE (50 mL) was added n-BuLi (12.8 mL, 20.48 mmol) at −78° C. and the mixture was stirred for 10 min under nitrogen. A solution of 1Ad (4.0 g, 10.24 mmol) in dry THE (20 mL) was added and the mixture was stirred for 5 min at −78° C. TLC (PE:EA=8:1) showed the reaction was complete. The reaction was poured into dilute HCl (pH=6; pH kept <8 during the process of quenching.) The mixture was extracted with EA (200 mL×2), the combined organic layers were dried, concentrated and purified by combi-flash eluting with $CH_3CN/H_2O$ (neutral) from 5/95 to 95/5 to give 22c (5.1 g, 8.60 mmol, 84% yield) as yellow solid.

Step 4. Synthesis of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-[2-[[tert-butyl(dimethyl)silyl]oxymethyl]-5-chloro-phenyl]methanol (22d)

To a solution of 22c (5.0 g, 8.44 mmol) in THF (30 mL) at −78° C., DIBAL-H (16.88 mL, 25.31 mmol) was added and the mixture was stirred at −78° C. for 30 min. TLC (PE/EA=8/1) showed SM $R_f$=0.5 has been completely consumed with the main product $R_f$=0.4. The reaction was poured into dilute HCl (pH=6, 400 mL, keeping the pH<8 during the process of quenching.) The mixture was extracted with EA (300 mL×2) and the combined organic layers were dried and concentrated to give the crude 22d (5.0 g) as a yellow solid.

Step 5. Synthesis of 2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (22e)

To a solution of 22d (3.0 g, 5.17 mmol) in THF (50 mL) was added tetrabutylammonium fluoride (5.17 mL, 5.17 mmol). The mixture solution was stirred at 25° C. for 40 min. The reaction mixture was poured into aqueous $NH_4Cl$ and extracted with EA (100 mL). The combined organic layers were washed with brine, dried over anhydrous $Na_2SO_4$ and the solvent was concentrated under reduced pressure. The crude product was purified by flash column (PE:EA=15:1 to 3:1) to give 22e (2 g, 4.08 mmol, 79% yield) as a white solid. LCMS [M+H]: 480.1.

Step 6. Synthesis of 4-chloro-7-[(3aR,4R,6R,6aR)-2,2-dimethyl-6-[(1R)-6-chloroisochroman-1-yl]-3a,4,6,6a-tetrahydrofuro[3,4-d][1,3]dioxol-4-yl]pyrrolo[2,3-d]pyrimidine (22f)

To a solution of 22e (2.0 g, 4.16 mmol) in THF (100 mL) and was added tributylphosphine (2.1 mL, 8.33 mmol), isopropyl (NE)-N-isopropoxycarbonyliminocarbamate (1.72 mL, 8.74 mmol) and pyridine (0.34 mL, 4.16 mmol), and the reaction mixture was stirred at 25° C. for 16 h.

TLC (PE/EA=3/1, $R_f$=0.4) showed that the starting material was consumed. The solvent was removed in vacuo and the crude product was purified by column chromatography on silica gel using petroleum ether/EtOAc (10:1-5:1) as eluent to give 22f (1.7 g, 3.68 mmol, 88% yield) as a yellow oil. LCMS [M+H]: 462.1.

Step 7. Synthesis of 4-methyl-7-[(3aR,4R,6R,6aR)-2,2-dimethyl-6-[(1R)-6-chloroisochroman-1-yl]-3a,4,6,6a-tetrahydrofuro[3,4-d][1,3]dioxol-4-yl]pyrrolo[2,3-d]pyrimidine (22g)

Methyl magnesium bromide (3.68 mL, 11.04 mmol) was added dropwise to a solution of ferric acetylacetonate (0.13 g, 0.37 mmol) and 22f (1.7 g, 3.68 mmol) in THF (100 mL) at 5° C. under nitrogen. The reaction mixture was warmed to rt and stirred for 1 h. TLC (EA:PE=1:1, $R_f$=0.3) showed the reaction was complete. Saturated $NH_4Cl$ was added dropwise to quench the reaction, which was extracted with EA (200 mL×2), then dried over $Na_2SO_4$ and concentrated. The residue was purified by flash column (PE:EA=10:1 to 1:1) to give 22g (900 mg, 1.93 mmol, 52.6% yield) as a white solid.

Step 8. Synthesis of (2R,3R,4S,5S)-2-(4-methylpyrrolo[2,3-d]pyrimidin-7-yl)-5-[(1R)-6-chloroisochroman-1-yl]tetrahydrofuran-3,4-diol (Ex. 22)

To a solution of HCl (6.0 mL, 12 mmol) in methanol (10 mL) and was added 22g (900 mg, 2.04 mmol) and the reaction mixture was stirred at 40° C. for 2 h. The reaction mixture was concentrated, and the residue was stirred with EA (50 ml) and filtered. The solid was purified by prep-HPLC eluting with $CH_3CN/H_2O$ (0.1% $NH_4OH$) from 5/95 to 95/5. The product fractions were extracted with EA (100 ml×2) and the extracts concentrated to yield Ex. 22 (550 mg, 1.34 mmol, 66% yield) as a white solid. LCMS [M+H]: 402.3. 1H NMR (400 M Hz, DMSO-d6): δ 8.67 (s, 1H), 7.76 (d, J=4.0 Hz, 1H), 7.22-7.31 (m, 3H), 6.81 (d, J=3.6 Hz, 1H), 6.31 (d, J=7.6 Hz, 1H), 5.26 (d, J=7.2 Hz, 1H), 5.13 (d, J=4.0 Hz, 1H), 4.90 (d, J=3.6 Hz, 1H), 4.48-4.54 (m, 1H), 4.42-4.43 (m, 1H), 4.23-4.27 (m, 1H), 3.84-3.86 (m, 1H), 3.66-3.72 (m, 1H), 2.91-2.99 (m, 1H), 2.70-2.74 (m, 1H), 2.67 (s, 3H). 1H NMR (400 M Hz, DMSO-d6+D2O): δ 8.86 (s, 1H), 7.77 (d, J=4 Hz, 1H), 7.22-7.31 (m, 3H), 6.82 (d, J=3.6 Hz, 1H), 6.31 (d, J=7.6 Hz, 1H), 4.90 (d, J=3.6 Hz, 1H), 4.49-4.53 (m, 1H), 4.42-4.43 (m, 1H), 4.24-4.28 (m, 1H), 3.83-3.85 (m, 1H), 3.66-3.72 (m, 1H), 2.91-2.99 (m, 1H), 2.70-2.75 (m, 1H), 2.69 (s, 3H).

Example 44. Synthesis of (2S,3S,4R,5R)-2-((1R)-6-chloro-3-methoxyisochroman-1-yl)-5-(4-methyl-7H-pyrrolo[2,3-d]pyrimidin-7-yl)tetrahydrofuran-3,4-diol (Ex. 44)

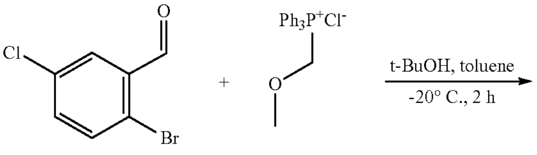

44a

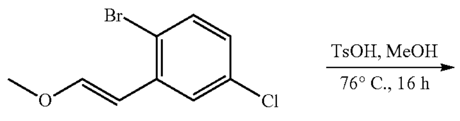

44b

-continued

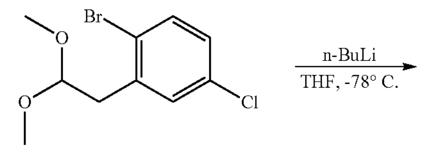

44c

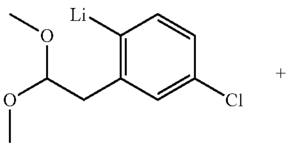

44d

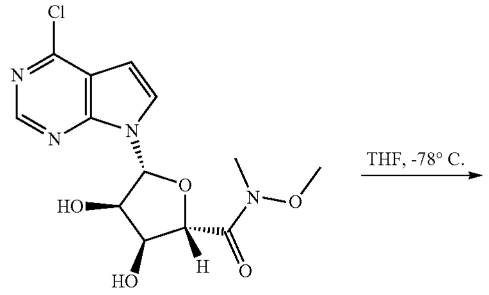

1Ad

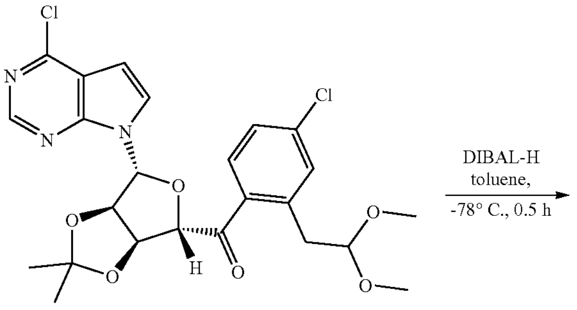

44e

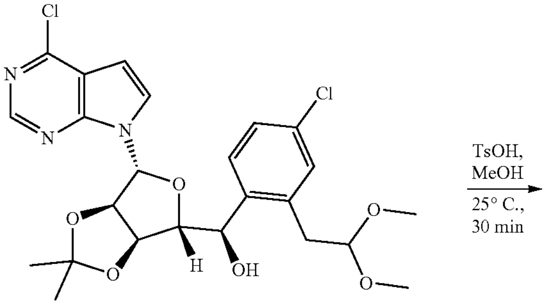

44f

-continued

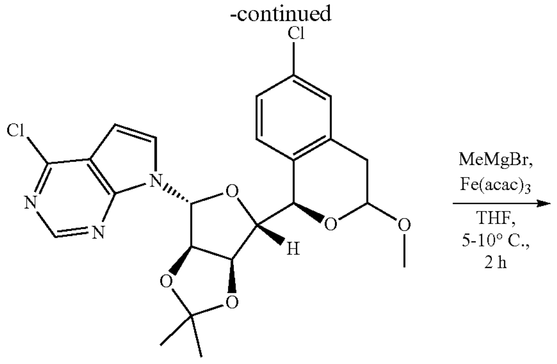

44g

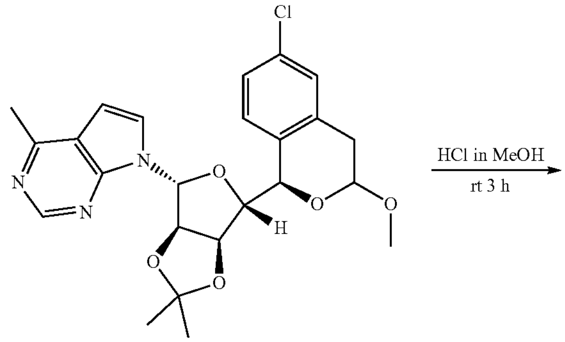

44h

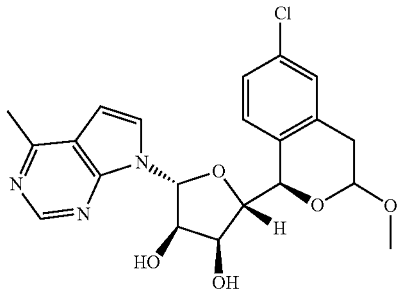

Ex. 44

Step 1. Synthesis of 1-bromo-4-chloro-2-(2-methoxyvinyl)benzene (44b)

To a solution of (methoxymethyl)triphenylphosphonium chloride (22.96 g, 66.98 mmol) in THF (100 mL) was added potassium tert-butoxide (7.16 g, 63.79 mmol) under $N_2$ at −10° C. After 5 minutes, 2-bromo-5-chloro-benzaldehyde (44a; 7.0 g, 31.9 mmol) was added. The solution was stirred at −10° C. for 2 h. TLC (PE=100%, $R_f$=0.8) showed the reaction was complete. The reaction mixture was poured into $H_2O$ (200 mL). The mixture was extracted with EA (200 mL), washed with water (60 mL) and brine (60 mL), dried over $Na_2SO_4$, filtered and concentrated. The crude product was purified by silica gel column chromatography, eluting with PE (100%) to give 44b (7.2 g, 29.09 mmol, 91.2% yield, mixture of E and Z isomers) as a yellow oil. $^1$H NMR (400 MHz, DMSO-d6) δ 7.99 (d, J=2.8 Hz, 1H), 7.61-7.56 (m, 2H), 7.43-7.40 (m, 1H), 7.15-7.10 (m, 2H), 6.58 (d, J=6.8 Hz, 1H), 5.93 (d, J=12.8 Hz, 2H), 5.44 (d, J=7.2 Hz), 3.84 (s, 3H), 3.71 (s, 3H).

Step 2. Synthesis of 1-bromo-4-chloro-2-(2-methoxyvinyl)benzene (44c)

To a mixture of p-toluenesulfonic acid (537 mg, 2.83 mmol) in methanol (70 mL) was added 44b (7.0 g, 28.28 mmol). The mixture was stirred at 66° C. for 16 h. TLC (PE=100%, $R_f$=0.4) showed the reaction was complete. The reaction mixture was poured into $H_2O$ (200 mL). The mixture was extracted with EA (200 mL), washed with water (60 mL) and brine (60 mL), dried over $Na_2SO_4$, filtered and concentrated. The crude product was purified by silica gel column chromatography, eluting with PE (100%) to give 44c (7.2 g, 25.7 mmol, 91% yield) as a yellow oil. $^1$H NMR (400 MHz, $CDCl_3$) δ 7.62 (d, J=8.8 Hz, 1H), 7.43 (d, J=2.4 Hz, 1H), 7.25 (dd, J=8.4, 2.8 Hz, 1H), 4.62 (t, J=5.2 Hz, 1H), 3.26 (s, 6H), 2.99 (d, J=5.6 Hz, 2H).

Step 3. Synthesis of [4-chloro-2-(2,2-dimethoxyethyl)phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (44e)

To a mixture of 44c (3.0 g, 10.73 mmol) in THF (30 mL) was added n-BuLi (2.04 g, 10.73 mmol) at −78° C. The resulting solution of 44d was stirred at −78° C. for 1 min, and 1Ad (3.24 g, 8.46 mmol) in THF (20 mL) was added at −78° C. The reaction mixture was stirred at −78° C. for 30 min. TLC (PE:EA=5:1, $R_f$=0.5) showed the reaction was complete. The reaction was quenched with $NH_4Cl$ (aq, 100 mL) and water (100 mL). The aqueous layer was extracted with EA (300 mL×3). The organic layers were concentrated to give a crude product which was purified by silica gel column chromatography, eluting with PE:EA=10:1 to give 44e (3 g, 5.74 mmol, 53.5% yield) as a yellow oil. LCMS [M+H]: 522.3

Step 4. Synthesis of (S)-[4-chloro-2-(2,2-dimethoxyethyl)phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (44f)

To a mixture of 44e (3.0 g, 5.74 mmol) in toluene (30 mL) was added DIBAL-H (1.33 mL, 11.49 mmol) at −78° C. The mixture was stirred at −78° C. for 30 min. LCMS showed the reaction was complete. The reaction mixture was poured into $H_2O$ (100 mL) and extracted with DCM (200 mL), dried over $Na_2SO_4$, filtered, and concentrated. The crude product was purified by silica gel column chromatography, eluting with DCM:MeOH=5:1 to give 44f (3 g, 5.72 mmol, 99.6% yield) as a yellow oil. LCMS [M+H]: 524.4

Step 5. Synthesis of 4-chloro-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (44g)

To a mixture of (S)-[4-chloro-2-(2,2-dimethoxyethyl)phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (2.0 g, 3.81 mmol) in methanol (20 mL) was added TsOH (0.03 mL, 5.72 mmol at 0° C. The mixture was stirred at 25° C. for 2 h. TLC (PE:EA=5:1, $R_f$=0.5) showed the reaction was complete. The reaction mixture was poured into $H_2O$ (30 mL) and extracted with DCM (50 mL×3). The organic phase was washed with saturated NaCl (100 mL), dried over $Na_2SO_4$, filtered and concentrated. The crude product which was purified by silica gel column chromatography, eluting with PE:EA=10:1 to give 44g (1.36 g, 2.76 mmol, 72% yield) as a yellow oil. LCMS [M+H]: 492.2

Step 6. Synthesis of 4-methyl-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (44h)

To a mixture of 44g (200 mg, 0.41 mmol) and ferric acetylacetonate (71.73 mg, 0.20 mmol) in THF (2 mL) was added MeMgBr (484 mg, 4.06 mmol) at −10° C. The reaction mixture was warmed to 0° C. and stirred for 1 h. TLC (PE:EA=5:1, $R_f$=0.7) showed the reaction was complete. The reaction mixture was poured into $H_2O$ (10 mL), extracted with DCM (10 mL×3), washed with saturated NaCl (20 mL), dried over $Na_2SO_4$, filtered, and concentrated. The crude product was purified by silica gel column chromatography, eluting with PE:EA=7:1 to give 44h (110 mg, 0.23 mmol, 57.4% yield) as a yellow oil. LCMS [M+H]: 472.4

Step 7. Synthesis of (2R,3R,4S,5S)-2-(4-methylpyrrolo[2,3-d]pyrimidin-7-yl)-5-[(1R)-6-chloro-3-methoxy-isochroman-1-yl]tetrahydrofuran-3,4-diol (Ex. 44)

To a mixture of 44h (110 mg, 0.23 mmol) in methanol (2 mL) was added HCl (42 mg, 1.17 mmol). The mixture was stirred at 25° C. for 1 h. TLC (PE:EA=5:1, $R_f$=0.7) and LCMS showed the reaction was complete. The reaction mixture was poured into $H_2O$ (10 mL), extracted with DCM (10 mL×3), washed with saturated NaCl (20 mL), dried over $Na_2SO_4$, filtered, and concentrated. The crude product was purified by silica gel column chromatography, eluting with PE:EA=7:1 to give a crude product which was further purified by prep-HPLC, eluting with $CH_3CN$ in $H_2O$ (0.10% $NH_3 \cdot H_2O$) from 10% to 95%) to give Ex. 44 (25 mg, 0.047 mmol, 20% yield) as a white solid. LCMS [M+H]: 432.4 $^1$H NMR (400 MHz, DMSO-d6) δ 8.67 (s, 1H), 7.79-7.81 (d, 1H), 7.22-7.32 (m, 3H), 6.82-6.84 (m, 1H), 6.31-6.34 (m, 1H), 5.15-5.30 (m, 3H), 4.82 (d, 1H), 4.46-4.58 (m, 2H), 3.89-3.91 (t, 1H), 3.38 (s, 3H), 3.08-3.13 (m, 1H), 2.77 (d, 1H), 2.67 (s, 3H). $^1$H NMR (400 MHz, DMSO-d6+$D_2O$) δ 8.68 (s, 1H), 7.81 (d, 1H), 7.22-7.32 (m, 3H), 6.83 (d, 1H), 6.32 (d, 1H), 5.26 (d, 1H), 4.83 (d, 1H), 4.78-4.57 (m, 2H), 3.89 (d, 1H), 3.08 (d, 1H), 2.77 (d, 1H), 2.67 (s, 3H).

Example 46. Synthesis of (1R)-6-chloro-1-[(2S,3S,4R,5R)-3,4-dihydroxy-5-(4-methylpyrrolo[2,3-d]pyrimidin-7-yl)tetrahydrofuran-2-yl]isochroman-3-one (Ex. 46)

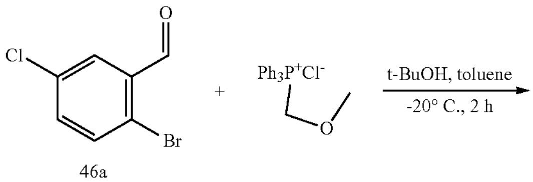

46a

-continued
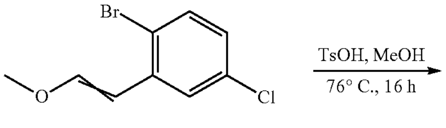
46b
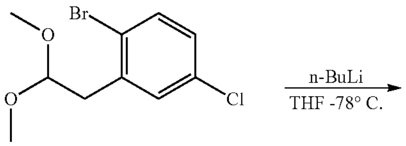
46c
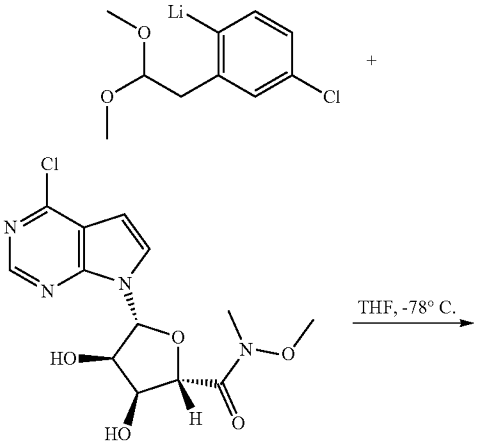
1Ad
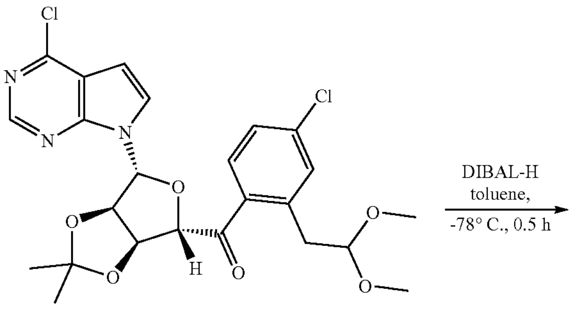
46d
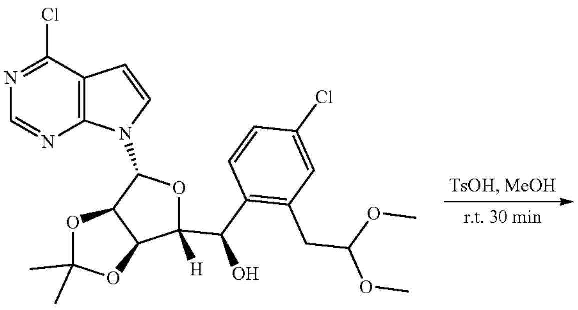
46e
-continued
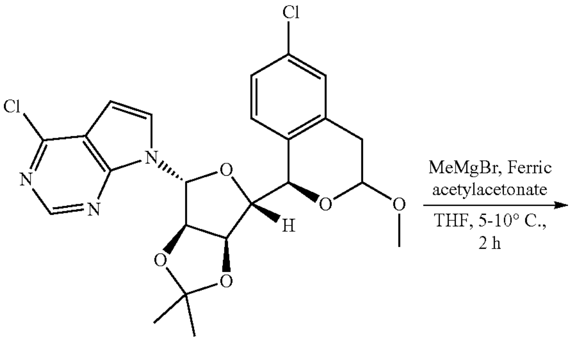
46f
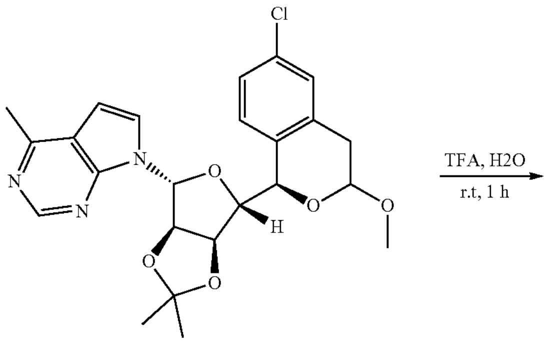
46g
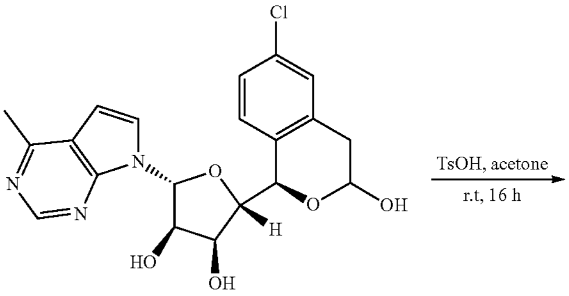
46h
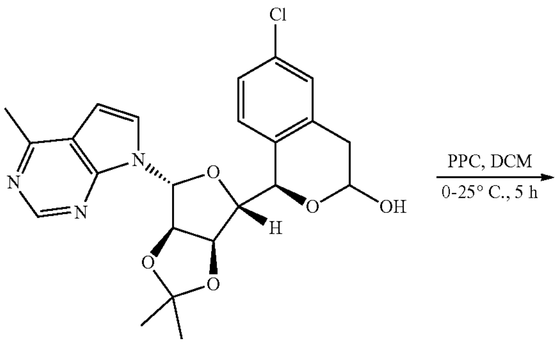
46i -continued

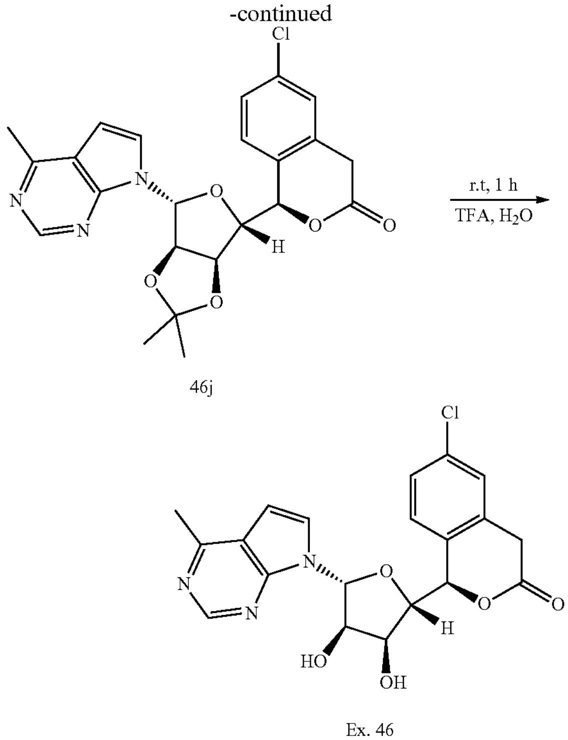

46j

Ex. 46

Step 1. Synthesis of 1-bromo-4-chloro-2-(2-methoxyvinyl)benzene (46b)

To a solution of (methoxymethyl)-triphenylphosphonium chloride (26.24 g, 76.55 mmol) in THF (70 mL) was added potassium tert-butoxide (4.65 mL, 72.91 mmol) at −25° C. under $N_2$. A few minutes later, 2-bromo-5-chloro-benzaldehyde (46a, 8.0 g, 36.45 mmol) was added. The solution was stirred at −25° C. for 2 h. The reaction was monitored by TLC (petroleum ether=100%, $R_f$=0.8). The reaction mixture was poured into water (200 mL). Ethyl acetate (200 mL) was added and the organic phase was separated. The solution was washed with water (100 mL) and brine (100 mL), dried ($Na_2SO_4$), filtered, and concentrated in vacuum to give the crude product which was purified by column chromatography on silica gel with petroleum ether (100%) to give 1-bromo-4-chloro-2-(2-methoxyvinyl)benzene (46b, 8.75 g, 35.351 mmol, 97% yield) as a yellow oil. LCMS [M+H]: 247.1.

Step 2. Synthesis of 1-bromo-4-chloro-2-(2,2-dimethoxyethyl)benzene (46c)

To a mixture of TsOH (672 mg, 3.54 mmol) in methanol (70 mL) was added 1-bromo-4-chloro-2-(2-methoxyvinyl) benzene (46b, 8.75 g, 35.35 mmol) and the mixture was stirred at 75° C. for 16 h. TLC (petroleum ether=100%, $R_f$=0.4) showed the reaction was complete. The reaction mixture was poured into water (200 mL) and ethyl acetate (200 mL) was added. The organic layer was washed with saturated NaCl (100 mL), dried over $Na_2SO_4$, filtered and concentrated in vacuum to give the crude product which was purified by column chromatography on silica gel with petroleum ether (100%) to give 1-bromo-4-chloro-2-(2,2-dimethoxyethyl)benzene (46c, 5.5 g, 19.674 mmol, 56% yield) as a yellow oil. LCMS [M+H]: 279.1.

Step 3. Synthesis of [4-chloro-2-(2,2-dimethoxyethyl)phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (46d)

To a mixture of 1-bromo-4-chloro-2-(2,2-dimethoxyethyl)benzene (46c, 5.5 g, 19.7 mmol) in THF (30 mL), BuLi (3.74 g, 19.7 mmol) was added at −78° C. and stirred for 1 min. (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1Ad, 5.94 g, 15.52 mmol) was added at −78° C. and the reaction was stirred for 30 min at −78° C. TLC (petroleum ether:ethyl acetate=5:1, $R_f$=0.5) showed the reaction was complete. The reaction was quenched with $NH_4Cl$ (100 mL) and water (100 mL). The aqueous layer was extracted with ethyl acetate (300 mL×3), dried over $Na_2SO_4$, and concentrated in vacuum. The crude product was purified by column chromatography on silica gel with petroleum ether:ethyl acetate (10:1) to give [4-chloro-2-(2,2-dimethoxyethyl)phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (46d, 2.0 g, 3.8286 mmol, 19.5% yield) as a yellow oil. LCMS [M+H]: 522.3.

Step 4. Synthesis of (S)-[4-chloro-2-(2,2-dimethoxyethyl)phenyl]-[(3aR,4R,6R,6aR)-4-(4-chloro-pyrrolo-[2,3-d]pyrimidin-7-yl)-2,2-dimethyl-3a,4,6,6a-tetrahydrofuro[3,4-d][1,3]dioxol-6-yl]methanol (46e)

To a mixture of [4-chloro-2-(2,2-dimethoxyethyl)phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (46d, 2.0 g, 3.83 mmol) in toluene (30 mL) was added DIBAL-H (0.89 mL, 7.66 mmol) at −78° C. The mixture was stirred at −78° C. for 30 min. The reaction was poured into water (100 mL) and extracted with DCM (200 mL). The aqueous layer was extracted with DMC (300 mL×3), dried over $Na_2SO_4$, and concentrated in vacuum. The crude product was purified by column chromatography on silica gel with DCM:MeOH=5:1 to give (S)-[4-chloro-2-(2,2-dimethoxyethyl)phenyl]-[(3aR,4R,6R,6aR)-4-(4-chloropyrrolo-[2,3-d]pyrimidin-7-yl)-2,2-dimethyl-3a,4,6,6a-tetrahydrofuro[3,4-d][1,3]dioxol-6-yl]methanol (46e, 2 g, 3.81 mmol, 100% yield) as a yellow oil. LCMS [M+H]: 524.3.

Step 5. Synthesis of 4-chloro-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (46f)

To a mixture of (S)-[4-chloro-2-(2,2-dimethoxyethyl)phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (46e, 2.0 g, 3.81 mmol) in methanol (20 mL) was added TsOH (0.03 mL, 5.72 mmol) at 0° C., then the mixture was stirred at 25° C. for 2 h. TLC (petroleum ether:ethyl acetate=5:1, $R_f$=0.5) and LCMS showed the reaction was complete. The reaction mixture was poured into water (30 mL) and extracted with DCM (50 mL×3). The organic layers were dried over $Na_2SO_4$ and concentrated in vacuum. The crude product was purified by column chromatography on silica gel with petroleum ether: ethyl acetate=10:1 to give 4-chloro-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (46f, 1.6 g, 3.25 mmol, 85% yield) as a yellow oil. LCMS [M+H]: 492.0.

Step 6. Synthesis of 4-methyl-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (46g)

To a mixture of 4-chloro-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (46f, 800 mg, 1.62 mmol) and ferric acetylacetonate (287 mg, 0.81 mmol) in THF (10 mL), was added methylmagnesium bromide (1937.48 mg, 16.25 mmol) at −10° C. The mixture was warmed to 0° C. and stirred for 1 h. TLC (petroleum ether:ethyl acetate=5:1, $R_f$=0.7) showed the reaction was complete. The reaction mixture was poured into water (30 mL) and extracted with DCM (50 mL×3). The organic layers were dried over $Na_2SO_4$ and concentrated in vacuum. The crude product was purified by column chromatography on silica gel with petroleum ether:ethyl acetate=7:1 to give 4-methyl-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (46g, 610 mg, 1.29 mmol, 80% yield) as a yellow oil. LCMS [M+H]: 472.1.

Step 7. Synthesis of (2R,3R,4S,5S)-2-(4-methylpyrrolo[2,3-d]pyrimidin-7-yl)-5-[(1R)-6-chloro-3-hydroxy-isochroman-1-yl]tetrahydrofuran-3,4-diol (46h)

To a mixture of 4-methyl-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (46g, 590 mg, 1.25 mmol) in water (6 mL) was added trifluoroacetic acid (228 mg, 2 mmol). The mixture was stirred at 25° C. for 1 h. TLC (petroleum ether:ethyl acetate=2:1, $R_f$=0.3) showed the reaction was complete. The reaction mixture was poured into water (30 mL) and extracted with ethyl acetate (50 mL×3). The organic layers was dried over $Na_2SO_4$, and concentrated in vacuum to give the crude product which was purified by column chromatography on silica gel with petroleum ether:ethyl acetate=7:1 to give (2R,3R,4S,5S)-2-(4-methylpyrrolo[2,3-d]pyrimidin-7-yl)-5-[(1R)-6-chloro-3-hydroxy-isochroman-1-yl]tetrahydrofuran-3,4-diol (46h, 280 mg, 0.54 mmol, 43% yield) as a yellow oil. LCMS [M+H]: 418.1.

Step 8. Synthesis of (1R)-6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]isochroman-3-ol (46i)

To a mixture of (2R,3R,4S,5S)-2-(4-methylpyrrolo[2,3-d]pyrimidin-7-yl)-5-[(1R)-6-chloro-3-hydroxy-isochroman-1-yl]tetrahydrofuran-3,4-diol (46h, 50 mg, 0.12 mmol) in acetone (10 mL) was added TsOH (8.24 mg, 0.05 mmol) at 0° C. The mixture was stirred at 25° C. for 3 h. TLC (petroleum ether:ethyl acetate=5:1, $R_f$=0.3) showed the reaction was complete. The reaction mixture was poured into water (30 mL) and extracted with DCM (50 mL×3). The organic layers was dried over $Na_2SO_4$, concentrated in vacuum to give the crude product which was purified by column chromatography on silica gel with petroleum ether: ethyl acetate=(7:1) to give (1R)-6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]isochroman-3-ol (46i, 76 mg, 0.13 mmol, 112% yield) as a white solid. LCMS [M+H]: 458.1.

Step 9. Synthesis of 6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]isochroman-3-one (46j)

To a mixture of 6-chloro-1-[(3aR,4R,6R,6aR)-2,2-dimethyl-4-(4-methylpyrrolo-[2,3-d]pyrimidin-7-yl)-3a,4,6,6a-tetrahydrofuro[3,4-d][1,3]dioxol-6-yl]isochroman-3-ol (46i, 75 mg, 0.16 mmol) in DCM (3 mL) was added PCC (0.09 mL, 0.49 mmol) at 0° C. and the mixture was stirred at 0° C. for 30 min. Then the reaction was warmed to 25° C. until the reaction was complete. The reaction mixture was poured into water (30 mL) and extracted with DCM (3×50 mL). The organic layers was dried over $Na_2SO_4$ and concentrated in vacuum to give 6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]isochroman-3-one (46j, 79 mg, 0.172 mmol, 100% yield) as a white solid which was used without further purification in the next step. LCMS [M+H]: 456.3.

Step 10. Synthesis of (1R)-6-chloro-1-[(2S,3S,4R,5R)-3,4-dihydroxy-5-(4-methylpyrrolo[2,3-d]pyrimidin-7-yl)tetrahydrofuran-2-yl]isochroman-3-one (Ex. 46)

To a mixture of (1R)-6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]isochroman-3-one (46j, 78 mg, 0.17 mmol) in water (2 mL), trifluoroacetic acid (31.19 mg, 0.27 mmol) was added and the mixture was stirred at 25° C. for 1 h. LCMS showed the reaction was complete. The reaction was neutralized with $NaHCO_3$ and purified by prep-HPLC, eluting with $CH_3CN$ in water (0.1% TFA) from 10% to 95%) to give (1R)-6-chloro-1-[(2S,3S,4R,5R)-3,4-dihydroxy-5-(4-methylpyrrolo[2,3-d]pyrimidin-7-yl)tetrahydrofuran-2-yl]isochroman-3-one (Ex. 46, 3.4 mg, 0.0078 mmol, 4.6% yield) as an off white solid. LCMS [M+H]: 416.0. $^1H$ NMR (400 MHz, DMSO-$d_6$) δ 8.74 (s, 1H), 7.58 (s, 1H), 7.30 (m, 3H), 6.86 (s, 1H), 6.23 (d, J=5.6 Hz, 1H), 5.73 (d, J=4.8 Hz, 1H), 4.48 (m, 2H), 4.26 (s, 1H), 3.77 (d, J=4.8 Hz, 2H), 2.72 (s, 3H). 1H NMR (400 MHz, DMSO-$d_6$+D2O) δ 8.82 (s, 1H), 7.62 (d, J=3.2 Hz, 1H), 7.29 (m, 3H), 6.93 (d, J=3.2 Hz, 1H), 6.24 (d, J=5.6 Hz, 1H), 5.73 (d, J=5.2 Hz, 1H), 4.49 (m, 2H), 4.26 (s, 1H), 3.76 (s, 2H), 2.76 (s, 3H).

Example 50. Synthesis of (2R,3R,4S,5S)-2-(4-methylpyrrolo[2,3-d]pyrimidin-7-yl)-5-[(1R)-6-chloro-3-hydroxy-isochroman-1-yl]tetrahydrofuran-3,4-diol (Ex. 50)

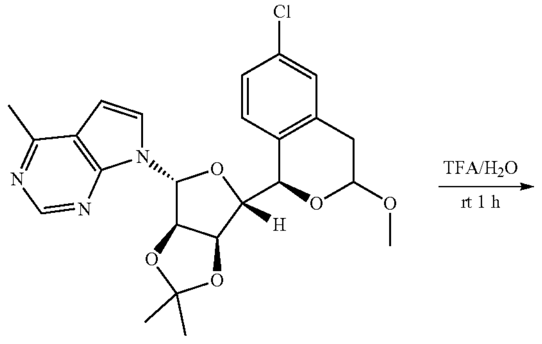

44h

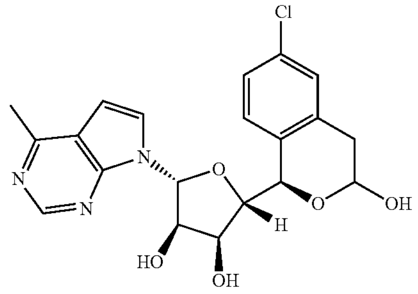

Ex. 50

To a mixture of 44h (100 mg, 0.21 mmol) in water (2 mL) was added trifluoroacetic acid (38.63 mg, 0.34 mmol). The mixture was stirred at 25° C. for 1 h. TLC (PE:EA=5:1, $R_f$=0.7) and LCMS showed the reaction was complete. The reaction mixture was poured into $H_2O$ (10 mL), extracted with DCM (10 mL×3), washed with saturated NaCl (20 mL), dried over $Na_2SO_4$, filtered, and concentrated. The crude product was purified by silica gel column chromatography, eluting with PE:EA=7:1 to give a crude product which was further purified by prep-HPLC, eluted with $CH_3CN$ in $H_2O$ (0.1% $NH_3$·$H_2O$) from 10% to 95%) to give Ex. 50 as a mixture of diastereomers (10 mg, 0.019 mmol, 9% yield) as white solid. [M+H]: 418.3. $^1$H NMR (400 MHz, DMSO-d6) δ 8.67 (s, 1H), 8.00 (d, 1H), 7.21-7.35 (m, 3H), 6.75-6.82 (m, 1H), 6.30-6.36 (m, 1H), 5.05-5.25 (m, 2H), 4.98-5.04 (m, 2H), 4.45-4.59 (m, 2H), 3.74-3.87 (m, 1H), 2.91-3.05 (m, 1H), 2.72-2.81 (m, 1H), 2.50-2.51 (m, 3H). $^1$H NMR (400 MHz, DMSO-d6+D2O) δ 8.66 (s, 1H), 7.81-8.00 (q, 1H), 7.22-7.34 (m, 3H), 6.79-6.81 (t, 1H), 6.30-6.34 (q, 1H), 4.98-5.05 (q, 2H), 4.45-4.59 (m, 2H), 3.74-3.87 (m, 1H), 2.79-2.91 (m, 1H), 2.72 (s, 1H), 2.68 (s, 3H).

Example 55. Synthesis (2R,3R,4S,5S)-2-(4-methylpyrrolo[2,3-d]pyrimidin-7-yl)-5-[(1R)-7-chloro-1,5-dihydro-2,4-benzodioxepin-1-yl]tetrahydrofuran-3,4-diol of (Ex. 55)

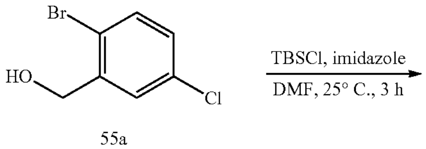

55a

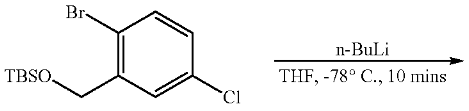

55b

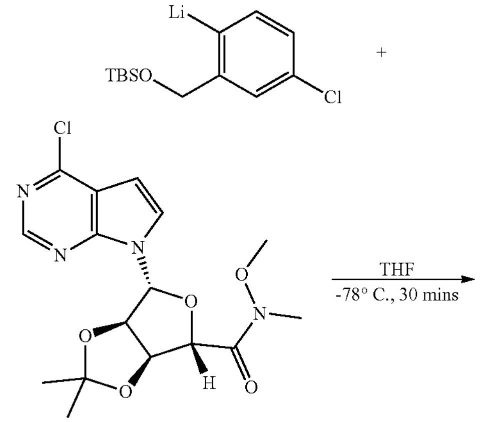

1Ad

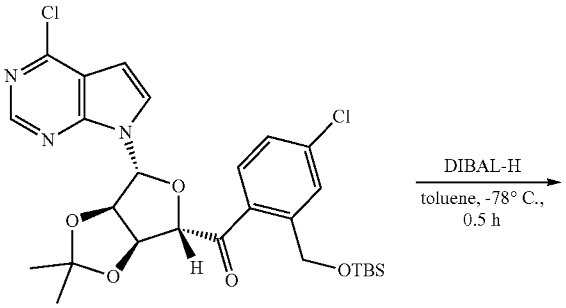

55c

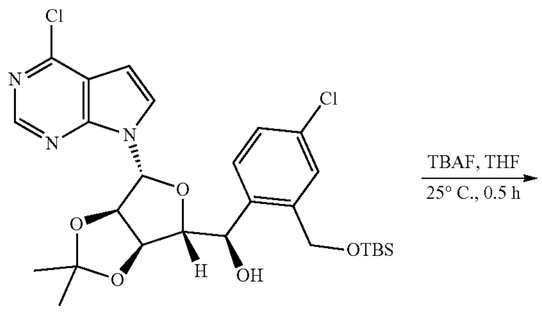

55d

-continued

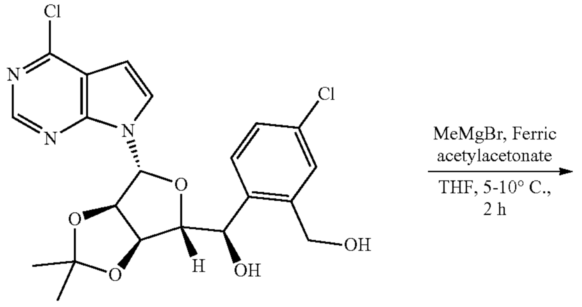

55e

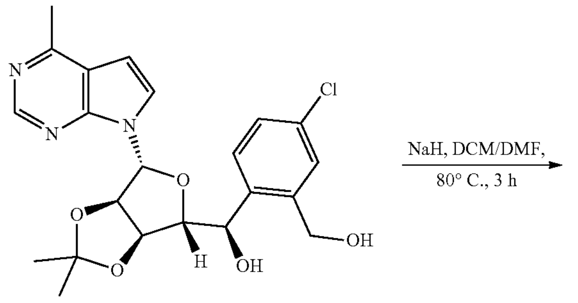

55f

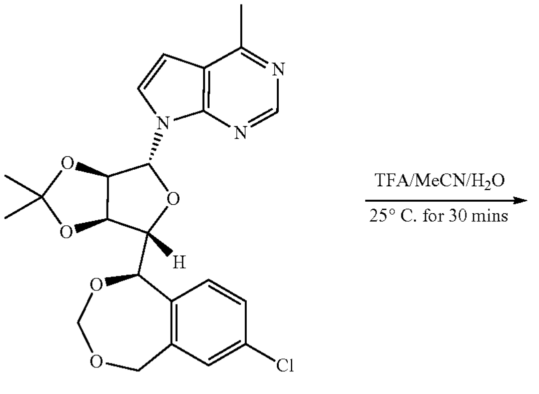

55g

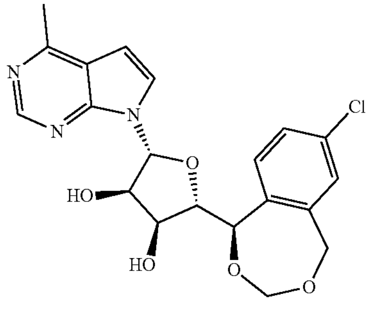

Ex. 55

Step 1. Synthesis of (2-bromo-5-chloro-phenyl) methoxy-tert-butyl-dimethyl-silane (55b)

To a solution of (2-bromo-5-chlorophenyl)methanol (55a, 6.0 g, 27.09 mmol) and imidazole (3.69 g, 54.18 mmol) in DCM (50 mL) was slowly added t-butylchlorodiphenylsilane (4.9 g, 32.51 mmol) at rt. The mixture was stirred at 30° C. for 3 h. TLC (petroleum ether, $R_f$=0.4) showed the reaction was complete. The reaction mixture was concentrated in vacuum to give the crude product which was purified by silica gel column chromatography (petroleum ether) to give (2-bromo-5-chloro-phenyl)methoxy-tert-butyl-dimethyl-silane (55b, 9.0 g, 26.81 mmol, 99% yield) as colorless oil. $^1$H NMR (400 MHz, DMSO-$d_6$): δ 7.51 (d, J=8.4, 1H), 7.81 (d, J=2.8, 1H), 7.22-7.19 (m, 1H), 4.57 (s, 1H), 0.83-0.81 (m, 9H), 0.02-0.01 (m, 6H).

Step 2. Synthesis of [2-[[tert-butyl(dimethyl)-silyl] oxymethyl]-4-chloro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (55c)

To a solution of (2-bromo-5-chloro-phenyl)methoxy-tert-butyl-dimethyl-silane (55b, 9 g, 26.8 mmol) in dry THF (50 mL) was stirred at −78° C. under Ar. n-BuLi (12.02 mL, 30.04 mmol) was added and stirred at −78° C. for 10 mins. (3aR,4R,6S,6aS)-4-(4-chloropyrrolo-[2,3-d]pyrimidin-7-yl)-N-methoxy-N,2,2-trimethyl-3a,4,6,6a-tetrahydrofuro[3,4-d][1,3]dioxole-6-carboxamide (1Ad, 4.6 g, 12.02 mmol) in anhydrous THE (50 mL) was added, then the reaction mixture was stirred at −78° C. for 30 mins. TLC (petroleum ether:ethyl acetate=5:1) and LCMS showed the reaction was complete. The mixture was adjusted to pH=6 with HCl (1N). The reaction was extracted with EtOAc (2×100 mL) and the organics washed with water (100 mL×2), then brine (50 mL×2). The organic layers were dried over $MgSO_4$, filtered, and concentrated. The crude product was purified by silica gel column chromatography (petroleum ether:ethyl acetate=10:1 to 5:1) to give [2-[[tert-butyl(dimethyl)-silyl] oxymethyl]-4-chloro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (55c, 4.03 g, 6.97 mmol, 58% yield). LCMS [M+H]: 578.2. $^1$H NMR (400 MHz, DMSO-$d_6$): δ 8.67 (s, 1H), 7.68 (d, J=3.6, 1H), 7.62 (d, J=8.4, 1H), 7.47-7.46 (m, 2H), 7.35 (d, J=8.0, 1H), 7.26-7.20 (m, 2H), 6.49 (d, J=3.6, 1H), 6.42 (s, 1H), 5.53-5.51 (m, 2H), 5.42 (d, J=5.6, 1H), 5.27-5.25 (m, 1H), 4.54-4.44 (m, 3H), 1.52 (s, 3H), 1.31 (s, 3H), 0.69 (s, 9H), 0.01-0.070 (m, 6H).

Step 3. Synthesis of (R)-[2-[[tert-butyl(dimethyl) silyl]oxymethyl]-4-chloro-phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (55d)

To a solution of [2-[[tert-butyl(dimethyl)silyl]oxymethyl]-4-chloro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (55c, 4.39 g, 7.59 mmol) in toluene (10 mL) was added diisobutylaluminum hydride dropwise (3.23 g, 22.77 mmol, 1 M in toluene) at −78° C. The reaction was stirred at −78° C. for 30 mins. The mixture was quenched with $NH_4Cl$ (50 mL). The reaction mixture was concentrated in vacuum and extracted with ethyl acetate (2×100 mL). The combined organic layers were dried over $MgSO_4$. The solvent was removed in vacuum to afforded crude (R)-[2-[[tert-butyl(dimethyl)silyl] oxymethyl]-4-chloro-phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (55d, 4.2 g) which was used without further purification in the next step. LCMS [M+H]: 580.2.

Step 4. Synthesis of (R)-[4-chloro-2-(hydroxymethyl)phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (55e)

To a solution of (R)-[2-[[tert-butyl(dimethyl)silyl]oxymethyl]-4-chloro-phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (55d, 4.2 g, 7.23 mmol) in THF (5 mL) was added TBAF (1 M) (3.78 mL, 14.47 mmol). The mixture was stirred at 25° C. for 2 h in $N_2$. The mixture was quenched with $NH_4Cl$ (50 mL). The reaction mixture was concentrated in vacuum and purified by silica gel column chromatography (petroleum ether:ethyl acetate=3:1) to give (R)-[4-chloro-2-(hydroxymethyl)phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (55e, 1.8 g, 3.78 mmol, 52% yield). $^1$H NMR (400 MHz, DMSO-$d_6$): δ 8.69 (d, J=3.2, 1H), 8.03 (d, J=3.6, 1H), 7.53 (d, J=8, 1H), 7.39-7.29 (m, 2H), 6.79 (d, J=3.6, 1H), 6.32 (d, J=3.6, 1H), 5.96 (d, J=4.4, 1H), 5.27-5.17 (m, 3H), 4.94-4.91 (m, 1H), 4.46-4.41 (m, 1H), 4.26-4.19 (m, 1H), 1.51 (s, 3H), 1.30 (s, 3H). LCMS [M+H]: 466.1.

Step 5. Synthesis of (R)-[4-chloro-2-(hydroxymethyl)phenyl]-[(6R)-2,2-dimethyl-4-(4-methylpyrrolo[2,3-d]pyrimidin-7-yl)-3a,4,6,6a-tetrahydrofuro[3,4-d][1,3]dioxol-6-yl]methanol (55f)

To a solution of ferric acetylacetonate (22.72 mg, 0.06 mmol) and (R)-[4-chloro-2-(hydroxymethyl)phenyl]-[(6R)-4-(4-chloropyrrolo[2,3-d]pyrimidin-7-yl)-2,2-dimethyl-3a,4,6,6a-tetrahydrofuro[3,4-d][1,3]dioxol-6-yl]methanol (55e, 300 mg, 0.64 mmol) in THF (5 mL) was added methylmagnesium bromide (721.9 mg, 6.43 mmol) at 0° C. under $N_2$. The reaction mixture was warmed to rt and stirred for 1 h. TLC (ethyl acetate:petroleum ether=5:1, $R_f$=0.6) showed the reaction was complete. Sat. $NH_4Cl$ was added dropwise to quench the reaction. The reaction mixture was extracted with ethyl acetate (2×50 mL), dried over $Na_2SO_4$ and concentrated in vacuum. The crude product was purified by silica gel column chromatography (petroleum ether:ethyl acetate=10:1 to 5:1) to give (R)-[4-chloro-2-(hydroxymethyl)phenyl]-[(6R)-2,2-dimethyl-4-(4-methylpyrrolo[2,3-d]pyrimidin-7-yl)-3a,4,6,6a-tetrahydrofuro[3,4-d][1,3]dioxol-6-yl]methanol (55f, 105 mg, 0.23 mmol, 37% yield) as a colorless oil. $^1$H NMR (400 MHz, DMSO-$d_6$): δ 8.74 (s, 1H), 7.82 (d, J=3.6, 1H), 7.53 (d, J=8, 1H), 7.39-7.35 (m, 2H), 6.81 (d, J=3.6, 1H), 6.27 (d, J=4, 1H), 6.00 (d, J=4.4, 1H), 5.25-5.15 (m, 3H), 4.92-4.90 (m, 1H), 4.47-4.41 (m, 1H), 4.24-4.19 (m, 2H), 2.68-2.62 (m, 3H), 1.51 (s, 3H), 1.30 (s, 3H). LCMS [M+H]: 446.1.

Step 6. Synthesis of 4-methyl-7-[(3aR,4R,6R,6aR)-2,2-dimethyl-6-[(1R)-7-chloro-1,5-dihydro-2,4-benzodioxepin-1-yl]-3a,4,6,6a-tetrahydrofuro[3,4-d][1,3]dioxol-4-yl]pyrrolo[2,3-d]pyrimidine (55g)

To a solution of (R)-[4-chloro-2-(hydroxymethyl)phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (55f, 150 mg, 0.34 mmol) in DCM (1.2 mL) and DMF (2.5 mL) was added sodium hydride (80.74 mg, 3.36 mmol). The mixture solution was stirred at 80° C. for 2 h. LCMS showed the reaction was complete. The reaction mixture was quenched with $NH_4Cl$ (50 mL). The solvent was removed in vacuum to give the crude product which was purified by silica gel column chromatography (DCM:MeOH=50:1) to give 4-methyl-7-[(3aR,4R,6R,6aR)-2,2-dimethyl-6-[(1R)-7-chloro-1,5-dihydro-2,4-benzodioxepin-1-yl]-3a,4,6,6a-tetrahydrofuro[3,4-d][1,3]dioxol-4-yl]pyrrolo[2,3-d]pyrimidine (55g, 160 mg, 0.33 mmol, 97% yield) as a yellow oil. $^1$H NMR (400 MHz, DMSO-$d_6$): δ 8.73 (s, 1H), 7.71 (d, J=3.6, 1H), 7.38 (d, J=1.6, 1H), 73.31-7.30 (m, 2H), 6.80 (d, J=3.6, 1H), 6.48 (d, J=4, 1H), 5.33-5.31 (m, 1H), 5.20-5.14 (m, 2H), 5.05-5.01 (m, 2H), 4.83-4.78 (m, 3H), 2.68-2.62 (m, 3H), 1.60 (s, 3H), 1.34 (s, 3H). LCMS [M+H]: 458.1.

Step 7. Synthesis of (2R,3R,4S,5S)-2-(4-methylpyrrolo[2,3-d]pyrimidin-7-yl)-5-[(1R)-7-chloro-1,5-dihydro-2,4-benzodioxepin-1-yl]tetrahydrofuran-3,4-diol (Ex. 55)

To a solution of 4-methyl-7-[(3aR,4R,6R,6aR)-2,2-dimethyl-6-[(1R)-7-chloro-1,5-dihydro-2,4-benzodioxepin-1-yl]-3a,4,6,6a-tetrahydrofuro[3,4-d][1,3]dioxol-4-yl]pyrrolo[2,3-d]pyrimidine (55g, 160 mg, 0.35 mmol) in water (1 mL) was added 2,2,2-trifluoroacetic acid (2.0 mL, 2 mmol) and the mixture was stirred at 25° C. for 30 mins. $NH_3$° water was added until pH=7 and the mixture was concentrated in vacuum. The residue was purified by prep-HPLC, eluting with MeCN in water (0.1% $NH_3$° water) from 10% to 90% to give (2R,3R,4S,5S)-2-(4-methylpyrrolo[2,3-d]pyrimidin-7-yl)-5-[(1R)-7-chloro-1,5-dihydro-2,4-benzodioxepin-1-yl]tetrahydrofuran-3,4-diol (Ex. 55.31 mg, 0.073 mmol, 21% yield) as a white solid. LCMS [M+H]: 418.1. $^1$H NMR (400 MHz, DMSO-$d_6$): δ 8.68 (s, 1H), 7.64 (d, J=4, 1H), 7.41 (s, 1H), 7.32 (d, J=1.2, 2H), 6.78 (d, J=3.6, 1H), 6.32 (d, J=8.0, 1H), 5.51 (d, J=4.4, 1H), 5.41 (d, J=7.2, 1H), 5.34-5.31 (m, 1H), 5.09 (d, J=4.8, 1H), 5.04 (d, J=6.4, 1H), 4.99-4.95 (m, 1H), 4.85-4.81 (m, 1H), 4.62-4.56 (m, 2H), 4.19-4.17 (m, 1H), 2.66 (s, 3H).

Example 69. Synthesis of (2S,3S,4R,5R)-2-((R)-6-chloroisochroman-1-yl)-5-(4-(methylamino)-7H-pyrrolo[2,3-d]pyrimidin-7-yl)tetrahydrofuran-3,4-diol (Ex. 69)

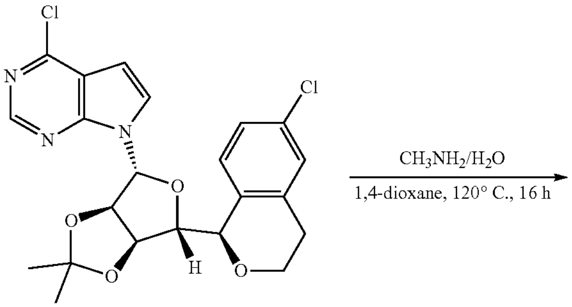

22f

-continued

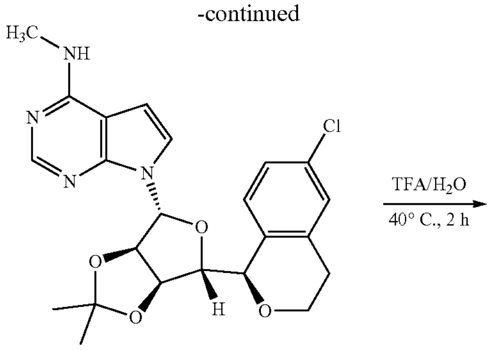

69a

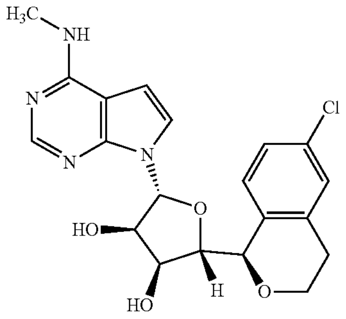

Ex. 69

Step 1. Synthesis of N-methyl-7-[(3aR,4R,6R,6aR)-2,2-dimethyl-6-[(1R)-6-chloroisochroman-1-yl]-3a,4,6,6a-tetrahydrofuro[3,4-d][1,3]dioxol-4-yl]pyrrolo[2,3-d]pyrimidin-4-amine (69a)

To a solution of 22f (100 mg, 0.22 mmol) in 1,4-dioxane (2 mL), methylamine in water (2.0 mL, 0.09 mmol) was added. The mixture was stirred at 120° C. for 16 h. The mixture was purified by prep-HPLC eluting with $CH_3CN/H_2O$ (neutral) from 5/95 to 95/5. The product fractions were lyophilized to give 69a (75 mg, 0.16 mmol, 75% yield) as a yellow solid. LCMS [M+H]: 457.1.

Step 2. Synthesis of (2S,3S,4R,5R)-2-((R)-6-chloroisochroman-1-yl)-5-(4-(methylamino)-7H-pyrrolo[2,3-d]pyrimidin-7-yl)tetrahydrofuran-3,4-diol (Ex. 69)

To a solution of 69a (75 mg, 0.16 mmol) in MeCN (1 mL), $TFA/H_2O$ (0.97 mL, 0.39 mmol) was added. The mixture was stirred at 40° C. for 2 h. The mixture was purified by prep-HPLC eluting with $CH_3CN/H_2O$ (0.1% $NH_4OH$) from 5/95 to 95/5 and lyophilized to give Ex. 69 (36.5 mg, 0.087 mmol, 53% yield) as a white solid. LCMS [M+H]: 417.3. 1H NMR (400 M Hz, DMSO-d6): δ 8.15 (s, 1H), 7.48-7.49 (m, 1H), 7.36-7.37 (m, 1H), 7.28-7.30 (m, 2H), 7.21-7.23 (m, 1H), 6.63 (d, J=3.2 Hz, 1H), 6.18 (d, J=7.6 Hz, 1H), 5.16 (d, J=7.6 Hz, 1H), 5.04 (d, J=4.0 Hz, 1H), 4.86-4.87 (m, 1H), 4.42-4.48 (m, 1H), 4.35-4.36 (m, 1H), 4.20-4.24 (m, 1H), 3.83-3.86 (m, 1H), 3.65-3.71 (m, 1H), 2.96 (d, J=7.6 Hz, 3H), 2.89-2.94 (m, 1H), 2.69-2.74 (m, 1H).

Example 76. Synthesis of (Ex. 76)

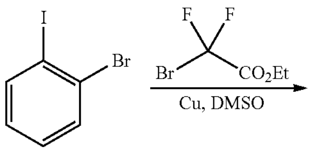

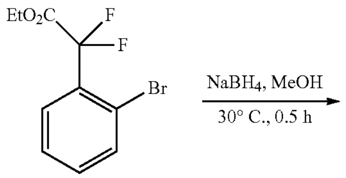

76a

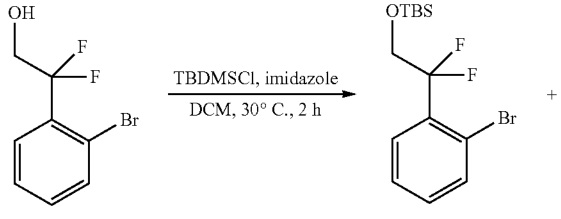

76b

76c

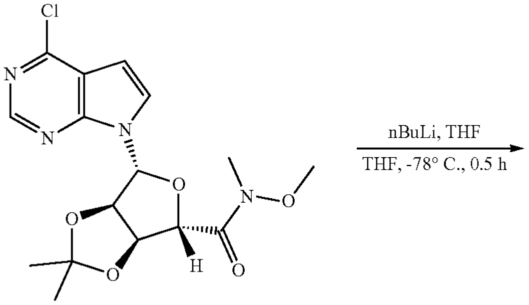

1Ad

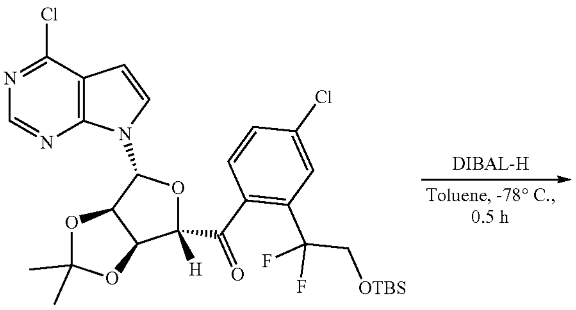

76d

-continued

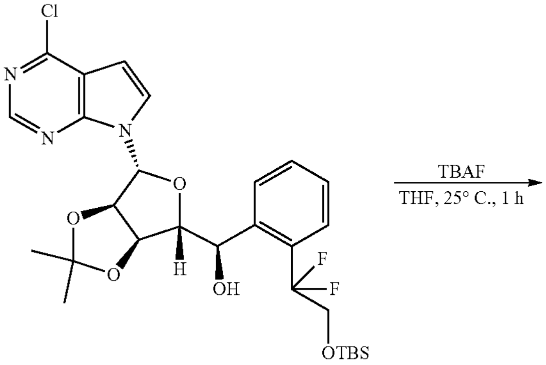

76e

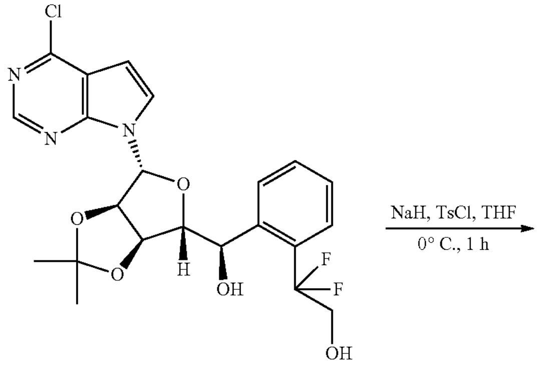

76f

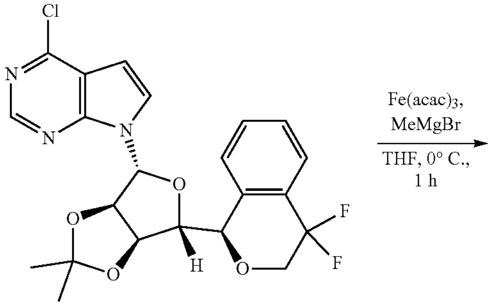

76g

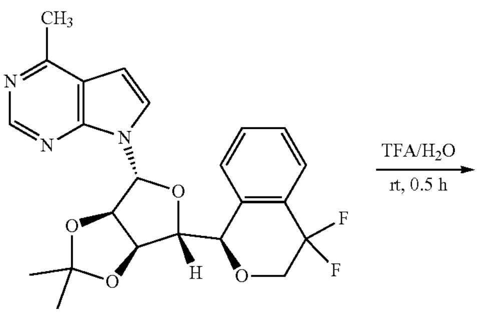

76h

-continued

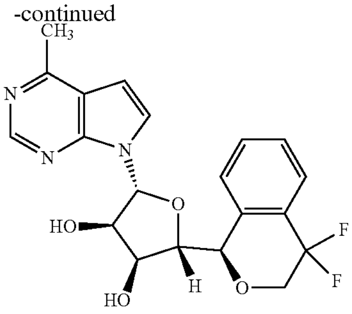

Ex. 76

Step 1. Synthesis of ethyl 2-(2-bromophenyl)-2,2-difluoro-acetate (76a)

To a solution of copper (898.6 mg, 14.14 mmol) in DMSO (10 mL) was added ethyl 2-bromo-2,2-difluoro-acetate (5739.98 mg, 28.28 mmol) and the mixture was stirred at rt under nitrogen. 1-bromo-2-iodo-benzene (2000 mg, 7.07 mmol) was added to the mixture 1 h later. After 16 h, added aqueous $NH_4Cl$ (50 mL) to the mixture and extracted with EA (50.0 mL×3). The organic phases were combined, washed with water (100 mL) and brine (100 mL), dried over $Na_2SO_4$, filtered and concentrated under vacuum. The residue was purified by flash column (PE:EA=40:1) to give 76a (750 mg, 2.66 mmol, 38% yield). 1H NMR (400 M Hz, $CDCl_3$): δ 7.75-7.73 (m, 1H), 7.65-7.62 (m, 1H), 7.46-7.42 (m, 1H), 7.38-7.34 (m, 1H), 4.36 (q, J=7.2 Hz, 2H), 1.32 (t, J=7.2 Hz, 3H).

Step 2. Synthesis of 2-(2-bromophenyl)-2,2-difluoro-ethanol (76b)

To a solution of 76a (5.8 g, 20.78 mmol) in methanol (50 mL) was added $NaBH_4$ (1.57 g, 41.57 mmol) at 0° C., and the reaction mixture was stirred at rt for 30 mins. TLC (PE:EA=10:1, $R_f$=0.1) showed the reaction was complete. The reaction was concentrated and HCl (1 M) was added. The mixture was extracted with EA (30.0 mL×3). The organic phases were combined, washed with water (50 mL) and brine (50 mL), dried over $Na_2SO_4$, filtered and concentrated. The residue was purified by flash column (PE: EA=10:1) to give 76b (5.1 g, 19.36 mmol, 93% yield) as an oil. 1H NMR (400 M Hz, $CDCl_3$): δ 7.67-7.633 (m, 2H), 7.40 (t, J=7.6 Hz, 1H), 7.33-7.26 (m, 1H), 4.21 (t, J=13.8 Hz, 2H).

Step 3. Synthesis of [2-(2-bromophenyl)-2,2-difluoro-ethoxy]-tert-butyl-dimethyl-silane (76c)

To a solution of 76b (5.1 g, 21.52 mmol) and imidazole (2.93 g, 43.03 mmol) in DCM (20 mL) was slowly added t-butylchlorodiphenylsilane (4.86 g, 32.27 mmol), and the reaction mixture was stirred for 2 h at rt. TLC (PE, $R_f$=0.7) showed a new spot and the SM was consumed. The solvent was removed in vacuo and the crude product was purified by column chromatography on silica gel (PE) to give 76c (6.2 g, 15.88 mmol, 74% yield) as white-off oil. 1H NMR (400 M Hz, $CDCl_3$): δ 7.67-7.633 (m, 2H), 7.39 (t, J=7.6 Hz, 1H), 7.32-7.29 (m, 1H), 4.23 (t, J=13.0 Hz, 2H), 0.82 (s, 9H), 0.0 (s, 6H).

Step 4. Synthesis of [2-[2-[tert-butyl(dimethyl)silyl]oxy-1,1-difluoro-ethyl]phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (76d)

To a solution of 76b (1.03 g, 2.95 mmol) in dry THE (10 mL) was added n-BuLi (1.5 mL, 2.4 mmol) at −78° C., and the mixture was stirred for 10 min under nitrogen. 1Ad (720 mg, 1.84 mmol) in dry THE (5 mL) was added and the mixture was stirred for 30 min at −78° C. TLC (PE:EA=10:1, starting material $R_f$=0.3, product $R_f$=0.4) showed the reaction was complete. The reaction was poured into dilute HCl (0.05 M), keeping the pH<8 during the process of quenching. The mixture was extracted with EA (200 mL×2), the combined organic layers were dried, concentrated and purified by silica gel column (PE:EA=100 to 10:1) to give 76d (610 mg, 1.02 mmol, 55% yield) as yellow oil. LCMS [M+H]: 594.3.

Step 5. Synthesis of (R)-[2-[2-[tert-butyl(dimethyl)silyl]oxy-1,1-difluoro-ethyl]phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (76e)

To a solution of 76d (610 mg, 1.03 mmol) in toluene (20 mL) was added diisobutylaluminum hydride (2.05 mL, 3.08 mmol) at −78° C. under nitrogen and the reaction mixture was stirred for 30 min at −78° C. The reaction mixture was diluted with saturated $NH_4Cl$ (aq) and the mixture was extracted with EA and washed with brine. The organic layer was dried with anhydrous $Na_2SO_4$ and the solvent was removed in vacuo to give 76e (600 mg, 0.93622 mmol, 91% yield) as a crude product which was used without further purification.

Step 6. Synthesis of 2,2-difluoro-2-[2-[(R)-hydroxy-[(3aR,4R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (76f)

To a solution of 76e (270 mg, 0.45 mmol) in THF (0.03 mL) was added TBAF (0.24 mL, 0.91 mmol) and the reaction mixture was stirred at rt for 1h. The reaction mixture was diluted with saturated $NH_4Cl$ solution (100 mL), the mixture was extracted with EA (50 mL×3), and the combined organics were washed with saturated NaCl (100 mL). The organics were dried with anhydrous $Na_2SO_4$ and the solvent was removed in vacuo. The residue was purified by silica gel chromatography (PE:EA=50:1 to 10:1) to give 76f (120 mg, 0.2291 mmol, 51% yield) as a solid. LCMS [M+H]: 482.3.

Step 7. Synthesis of 4-chloro-7-[(3aR,4R,6aR)-2,2-dimethyl-6-[(1R)-4,4-difluoroisochroman-1-yl]-3a,4,6,6a-tetrahydrofuro[3,4-d][1,3]dioxol-4-yl]pyrrolo[2,3-d]pyrimidine (76g)

To a solution of 76f (100 mg, 0.21 mmol) in THF (4 mL) was added NaH (33.2 mg, 0.83 mmol) and stirred for 10 min. TSCl (39.56 mg, 0.21 mmol) was added and the reaction was stirred for 1 h. The reaction mixture was poured into saturated $NH_4Cl$ solution, extracted with EA the organics were washed with saturated NaCl. The organic phase was dried over anhydrous $Na_2SO_4$ and the solvent was concentrated under reduced pressure to give a crude product which was purified by prep-TLC (PE:EA=5:1, $R_f$=0.3) to give 76g (50 mg, 0.10 mmol, 48% yield) as a white solid. LCMS [M+H]: 464.2.

Step 8. Synthesis of 4-methyl-7-[(3aR,4R,6R,6aR)-2,2-dimethyl-6-[(1R)-4,4-difluoroisochroman-1-yl]-3a,4,6,6a-tetrahydrofuro[3,4-d][1,3]dioxol-4-yl]pyrrolo[2,3-d]pyrimidine (76h)

To a solution of 76g (50 mg, 0.11 mmol) and ferric acetylacetonate (3.81 mg, 0.01 mmol) in THF (6 mL) was added methylmagnesium bromide, 3.2 M in MeTHF (0.36 mL, 1.08 mmol) at 0° C. under nitrogen. The reaction was stirred at rt for 1 hour. The mixture was poured into aqueous $NH_4Cl$ (30 mL) and extracted with EA (30.0 mL×3). The organic phases were combined, dried over $Na_2SO_4$, filtered and concentrated under vacuum. The residue was purified by flash column (PE:EA=8:1-PE:EA=3:1) to give 76h (45 mg, 0.10148 mmol, 94% yield). LCMS [M+H]: 444.3.

Step 9. Synthesis of (2R,3R,4S,5S)-2-(4-methylpyrrolo[2,3-d]pyrimidin-7-yl)-5-[(1R)-4,4-difluoroisochroman-1-yl]tetrahydrofuran-3,4-diol (Ex. 76)

To a solution of 76h (45 mg, 0.10 mmol) in water (1 mL) was added TFA (0.5 mL, 6.49 mmol) and the mixture was stirred at rt for 30 mins. The residue was purified by pre-HPLC, eluted with $CH_3CN$ in $H_2O$ (0.1% $NH_4OH$) from 5.0% to 95.0% to give Ex. 76 (8.58 mg, 0.021 mmol, 20.5% yield) as a white solid. LCMS [M+H]: 404.3. 1H NMR (400 MHz, DMSO-d6) δ 8.68 (s, 1H), 7.75-7.72 (m, 2H), 7.57-7.48 (m, 3H), 6.81 (d, J=3.6 Hz, 1H), 6.34 (d, J=8 Hz, 1H), 5.35 (d, J=6.8 Hz, 1H), 5.20 (d, J=4 Hz, 1H), 5.09 (m, 1H), 4.61 (d, J=3.2 Hz, 1H), 4.56-4.46 (m, 2H), 4.16-4.07 (m, 1H), 3.82 (t, J=4.4 Hz, 1H), 2.68 (s, 3H). 1H NMR (400 MHz, DMSO-d6+D2O) δ 8.66 (s, 1H), 7.74-7.71 (m, 2H), 7.55-7.46 (m, 3H), 6.81 (d, J=3.6 Hz, 1H), 6.32 (d, J=8 Hz, 1H), 5.08 (m, 1H), 4.60 (d, J=3.2 Hz, 1H), 4.55-4.46 (m, 2H), 4.14-4.04 (m, 1H), 3.80 (d, J=5.2 Hz, 1H), 2.66 (s, 3H).

Example 81. Synthesis of (2R,3R,4S,5S)-2-(4-aminopyrrolo[2,3-d]pyrimidin-7-yl)-5-[(1R)-7-chloro-1,5-dihydro-2,4-benzodioxepin-1-yl]tetrahydrofuran-3,4-diol (Ex. 81)

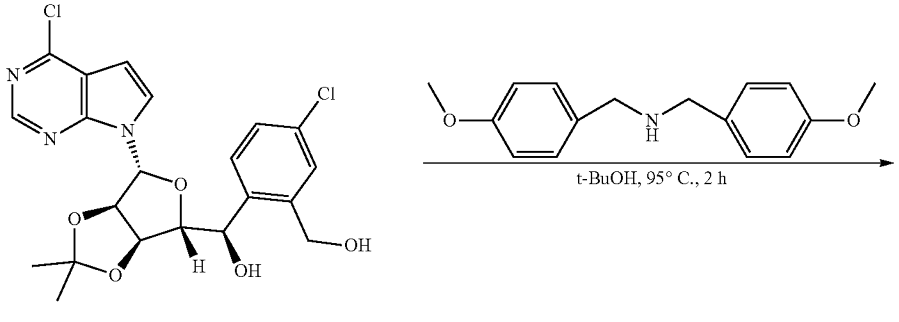

55e

-continued

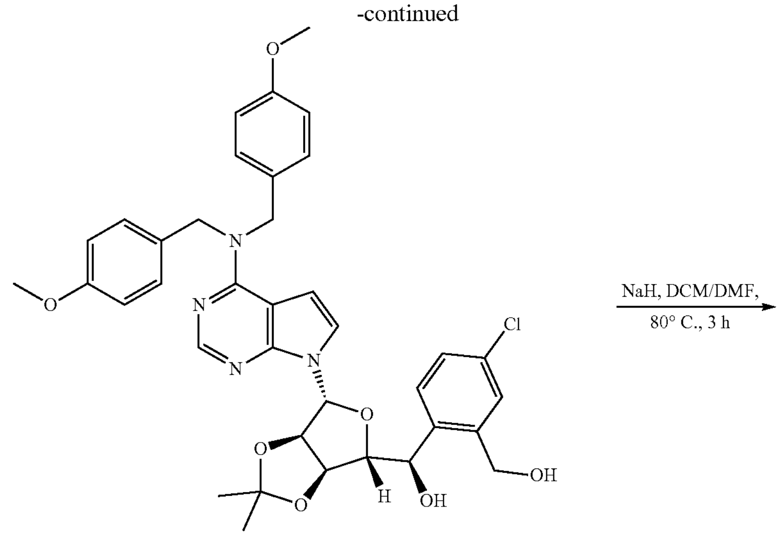

81a

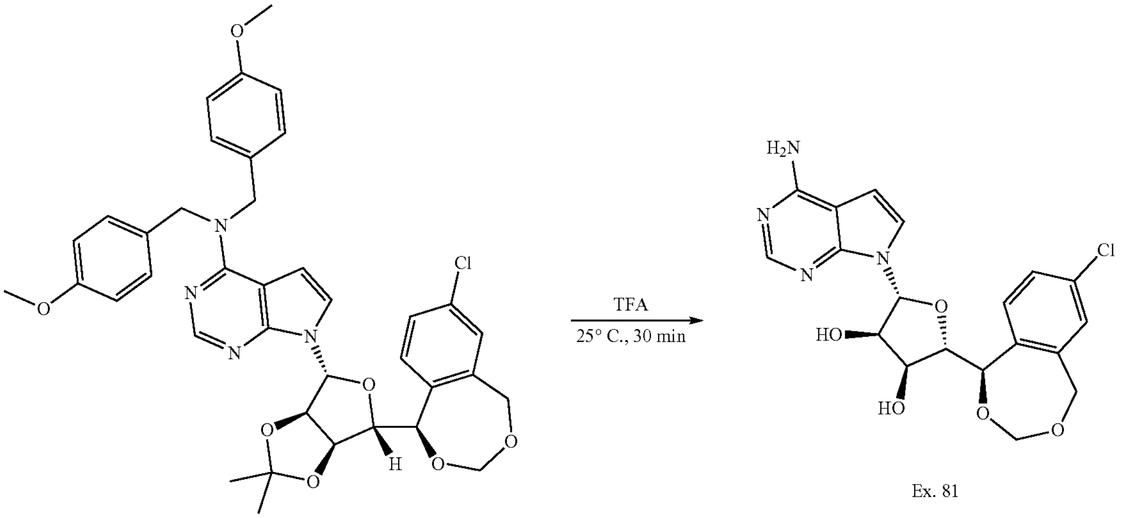

81b

Ex. 81

Step 1. Synthesis of (R)-[4-chloro-2-(hydroxymethyl)phenyl]-[(3aR,4R,6R,6aR)-4-[4-[bis[(4-methoxyphenyl)methyl]amino]pyrrolo[2,3-d]pyrimidin-7-yl]-2,2-dimethyl-3a,4,6,6a-tetrahydrofuro[3,4-d][1,3]dioxol-6-yl]methanol (81a)

A mixture of $K_2CO_3$ (292.98 mg, 2.12 mmol), (R)-[4-chloro-2-(hydroxymethyl)phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (55e, 300 mg, 0.64 mmol) and bis-(4-methoxybenzyl)amine (331 mg, 1.29 mmol) in tert-butanol (5 mL) was stirred at 95° C. for 2 h under $N_2$. LCMS showed the reaction was complete. The reaction was concentrated in vacuum to dryness and the residue was extracted with EtOAc (2×50 mL) and the organic layers were washed with water (2×10 mL), then brine (2×10 mL). The organics layers were dried with $MgSO_4$, filtered, and concentrated in vacuum. The crude product was purified by silica gel column chromatography (ethyl acetate:petroleum ether=1:1) to give (R)-[4-chloro-2-(hydroxymethyl)phenyl]-[(3aR,4R,6R,6aR)-4-[4-[bis[(4-methoxyphenyl)methyl]amino]pyrrolo[2,3-d]pyrimidin-7-yl]-2,2-dimethyl-3a,4,6,6a-tetrahydrofuro[3,4-d][1,3]dioxol-6-yl]methanol (81a, 80 mg, 0.10 mmol, 16% yield) as a white solid. LCMS [M+H]: 687.2.

Step 2. Synthesis of N,N-bis[(4-methoxyphenyl)methyl]-7-[(3aR,4R,6R,6aR)-2,2-dimethyl-6-[(1R)-7-chloro-1,5-dihydro-2,4-benzodioxepin-1-yl]-3a,4,6,6a-tetrahydrofuro[3,4-d][1,3]dioxol-4-yl]pyrrolo[2,3-d]pyrimidin-4-amine (81b)

To a solution of (R)-[4-chloro-2-(hydroxymethyl)phenyl]-[(3aR,4R,6R,6aR)-4-[4-[bis[(4-methoxyphenyl)methyl]amino]pyrrolo[2,3-d]pyrimidin-7-yl]-2,2-dimethyl-3a,4,6,6a-tetrahydrofuro[3,4-d][1,3]dioxol-6-yl]methanol (81a, 80 mg, 0.12 mmol) in DCM (1.2 mL) and DMF (2.5 mL) was added sodium hydride (28 mg, 1.16 mmol). The mixture was stirred at 80° C. for 2 h. The reaction mixture was quenched with $NH_4Cl$ (50 mL). The solvent was removed in vacuum to give N,N-bis[(4-methoxyphenyl)

methyl]-7-[(3aR,4R,6R,6aR)-2,2-dimethyl-6-[(1R)-7-chloro-1,5-dihydro-2,4-benzodioxepin-1-yl]-3a,4,6,6a-tetrahydrofuro[3,4-d][1,3]dioxol-4-yl]pyrrolo[2,3-d]pyrimidin-4-amine (81b, 90 mg, 0.10 mmol, 87% yield) as yellow oil. LCMS [M+H]: 699.3.

Step 3. Synthesis of (2R,3R,4S,5S)-2-(4-aminopyrrolo[2,3-d]pyrimidin-7-yl)-5-[(1R)-7-chloro-1,5-dihydro-2,4-benzodioxepin-1-yl]tetrahydrofuran-3,4-diol (Ex. 81)

To a solution of N,N-bis[(4-methoxyphenyl)methyl]-7-[(3aR,4R,6R,6aR)-2,2-dimethyl-6-[(1R)-7-chloro-1,5-dihydro-2,4-benzodioxepin-1-yl]-3a,4,6,6a-tetrahydrofuro[3,4-d][1,3]dioxol-4-yl]pyrrolo[2,3-d]pyrimidin-4-amine (81b, 90 mg, 0.13 mmol) in water (1 mL) was added 2,2,2-trifluoroacetic acid (0.74 mL, 0.74 mmol). The reaction mixture was stirred at 25° C. for 30 mins. $NH_3$° water was added until pH=7 and the mixture was concentrated in vacuum. The residue was purified by prep-HPLC, eluting with MeCN in water (0.1% $NH_3$° water) from 10% to 90% to give crude product. The crude product was further purified by prep-HPLC, eluted with MeCN in water (0.1% TFA) from 10% to 90% to give (2R,3R,4S,5S)-2-(4-aminopyrrolo[2,3-d]pyrimidin-7-yl)-5-[(1R)-7-chloro-1,5-dihydro-2,4-benzodioxepin-1-yl]tetrahydrofuran-3,4-diol (Ex. 81, 2.7 mg, 0.0063 mmol, 5% yield) as a white solid. LCMS [M+H]: 419.1. $^1$H NMR (400 MHz, DMSO-$d_6$+D2O) δ: 8.33 (s, 1H), 7.51 (d, J=3.6, 1H), 7.45 (s, 1H), 7.42 (d, J=1.6, 2H), 6.94 (d, J=3.2, 1H), 6.32 (d, J=8.0, 1H), 5.33 (d, J=6, 1H), 5.07-5.03 (m, 2H), 4.97 (d, J=1.2, 1H), 4.83 (d, J=14.4, 1H), 4.61 (d, J=4.8, 1H), 4.54-4.51 (m, 1H), 4.17 (d, J=4.8, 1H).

Example 82. Synthesis of (1R)-6-chloro-1-[(2S,3S,4R,5R)-5-(4-aminopyrrolo[2,3-d]pyrimidin-7-yl)-3,4-dihydroxy-tetrahydrofuran-2-yl]isochroman-3-one; 2,2,2-trifluoroacetic Acid (Ex. 82)

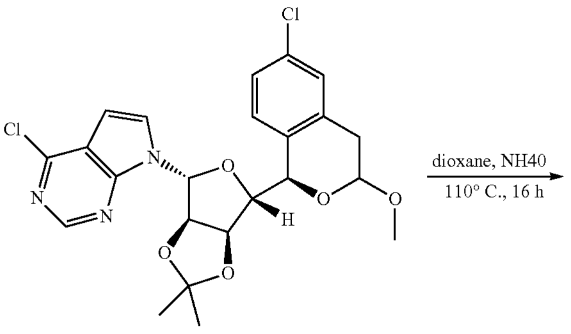

46f

-continued

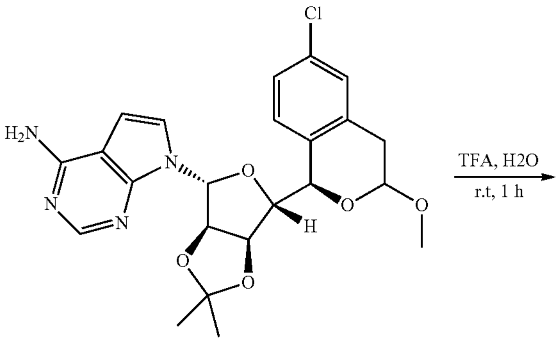

82a

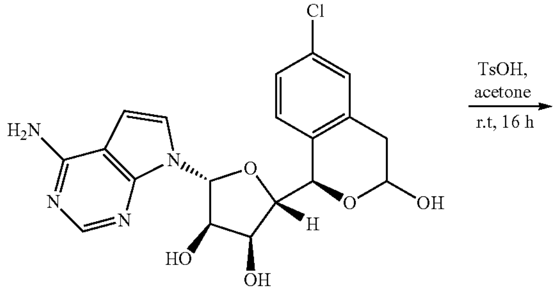

82b

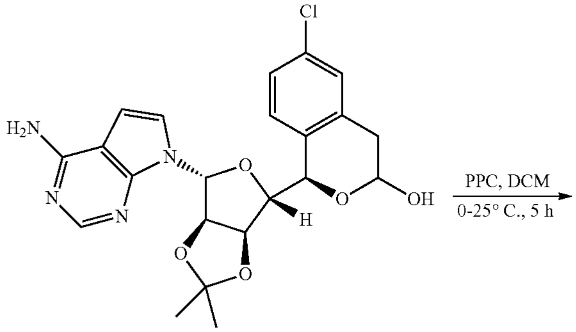

82c

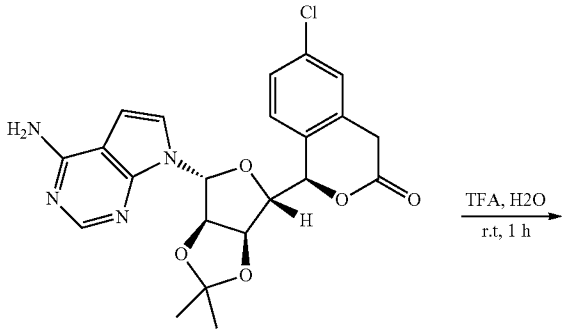

82d

-continued

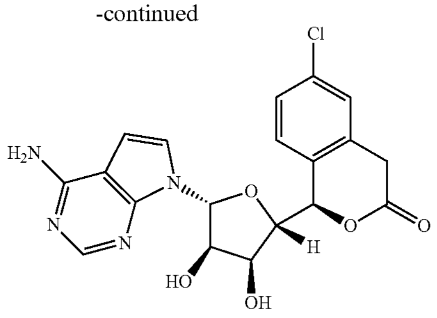

Ex. 82

Step 1. Synthesis of 7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidin-4-amine (82a)

To a mixture of 4-chloro-7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidine (46f, 700 mg, 1.42 mmol) in 1,4-dioxane (8 mL), ammonium hydroxide (0.03 mL, 14.22 mmol) was added. The mixture was stirred at 120° C. overnight. TLC (petroleum ether:ethyl acetate=5:1, $R_f$=0.5) and LCMS showed the reaction was complete. The reaction mixture was poured into water (30 mL) and extracted with DCM (50 mL×3). The organic layers were washed with saturated NaCl (100 mL), dried over $Na_2SO_4$, filtered, concentrated in vacuum to give the crude product which was purified by column chromatography on silica gel with petroleum ether:ethyl acetate=7:1 to give 7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidin-4-amine (82a, 460 mg, 0.97 mmol, 68% yield) as a yellow solid. LCMS [M+H]: 458.1.

Step 2. Synthesis of (2R,3R,4S,5S)-2-(4-aminopyrrolo[2,3-d]pyrimidin-7-yl)-5-[(1R)-6-chloro-3-hydroxy-isochroman-1-yl]tetrahydrofuran-3,4-diol (82b)

To a mixture of 7-[(3aR,4R,6R,6aR)-2,2-dimethyl-6-[(1R)-6-chloro-3-methoxy-isochroman-1-yl]-3a,4,6,6a-tetrahydrofuro[3,4-d][1,3]dioxol-4-yl]pyrrolo[2,3-d]pyrimidin-4-amine (82a, 460 mg, 0.97 mmol) in water (5 mL) was added trifluoroacetic acid (177 mg, 1.56 mmol). The reaction mixture was stirred at 25° C. for 1 h. TLC (petroleum ether:ethyl acetate=3:1, $R_f$=0.3) and LCMS showed the reaction was complete. The reaction was neutralized with $NaHCO_3$ and purified by column chromatography on silica gel with petroleum ether:ethyl acetate=7:1 to give the crude product which was further purified by prep-HPLC, eluted with $CH_3CN$ in water (0.1% $NH_3$/water) from 10% to 95%) to give (2R,3R,4S,5S)-2-(4-aminopyrrolo[2,3-d]pyrimidin-7-yl)-5-[(1R)-6-chloro-3-hydroxy-isochroman-1-yl]tetrahydrofuran-3,4-diol (82b, 50 mg, 0.11 mmol, 12% yield) as an off-white solid. LCMS [M+H]: 419.1.

Step 3. Synthesis of (1R)-6-chloro-1-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]isochroman-3-ol (82c)

To a mixture of (2R,3R,4S,5S)-2-(4-aminopyrrolo[2,3-d]pyrimidin-7-yl)-5-[(1R)-6-chloro-3-hydroxy-isochroman-1-yl]tetrahydrofuran-3,4-diol (82b, 230.5 mg, 0.55 mmol) in acetone (10 mL), TsOH (38 mg, 0.22 mmol) was added at 0° C. The reaction mixture was stirred at 25° C. for 3 h. TLC (petroleum ether:ethyl acetate=5:1, $R_f$=0.3) and LCMS showed the reaction was complete. The reaction mixture was poured into water (10 mL) and extracted with DCM (10 mL×3). The organic layers were washed with saturated NaCl (100 mL), dried over $Na_2SO_4$, filtered, and concentrated in vacuum. The crude product was purified by column chromatography on silica gel with petroleum ether:ethyl acetate=7:1) to give (1R)-6-chloro-1-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]isochroman-3-ol (82c, 180 mg, 0.32 mmol, 58% yield) as a white solid. LCMS [M+H]: 458.1.

Step 4. Synthesis of 6-chloro-1-[(3aR,4R,6R,6aR)-4-(4-aminopyrrolo-[2,3-d]pyrimidin-7-yl)-2,2-dimethyl-3a,4,6,6a-tetrahydrofuro[3,4-d][1,3]dioxol-6-yl]isochroman-3-one (82d)

To a mixture of 6-chloro-1-[(3aR,4R,6R,6aR)-4-(4-aminopyrrolo[2,3-d]pyrimidin-7-yl)-2,2-dimethyl-3a,4,6,6a-tetrahydrofuro[3,4-d][1,3]dioxol-6-yl]isochroman-3-ol (82c, 44 mg, 0.10 mmol) in DCM (10 mL) was added PCC (0.05 mL, 0.29 mmol) at 0° C. The mixture was stirred at 0° C. for 30 min, then warmed to 25° C. until the reaction was complete. The reaction mixture was poured into water (10 mL) and extracted with DCM (2×10 mL). The organics were concentrated in vacuum to give 6-chloro-1-[(3aR,4R,6R,6aR)-4-(4-aminopyrrolo-[2,3-d]pyrimidin-7-yl)-2,2-dimethyl-3a,4,6,6a-tetrahydrofuro[3,4-d][1,3]dioxol-6-yl]isochroman-3-one (82d, 35 mg, 0.076 mmol, 79.5% yield) as a white solid. The crude product was used without further purification in the next step. LCMS [M+H]: 457.1.

Step 5. Synthesis of (1R)-6-chloro-1-[(2S,3S,4R,5R)-5-(4-aminopyrrolo[2,3-d]pyrimidin-7-yl)-3,4-dihydroxy-tetrahydrofuran-2-yl]isochroman-3-one; 2,2,2-trifluoroacetic acid (Ex. 82)

To a mixture of (1R)-6-chloro-1-[(3aR,4R,6R,6aR)-4-(4-aminopyrrolo-[2,3-d]pyrimidin-7-yl)-2,2-dimethyl-3a,4,6,6a-tetrahydrofuro[3,4-d][1,3]dioxol-6-yl]isochroman-3-one (82d, 35 mg, 0.08 mmol) in water (2 mL) was added trifluoroacetic acid (14 mg, 0.12 mmol) and the mixture was stirred at 25° C. for 1h. TLC (petroleum ether:ethyl acetate=3:1, $R_f$=0.3) and LCMS showed the reaction was complete. The reaction was neutralized with $NaHCO_3$ and extracted with DCM (3×3 mL), the organics were washed with saturated NaCl (20 mL), dried over $Na_2SO_4$, filtered, concentrated in vacuum. The crude product was purified by column chromatography on silica gel with petroleum ether: ethyl acetate=7:1 and further purified by prep-HPLC, eluted with $CH_3CN$ in water (0.1% TFA) from 10% to 95% to give (1R)-6-chloro-1-[(2S,3S,4R,5R)-5-(4-aminopyrrolo[2,3-d]pyrimidin-7-yl)-3,4-dihydroxy-tetrahydrofuran-2-yl]isochroman-3-one; 2,2,2-trifluoroacetic acid (Ex. 82, 3 mg, 0.0052 mmol, 7% yield) as a white solid. LCMS [M+H]: 417.1. $^1$H NMR (400 MHz, DMSO-$d_6$) δ: 8.50-8.64 (m, 2H), 8.30 (s, 1H), 7.30-7.44 (m, 4H), 6.91 (s, 1H), 6.10 (s, 1H), 5.83 (s, 1H), 5.55-5.67 (m, 2H), 4.37-4.41 (m, 3H), 3.74 (m, 2H). $^1$H NMR (400 MHz, DMSO-$d_6$+D2O) δ 8.30 (s, 1H), 7.31-7.42 (m, 4H), 6.93 (s, 1H), 6.10 (d, J=4 Hz, 1H), 5.83 (s, 1H), 4.38-4.43 (m, 3H), 3.74 (m, 2H).

Example 83. Synthesis of (2R,3R,4S,5S)-2-(4-methylpyrrolo[2,3-d]pyrimidin-7-yl)-5-[(1R)-6-chloro-5-fluoro-isochroman-1-yl]tetrahydrofuran-3,4-diol (Ex. 83)
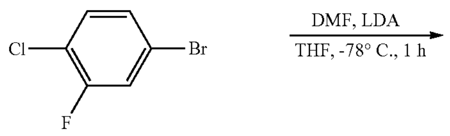
83a
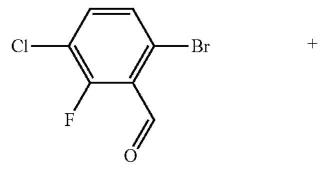
83b
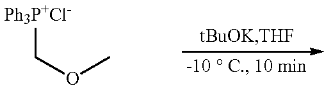
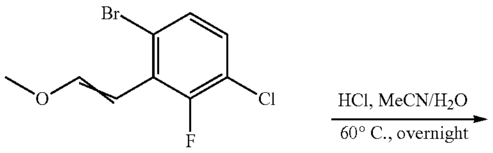
83c
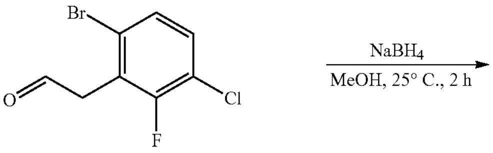
83d
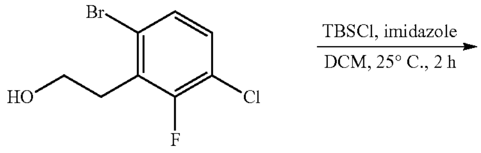
83e
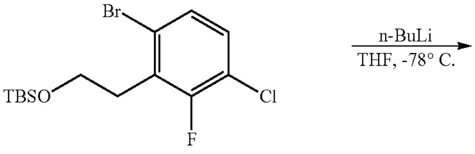
83f
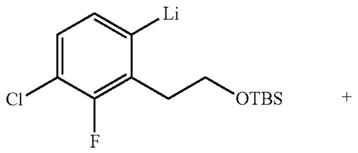
-continued
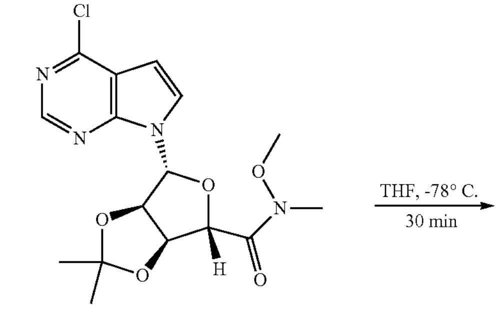
1Ad
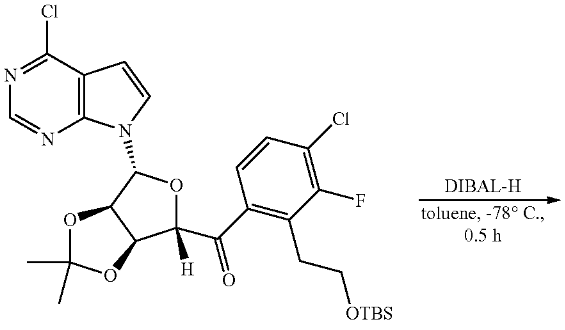
83g
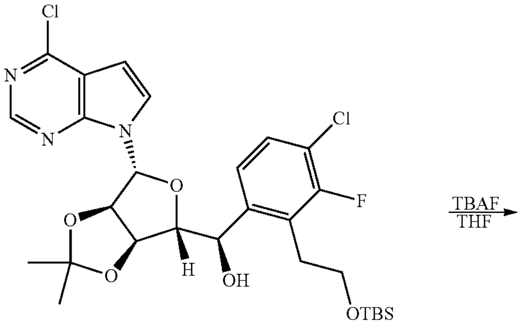
83h
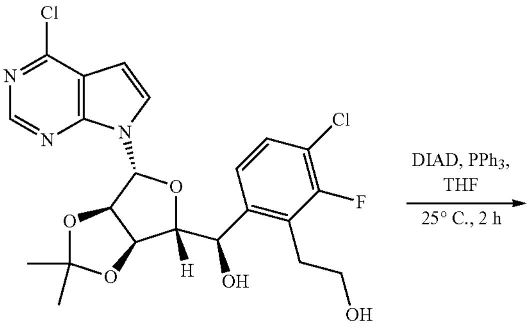
83i -continued

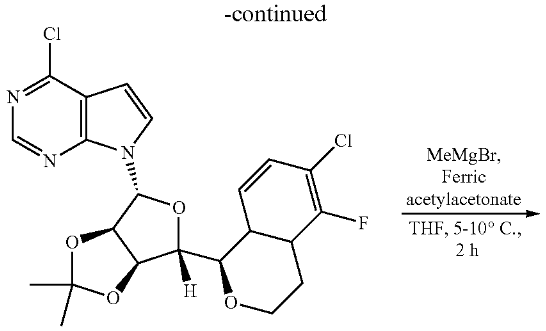

83j

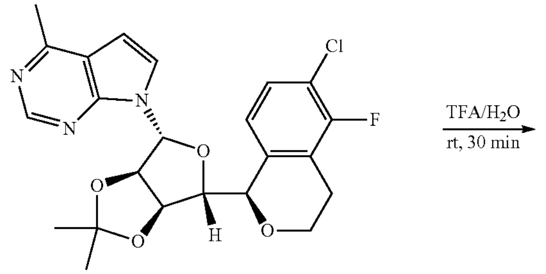

83k

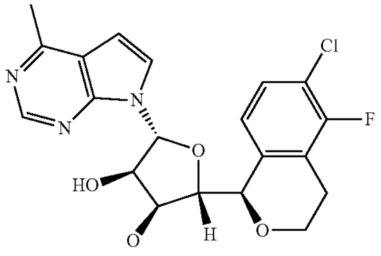

Ex. 83

Step 1. Synthesis of 6-bromo-3-chloro-2-fluorobenzaldehyde (83b)

To a solution of 4-bromo-1-chloro-2-fluoro-benzene (83a, 10 g, 47.75 mmol) in THF (60 mL) was added LDA (30 mL, 57.3 mmol) at −78° C. The reaction mixture was stirred at −78° C. for 1 h, then DMF (7.4 mL, 95.5 mmol) was added to the mixture and the reaction was stirred at −78° C. for 1h. The reaction was quenched with $NH_4Cl$ (aq, 100 mL) and water (100 mL). The aqueous layer was extracted with ethyl acetate (3×300 mL). The organic layers were concentrated in vacuum to give the crude product which was purified by silica gel column chromatography, eluted with petroleum ether:ethyl acetate=10:1 to give 6-bromo-3-chloro-2-fluorobenzaldehyde (83b, 6.1 g, 25.69 mmol, 54% yield) as a yellow oil. $^1$H NMR (400 MHz, $CDCl_3$) 10.39 (s, 1H), 7.86 (s, 1H), 7.56 (dd, J=8 Hz, 1H).

Step 2. Synthesis of 1-bromo-4-chloro-3-fluoro-2-[(E)-2-methoxyvinyl]benzene (83c)

To a solution of (methoxymethyl)triphenylphosphonium chloride (83b, 18.2 g, 53.06 mmol) in THF (60 mL) was added potassium t-butoxide 1.0 M in THF (5.67 g, 50.54 mmol) at −10° C. The reaction was stirred at −10° C. for 10 mins. The reaction was diluted with water (150 mL) and extracted with ethyl acetate (150 mL). The organic layer was concentrated in vacuum and the residue was purified by silica gel column chromatography, eluted with petroleum ether:ethyl acetate=10:1 to give 1-bromo-4-chloro-3-fluoro-2-[(E)-2-methoxyvinyl]benzene (83c, 4.50 g, 16.1 mmol, 64% yield) as a white solid. $^1$H NMR (400 MHz, DMSO-$d_6$) 7.64 (s, 1H), 7.51 (dd, J=10.8 Hz, 1H), 7.24 (dd, J=13.2 Hz, 1H), 5.73 (d, J=13.2 Hz, 1H), 3.71 (s, 3H).

Step 3. Synthesis of 2-(6-bromo-3-chloro-2-fluoro-phenyl)acetaldehyde (83d

To a solution of 1-bromo-4-chloro-3-fluoro-2-[(E)-2-methoxyvinyl]benzene (83c, 4.5 g, 16.95 mmol) in acetone (45 mL) was added HCl (1.86 g, 50.85 mmol) and the mixture was stirred at 60° C. overnight. TLC (petroleum ether) showed the reaction was complete. The reaction mixture was concentrated in vacuum and extracted with ethyl acetate (50 mL). The organic layer was concentrated in vacuum to afford 2-(6-bromo-3-chloro-2-fluoro-phenyl)acetaldehyde (83d, 4.0 g, 14.32 mmol, 84.5% yield) as a yellow solid. $^1$H NMR (400 MHz, DMSO-$d_6$) 9.72 (s, 1H), 7.71 (s, 1H), 7.58 (d, J=11.2 Hz, 1H), 4.02 (d, J=8.4 Hz, 2H).

Step 4. Synthesis of 2-(6-bromo-3-chloro-2-fluoro-phenyl)ethanol (83e)

To a solution of 2-(6-bromo-3-chloro-2-fluoro-phenyl) acetaldehyde (83d, 3.3 g, 13.12 mmol) in methanol (30 mL) was added sodium borohydride (1.5 g, 39.37 mmol) at 0° C. The reaction mixture was stirred at rt. for 1 h. TLC (petroleum ether) showed the reaction was complete. The mixture was concentrated in vacuum and the residue was extracted with ethyl acetate (50 mL), washed with brine (50 mL) and the organic layer was concentrated in vacuum to obtain 2-(6-bromo-3-chloro-2-fluoro-phenyl)ethanol (83e, 3.20 g, 11.99 mmol, 91% yield) as a yellow oil. $^1$H NMR (400 MHz, DMSO-$d_6$) 7.62 (s, 1H), 7.48 (dd, J=9.2 Hz, 1H), 4.85 (t, J=5.6 Hz, 1H), 7.52 (dd, J=12.8 Hz, 2H), 2.88 (dd, J=7.2 Hz, 2H).

Step 5. Synthesis of tert-butyl-[2-(3-chloro-2,6-difluoro-phenyl)ethoxy]-dimethyl-silane (83f)

To a solution of 2-(3-chloro-2,6-difluoro-phenyl)ethanol (83e, 3.20 g, 16.62 mmol) in DCM (30 mL) was added tert-butyldimethylchlorosilane (3.01 g, 19.94 mmol) and imidazole (2.26 g, 33.23 mmol). The reaction was stirred at 25° C. for 2 h. The reaction mixture was concentrated in vacuum and the residue was extracted with ethyl acetate (3×50 mL) and washed with brine (3×50 mL). The organic layers were concentrated in vacuum to give the crude product which was purified by silica gel column chromatography, to yield tert-butyl-[2-(3-chloro-2,6-difluoro-phenyl)ethoxy]-dimethyl-silane (83f, 3.9 g, 12.07 mmol, 73% yield) as an colorless oil. LCMS [M+H]: 306.8.

Step 6. Synthesis of [2-[2-[tert-butyl(dimethyl)silyl]oxyethyl]-4-chloro-3-fluoro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (83g)

To a solution of 2-(6-bromo-3-chloro-2-fluoro-phenyl) ethoxy-tert-butyl-dimethyl-silane (83f, 3074 mg, 8.36 mmol) in THF (20 mL) was added n-BuLi (535.5 mg, 8.36 mmol) at −78° C. The mixture was stirred for 10 min under $N_2$. (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1Ad, 1.6 g, 4.18 mmol) in THF (10 mL) was added. The mixture was stirred for 30 min at −78° C. TLC (petroleum ether:ethyl acetate=10:1) showed the reaction was complete. The reaction was added to dilute HCl (0.05 mol/L) and kept the pH<8 during the process of quenching. The mixture was extracted with ethyl acetate (2×200 mL), the combined organic layers were dried, concentrated in vacuum and purified by silica gel column chromatography (petroleum ether:ethyl acetate=100% to 10:1) to give [2-[2-[tert-butyl(dimethyl)silyl]oxyethyl]-4-chloro-3-fluoro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (83g, 1.2 g, 1.87 mmol, 45% yield) as a yellow oil. LCMS [M+H]: 610.1.

Step 7. Synthesis of (R)-[2-[2-[tert-butyl(dimethyl)silyl]oxyethyl]-4-chloro-3-fluoro-phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (83h)

To a solution of [2-[2-[tert-butyl(dimethyl)silyl]oxyethyl]-4-chloro-3-fluoro-phenyl]-[(3aR,6S,6aS)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanone (83g, 1.1 g, 1.8 mmol) in toluene (15 mL) was added diisobutylaluminum hydride (3.6 mL, 5.4 mmol) at −78° C. under $N_2$. The reaction mixture was stirred at −78° C. for 30 min. Water (50 mL) was added, and the mixture was extracted with ethyl acetate (100 mL) and washed with saturated NaCl (2×50 mL). The organic layers were dried over anhydrous $Na_2SO_4$ and the solvent was removed in vacuum to give (R)-[2-[2-[tert-butyl(dimethyl)silyl]oxyethyl]-4-chloro-3-fluoro-phenyl]-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methanol (83h, 1.0 g, 1.55 mmol, 86% yield) which was used for the next step directly. LCMS [M+H]: 612.2.

Step 8. Synthesis of 2-[3-chloro-2-fluoro-6-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (83i)

To a solution of (R)-[2-[2-[tert-butyl(dimethyl)silyl]oxyethyl]-4-chloro-3-fluoro-phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (83h, 1.0 g, 1.63 mmol) in THF (3 mL) was added TBAF (0.85 mL, 3.26 mmol). The reaction mixture was stirred at rt for 1 h. TLC (petroleum ether:ethyl acetate=10:1) showed the reaction was complete. The mixture was concentrated in vacuum and purified by silica gel column chromatography (petroleum ether:ethyl acetate=50:1 to 10:1) to give 2-[3-chloro-2-fluoro-6-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (83i, 670 mg, 1.30 mmol, 80% yield) as a white solid. LCMS [M+H]: 498.1.

Step 9. Synthesis of 4-chloro-7-[(3aR,4R,6R,6aR)-2,2-dimethyl-6-[(1R)-6-chloro-5-fluoro-isochroman-1-yl]-3a,4,6,6a-tetrahydrofuro[3,4-d][1,3]dioxol-4-yl]pyrrolo[2,3-d]pyrimidine (83j)

To a solution of 2-[3-chloro-2-fluoro-6-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (83i, 500 mg, 1 mmol) in THF (5 mL) was added $PPh_3$ (526 mg, 2.01 mmol), DIAD (0.56 mL, 2.01 mmol) under Ar. The reaction mixture was stirred at 25° C. for 1 h. The mixture was concentrated in vacuum and the residue was purified by silica gel column chromatography to yield 4-chloro-7-[(3aR,4R,6R,6aR)-2,2-dimethyl-6-[(1R)-6-chloro-5-fluoro-isochroman-1-yl]-3a,4,6,6a-tetrahydrofuro[3,4-d][1,3]dioxol-4-yl]pyrrolo[2,3-d]pyrimidine (83j, 390 mg, 0.77 mmol, 77% yield). LCMS [M+H]: 480.1.

Step 10. Synthesis of 4-methyl-7-[(3aR,4R,6R,6aR)-2,2-dimethyl-6-[(1R)-6-chloro-5-fluoro-isochroman-1-yl]-3a,4,6,6a-tetrahydrofuro[3,4-d][1,3]dioxol-4-yl]pyrrolo[2,3-d]pyrimidine (83k)

To a solution of 4-chloro-7-[(3aR,4R,6R,6aR)-2,2-dimethyl-6-[(1R)-6-chloro-5-fluoro-isochroman-1-yl]-3a,4,6,6a-tetrahydrofuro[3,4-d][1,3]dioxol-4-yl]pyrrolo[2,3-d]pyrimidine (83j, 100 mg, 0.21 mmol) in THF (2 mL) was added ferric acetylacetonate (7.35 mg, 0.02 mmol) and methylmagnesium bromide (0.21 mL, 0.63 mmol) dropwise under $N_2$. The reaction was stirred at rt for 30 min. The mixture was extracted with ethyl acetate (3×10 mL) and washed with water (2×10 mL). The organic layer was concentrated in vacuum to yield 4-methyl-7-[(3aR,4R,6R,6aR)-2,2-dimethyl-6-[(1R)-6-chloro-5-fluoro-isochroman-1-yl]-3a,4,6,6a-tetrahydrofuro[3,4-d][1,3]dioxol-4-yl]pyrrolo[2,3-d]pyrimidine (83k, 90 mg, 0.19 mmol, 89% yield) as a yellow oil. LCMS [M+H]: 460.2.

Step 11. Synthesis of (2R,3R,4S,5S)-2-(4-methylpyrrolo[2,3-d]pyrimidin-7-yl)-5-[(1R)-6-chloro-5-fluoro-isochroman-1-yl]tetrahydrofuran-3,4-diol (Ex. 83)

To a solution of 4-methyl-7-[(3aR,4R,6R,6aR)-2,2-dimethyl-6-[(1R)-6-chloro-5-fluoro-isochroman-1-yl]-3a,4,6,6a-tetrahydrofuro[3,4-d][1,3]dioxol-4-yl]pyrrolo[2,3-d]pyrimidine (83k, 100 mg, 0.22 mmol) in water (2 mL) was added TFA (1.1 mL, 12.34 mmol). The mixture was stirred at rt for 30 mins. The residue was purified by pre-HPLC, eluted with $CH_3CN$ in water (0.1% $NH_4OH$) from 5% to 95% to give (2R,3R,4S,5S)-2-(4-methylpyrrolo[2,3-d]pyrimidin-7-yl)-5-[(1R)-6-chloro-5-fluoro-isochroman-1-yl]tetrahydrofuran-3,4-diol (Ex. 83, 18 mg, 0.042 mmol, 19% yield) as a white solid. $^1H$ NMR (400 MHz, DMSO-$d_6$) 8.67 (s, 1H), 7.78 (d, J=4 Hz, 1H), 7.32-7.28 (m, 2H), 6.82 (d, J=4 Hz, 1H), 6.31 (d, J=7.6 Hz, 1H), 5.31 (d, J=6.8 Hz, 1H), 5.20 (d, J=4 Hz, 1H), 4.91 (d, J=7.2 Hz, 1H), 4.52-4.46 (m, 2H), 4.32 (s, 1H), 3.88 (t, J=4 Hz, 1H), 3.69 (s, 1H), 2.73 (s, 2H), 2.67 (d, J=8 Hz, 3H). $^1H$ NMR (400 MHz, DMSO-$d_6$+D2O) 8.67 (s, 1H), 7.78 (d, J=4 Hz, 1H), 7.32-7.28 (m, 2H), 6.82 (d, J=4 Hz, 1H), 6.31 (d, J=7.6 Hz, 1H), 4.91 (d, J=7.2 Hz, 1H), 4.52-4.46 (m, 2H), 4.32 (s, 1H), 3.88 (t, J=4 Hz, 1H), 3.69 (s, 1H), 2.73 (s, 2H), 2.67 (d, J=8 Hz, 3H).

Example 86. Synthesis of (2R,3R,4S,5S)-2-(4-amino-5-fluoro-pyrrolo[2,3-d]pyrimidin-7-yl)-5-[(1R)-6-chloroisochroman-1-yl]tetrahydrofuran-3,4-diol (Ex. 86)

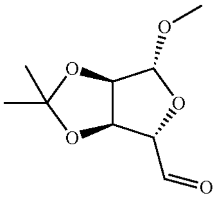

+

86a

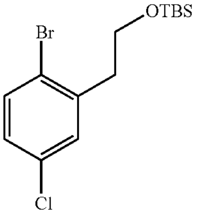

n-BuLi
THF, -78° C.
10 min

22b

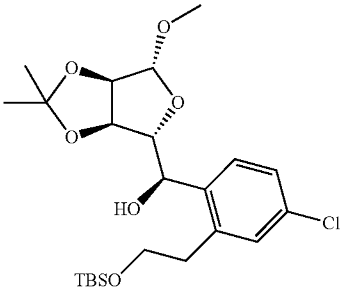

TBAF, THF
rt, 1 h

86b

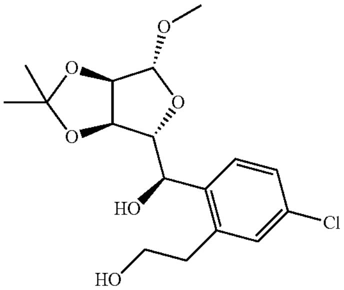

$PPh_3$, DIAD
THF, 25° C., 3 h

86c

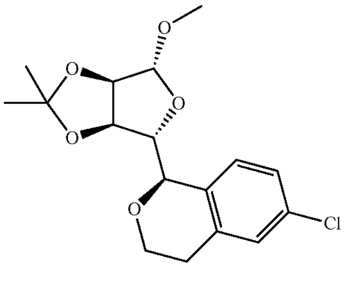

TFA/$H_2O$
40° C., 18 h

86d

-continued

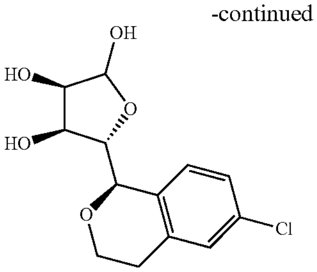

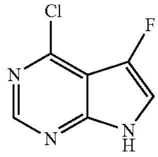

86f $PBu_3$, DIAD, THF,
25° C., 3 h

86e

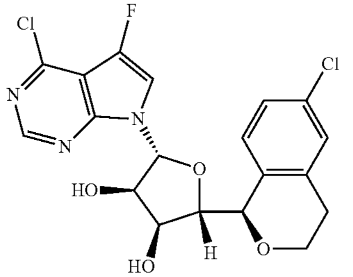

$NH_3$•$H_2O$,
1,4-dioxane
120° C., 18 h

86g

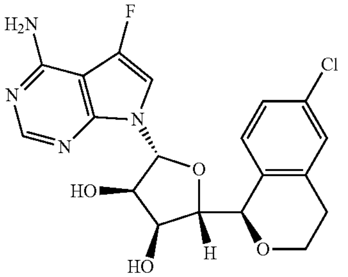

Ex. 86

Step 1. Synthesis of (R)-[2-[2-[tert-butyl(dimethyl) silyl]oxyethyl]-4-chloro-phenyl]-[(3aR,4R,6R,6aR)-4-methoxy-2,2-dimethyl-3a,4,6,6 atetrahydrofuro[3,4-d][1,3]dioxol-6-yl]methanol (86b)

To a solution of 2-(2-bromo-5-chloro-phenyl)ethoxy-tert-butyl-dimethyl-silane (22b, 23.6 g, 68 mmol) in dry THF (50 mL) was added n-BuLi (34 mL, 54.4 mmol) at −78° C. The reaction mixture was stirred at −78° C. for 10 min under $N_2$. (3aR,4R,6S,6aR)-4-methoxy-2,2-dimethyl-3a,4,6,6a-tetra-hydrofuro[3,4-d][1,3]dioxole-6-carbaldehyde (86a, 5.5 g, 27.2 mmol) in dry THF (10 mL) was added to the mixture. The mixture was stirred for 5 min at −78° C. The reaction was added into dilute HCl (300 mL, 0.6 M), and maintaining pH=6. The mixture was concentrated in vacuum to give the crude product which was purified was purified by silica gel column chromatography, eluting with petroleum ether:ethyl acetate=5:1 to give (R)-[2-[2-[tert-butyl(dimethyl)silyl]oxy-ethyl]-4-chloro-phenyl]-[(3aR,4R,6R,6aR)-4-methoxy-2,2-dimethyl-3a,4,6,6 atetrahydrofuro[3,4-d][1,3]dioxol-6-yl] methanol (86b, 5.8 g, 11.6 mmol, 43% yield) as a yellow oil. $^1H$ NMR (400 MHz, $CDCl_3$) δ 7.54 (d, J=8.4 Hz, 1H), 7.22-7.29 (m, 2H), 5.36 (s, 2H), 4.95 (d, J=6.0 Hz, 1H), 4.68 (d, J=5.6 Hz, 1H), 4.50 (s, 1H), 4.31 (s, 1H), 3.83-3.90 (m, 2H), 3.43 (s, 3H), 2.78-2.99 (m, 2H), 1.47 (s, 3H), 1.30 (s, 3H), 0.87 (s, 9H), 0.02 (s, 6H).

Step 2. Synthesis 2-[5-chloro-2-[(R)-hydroxy-[(3aR,4R,6R,6aR)-4-methoxy-2,2-dimethyl-3a,4,6,6a-tetrahydrofuro[3,4-d][1,3]dioxol-6-yl]methyl]phenyl] ethanol (86c)

To a solution of (R)-[2-[2-[tert-butyl(dimethyl)silyl]oxyethyl]-4-chloro-phenyl]-[(3aR,4R,6R,6aR)-4-methoxy-2,2-dimethyl-3a,4,6,6a-tetrahydrofuro[3,4-d][1,3]dioxol-6-yl] methanol (86b, 4.8 g, 10.1 mmol) in THF (10 mL) was added tetrabutylammonium fluoride (10.1 mL, 10.1 mmol) at rt. The mixture was stirred at rt for 1 h. The mixture was poured into 50 ml of $NH_4Cl$ (aq) and extracted with ethyl acetate (2×50 mL). The organic layers were concentrated in vacuum to give the crude product which was purified by silica gel column chromatography, eluting with petroleum ether to petroleum ether:ethyl acetate=5:1) to give 2-[5-chloro-2-[(R)-hydroxy-[(3aR,4R,6R,6aR)-4-methoxy-2,2-dimethyl-3a,4,6,6a-tetrahydrofuro[3,4-d][1,3]dioxol-6-yl] methyl]phenyl]ethanol (86c, 3.8 g, 9.5 mmol, 94% yield) as a colorless oil. $^1$H NMR (400 MHz, $CDCl_3$) δ 7.54 (d, J=8.4 Hz, 1H), 7.22-7.29 (m, 2H), 5.01 (s, 2H), 4.95 (d, J=6.0 Hz, 1H), 4.65 (d, J=6.0 Hz, 1H), 4.55 (s, 1H), 4.33 (br, 1H), 3.85-3.96 (m, 2H), 3.41 (s, 3H), 2.78-3.06 (m, 2H), 1.47 (s, 3H), 1.30 (s, 3H).

Step 3. Synthesis of (1R)-6-chloro-1-[(3aR,4R,6R,6aR)-4-methoxy-2,2-dimethyl-3a,4,6,6a-tetrahydrofuro[3,4-d][1,3]dioxol-6-yl]isochromane (86d)

To a solution of 2-[5-chloro-2-[(R)-hydroxy-[(3aR,4R,6R,6aR)-4-methoxy-2,2-dimethyl-3a,4,6,6 atetrahydrofuro [3,4-d][1,3]dioxol-6-yl]methyl]phenyl]ethanol (86c, 2.3 g, 6.4 mmol) in THF (50 mL was added isopropyl(NE)-N-isopropoxycarbonyliminocarbamate (2.5 mL, 12.8 mmol) and triphenylphosphine (3.3 g, 12.8 mmol), and the reaction mixture was stirred at 25° C. for 16 h. The mixture was concentrated in vacuum to give a crude product which was purified by silica gel column chromatography, eluting with petroleum ether:ethyl acetate=20:1 to 5:1 to give (1R)-6-chloro-1-[(3aR,4R,6R,6aR)-4-methoxy-2,2-dimethyl-3a,4,6,6a-tetrahydrofuro[3,4-d][1,3]dioxol-6-yl]isochromane (86d, 2.1 g, 6.1 mmol, 96% yield) as a white solid. $^1$H NMR (400 MHz, $CDCl_3$) δ 7.58 (d, J=8.4 Hz, 1H), 7.12-7.17 (m, 2H), 5.09 (s, 2H), 4.56-4.62 (m, 2H), 4.14-4.28 (m, 2H), 3.71-3.77 (m, 1H), 3.70 (s, 3H), 2.65-3.01 (m, 2H), 1.47 (s, 3H), 1.25 (s, 3H).

Step 4. Synthesis of (3R,4S,5S)-5-[(1R)-6-chloroisochroman-1-yl]tetrahydrofuran-2,3,4-triol (86e)

To a solution of (1R)-6-chloro-1-[(3aR,4R,6R,6aR)-4-methoxy-2,2-dimethyl-3a,4,6,6a-tetrahydrofuro[3,4-d][1,3] dioxol-6-yl]isochromane (86d, 1.6 g, 4.7 mmol) in trifluoroacetic acid (16 mL, 215.4 mmol) was added water (10 mL) at rt. The mixture was stirred at 40° C. for 24 h. The reaction mixture was concentrated in vacuum and purified by silica gel column chromatography, eluting with petroleum ether: ethyl acetate=5:1 to 1:1 to give (3R,4S,5S)-5-[(1R)-6-chloroisochroman-1-yl]tetrahydrofuran-2,3,4-triol (86e, 700 mg, 2.4 mmol, 42% yield) as a colorless oil. LCMS [M+H]: 286.1.

Step 5. Synthesis of (2R,3R,4S,5S)-2-(4-chloro-5-fluoro-pyrrolo[2,3-d]pyrimidin-7-yl)-5-[(1R)-6-chloroisochroman-1-yl]tetrahydrofuran-3,4-diol (86g)

To a solution of 4-chloro-5-fluoro-7H-pyrrolo[2,3-d]pyrimidine (86f, 461 mg, 2.7 mmol) and pyridine (0.8 mL, 9.8 mmol) in dry THF (10 mL) was added tributylphosphane (1.2 mL, 4.9 mmol) and DIAD (1.0 mL, 5.1 mmol) under $N_2$. (3R,4S,5S)-5-[(1R)-6-chloroisochroman-1-yl]tetrahydrofuran-2,3,4-triol (86e, 700 mg, 2.4 mmol) and pyridine (0.8 mL, 9.8 mmol) was added at once. The reaction mixture was stirred at 30° C. for 1.5 h under $N_2$. The reaction mixture was concentrated in vacuum and the residue was purified by silica gel column chromatography, eluting with petroleum ether:ethyl acetate=5:1 to 1:1) to give (2R,3R,4S,5S)-2-(4-chloro-5-fluoro-pyrrolo[2,3-d]pyrimidin-7-yl)-5-[(1R)-6-chloroisochroman-1-yl]tetrahydrofuran-3,4-diol (86g, 160 mg, 0.4 mmol, 15% yield) as a yellow oil. LCMS [M+H]: 440.1.

Step 6. Synthesis of (2R,3R,4S,5S)-2-(4-amino-5-fluoro-pyrrolo[2,3-d]pyrimidin-7-yl)-5-[(1R)-6-chloroisochroman-1-yl]tetrahydrofuran-3,4-diol (Ex. 86)

A mixture solution of (2R,3R,4S,5S)-2-(4-chloro-5-fluoro-pyrrolo[2,3-d]pyrimidin-7-yl)-5-[(1R)-6-chloroisochroman-1-yl]tetrahydrofuran-3,4-diol (86g, 156 mg, 0.35 mmol) in ammonium hydroxide (10 mL, 260 mmol) and 1,4-dioxane (10 mL) was stirred at 105° C. in a sealed tube overnight. The mixture solution was concentrated in vacuum and the residue was purified by prep-HPLC, eluting with $CH_3CN$ in water from 5% to 95%. The product fraction were extracted with ethyl acetate (2×50 ml) and concentrated in vacuum to give a yellow solid which was triturated with petroleum ether:ethyl acetate=100:1 (50 ml), filtered, and dried in vacuum to afford (2R,3R,4S,5S)-2-(4-amino-5-fluoro-pyrrolo[2,3-d]pyrimidin-7-yl)-5-[(1R)-6-chloroisochroman-1-yl]tetrahydrofuran-3,4-diol (Ex. 86.74 mg, 0.17 mmol, 49% yield) as a white solid. LCMS [M+H]: 421.1. $^1$H NMR (400 MHz, DMSO-d6) δ 8.08 (s, 1H), 7.23-7.31 (m, 4H), 7.01 (s, 2H), 6.23 (d, J=7.6 Hz, 1H), 5.23 (d, J=6.8 Hz, 1H), 5.08 (s, 1H), 4.87 (s, 1H), 4.35-4.39 (m, 2H), 4.23-4.26 (m, 1H), 3.79-3.82 (m, 1H), 3.66-3.71 (m, 1H), 2.89-2.96 (m, 1H), 2.70-2.74 (m, 1H). $^1$H NMR (400 MHz, DMSO-d6+D2O) δ 8.08 (s, 1H), 7.23-7.30 (m, 4H), 6.23 (d, J=6.0 Hz, 1H), 4.87 (s, 1H), 4.35-4.39 (m, 2H), 4.23-4.26 (m, 1H), 3.79-3.81 (m, 1H), 3.65-3.71 (m, 1H), 2.89-2.96 (m, 1H), 2.70-2.74 (m, 1H). $^{19}$F NMR (377 MHz, DMSO-d6) δ-166.8.

Example 88. Synthesis of (2R,3R,4S,5S)-2-(4-aminopyrrolo[2,3-d]pyrimidin-7-yl)-5-[(1R)-6,7-dichloroisochroman-1-yl]tetrahydrofuran-3,4-diol (Ex. 88

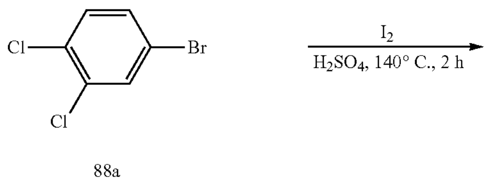

88a

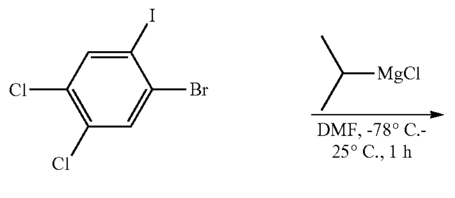

88b

-continued
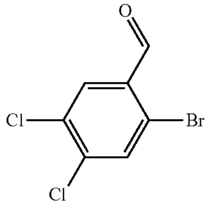
88c
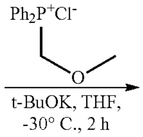
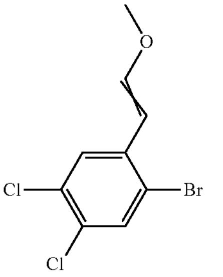
88d
2 N HCl
acetone, 70° C.,
2 h
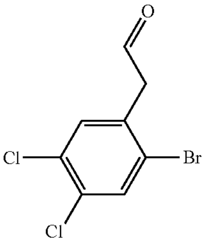
88e
$NaBH_4$, MeOH
0° C., 1 h
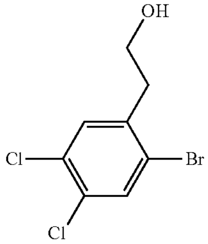
88f
TBSCl, imidazole
DMF, rt
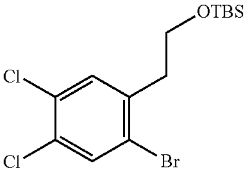
88g
n-BuLi
THF, -78° C.
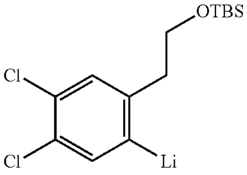
+
-continued
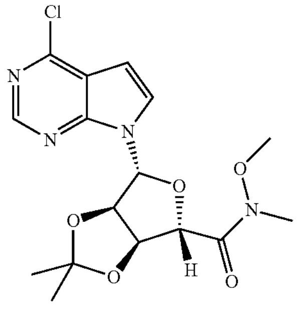
1Ad
THF
-78° C.
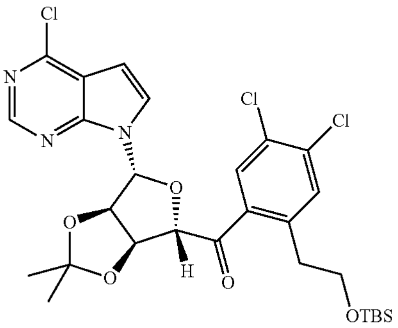
88h
DIBAL-H
toluene, -78° C.,
0.5 h
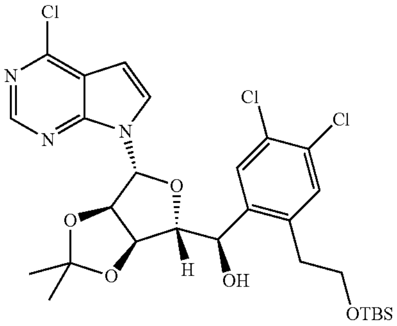
88i
TBAF, THF
25° C., 1 h
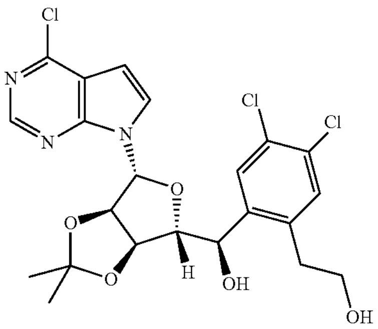
88j
DIAD, $P(nBu)_3$,
THF
-78° C., 2.5 h -continued

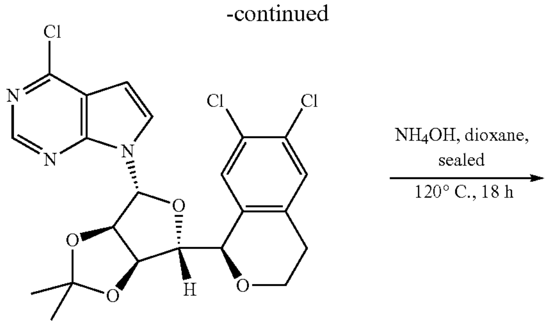

88k

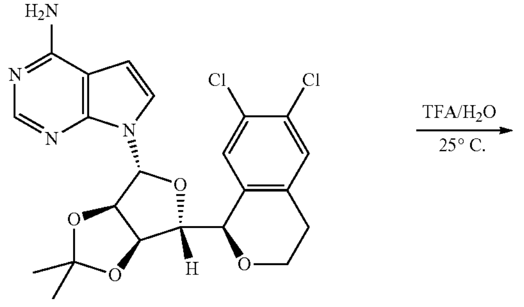

881

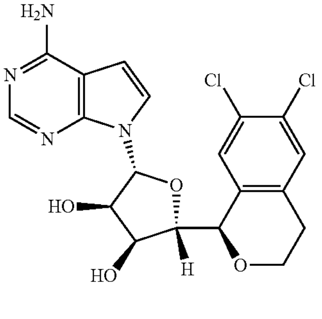

Ex. 88

Step 1. Synthesis of 1-bromo-4,5-dichloro-2-iodo-benzene (88b

To a solution of 4-bromo-1,2-dichlorobenzene (88a, 25 g, 110.67 mmol), 12 (42.13) g, 166 mmol) in $H_2SO_4$ (353.95 mL, 6640.1 mmol) was stirred at 140° C. for 72 h under Ar. The reaction was diluted with water (5000 mL), extracted with EtOAc (1500 ml), washed with $Na_2SO_3$ (aq, 2×100 mL) and saturated brine (800 ml×1). The crude product was dried over $MgSO_4$, filtered and concentrated in vacuum to give the crude product which was then purified by silica gel column chromatography, eluted with 2% EtOAc in petroleum ether to give 1-bromo-4,5-dichloro-2-iodo-benzene (88b, 40 g, 113.7 mmol, 100% yield) as a white solid. $^1H$ NMR (400 MHz, $CDCl_3$) δ 7.84 (s, 1H), 7.62 (s, 1H).

Step 2. Synthesis of 2-bromo-4,5-dichloro-benzaldehyde (88c)

To a solution of 1-bromo-4,5-dichloro-2-iodo-benzene (88b, 5 g, 14.21 mmol) in THF (20 mL) was stirred at −78° C. for 15 min under Ar. Isopropylmagnesium bromide[1 M solution in THF] (15.6 mL, 15.63 mmol) was added slowly and stirred for 15 min. DMF (1.2 mL, 15.63 mmol) was added and stirred for 1h at rt. The reaction mixture was extracted with EtOAc (80 mL), washed with $Na_2SO_3$ (aq, 2×30 mL) and saturated brine (2×30 mL), dried over $MgSO_4$, filtered, and concentrated in vacuum. The crude product was then purified by silica gel column chromatography, eluting with 0.1% of EtOAc in petroleum ether to give 2-bromo-4,5-dichloro-benzaldehyde (88c, 2.7 g, 10.6 mmol, 75% yield) as a white solid. $^1H$ NMR (400 MHz, $CDCl_3$) δ 10.16 (d, J=4.0 Hz, 1H), 7.89 (d, J=4.0 Hz, 1H), 7.10 (d, J=4.0 Hz, 1H).

Step 3. Synthesis of 1-bromo-4,5-dichloro-2-[(E)-2-methoxyvinyl]benzene (88d)

A solution of (methoxymethyl)triphenylphosphonium chloride (7.29 g, 21.27 mmol) and t-BuOK (2.39 g, 21.27 mmol) in THF (10 mL) was stirred at −25° C. under Ar for 15 min. 2-bromo-4,5-dichloro-benzaldehyde (88c, 2.7 g, 10.63 mmol) in THE was added and stirred at −25° C. for 1.5 h. The reaction mixture was extracted with EtOAc (100 mL), washed with water (2×30 mL), then saturated brine (30 mL), dried over $MgSO_4$, filtered, and concentrated in vacuum. The crude product was purified by silica gel column chromatography, eluting with 0.1% EtOAc in petroleum ether to give 1-bromo-4,5-dichloro-2-[(E)-2-methoxyvinyl]benzene (88d, 1.1 g, 0.0039 mmol, 75% yield) as a white solid. $^1H$ NMR (400 MHz, $CDCl_3$) δ 7.54-7.53 (d, J=4.0 Hz, 1H), 7.37-7.35 (d, J=8.0 Hz, 1H), 6.94-6.89 (m, 1H), 5.88-5.85 (d, J=12.0 Hz, 1H), 3.66 (s, 3H).

Step 4. Synthesis of 2-(2-bromo-4,5-dichloro-phenyl)acetaldehyde (88e)

A solution of 1-bromo-4,5-dichloro-2-[(E)-2-methoxyvinyl]benzene (88d, 1.1 g, 3.9 mmol) and hydrochloric acid 2N (aq) (0.7 g, 19.51 mmol) in acetone (5 mL) was stirred at 70° C. for 2 h under Ar. The reaction was concentrated in vacuum to give 2-(2-bromo-4,5-dichloro-phenyl)acetaldehyde (88e, 830 mg, 3.09 mmol, 79% yield) as a colorless oil. LCMS [M+H]: 267.1.

Step 5. Synthesis of 2-(2-bromo-4,5-dichloro-phenyl)ethanol (88f)

A solution of 2-(2-bromo-4,5-dichloro-phenyl)acetaldehyde (88e, 830 mg, 3.1 mmol) in methanol (5 mL) was stirred at 0° C. for 15 min under Ar. $NaBH_4$ (352 mg, 9.29 mmol) was added and stirred at 0° C. for 30 min. The reaction mixture was extracted with EtOAc (50 mL), washed with water (2×20 mL) and saturated brine (10 mL), dried over $MgSO_4$, filtered, and concentrated in vacuum to give 2-(2-bromo-4,5-dichloro-phenyl)ethanol (88f, 800 mg, 3.0 mmol, 96% yield) as a colorless oil. $^1H$ NMR (400 MHz, $CDCl_3$) δ 7.71 (s, 1H), 7.39 (s, 1H), 3.90-3.86 (m, 2H), 2.99-2.95 (m, 2H), 1.46-1.43 (m, 1H).

Step 6. Synthesis of 2-(2-bromo-4,5-dichloro-phenyl)ethoxy-tert-butyl-dimethyl-silane (88g)

To a solution of 2-(2-bromo-4,5-dichloro-phenyl)ethanol (88f, 810 mg, 3 mmol) in DCM (10 mL) was added imidazole (409 mg, 6.0 mmol) followed by t-butylchlorodiphenylsilane (678 mg, 4.5 mmol) and the reaction was stirred at 25° C. for 2 h. The reaction mixture was diluted with EtOAc (50 mL), washed with water (2×20 mL) and saturated brine (10 mL), dried over $MgSO_4$, filtered, concentrated in vacuum. The crude product was purified by flash column chromatography eluting with 10% EtOAc in PE to give 2-(2-bromo-4,5-dichloro-phenyl)ethoxy-tert-butyl-dimethyl-silane (88g, 910 mg, 2.37 mmol, 79% yield) as a colorless oil. $^1$H NMR (400 MHz, $CDCl_3$) δ 7.66 (s, 1H), 7.40 (s, 1H), 3.83 (m, 2H), 2.93 (t, 2H), 7.40 (s, 9H), 0.00 (s, 6H).

Step 7. Synthesis of [2-[2-[tert-butyl(dimethyl)silyl]oxyethyl]-4,5-dichloro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (88h)

A solution of [2-(2-bromo-4,5-dichloro-phenyl)-2,2-difluoro-ethoxy]-tert-butyl-dimethyl-silane (88g, 713.49 mg, 1.7 mmol in THF (6.5 mL) was stirred at −78° C. for 20 min under Ar. n-BuLi (83.67 mg, 1.31 mmol) was added and stirred at −78° C. for 5 min. (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1Ad, 250 mg, 0.65 mmol) in THF (3 mL) was added and stirred for 5 min. TLC showed the reaction was complete. The reaction was quenched with ethyl acetate (25 mL). The reaction mixture was extracted with EtOAc (25 mL), washed with water (2×10 mL) and saturated brine (10 mL), dried over $MgSO_4$, filtered, and concentrated in vacuum. The crude product was then purified by silica gel column chromatography, eluting with 20% EtOAc in petroleum ether to give [2-[2-[tert-butyl(dimethyl)silyl]oxyethyl]-4,5-dichloro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (88h, 210 mg, 0.33 mmol, 51% yield) as a yellow oil. LCMS [M+H]: 626.2.

Step 8. Synthesis of give (R)-[2-[2-[tert-butyl(dimethyl)silyl]oxyethyl]-4,5-dichloro-phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (88i)

A solution of [2-[2-[tert-butyl(dimethyl)silyl]oxyethyl]-4,5-dichloro-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (88h, 250 mg, 0.39 mmol) in toluene (5 mL) was stirred at −78° C. for 5 min under Ar. DIBAL-H (0.13 mL, 1.1 mmol) was added and stirred for 2.5 h. The mixture was purified by prep-HPLC to give (R)-[2-[2-[tert-butyl(dimethyl)silyl]oxyethyl]-4,5-dichloro-phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (88i, 195 mg, 0.31 mmol, 80% yield) as a white solid. LCMS [M+H]: 628.2.

Step 9. Synthesis of 2-[4,5-dichloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (88j)

A solution of (R)-[2-[2-[tert-butyl(dimethyl)silyl]oxy-1,1-difluoro-ethyl]-4,5-dichloro-phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (88i, 205 mg, 0.31 mmol) in THF (8 mL) was stirred at 25° C. for 5 min under Ar. Tetrabutylammonium fluoride (0.17 mL, 0.62 mmol) was added and stirred for 2.5 h. The mixture was purified by prep-HPLC (MeCN in water, from 10% to 90%) to give 2-[4,5-dichloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (88j, 100 mg, 0.19 mmol, 63% yield) as a white solid. LCMS [M+H]: 514.2.

Step 10. Synthesis of 4-chloro-7-[(3aR,4R,6R,6aR)-2,2-dimethyl-6-[(1R)-6,7-dichloroisochroman-1-yl]-3a,4,6,6a-tetrahydrofuro[3,4-d][1,3]dioxol-4-yl]pyrrolo[2,3-d]pyrimidine (88k)

A solution of 2-[4,5-dichloro-2-[(R)-hydroxy-[(3aR,4R,6R,6aR)-4-(4-chloropyrrolo-[2,3-d]pyrimidin-7-yl)-2,2-dimethyl-3a,4,6,6a-tetrahydrofuro[3,4-d][1,3]dioxol-6-yl]methyl]phenyl]ethanol (88j, 100 mg, 0.19 mmol) and $PPh_3$ (101.9 mg, 0.39 mmol) in THF (3 mL) was stirred at 25° C. for 5 min under Ar. DIAD (0.11 mL, 0.39 mmol) was added and stirred for 2 h. The reaction mixture was extracted with EtOAc (200 mL), washed with water (2×100 mL) and saturated brine (100 mL), dried over $MgSO_4$, filtered, and concentrated in vacuum. The crude product was then purified by silica gel column chromatography, eluting with 50% EtOAc in petroleum ether to give 4-chloro-7-[(3aR,4R,6R,6aR)-2,2-dimethyl-6-[(1R)-6,7-dichloroisochroman-1-yl]-3a,4,6,6a-tetrahydrofuro[3,4-d][1,3]dioxol-4-yl]pyrrolo[2,3-d]pyrimidine (88k, 70 mg, 0.14 mmol, 72.5% yield) as a white solid. LCMS [M+H]: 496.1.

Step 11. Synthesis of 7-[(3aR,4R,6R,6aR)-2,2-dimethyl-6-[(1R)-6,7-dichloroisochroman-1-yl]-3a,4,6,6a-tetrahydrofuro[3,4-d][1,3]dioxol-4-yl]pyrrolo[2,3-d]pyrimidin-4-amine (88l)

A solution of 4-chloro-7-[(3aR,4R,6R,6aR)-2,2-dimethyl-6-[(1R)-6,7-dichloroisochroman-1-yl]-3a,4,6,6a-tetrahydrofuro[3,4-d][1,3]dioxol-4-yl]pyrrolo[2,3-d]pyrimidine (88k, 70 mg, 0.14 mmol) and $NH_3$. water (0.54 mL, 14.09 mmol) in 1,4-dioxane (2 mL) was stirred at 120° C. for 16 h. The mixture was concentrated in vacuum to give 7-[(3aR,4R,6R,6aR)-2,2-dimethyl-6-[(1R)-6,7-dichloroisochroman-1-yl]-3a,4,6,6a-tetrahydrofuro[3,4-d][1,3]dioxol-4-yl]pyrrolo[2,3-d]pyrimidin-4-amine (88l, 65 mg, 0.14 mmol, 97% yield) as a white solid. LCMS [M+H]: 477.2.

Step 12. Synthesis of (2R,3R,4S,5S)-2-(4-aminopyrrolo[2,3-d]pyrimidin-7-yl)-5-[(1R)-6,7-dichloroisochroman-1-yl]tetrahydrofuran-3,4-diol (Ex. 88)

A solution of 7-[(3aR,4R,6R,6aR)-2,2-dimethyl-6-[(1R)-6,7-dichloroisochroman-1-yl]-3a,4,6,6a-tetrahydrofuro[3,4-d][1,3]dioxol-4-yl]pyrrolo[2,3-d]pyrimidin-4-amine (88l, 70 mg, 0.15 mmol) and TFA (502 mg, 4.4 mmol) in water (2 mL) was stirred at 25° C. for 1.5 h. LCMS showed the reaction was complete. The mixture was concentrated in vacuum to give the crude product which was purified by prep-HPLC, eluted with water:$CH_3CN$ (0.1% $NH_4OH$, from 90:10 to 5:95) to give (2R,3R,4S,5S)-2-(4-aminopyrrolo[2,3-d]pyrimidin-7-yl)-5-[(1R)-6,7-dichloroisochroman-1-yl]tetrahydrofuran-3,4-diol (Ex. 88, 5.1 mg, 0.011 mmol, 8% yield) as a white solid. LCMS [M+H]: 437.2. $^1$H NMR (400 MHz, DMSO-$d_6$) δ 8.26 (s, 1H), 7.97-8.07 (m, 1.4H), 7.58 (m, 2H), 7.52 (s, 1H), 6.85 (s, 1H), 6.18-6.20 (d, J=8 Hz, 1H), 5.17-5.30 (m, 2H), 4.88-4.89 (d, J=2.8 Hz, 1H), 4.43-4.47 (m, 2H), 4.23-4.24 (m, 1H), 3.84-3.85 (d, J=4 Hz, 1H), 3.64-3.65 (m, 1H), 2.88-2.95 (m, 1H), 2.67-2.75 (m, 1H). $^1$H NMR (400 MHz, DMSO-$d_6$+D2O) δ 8.25 (s, 1H), 7.59-7.60 (d, J=6.8 Hz, 1H), 7.54 (s, 1H), 7.51 (s, 1H), 6.87-6.88 (d, J=3.2 Hz, 1H), 6.19-6.20 (d, J=7.6 Hz, 1H), 4.90 (s, 1H), 4.47-4.50 (m, 1H), 4.42-4.43 (d, J=4 Hz, 1H), 4.22-4.26 (m, 1H), 3.86-3.87 (d, J=5.2 Hz, 2H), 2.93-2.90 (m, 1H), 2.70-2.75 (m, 1H).
Example 89. Synthesis of (2R,3R,4S,5S)-2-(4-methylpyrrolo[2,3-d]pyrimidin-7-yl)-5-[(7S)-2-chloro-5,7-dihydro-4H-thieno[2,3-c]pyran-7-yl]tetrahydrofuran-3,4-diol; 2,2,2-trifluoroacetic Acid (Ex. 89)
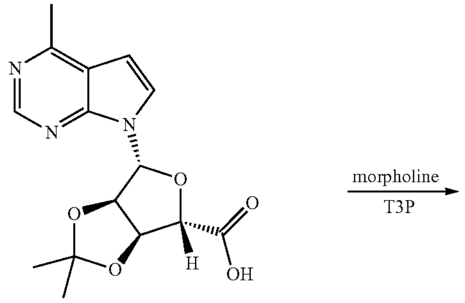
89a
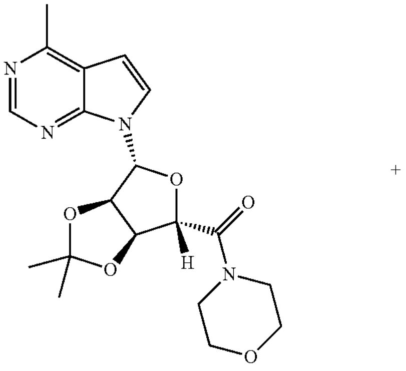
89b
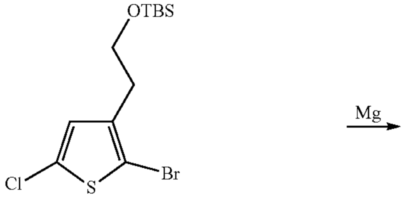
89c
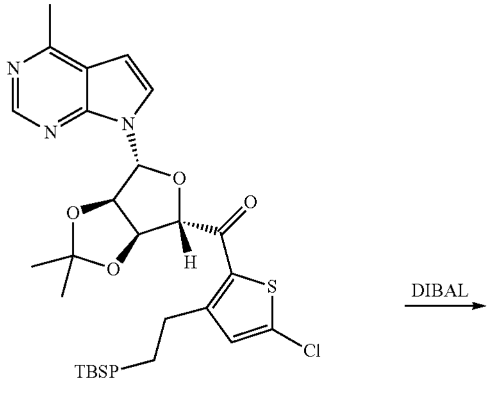
89d
-continued
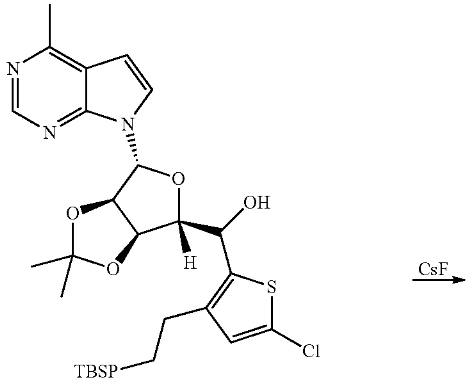
89e
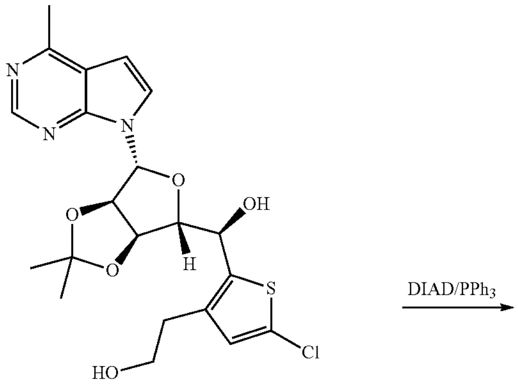
89f
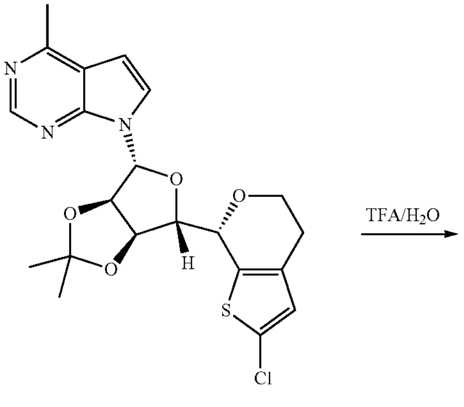
89g -continued

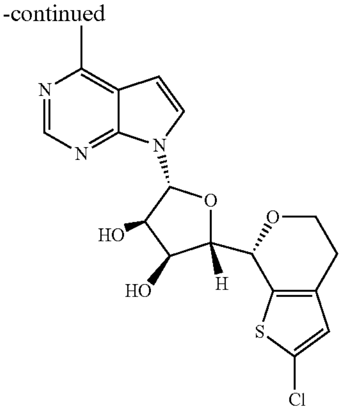

Ex. 89

Step 1. Synthesis of morpholino-[(3aR,4R,6S,6aS)-2,2-dimethyl-4-(4-methylpyrrolo[2,3-d]pyrimidin-7-yl)-3a,4,6,6a-tetrahydrofuro[3,4-d][1,3]dioxol-6-yl]methanone (89b)

To a solution of (3aR,4R,6S,6aS)-2,2-dimethyl-4-(4-methylpyrrolo[2,3-d]pyrimidin-7-yl)-3a,4,6,6a-tetrahydrofuro[3,4-d][1,3]dioxole-6-carboxylic acid (89a, 9.0 g, 28.19 mmol) in ethyl acetate (100 mL) was added morpholine (2.46 g, 28.19 mmol) and T3P (35 mL, 28.19 mmol) under ice bath. then the reaction was stirred at rt for 3h. To the solution was added $NaHCO_3$ (aq), adjusting the pH to 8. The mixture was extracted with EA (200 mL×3). The combined organics were concentrated, and the residue was purified by flash column chromatography (PE:EA=5:1 to 1:1) to give morpholino-[(3aR,4R,6S,6aS)-2,2-dimethyl-4-(4-methylpyrrolo[2,3-d]pyrimidin-7-yl)-3a,4,6,6a-tetrahydrofuro[3,4-d][1,3]dioxol-6-yl]methanone (89b, 9.5 g, 24.2 mmol, 86% yield) as a yellow oil. LCMS [M+H]: 389.3.

Step 2. Synthesis of 3-[2-[tert-butyl(dimethyl)silyl]oxyethyl]-5-chloro-2-thienyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (89d)

Magnesium (123 mg, 5.06 mmol) in a 20 mL vial was etched with a spatula and stirred vigorously, then heat-gun dried under vacuum and back-filled with nitrogen when cool. A solution of 2-(2-bromo-5-chloro-3-thienyl)ethoxy-tert-butyl-dimethyl-silane (89c, 1.5 g, 4.22 mmol) in THF (1 mL) was added, followed by diisobutylaluminum hydride, 1 M in toluene (0.05 mL, 0.05 mmol). After 4 h the solution was dark and most of the magnesium was consumed, and was used as 0.82 M solution of bromo-[3-[2-[tert-butyl(dimethyl)silyl]oxyethyl]-5-chloro-2-thienyl]magnesium. Into a dry flask was placed morpholino-[(3aR,4R,6S,6aS)-2,2-dimethyl-4-(4-methylpyrrolo[2,3-d]pyrimidin-7-yl)-3a,4,6,6a-tetrahydrofuro[3,4-d][1,3]dioxol-6-yl]methanone (89b, 578.37 mg, 1.49 mmol), which had been dried under vacuum, and 3 mL THF. The solution was cooled in an ice bath and bromo-[3-[2-[tert-butyl(dimethyl)silyl]oxyethyl]-5-chloro-2-thienyl]magnesium (2.72 mL, 2.23 mmol) added dropwise via syringe. The ice bath was removed, and the reaction stirred for 1 h. An additional portion of bromo-[3-[2-[tert-butyl(dimethyl)silyl]oxyethyl]-5-chloro-2-thienyl]magnesium (0.91 mL, 0.75 mmol) was added and stirred 1 h before quenching with EtOAc. The reaction was poured into $NH_4Cl$, the organics were separated, and the aqueous layer extracted with EtOAc. The organic layers were combined, washed with water followed by brine and dried over $Na_2SO_4$. The solvent was evaporated in vacuo and the residue purified by flash column chromatography to give [3-[2-[tert-butyl(dimethyl)silyl]oxyethyl]-5-chloro-2-thienyl]-[(3aR,4R,6S,6aS)-2,2-dimethyl-4-(4-methylpyrrolo[2,3-d]pyrimidin-7-yl)-3a,4,6,6a-tetrahydrofuro[3,4-d][1,3]dioxol-6-yl]methanone (89d, 320 mg, 0.553 mmol, 37% yield).

Step 3. Synthesis of (R)-[3-[2-[tert-butyl(dimethyl)silyl]oxyethyl]-5-chloro-2-thienyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (89e)

A 50 mL round bottom flask containing a solution of [3-[2-[tert-butyl(dimethyl)silyl]oxyethyl]-5-chloro-2-thienyl]-[(3aR,4R,6S,6aS)-2,2-dimethyl-4-(4-methylpyrrolo[2,3-d]pyrimidin-7-yl)-3a,4,6,6a-tetrahydrofuro[3,4-d][1,3]dioxol-6-yl]methanone (89d, 328 mg, 0.57 mmol) in toluene (6 mL) was sparged with nitrogen for 5 min then cooled to −78° C. and charged with diisobutylaluminum hydride, 1 M in toluene (1.18 mL, 1.42 mmol) dropwise over 5 min. The yellow solution was stirred at −78° C. for 75 min. The reaction mixture was warmed to 0° C., slowly charged with water (80 μL), 15% sodium hydroxide (80 μL), and water (200 L), and stirred at rt for 15 min. The mixture was then diluted with ether, dried with $MgSO_4$, stirred for 15 min, and filtered. The filtrate was concentrated under reduced pressure and purified by flash column chromatography (0 to 45% EtOAc in hexanes, wet-loaded in DCM/hexanes) to yield (S)-[3-[2-[tert-butyl(dimethyl)silyl]oxyethyl]-5-chloro-2-thienyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (61 mg, 0.105 mmol, 18.5% yield) and (R)-[3-[2-[tert-butyl(dimethyl)silyl]oxyethyl]-5-chloro-2-thienyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (89e, 120 mg, 0.207 mmol, 36.5% yield) as fluffy white solids. $^1H$ NMR (500 MHz, methanol-$d_4$) δ 8.59 (d, J=5.0 Hz, 1H), 7.92 (d, J=3.8 Hz, 1H), 6.83 (d, J=0.8 Hz, 1H), 6.70 (dd, J=3.8, 6.2 Hz, 1H), 6.50-6.25 (m, 1H), 5.26-5.11 (m, 1H), 5.09-5.02 (m, 1H), 4.45 (ddd, J=2.5, 4.5, 15.6 Hz, 1H), 3.75 (q, J=6.6 Hz, 2H), 2.72 (dt, J=6.5, 19.3 Hz, 2H), 2.01 (s, 2H), 1.61 (d, J=4.9 Hz, 3H), 1.35 (d, J=7.4 Hz, 3H), 0.83 (d, J=9.7 Hz, 8H), −0.06 (d, J=4.5 Hz, 5H).

Step 4. Synthesis of 2-[5-chloro-2-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]-3-thienyl]ethanol (89f)

Into a round bottom flask was placed (R)-[3-[2-[tert-butyl(dimethyl)silyl]oxyethyl]-5-chloro-2-thienyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (89e, 123 mg, 0.21 mmol), DMSO (5 mL), and cesium fluoride (98 mg, 0.64 mmol). The mixture was stirred for 1 h, then purified directly by reverse-phase chromatography (10%-70% MeCN/water/0.1% TFA). Product fractions were lyophilized to give 2-[5-chloro-2-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d]

[1,3]dioxol-6-yl]methyl]-3-thienyl]ethanol; 2,2,2-trifluoroacetic acid (89f, 70 mg, 0.120 mmol, 56% yield). $^1$H NMR (500 MHz, Methanol-$d_4$) δ 8.96 (d, J=9.5 Hz, 1H), 8.33 (dd, J=3.9, 28.5 Hz, 1H), 7.15 (dd, J=3.9, 8.6 Hz, 1H), 6.61 (dd, J=3.7, 18.7 Hz, 1H), 5.27 (d, J=3.4 Hz, 1H), 5.18 (ddd, J=3.0, 5.9, 8.5 Hz, 1H), 5.12 (dd, J=1.9, 5.9 Hz, 1H), 4.58-4.44 (m, 1H), 3.79-3.63 (m, 2H), 2.96 (d, J=4.9 Hz, 3H), 2.86-2.66 (m, 2H), 1.63 (s, 3H), 1.39 (s, 3H). LCMS: LCMS [M+H]: 466.0.

Step 5. Synthesis of 4-methyl-7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidine (89g)

Into a vial was placed 2-[5-chloro-2-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]-3-thienyl]ethanol (89f, 110 mg, 0.19 mmol) in THF (2 mL). Pyridine (0.03 mL, 0.38 mmol) was added and the mixture stirred for 20 minutes then triphenylphosphine (99.5 mg, 0.38 mmol) and diisopropyl azodicarboxylate (0.07 mL, 0.38 mmol) was added and stirred for 2.5 h. Additional diisopropyl azodicarboxylate (0.07 mL, 0.38 mmol) and triphenylphosphine (99.5 mg, 0.38 mmol) were added. After 1 h, the solvent was evaporated and the residue purified by flash column chromatography (0-60% EtOAc/hexane) to yield 4-methyl-7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidine (89g, 94.5 mg, 0.21 mmol, 111% yield). LCMS [M+H]: 448.1.

Step 6. Synthesis of (2R,3R,4S,5S)-2-(4-methylpyrrolo[2,3-d]pyrimidin-7-yl)-5-[(7S)-2-chloro-5,7-dihydro-4H-thieno[2,3-c]pyran-7-yl]tetrahydrofuran-3,4-diol; 2,2,2-trifluoroacetic Acid (Ex. 89)

Into a vial was placed 4-methyl-7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidine (89g, 94.5 mg, 0.21 mmol) in water (0.50 mL) and 2,2,2-trifluoroacetic acid (0.16 mL, 2.11 mmol) added. The reaction was stirred for 3 h, then diluted with EtOAc and $NaHCO_3$. The organics were separated and washed with water and brine. The solvent was evaporated in vacuo, and the residue was purified by reverse phase chromatography (0-70% MeCN/water/0.1% TFA) to yield (2R,3R,4S,5S)-2-(4-methylpyrrolo[2,3-d]pyrimidin-7-yl)-5-[(7S)-2-chloro-5,7-dihydro-4H-thieno[2,3-c]pyran-7-yl]tetrahydrofuran-3,4-diol; 2,2,2-trifluoroacetic acid (Ex. 89, 2.3 mg, 0.0042 mmol, 2% yield). $^1$H NMR (500 MHz, Methanol-d4) δ 8.78 (s, 1H), 7.92 (s, 1H), 6.97 (s, 1H), 6.76 (s, 1H), 6.46 (d, J=7.5 Hz, 1H), 4.22 (dd, J=5.4, 12.1 Hz, 2H), 3.98-3.76 (m, 1H), 2.84 (s, 5H). LCMS [M+H]: 408.0.

Example 90. Synthesis of (2R,3R,4S,5S)-2-(4-aminopyrrolo[2,3-d]pyrimidin-7-yl)-5-[(7S)-2-chloro-5,7-dihydro-4H-thieno[2,3-c]pyran-7-yl]tetrahydrofuran-3,4-diol; 2,2,2-trifluoroacetic Acid (Ex. 90)

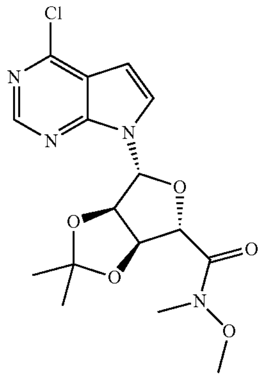

1Ad

+

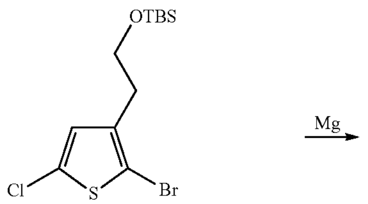

89c

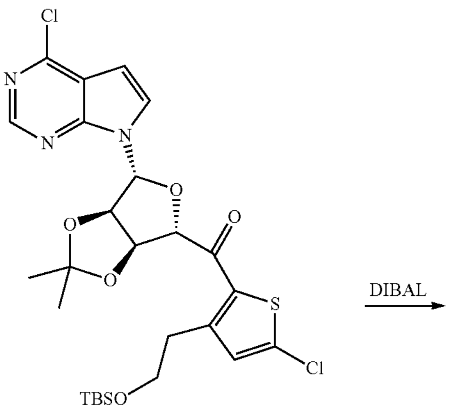

90a

-continued
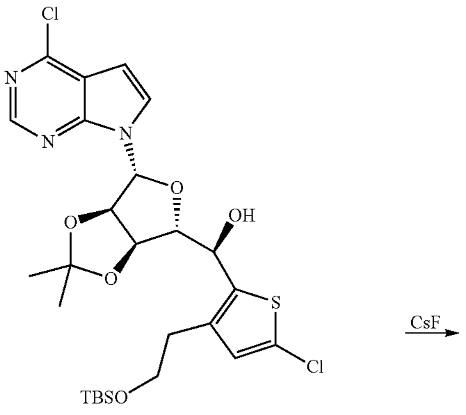
90b
-continued
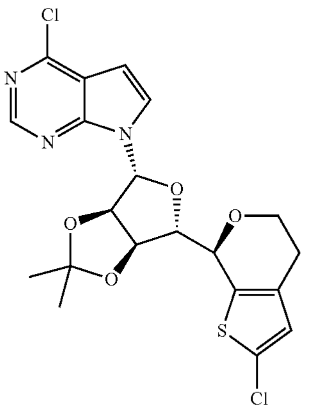
90d2
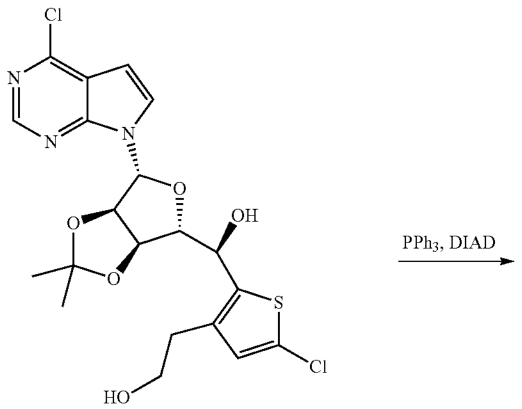
90c
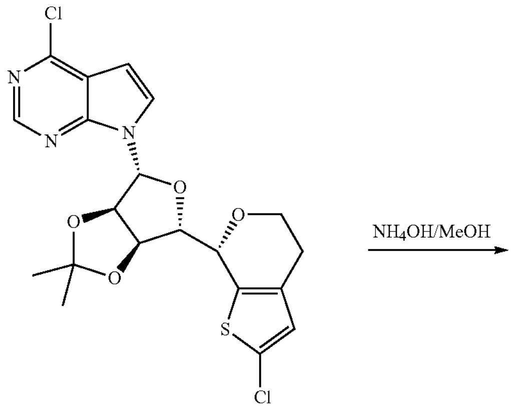
90d1
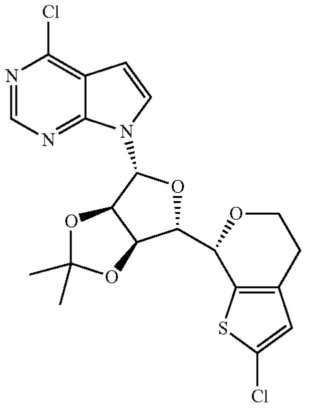
90d1
+
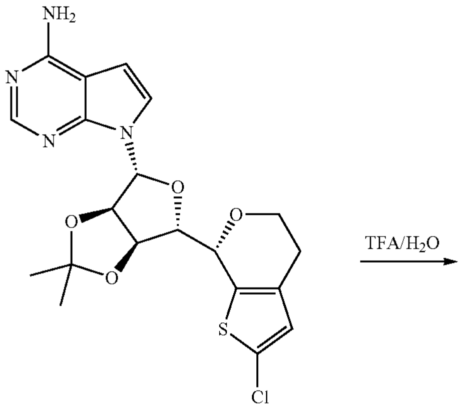
90e -continued

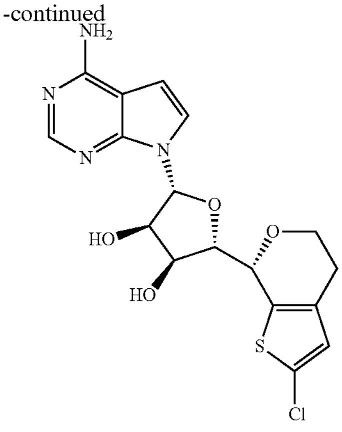

Ex. 90

Step 1. Synthesis of [3-[2-[tert-butyl(dimethyl)silyl]oxyethyl]-5-chloro-2-thienyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (90a)

A 20 mL vial containing magnesium (43.52 mg, 1.79 mmol) and a stir bar was heat-gun dried under vacuum and back-filled with nitrogen when cool. A solution of 2-(2-bromo-5-chloro-3-thienyl)ethoxy-tert-butyl-dimethyl-silane (89c, 0.07 mL, 1.79 mmol) in 2 mL THE was added, followed by diisobutylalumanylium hydride (0.02 mL, 0.02 mmol). The reaction was stirred for 5 h at room temperature until most of the magnesium was consumed. The solution was cooled to −78° C. and (3aR,4R,6S,6aS)-4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1Ad, 527 mg, 1.38 mmol) in THF (3 mL) was added and stirred cold 30 minutes before warming to room temperature. The reaction was stirred at rt for 3 h, then cooled back to −78° C. and quenched with EtOAc followed by $NH_4Cl$. The mixture was warmed to room temperature. The organics were separated, washed with water and brine and dried over $Na_2SO_4$. The residue was purified twice by flash column chromatography (0-70% EtOAc/hexane) to give [3-[2-[tert-butyl(dimethyl)silyl]oxyethyl]-5-chloro-2-thienyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (90a, 104 mg, 0.17 mmol, 13% yield). LCMS [M+H]: 599.8.

Step 2. Synthesis of (R)-[3-[2-[tert-butyl(dimethyl)silyl]oxyethyl]-5-chloro-2-thienyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (90b)

A solution of [3-[2-[tert-butyl(dimethyl)silyl]oxyethyl]-5-chloro-2-thienyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (90a, 104 mg, 0.17 mmol) in toluene (2 mL) was sparged with Ar for 5 min, cooled to −78° C., and then charged with diisobutylaluminum hydride, 1 M in toluene (0.36 mL, 0.44 mmol) dropwise over 5 min. The yellow solution was stirred at −78° C. for 75 min. The reaction mixture was warmed up to 0° C., slowly charged with water (80 μL), 15% sodium hydroxide (80 μL), and water (200 μL), and stirred at rt for 15 min. The mixture was then diluted with EtOAc, the organics were separated, and the aqueous phase extracted again with EtOAc. The organics were combined, washed with water and brine, dried with $MgSO_4$, and filtered. The filtrate was concentrated under reduced pressure and purified by flash column chromatography (0-45% EtOAc/hexanes, wet-loaded in DCM+hexanes) to yield (R)-[3-[2-[tert-butyl(dimethyl)silyl]oxyethyl]-5-chloro-2-thienyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (90b, 97 mg, 0.162 mmol, 93% yield) as a fluffy white solid. $^1H$ NMR (500 MHz, Methanol-$d_4$) δ 8.59 (d, J=5.0 Hz, 1H), 7.92 (d, J=3.8 Hz, 1H), 6.83 (d, J=0.8 Hz, 1H), 6.70 (dd, J=3.8, 6.2 Hz, 1H), 6.50-6.25 (m, 1H), 5.26-5.11 (m, 1H), 5.09-5.02 (m, 1H), 4.45 (ddd, J=2.5, 4.5, 15.6 Hz, 1H), 3.75 (q, J=6.6 Hz, 2H), 2.72 (dt, J=6.5, 19.3 Hz, 2H), 1.61 (d, J=4.9 Hz, 3H), 1.35 (d, J=7.4 Hz, 3H), 0.83 (d, J=9.7 Hz, 9H), −0.06 (d, J=4.5 Hz, 6H).

Step 3. Synthesis of 2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]-3-thienyl]ethanol (90c)

To a solution of (R)-[3-[2-[tert-butyl(dimethyl)silyl]oxyethyl]-5-chloro-2-thienyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (90b, 202 mg, 0.34 mmol) in DMSO (5 mL), cesium fluoride (154 mg, 1.01 mmol) added and the reaction stirred for 1 h. The mixture was purified directly by reverse phase chromatography (10%-70% MeCN/water/0.1% TFA) to give 2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]-3-thienyl]ethanol; 2,2,2-trifluoroacetic acid (90c, 62 mg, 0.103 mmol, 31% yield). LCMS [M+H]: 487.5.

Step 4. Synthesis of 4-chloro-7-[(3aR,4R,6S,6aR)-2,2-dimethyl-6-[(7R)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidine (90d1) and (90d2)

To a solution of 2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]-3-thienyl]ethanol (90c, 58 mg, 0.12 mmol) in THF (2 mL), was added triphenylphosphine (61.86 mg, 0.24 mmol) and diisopropyl azodicarboxylate (0.05 mL, 0.24 mmol). After 2.5 h diisopropyl azodicarboxylate (0.05 mL, 0.24 mmol) and triphenylphosphine (61.86 mg, 0.24 mmol) were added. After 1 h, the reaction was cooled to room temperature and partitioned between EtOAc and water. The layers were separated, and the aqueous layer again extracted with EtOAc and the organics were combined, washed with water and brine, dried over $MgSO_4$, filtered, and concentrated in vacuo. The residue was purified by flash column chromatography (0-80% EtOAc/DCM). Fractions containing product were collected and a second set containing trifluoromethyl ester of the primary alcohol were also collected separately. Those containing the ester were combined and taken up in THF, $NaHCO_3$ was added and stirred for 2 h after which they were diluted with EtOAc, the organics washed with water, brine and the solvent evaporated to give 90c, 2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]-3-thienyl]ethanol. This was then subjected to the original reaction conditions for 3 h, worked up and purified as described above, and combined with the product previously obtained to give 4-chloro-7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidine (90d1, 15 mg, 0.032 mmol, 27% yield); LCMS (M+H): 468.1, and 4-chloro-7-((3aR,4R,6S,6aR)-6-((7R)-2-chloro-4,7-dihydro-5H-thieno[2,3-c]pyran-7-yl)-2,2-dimethyltetrahydrofuro[3,4-d][1,3]dioxol-4-yl)-7H-pyrrolo[2,3-d]pyrimidine (90d2, 6 mg, 12%).

Step 5. Synthesis of 7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidin-4-amine (90e)

To a solution of 4-chloro-7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidine (90d1, 15 mg, 0.03 mmol) in 1,4-dioxane (1 mL), ammonium hydroxide (0.1 mL, 2.4 mmol) was added, the vial capped and placed in the microwave for 14 h at 120° C. The solvent was evaporated in vacuo, EtOAc (1 mL) added and the mixture was evaporated in vacuo twice to give 7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidin-4-amine (90e, 14 mg, 0.031 mmol, 97% yield). LCMS [M+H]: 449.0/450.9.

Step 6. Synthesis of (2R,3R,4S,5S)-2-(4-aminopyrrolo[2,3-d]pyrimidin-7-yl)-5-[(7S)-2-chloro-5,7-dihydro-4H-thieno[2,3-c]pyran-7-yl]tetrahydrofuran-3,4-diol; 2,2,2-trifluoroacetic Acid (Ex. 90)

A solution of 7-[(3aR,4R,6S,6aR)-2,2-dimethyl-6-[(7S)-2-chloro-5,7-dihydro-4H-thieno[2,3-c]pyran-7-yl]-3a,4,6,6a-tetrahydrofuro[3,4-d][1,3]dioxol-4-yl]pyrrolo[2,3-d]pyrimidin-4-amine (90e, 6.0 mg, 0.01 mmol) in water (1 mL) and 2,2,2-trifluoroacetic acid; TFA (0.0 mL, 0.01 mmol was stirred for 2 h and purified by reverse phase HPLC to yield (2R,3R,4S,5S)-2-(4-aminopyrrolo[2,3-d]pyrimidin-7-yl)-5-[(7S)-2-chloro-5,7-dihydro-4H-thieno[2,3-c]pyran-7-yl]tetrahydrofuran-3,4-diol; 2,2,2-trifluoroacetic acid (Ex. 90, 1.1 mg, 0.0021 mmol, 16% yield). $^1$H NMR (500 MHz, Methanol-d4) δ 8.26 (s, 1H), 7.80-7.56 (m, 1H), 6.96 (d, J=3.7 Hz, 1H), 6.77 (s, 1H), 6.37 (d, J=7.6 Hz, 1H), 4.65 (dd, J=5.1, 7.5 Hz, 1H), 4.31 (dd, J=5.9, 11.1 Hz, 1H), 4.25-4.17 (m, 2H), 3.83 (td, J=3.6, 11.1 Hz, 1H), 2.91-2.75 (m, 1H), 2.59 (d, J=16.2 Hz, 1H). Water peak at 5 ppm obscuring multiplet. LCMS [M+H]: 409.1.

Example 91. Synthesis of (2R,3R,4S,5S)-2-(4-aminopyrrolo[2,3-d]pyrimidin-7-yl)-5-[(7R)-2-chloro-5,7-dihydro-4H-thieno[2,3-c]pyran-7-yl]tetrahydrofuran-3,4-diol; 2,2,2-trifluoroacetic Acid (Ex. 91)

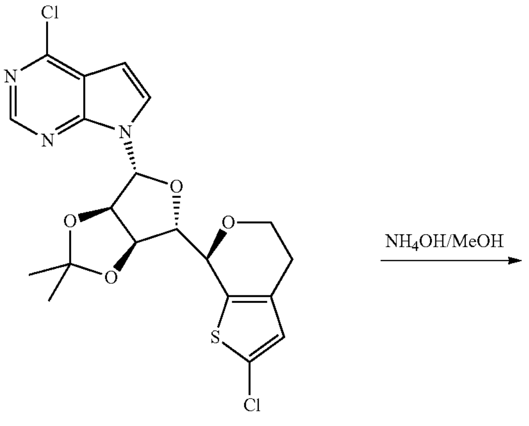

90d2

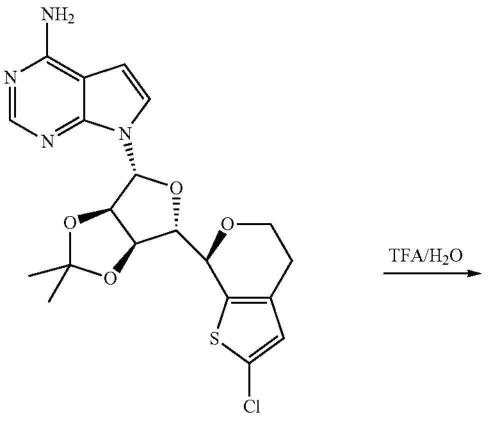

91a

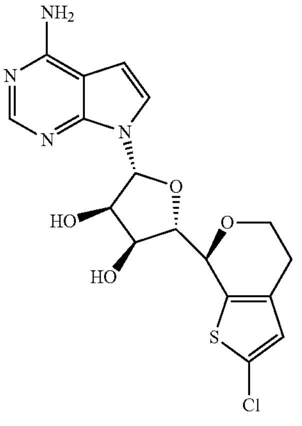

Ex. 91

Starting from 4-chloro-7-((3aR,4R,6S,6aR)-6-((7R)-2-chloro-4,7-dihydro-5H-thieno[2,3-c]pyran-7-yl)-2,2-dimethyltetrahydrofuro[3,4-d][1,3]dioxol-4-yl)-7H-pyrrolo[2,3-d]pyrimidine (90d2) and following the same procedures used for Ex. 90, (2R,3R,4S,5S)-2-(4-amino-7H-pyrrolo[2,3-d]pyrimidin-7-yl)-5-((S)-2-chloro-4,7-dihydro-5H-thieno[2, 3-c]pyran-7-yl)tetrahydrofuran-3,4-diol (Ex. 91, 1.1 mg, 7% yield) was obtained. LCMS [M+H]: 409.0. $^{1}$H NMR (500 MHz, Methanol-d4) δ 8.22 (s, 1H), 7.70 (d, J=3.8 Hz, 1H), 6.90 (d, J=3.8 Hz, 1H), 6.71 (s, 1H), 6.31 (d, J=6.1 Hz, 1H), 4.98 (d, J=2.4 Hz, 1H), 4.50 (t, J=5.7 Hz, 1H), 4.41 (dd, J=3.1, 5.2 Hz, 1H), 4.39-4.28 (m, 2H), 3.85 (td, J=3.5, 11.2 Hz, 1H), 2.78 (d, J=17.0 Hz, 1H), 2.55 (d, J=16.1 Hz, 1H).
Example 94. Synthesis of (2R,3R,4S,5S)-2-(4-methylpyrrolo[2,3-d]pyrimidin-7-yl)-5-[(1R,4R)-6-chloro-4-fluoro-isochroman-1-yl]tetrahydrofuran-3,4-diol; 2,2,2-trifluoroacetic Acid (Ex. 94)
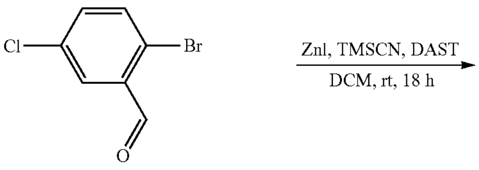
44a
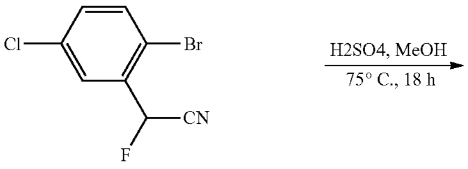
94a
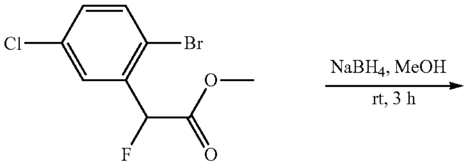
94b
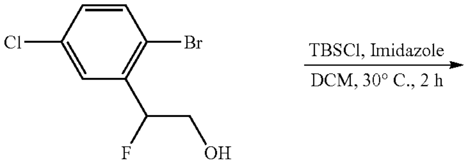
94c
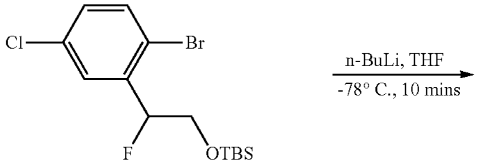
94d
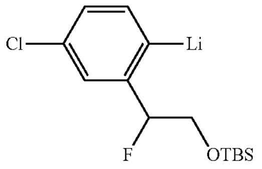
+
-continued
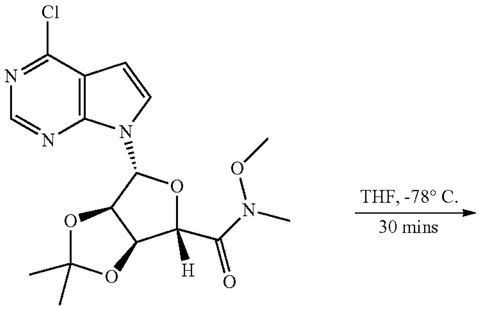
1Ad
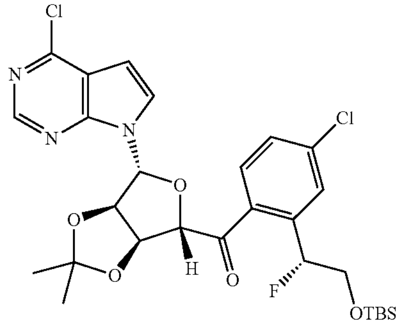
94e1
+
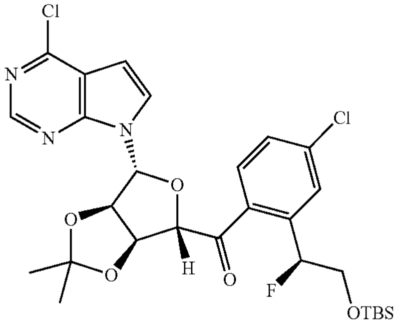
94e2
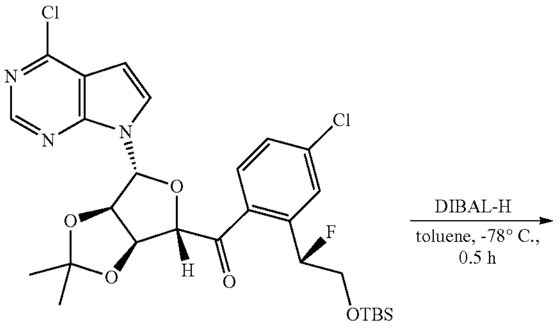
94e2

-continued

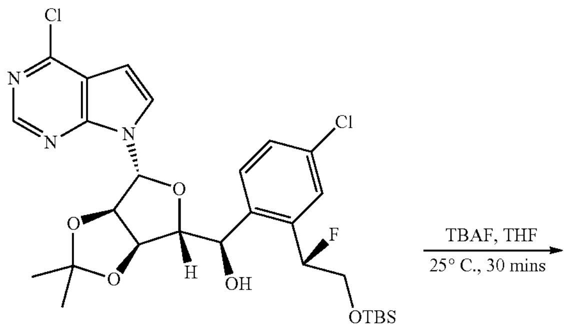

94f

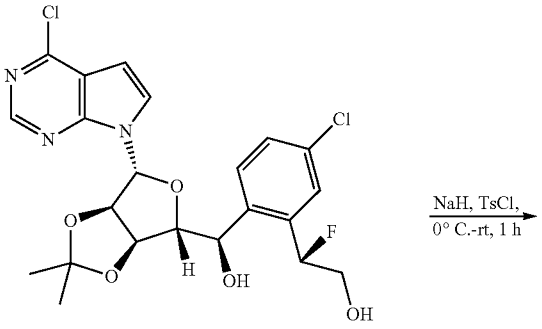

94g

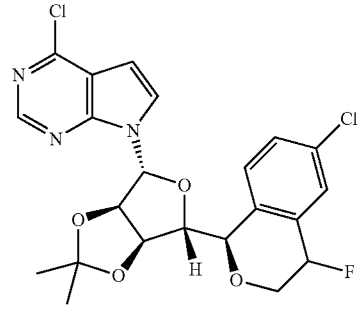

+

94h1

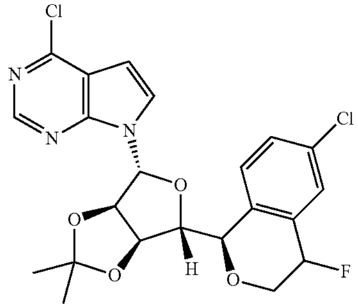

94h2

-continued

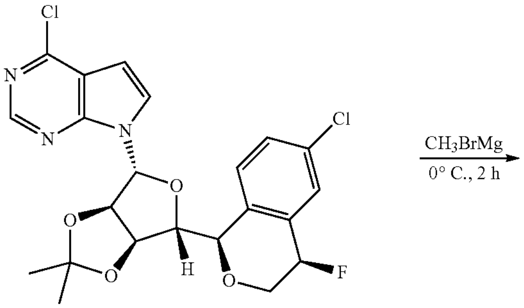

94h1

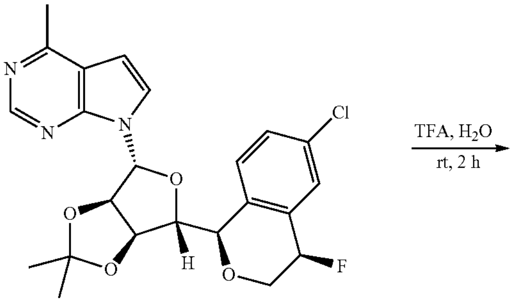

94i

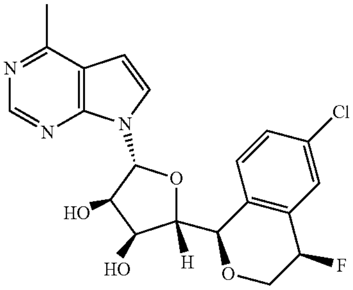

Ex. 94

Step 1. Synthesis of 2-(2-bromo-5-chloro-phenyl)-2-fluoro-acetonitrile (94a)

To a solution of 2-bromo-5-chloro-benzaldehyde (44a, 8000 mg, 31.9 mmol) and zinc iodide (21 mg, 0.07 mmol) in DCM (100 mL) was added trimethylsilylformonitrile (3360 mg, 33.9 mmol) at 0° C. The mixture was stirred at 25° C. for 18 h. Then DAST (5600 mg, 34.7 mmol) in DCM (80 mL) was added and the mixture was cooled to 0° C. The mixture was stirred at 25° C. for 18 h. The mixture was washed with HCl (50 mL, 1 M), $H_2O$ (50 mL) and $NaHCO_3$ (50 mL, aq). The reaction mixture was dried over $MgSO_4$, filtered, and concentrated in vacuum. The crude product was purified by silica gel column chromatography to give 2-(2-bromo-5-chloro-phenyl)-2-fluoro-acetonitrile (94a, 4670 mg, 16.10 mmol, 50.5% yield). $^1H$ NMR (400 MHz, DMSO-d6): δ 7.87-7.84 (m, 1H), 7.81 (s, 1H), 7.63-7.61 (m, 1H), 6.55 (d, J=43.6, 1H).

Step 2. Synthesis of 2-(2-bromo-5-chloro-phenyl)-2-fluoro-acetate (94b)

To a solution of 2-(2-bromo-5-chloro-phenyl)-2-fluoro-acetonitrile (94a, 4.47 g, 17.99 mmol) in methanol (50 mL)

was added, dropwise, sulfuric acid (10 mL, 187.6 mmol) at 75° C. The reaction was stirred at 75° C. for 18 h. TLC (PE, $R_f$=0.3) showed the reaction was complete. The mixture was quenched with $NaHCO_3$ (aq). The mixture was concentrated in vacuum and extracted with EA (2×100 mL). The combined organic layers were dried over $MgSO_4$. The solvent was removed in vacuum to afforded methyl 2-(2-bromo-5-chloro-phenyl)-2-fluoro-acetate (94b, 4.8 g, 14.7 mmol, 73% yield). $^1$H NMR (400 MHz, DMSO-d6): δ 7.67 (d, J=8.8, 1H), 7.60 (d, J=2, 1H), 7.53-7.50 (m, 1H), 6.36 (d, J=45, 1H), 3.752 (s, 3H).

Step 3. Synthesis of 2-(2-bromo-5-chloro-phenyl)-2-fluoro-ethanol (94c)

To a solution of methyl 2-(2-bromo-5-chloro-phenyl)-2-fluoro-acetate (94b, 4.8 g, 17.05 mmol) in methanol (40 mL) was added $NaBH_4$ (1.29 g, 34.1 mmol). The reaction was stirred at 25° C. for 2 h. TLC (PE:EA=4:1, $R_f$=0.5) showed the reaction was complete. The mixture was quenched with HCl (1N). Then, the mixture was concentrated in vacuum and extracted with EA (2×100 mL). The combined organic layers were dried over $MgSO_4$. The solvent was removed in vacuum to afford 2-(2-bromo-5-chloro-phenyl)-2-fluoro-ethanol (94c, 3.8 g, 15 mmol, 80% yield). $^1$H NMR (400 MHz, DMSO-d6): δ 7.69 (d, J=8.4, 1H), 7.60 (d, J=2.8, 1H), 7.43-7.40 (m, 1H), 5.78-5.76 (m, 1H), 5.40-5.37 (m, 1H), 3.83-3.65 (m, 2H).

Step 4. Synthesis of [2-(2-bromo-5-chloro-phenyl)-2-fluoro-ethoxy]-tert-butyl-dimethyl-silane (94d)

To a solution of 2-(2-bromo-5-chloro-phenyl)-2-fluoro-ethanol (94c, 3.8 g, 14.99 mmol) and imidazole (2.04 g, 29.98 mmol) in DCM (50 mL) was slowly added t-butylchlorodiphenylsilane (2.71 g, 17.99 mmol). The reaction mixture was stirred at 30° C. for 2 h. TLC (PE, $R_f$=0.4) showed the reaction was complete. The solvent was removed in vacuum and the crude product was purified by silica gel column chromatography (PE) to give [2-(2-bromo-5-chloro-phenyl)-2-fluoro-ethoxy]-tert-butyl-dimethyl-silane (94d, 5 g, 13.6 mmol, 91% yield) as a pale yellow oil. $^1$H NMR (400 MHz, DMSO-d6): δ 7.69 (d, J=8.4, 1H), 7.48-7.41 (m, 2H), 5.82-5.71 (m, 1H), 4.05-3.85 (m, 2H), 0.82 (s, 9H), 0.00-0.06 (m, 6H).

Step 5. Synthesis of [4-chloro-2-[(1R)-2-[tert-butyl (dimethyl)silyl]oxy-1-fluoro-ethyl]-phenyl]-[(3aR, 4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (94e1) and [4-chloro-2-[(1S)-2-[tert-butyl(dimethyl)silyl]oxy-1-fluoro-ethyl]phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (94e2)

To a solution of [2-(2-bromo-5-chloro-phenyl)-2-fluoro-ethoxy]-tert-butyl-dimethyl-silane (3.63 g, 9.87 mmol) in dry THE (8 mL) was stirred at −78° C. under Ar. The n-BuLi (4.7 mL, 11.76 mmol) was added and the reaction mixture was stirred for 10 mins. Then (3aR,4R,6S,6aS)-4-(4-chloropyrrolo2,3-d]pyrimidin-7-yl)-N-methoxy-N,2,2-trimethyl-3a,4,6,6a-tetrahydrofuro[3,4-d][1,3]dioxole-6-carboxamide (1Ad, 1.8 g, 4.7 mmol) in anhydrous THE (2.00 mL) was added. The mixture was stirred at −78° C. for 30 mins. TLC (PE:EA=5:1, $R_f$=0.5) showed the reaction was complete. The reaction was quenched with $CH_3COOH$. The mixture was combined with another batch to work up. The reaction was extracted in EtOAc (100 mL×3) and the organics were washed with water (50 mL×3), then saturated brine (50 mL×3). The organics were dried over $MgSO_4$, filtered, and concentrated in vacuum to give crude product which was further purified by SFC to give [4-chloro-2-[(1S)-2-[tert-butyl(dimethyl)silyl]oxy-1-fluoro-ethyl]phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (94e2, 300 mg, 0.49 mmol, 10.5% yield). LCMS [M+H]: 610.2. $^1$H NMR (400 MHz, DMSO-d6): δ 8.59 (s, 1H), 8.09-8.02 (m, 2H), 7.85-7.75 (m, 2H), 6.84 (d, J=3.6, 1H), 6.69 (s, 1H), 5.62-5.54 (m, 2H), 5.50-5.37 (m, 1H), 3.97-3.74 (m, 2H), 1.74 (s, 3H), 1.46 (s, 3H), 0.90 (s, 9H), −0.02 (d, J=13.6, 6H) and [4-chloro-2-[(1R)-2-[tert-butyl(dimethyl)silyl]oxy-1-fluoro-ethyl]-phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (94e1, 800 mg, 1.31 mmol, 28% yield). LCMS [M+H]: 610.2. $^1$H NMR (400 MHz, DMSO-d6): δ 8.52 (s, 1H), 7.77 (d, J=9.2, 1H), 7.69 (d, J=3.6, 1H), 7.28-7.26 (m, 1H), 6.48-6.46 (m, 2H), 5.77 (s, 1H), 5.71-5.51 (m, 2H), 5.44-5.31 (m, 1H), 3.97-3.33 (m, 2H), 1.59 (s, 3H), 1.42 (s, 3H), 0.83 (s, 9H), 0.01-0.01 (m, 6H).

Step 6. Synthesis of (R)-[4-chloro-2-[(1S)-2-[tert-butyl(dimethyl) silyl]oxy-1-fluoro-ethyl]phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (94f)

To a solution of [4-chloro-2-[(1S)-2-[tert-butyl(dimethyl) silyl]oxy-1-fluoro-ethyl]phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (94e2, 300 mg, 0.49 mmol) in toluene (7 mL) was added DIBAL-H (0.17 mL, 1.47 mmol). The mixture was stirred at −78° C. for 30 min under $N_2$. The solution was quenched with $CH_3COOH$. The mixture was combined with another batch to work up. The mixture was extracted with EtOAc (15 mL×3) and the organic layers were washed with water (20 mL×3), then brine (20 mL×3). The organic layers were dried over $MgSO_4$, filtered, and concentrated in vacuum. The crude product was purified by flash column chromatography on silica gel (PE:EA=5:1) to give (R)-[4-chloro-2-[(1S)-2-[tert-butyl(dimethyl) silyl]oxy-1-fluoro-ethyl]phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (94f, 300 mg, 0.49 mmol). LCMS [M+H]: 612.2. $^1$H NMR (400 MHz, DMSO-d6): δ 8.75 (s, 1H), 7.70 (d, J=12.8, 1H), 7.49 (s, 1H), 7.73-7.41 (m, 1H), 7.35-7.32 (m, 1H), 6.67-6.66 (m, 1H), 6.63 (d, J=1.6, 1H), 5.87-5.72 (s, 1H), 5.29-5.19 (m, 2H), 5.12-5.11 (m, 1H), 4.65 (s, 1H), 3.97-3.81 (m, 2H), 1.59 (s, 3H), 1.24 (s, 3H), 0.87 (s, 9H), 0.02-0.00 (m, 6H).

Step 7. Synthesis of give (2S)-2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]-2-fluoro-ethanol (94g)

To a solution of (R)-[4-chloro-2-[(1S)-2-[tert-butyl(dimethyl) silyl]oxy-1-fluoro-ethyl]phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (94f, 300 mg, 0.49 mmol) in THF (5 mL) was added TBAF (1 M) (0.26 mL, 0.98 mmol). The mixture was stirred at 25° C. for 30 mins under $N_2$. The mixture was combined with another batch to work up. The reaction was quenched with $NH_4Cl$, extracted with EA (10 mL×3). The combined organic extracts were washed with brine, dried over $MgSO_4$, filtered, concentrated in vacuum, and purified by silica gel column chromatography (PE:EA=1:1) to give (2S)-2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]-2-fluoro-ethanol (94g, 200 mg, 0.40 mmol, 82% yield). LCMS [M+H]: 498.1. $^1H$ NMR (400 MHz, DMSO-d6): δ 8.67 (s, 1H), 7.65 (d, J=8, 1H), 7.52-7.50 (m, 1H), 7.45-7.42 (m, 1H), 7.35-7.31 (m, 1H), 6.79 (s, 1H), 6.68 (d, J=3.6, 1H), 5.31-5.14 (m, 4H), 4.69 (s, 1H), 4.15-3.85 (m, 2H), 1.62 (s, 3H), 1.33 (s, 3H).

Step 8. Synthesis of (7S)-4-chloro-7-[(3aR,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94h1) and (7S)-4-chloro-7-[(3aR,6R,6aR)-2,2-dimethyl-6-[(1S,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94h2)

To a solution of 2-[5-chloro-2-[(R)-hydroxy-[(3aR,6R,6aR)-2,2-dimethyl-4-[(7S)-4-chloropyrrolo[2,3-d]pyrimidin-7-yl]-3a,4,6,6a-tetrahydrofuro[3,4-d][1,3]dioxol-6-yl]methyl]phenyl]-2-fluoro-ethanol (94g, 200 mg, 0.40 mmol) in THF (mL) was added NaH (19.26 mg, 0.80 mmol) at 25° C. and stirred for 10 mins. Tosyl chloride (76.52 mg, 0.40 mmol) was added and stirred for 1 h. The reaction mixture was combined with another batch to work up. The mixture was quenched with $H_2O$ and extracted with EA (10 mL×3). The combined organic layers were washed with brine (10 mL), dried over $MgSO_4$, filtered, and concentrated in vacuum. The crude product was purified by prep-HPLC, eluting with $CH_3CN$ in $H_2O$ (0.1% $NH_4OH$) from 5% to 95% to give (7S)-4-chloro-7-[(3aR,6R,6aR)-2,2-dimethyl-6-[(1S,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94h2, 15 mg, 0.031 mmol, 8% yield); LCMS [M+H]: 480.1, and (7S)-4-chloro-7-[(3aR,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94h1, 34 mg, 0.071 mmol, 17.6% yield). LCMS [M+H]: 480.1. $^1H$ NMR (400 MHz, DMSO-d6): δ 8.60 (s, 1H), 7.60 (d, J=4, 1H), 7.43-7.42 (m, 1H), 7.36-7.33 (m, 1H), 7.15 (d, J=8.4, 1H), 6.60 (d, J=3.6, 1H), 6.55 (d, J=3.6, 1H), 5.25 (d, J=50.8, 1H), 4.99-4.97 (m, 1H), 4.86-4.84 (m, 1H), 4.78-4.74 (m, 2H), 4.43-4.36 (m, 1H), 3.83-3.71 (m, 1H), 1.55 (s, 3H), 1.19 (s, 3H).

Step 9. Synthesis of 4-methyl-7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94i)

To a solution of tetrakis(triphenylphosphine)palladium (2.4 mg) and 4-chloro-7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94h1, 10 mg, 0.02 mmol) in THE (4 mL) was added dimethyl zinc (20 mg, 0.21 mmol). The mixture was stirred at 70° C. for 3 h. LCMS showed 20% of desired product. Another batch was combined with this reaction and concentrated in vacuum to give crude 4-methyl-7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94i) which was used for the next step directly. LCMS [M+H]: 460.3.

Step 10. Synthesis of (2R,3R,4S,5S)-2-(4-methylpyrrolo[2,3-d]pyrimidin-7-yl)-5-[(1R,4R)-6-chloro-4-fluoro-isochroman-1-yl]tetrahydrofuran-3,4-diol; 2,2,2-trifluoroacetic Acid (Ex. 94)

To a solution of 4-methyl-7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94i, 30 mg, 0.07 mmol) in water (1 mL) was added TFA (1.13 mL, 7.77 mmol). The mixture was stirred at 25° C. for 2 h. The residue was purified by prep-HPLC, eluting with $CH_3CN$ in $H_2O$ (0.1% TFA) from 5% to 95% to give a crude product which was further purified by prep-HPLC, eluted with $CH_3CN$ in $H_2O$ (0.1% $NH_3/H_2O$) from 5% to 95% to give (2R,3R,4S,5S)-2-(4-methylpyrrolo[2,3-d]pyrimidin-7-yl)-5-[(1R,4R)-6-chloro-4-fluoro-isochroman-1-yl]tetrahydrofuran-3,4-diol; 2,2,2-trifluoroacetic acid (Ex. 94, 3.5 mg, 0.0065 mmol, 10% yield) as a white solid. LCMS [M+H]: 420.3. $^1H$ NMR (400 MHz, DMSO-d6+D2O): δ 8.83 (s, 1H), 7.87 (d, J=3.2, 1H), 7.67 (s, 1H), 7.55-7.49 (m, 2H), 6.96 (s, 1H), 6.35 (d, J=8, 1H), 5.52 (d, J=50.4, 1H), 5.02-5.00 (m, 1H), 4.94-4.91 (m, 1H), 4.61 (d, J=2.8, 1H), 4.53-4.46 (m, 2H), 3.99-3.82 (m, 2H), 2.67 (s, 3H).

Example 95. Synthesis of (2R,3R,4S,5S)-2-(4-aminopyrrolo[2,3-d]pyrimidin-7-yl)-5-[(1R,4R)-6-chloro-4-fluoro-isochroman-1-yl]tetrahydrofuran-3,4-diol (Ex. 95)

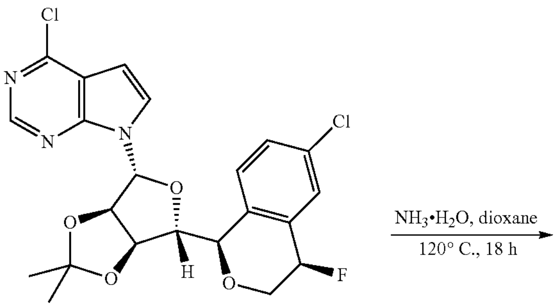

94h1

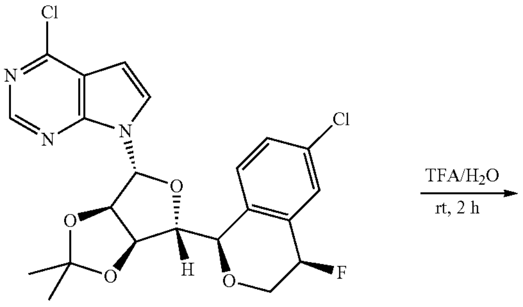

945a

-continued

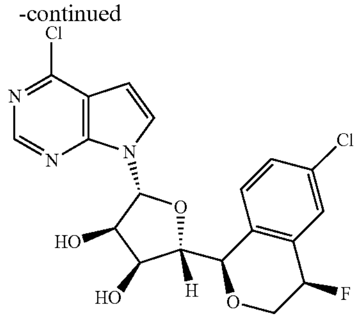

Ex. 95

Step 1. Synthesis of 7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidin-4-amine (95a)

To a solution of 4-chloro-7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidine (94h1, 35 mg, 0.07 mmol) in 1,4-dioxane (2.5 mL) was added ammonia (2.5 mL, 0.07 mmol). The mixture was sealed and stirred at 120° C. for 16 h. The reaction mixture was concentrated in vacuum to give crude 7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidin-4-amine (95a) which was used for the next step directly. LCMS [M+H]: 461.2.

Step 2. Synthesis of (2R,3R,4S,5S)-2-(4-aminopyrrolo[2,3-d]pyrimidin-7-yl)-5-[(1R,4R)-6-chloro-4-fluoro-isochroman-1-yl]tetrahydrofuran-3,4-diol (Ex. 95)

To a solution of 7-[(3aR,4R,6R,6aR)-2,2-dimethyl-6-[(1R,4R)-6-chloro-4-fluoro-isochroman-1-yl]-3a,4,6,6a-tetrahydrofuro[3,4-d][1,3]dioxol-4-yl]pyrrolo[2,3-d]pyrimidin-4-amine (95a, 25 mg, 0.05 mmol) in water (1 mL) was added 2,2,2-trifluoroacetic acid (1.0 mL, 12.98 mmol). The mixture was stirred at 25° C. for 30 mins. The residue was purified by prep-HPLC, eluting with $CH_3CN$ in $H_2O$ (0.1% $NH_4OH$) from 5% to 95% to give (2R,3R,4S,5S)-2-(4-aminopyrrolo[2,3-d]pyrimidin-7-yl)-5-[(1R,4R)-6-chloro-4-fluoro-isochroman-1-yl]tetrahydrofuran-3,4-diol (Ex. 95.6 mg, 0.014 mmol, 25% yield) as a white solid. LCMS [M+H]: 421.1. $^1H$ NMR (400 MHz, DMSO-d6+D2O): δ 8.07 (s, 1H), 7.65 (s, 1H), 7.51 (s, 2H), 7.38 (d, J=4, 1H), 6.67 (d, J=4.4, 1H), 6.21 (d, J=8, 1H), 5.59-5.46 (d, J=50, 1H), 4.88 (d, J=2.8, 1H), 4.52 (d, J=2.8, 1H), 4.46-4.34 (m, 2H), 3.96-3.87 (m, 1H), 3.81 (d, J=4.8, 1H).

Example 92. Synthesis of (2R,3R,4S,5S)-2-(4-methylpyrrolo[2,3-d]pyrimidin-7-yl)-5-[(1R,4S)-6-chloro-4-fluoro-isochroman-1-yl]tetrahydrofuran-3,4-diol (Ex. 92)

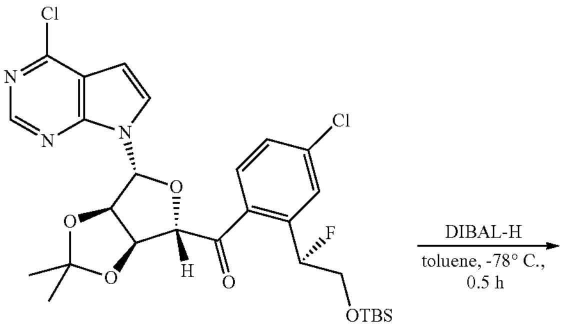

94e1

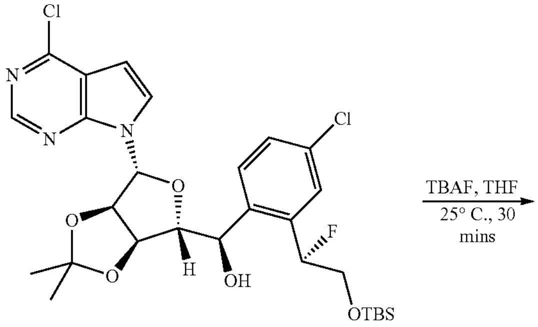

92a

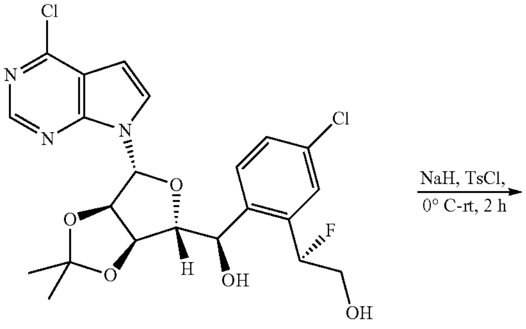

92b

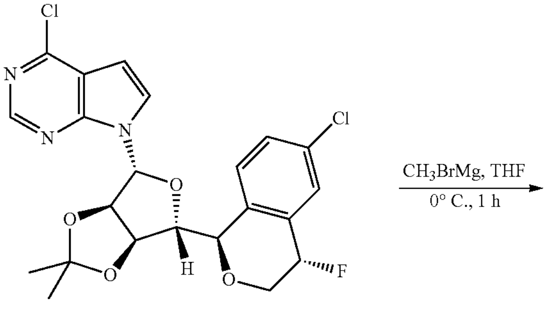

92c

-continued

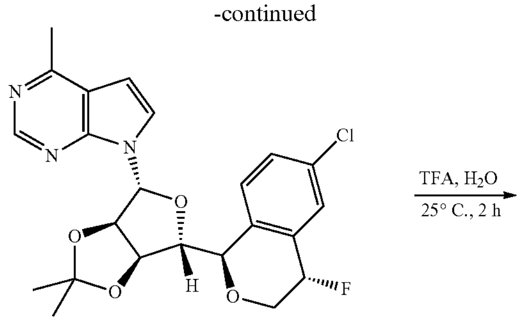

92d

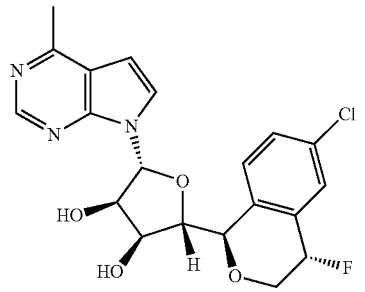

Ex. 92

Step 1. Synthesis of (R)-[4-chloro-2-[(1R)-2-[tert-butyl(dimethyl)silyl]oxy-1-fluoro-ethyl]phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (92a)

To a solution of [4-chloro-2-[(1R)-2-[tert-butyl(dimethyl)silyl]oxy-1-fluoro-ethyl]phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]methanone (94e1, 800 mg, 1.31 mmol) in toluene (7 mL) was added DIBAL (0.45 mL, 3.93 mmol). The mixture was stirred at −78° C. for 30 mins under $N_2$. The solution was quenched with $NH_4Cl$. The mixture was combined with another batch to work up. The mixture was extracted with EtOAc (15 mL×3) and the organic layers were washed with water (20 mL×3), then brine (20 mL×3). The organic layers were dried over $MgSO_4$, filtered, concentrated in vacuum. The crude product was purified by flash column chromatography on silica gel (PE:EA=5:1) to give (R)-[4-chloro-2-[(1R)-2-[tert-butyl(dimethyl)silyl]oxy-1-fluoro-ethyl]phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (92a, 520 mg, 0.85 mmol, 65% yield). LCMS [M+H]: 612.2. $^1$H NMR (400 MHz, DMSO-d6): δ 8.68 (s, 1H), 7.69 (d, J=8, 1H), 7.40 (s, 1H), 7.34 (d, J=3.6, 1H), 6.67 (d, J=3.6, 1H), 6.46 (d, J=1.2, 1H), 5.86 (d, J=4.8, 1H), 5.83-5.68 (m, 1H), 5.34 (s, 1H), 5.27-5.16 (m, 1H), 5.16-5.16 (m, 1H), 4.52 (s, 1H), 4.02-3.78 (m, 2H), 1.58 (s, 3H), 1.26 (s, 3H), 0.83 (s, 9H), 0.02-0.00 (m, 6H).

Step 2. Synthesis of (2R)-2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]-2-fluoro-ethanol (92b)

To a solution of (R)-[4-chloro-2-[(1R)-2-[tert-butyl(dimethyl)silyl]oxy-1-fluoro-ethyl]phenyl]-[(3aR,4R,6R,6aR)-

4-(4-chloropyrrolo[2,3-d]pyrimidin-7-yl)-2,2-dimethyl-3a,4,6,6a-tetrahydrofuro[3,4-d][1,3]dioxol-6-yl]methanol (92a, 520 mg, 0.85 mmol) in THF (5 mL) was added TBAF (1 M) (0.44 mL, 1.7 mmol). The mixture was stirred at 25° C. for 30 mins under $N_2$. The mixture was combined with another batch to work up. The solution was quenched with $NH_4Cl$ and washed with EA, and the solvent was removed in vacuum. The crude product was purified by flash column chromatography (PE:EA=3:1) to give (2R)-2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]-2-fluoro-ethanol (92b, 330 mg, 0.66 mmol, 78% yield). LCMS [M+H]: 498.1. $^1$H NMR (400 MHz, DMSO-d6): δ 8.68 (s, 1H), 7.73 (d, J=8.4, 1H), 7.45-7.40 (m, 2H), 7.33 (d, J=4, 1H), 6.67 (d, J=4, 1H), 6.39 (d, J=1.6, 1H), 5.88-5.73 (m, 2H), 5.33 (s, 1H), 5.28-5.25 (m, 1H), 5.17-5.15 (m, 1H), 4.48 (s, 1H), 3.99-3.67 (m, 2H), 1.59 (s, 3H), 1.32 (s, 3H).

Step 3. Synthesis of 4-chloro-7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidine (92c)

To a solution of (2R)-2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]-2-fluoro-ethanol (92b, 300 mg, 0.60 mmol) in THF (mL) was added NaH (28.9 mg, 1.2 mmol) at 0° C. and stirred for 10 mins. Tosyl chloride (115 mg, 0.60 mmol) was added to the mixture and stirred for 1 h. The mixture was combined with another batch to work up. The mixture was quenched with $H_2O$ and extracted with EA (10 mL×3). The combined organic layers were washed with brine (10 mL), dried over $MgSO_4$, filtered and concentrated in vacuum. The crude product was purified by silica gel column chromatography (PE:EA=5:1) to give 4-chloro-7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidine (92c, 90 mg, 0.192 mmol). LCMS [M+H]: 480.1. $^1$H NMR (400 MHz, DMSO-d6): δ 8.61 (d, J=6, 1H), 7.46-7.43 (m, 2H), 7.19 (d, J=8, 1H), 6.98 (d, J=8.4, 1H), 6.62 (d, J=3.6, 1H), 6.37 (d, J=3.2, 1H), 5.57-5.41 (m, 1H), 5.08-5.05 (m, 1H), 4.89-4.85 (m, 2H), 4.53-4.51 (m, 1H), 4.33-4.27 (m, 1H), 3.79-3.72 (m, 1H), 1.54 (s, 3H), 1.25 (s, 3H).

Step 4. Synthesis of 4-methyl-7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidine (92d)

To a solution of 4-chloro-7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidine (92c, 10 mg, 0.02 mmol) and ferric acetylacetonate (0.74 mg, 0.002 mmol) in THF (4 mL) was slowly added methylmagnesium bromide (23 mg, 0.21 mmol) at −30° C. The mixture was stirred at 0° C. for 1 h. The mixture was concentrated in vacuum to give crude 4-methyl-7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidine (92d) which was used for the next step directly. LCMS [M+H]: 460.2.

Step 5. Synthesis of (2R,3R,4S,5S)-2-(4-methylpyrrolo[2,3-d]pyrimidin-7-yl)-5-[(1R,4S)-6-chloro-4-fluoro-isochroman-1-yl]tetrahydrofuran-3,4-diol (Ex. 92)

To a solution of 4-methyl-7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidine (92d, 10 mg, 0.02 mmol) in water (1 mL) was added TFA (1.0 mL, 6.86 mmol). The mixture was stirred at 25° C. for 2 h. The mixture was purified by prep-HPLC, eluted with $CH_3CN$ in $H_2O$ (0.1% $NH_4OH$) from 5% to 95% to give (2R,3R,4S,5S)-2-(4-methylpyrrolo[2,3-d]pyrimidin-7-yl)-5-[(1R,4S)-6-chloro-4-fluoro-isochroman-1-yl]tetrahydrofuran-3,4-diol (Ex. 92, 7 mg, 0.016 mmol, 75% yield) as a white solid. LCMS [M+H]: 420.2. $^1$H NMR (400 MHz, DMSO-d6+D2O): δ 8.67 (s, 1H), 7.75 (d, J=3.6, 1H), 7.55 (d, J=1.6, 1H), 7.36 (d, J=8.8, 1H), 7.25 (d, J=8.4, 1H), 6.82 (d, J=4, 1H), 6.25 (d, J=7.2, 1H), 5.67-5.52 (m, 1H).

Example 93. Synthesis of (2R,3R,4S,5S)-2-(4-aminopyrrolo[2,3-d]pyrimidin-7-yl)-5-[(1R,4S)-6-chloro-4-fluoro-isochroman-1-yl]tetrahydrofuran-3,4-diol (Ex. 93)

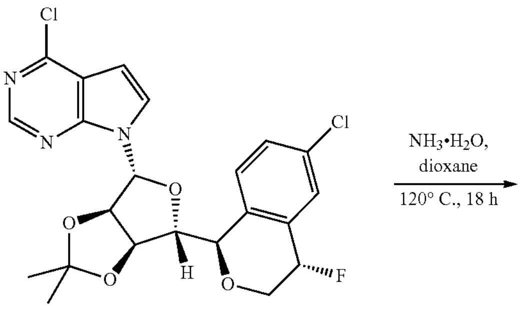

92c

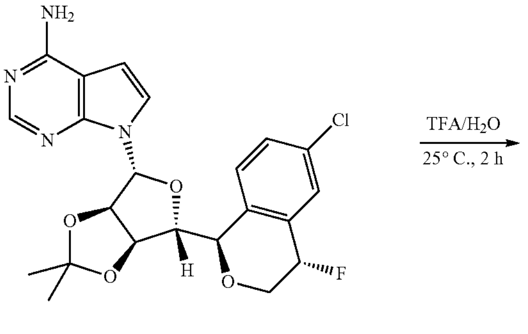

93a

-continued

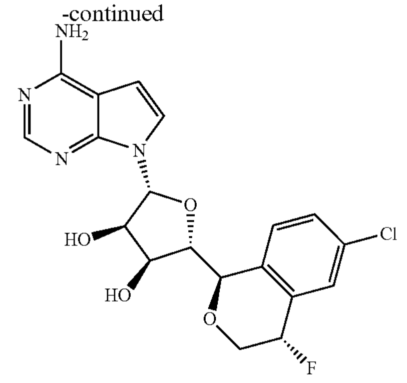

Ex. 93

Step 1. Synthesis of 7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidin-4-amine (93a)

To a solution of 4-chloro-7-[(3aR,4R,6R,6aR)-2,2-dimethyl-6-[(1R,4S)-6-chloro-4-fluoro-isochroman-1-yl]-3a,4,6,6a-tetrahydrofuro[3,4-d][1,3]dioxol-4-yl]pyrrolo[2,3-d]pyrimidine (92c, 10 mg, 0.02 mmol) in 1,4-dioxane (2.5 mL) was added ammonia (2.5 mL, 0.02 mmol). The mixture was sealed and stirred at 120° C. for 16 h. The mixture was concentrated in vacuum to give crude 7-[(3aR,4R,6R,6aR)-2,2-dimethyl-6-[(1R,4S)-6-chloro-4-fluoro-isochroman-1-yl]-3a,4,6,6a tetrahydrofuro[3,4-d][1,3]dioxol-4-yl]pyrrolo[2,3-d]pyrimidin-4-amine (93a) which was used for the next step directly. LCMS [M+H]: 461.2.

Step 2. Synthesis of (2R,3R,4S,5S)-2-(4-aminopyrrolo[2,3-d]pyrimidin-7-yl)-5-[(1R,4S)-6-chloro-4-fluoro-isochroman-1-yl]tetrahydrofuran-3,4-diol (Ex. 93)

To a solution of 7-[(3aR,4R,6R,6aR)-2,2-dimethyl-6-[(1R,4S)-6-chloro-4-fluoro isochroman-1-yl]-3a,4,6,6a-tetrahydrofuro[3,4-d][1,3]dioxol-4-yl]pyrrolo[2,3-d]pyrimidin-4-amine (93a, 10 mg, 0.02 mmol) in water (2 mL) was added 2,2,2-trifluoroacetic acid (1 mL, 13 mmol). The mixture was stirred at 25° C. for 60 min. The residue was purified by pre-HPLC, eluting with $CH_3CN$ in $H_2O$ (0.1% $NH_4OH$) from 5% to 95% to give (2R,3R,4S,5S)-2-(4-aminopyrrolo[2,3-d]pyrimidin-7-yl)-5-[(1R,4S)-6-chloro-4-fluoro-isochroman-1-yl]tetrahydrofuran-3,4-diol (5 mg, 0.011 mmol, 53% yield) as a white solid. LCMS [M+H]: 421.1. $^1$H NMR (400 MHz, DMSO d6+D2O): δ 8.06 (s, 1H), 7.55 (s, 1H), 7.39-7.32 (m, 1H), 7.28 (d, J=19.2, 1H), 7.25 (d, J=8, 1H), 6.65 (d, J=3.6, 1H), 6.11 (d, J=7.2, 1H), 5.64-5.51 (m, 1H), 4.99-4.98 (m, 1H), 4.53-4.50 (m, 1H), 4.40-4.33 (m, 1H), 4.31-4.25 (m, 1H), 4.12-3.98 (m, 1H), 3.95-3.91 (m, 1H).

Example 97. Synthesis of (2R,3R,4S,5S)-2-(4-methylpyrrolo[2,3-d]pyrimidin-7-yl)-5-[(4R)-7,8-difluoro-4H-1,3-benzodioxin-4-yl]tetrahydrofuran-3,4-diol (Ex. 97)
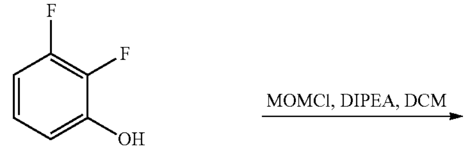
97a
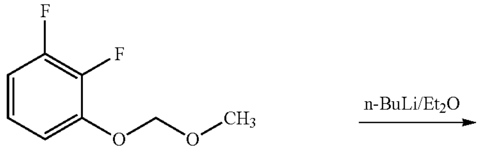
97b
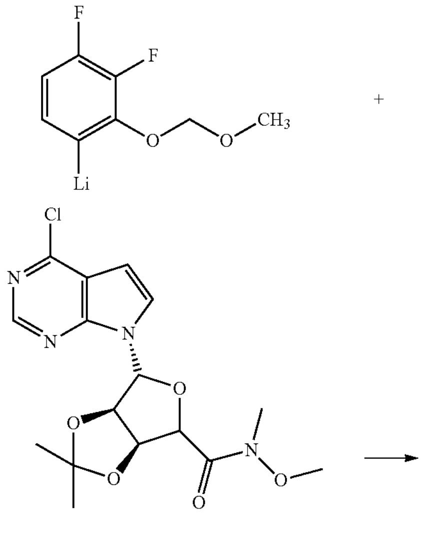
1Ad
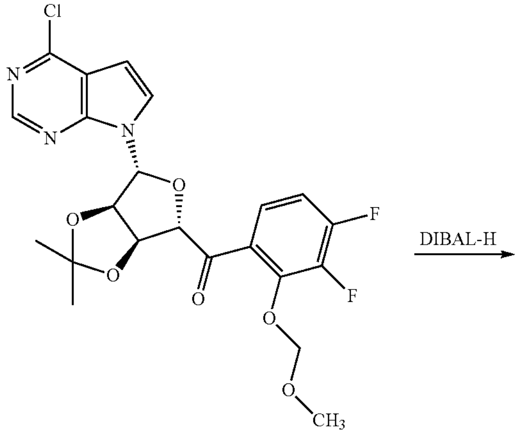
97c
-continued
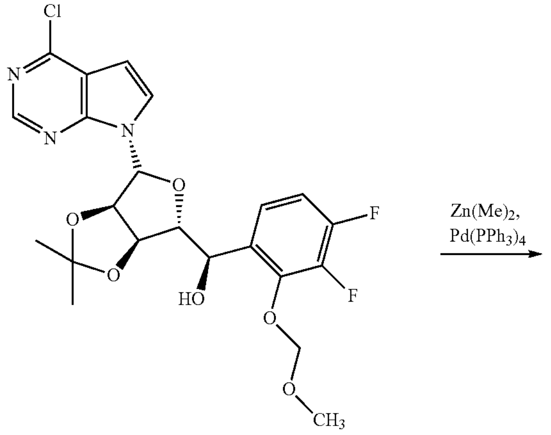
97d
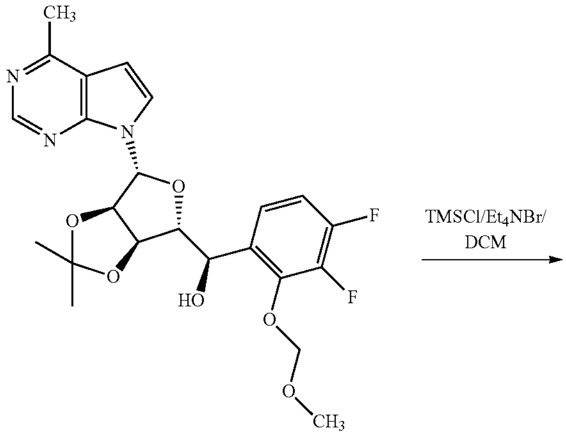
97e
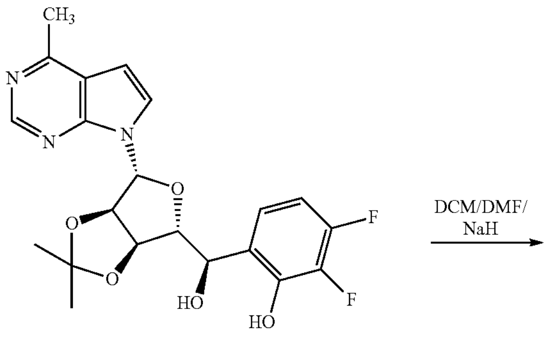
97f -continued

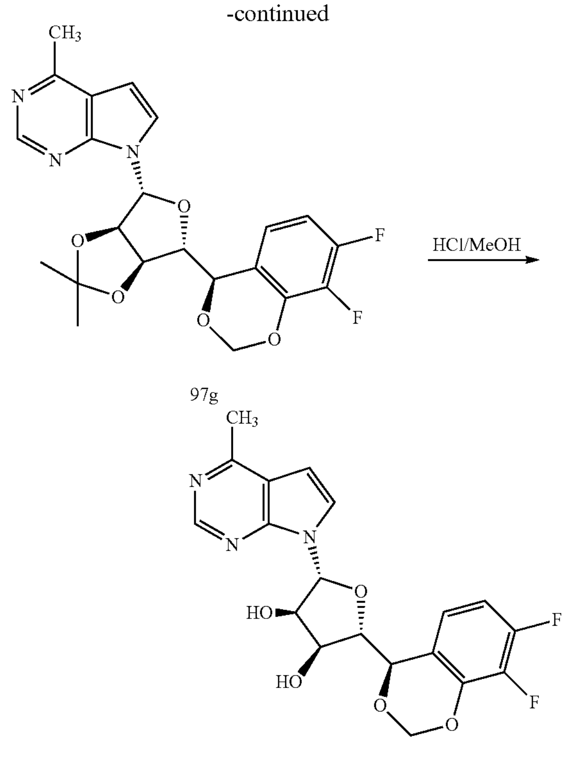

97g

Ex. 97

Step 1. Synthesis of 1,2-difluoro-3-(methoxymethoxy)benzene (97b)

To a clear colorless solution of 2,3-difluorophenol (97a, 3.08 g, 23.68 mmol) and N,N-diisopropylethylamine (4.95 mL, 28.41 mmol) under nitrogen at 0° C. in an ice bath was added chloromethyl methyl ether (2.16 mL, 28.41 mmol) dropwise. The ice bath was removed, and the clear orange reaction stirred at rt. After 35 min, TLC (2% EtOAc/hexanes) shows a clean product spot (rf=0.23) with no remaining phenol. The reaction was concentrated and purified by flash column chromatography (0-3% EtOAc/hexanes, ramping up to 30% to flush out product because peak tails). The product fractions were concentrated to 1,2-difluoro-3-(methoxymethoxy)benzene (97b, 2.79 g, 16.022 mmol, 68% yield), as a clear pale yellow oil. LCMS does not show good ionization.

Step 2. Synthesis of [3,4-difluoro-2-(methoxymethoxy)phenyl]-[(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl] methanone (97c)

A solution of 1,2-difluoro-3-(methoxymethoxy)benzene (97b, 181.96 mg, 1.04 mmol) in diethyl ether (2 mL) was chilled in an ice bath. n-BuLi (0.67 mL, 1.07 mmol) was added drop-wise and the solution was stirred cold for 3 min (yielding a milky mixture), and the ice bath was removed. The reaction becomes a pale yellow suspension. After 2 h, the reaction was returned to an ice bath, and a solution of (3aR,4R,6S,6aS)-4-(4-chloropyrrolo[2,3-d]pyrimidin-7-yl)-N methoxy-N,2,2-trimethyl-3a,4,6,6a-tetrahydrofuro[3,4-d][1,3]dioxole-6-carboxamide (1Ad, 150 mg, 0.39 mmol) in diethyl ether (1 mL) was added. The bath was removed, and the reaction stirred at rt to yield an orange-red opaque mixture. After 2 h, LCMS showed that the reaction was complete. The reaction was cooled on an ice bath and added sat'd $NH_4Cl$ followed by EtOAc. The layers were separated and the aqueous extracted 2×EtOAc. The combined organics were washed with brine, filtered through cotton and concentrated to an orange oil, which was purified by flash column chromatography, 5%-40% EtOAc/hexanes to yield [3,4-difluoro-2-(methoxymethoxy)phenyl]-[(3aR,4R,6S,6aS)-4-(4-chloropyrrolo[2,3-d]pyrimidin-7-yl)-2,2-dimethyl-3a,4,6,6a tetrahydrofuro[3,4-d][1,3]dioxol-6-yl] methanone (97c, 77 mg, 0.15529 mmol, 40% yield). LCMS [M+H]: 496.0.

Step 3. Synthesis of (R)-[3,4-difluoro-2-(methoxymethoxy)phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl] methanol (97d)

An amber solution of [3,4-difluoro-2-(methoxymethoxy) phenyl]-[(3aR,4R,6S,6aS)-4-(4-chloropyrrolo[2,3-d]pyrimidin-7-yl)-2,2-dimethyl-3a,4,6,6a tetrahydrofuro[3,4-d][1,3]dioxol-6-yl]methanone (97c, 163 mg, 0.33 mmol) in toluene (5 mL) under $N_2$ was cooled to −78° C., and then charged with diisobutylaluminum hydride (1 M in toluene; 0.66 mL, 0.66 mmol) slowly dropwise. The resulting clear yellow solution was stirred at −78° C. for 1 h. LCMS shows some starting material remains. An additional portion of diisobutylaluminum hydride (1 M in toluene; 0.2 mL, 0.2 mmol) was added. After 30 min, the reaction was transferred to an ice bath and allowed to warm to 0° C. and quenched by slow addition of several mL of EtOAc, followed by several addition of a saturated aqueous solution of Rochelle's salt. The ice bath was removed, additional EtOAc and sat'd Rochelle's salt was added, and the mixture stirred vigorously. The layers were separated and the aqueous was extracted with EtOAc. The combined organic layers were washed with brine, filtered through cotton, and concentrated to yield (R)-[3,4-difluoro-2-(methoxymethoxy) phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (97d, 170 mg, 0.34145 mmol, 104% yield), which was used in the next reaction without further purification. LCMS [M+H]: 498.0.

Step 4. Synthesis of (R)-[3,4-difluoro-2-(methoxymethoxy)phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl] methanol (97e)

To (R)-[3,4-difluoro-2-(methoxymethoxy)phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl] methanol (97d, 170 mg, 0.34 mmol) and tetrakis (triphenylphosphine)palladium(0) (19.73 mg, 0.02 mmol) under nitrogen in a capped 2 mL microwave vial was added THF (10 mL). The mixture was sparged with nitrogen for 10 min. Dimethylzinc (2 M in hexanes; 0.75 mL, 1.5 mmol) was added carefully via syringe (gas evolution) to yield a lighter yellow solution, which was heated to 70° C. Reaction gradually becomes dark orange. After 2 h, LCMS showed the reaction was complete. The reaction was cooled to rt and quenched with sat'd $NaHCO_3$ and extracted 2×EtOAc. The combined organics were washed with brine, filtered through cotton, and concentrated. The crude product was purified by flash column chromatography, 14%-100% EtOAc/hexanes to yield (R)-[3,4-difluoro-2-(methoxymethoxy)phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (97e, 111 mg, 0.23248 mmol, 68% yield). LCMS [M+H]: 478.1.

Step 5. Synthesis of 2,3-difluoro-6-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]phenol (97f)

To a mixture of (R)-[3,4-difluoro-2-(methoxymethoxy)phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (97e, 85 mg, 0.18 mmol) and tetraethylammonium bromide (112.24 mg, 0.53 mmol) was added DCM (4 mL) and the resulting yellow solution was chilled on an ice bath. Chlorotrimethylsilane (0.07 mL, 0.53 mmol) was added and the reaction was allowed to warm to rt in the ice bath and stirred at rt overnight. Added an additional tetraethylammonium bromide (112.24 mg, 0.53 mmol) and chlorotrimethylsilane (0.07 mL, 0.53 mmol). After 4 h, the reaction was concentrated and purified by flash column chromatography (100% DCM-8% MeOH/DCM) to yield 2,3-difluoro-6-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]phenol (97f, 43 mg, 0.01 mmol, 56% yield). LCMS [M+H]: 434.1.

Step 6. Synthesis of 4-methyl-7-[(3aR,4R,6R,6aR)-2,2-dimethyl-6-[(4R)-7,8-difluoro-4H-1,3-benzodioxin-4-yl]-3a,4,6,6a-tetrahydrofuro[3,4-d][1,3]dioxol-4-yl]pyrrolo[2,3-d]pyrimidine (97g)

To an orange solution of 2,3-difluoro-6-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]phenol (97f, 56 mg, 0.13 mmol) in DMF (5 mL) and DCM (2.5 mL) under nitrogen was added sodium hydride (51.68 mg, 1.29 mmol) and the reaction was heated to 80° C. After 5 h, the reaction was chilled on an ice bath and quenched with sat'd aqueous $NH_4Cl$, diluted with brine, and extracted 3×EtOAc. The combined organics were washed 3× brine, filtered through cotton, concentrated and dried under high vacuum. The crude product was purified by flash column chromatography, 13%-100% EtOAc/hexanes to yield 4-methyl-7-[(3aR,4R,6R,6aR)-2,2-dimethyl-6-[(4R)-7,8-difluoro-4H-1,3-benzodioxin-4-yl]-3a,4,6,6a-tetrahydrofuro[3,4-d][1,3]dioxol-4-yl]pyrrolo[2,3-d]pyrimidine (97g, 31 mg, 0.0696 mmol, 54% yield). LCMS [M+H]: 446.0.

Step 7. Synthesis of (2R,3R,4S,5S)-2-(4-methylpyrrolo[2,3-d]pyrimidin-7-yl)-5-[(4R)-7,8-difluoro-4H-1,3-benzodioxin-4-yl]tetrahydrofuran-3,4-diol (Ex. 97)

A clear solution of 4-methyl-7-[(3aR,4R,6R,6aR)-2,2-dimethyl-6-[(4R)-7,8-difluoro-4H-1,3-benzodioxin-4-yl]-3a,4,6,6a-tetrahydrofuro[3,4-d][1,3]dioxol-4-yl]pyrrolo[2,3-d]pyrimidine (97g, 29 mg, 0.07 mmol) in methanol (2 mL) was chilled briefly on an ice bath, then hydrochloric acid (2 mL, 4 mmol) was added and the resulting faintly hazy solution was stirred at rt. After 5 h, the reaction was chilled on an ice bath and carefully basified to pH~8 with 1N NaOH, then extracted 3×EtOAc. The combined extracts were washed with brine, filtered through cotton and concentrated. The crude product was purified by flash column chromatography, 0-10% MeOH/DCM to yield (2R,3R,4S,5S)-2-(4-methylpyrrolo[2,3-d]pyrimidin-7-yl)-5-[(4R)-7,8-difluoro-4H-1,3-benzodioxin-4-yl]tetrahydrofuran-3,4-diol (Ex. 97, 20 mg, 0.0449 mmol, 69% yield). LCMS [M+H]: 406.1. $^1H$ NMR (500 MHz, DMSO-d6) δ 8.66 (s, 1H), 7.76 (d, J=3.8 Hz, 1H), 7.15-7.07 (m, 1H), 7.00 (q, J=9.3 Hz, 1H), 6.80 (d, J=3.7 Hz, 1H), 6.31 (d, J=7.7 Hz, 1H), 5.62 (d, J=5.7 Hz, 1H), 5.35 (d, J=6.9 Hz, 1H), 5.31 (d, J=5.7 Hz, 1H), 5.26-5.22 (m, 2H), 4.56 (td, J=5.1, 7.3 Hz, 1H), 4.41 (dd, J=1.4, 4.5 Hz, 1H), 3.94 (t, J=4.9 Hz, 1H), 2.66 (s, 3H). $D_2O$ exchange: 1H NMR (500 MHz, DMSO-d6) δ 8.66 (s, 1H), 7.75 (d, J=3.8 Hz, 1H), 7.13-7.07 (m, 1H), 6.99 (td, J=7.2, 9.2, 9.6 Hz, 1H), 6.80 (d, J=3.8 Hz, 1H), 6.30 (d, J=7.7 Hz, 1H), 5.61 (d, J=5.7 Hz, 1H), 5.30 (d, J=5.8 Hz, 1H), 5.23 (d, J=4.4 Hz, 1H), 4.55 (dd, J=5.1, 7.7 Hz, 1H), 4.40 (dd, J=1.4, 4.5 Hz, 1H), 3.93 (dd, J=1.4, 5.1 Hz, 1H), 2.66 (s, 3H).

Example 98. Synthesis of (2R,3S,4R,5R)-2-[(1R)-6-chloro-1,2,3,4-tetrahydroisoquinolin-1-yl]-5-(4-methylpyrrolo[2,3-d]pyrimidin-7-yl)tetrahydrofuran-3,4-diol; 2,2,2-trifluoroacetic Acid (Ex. 98)

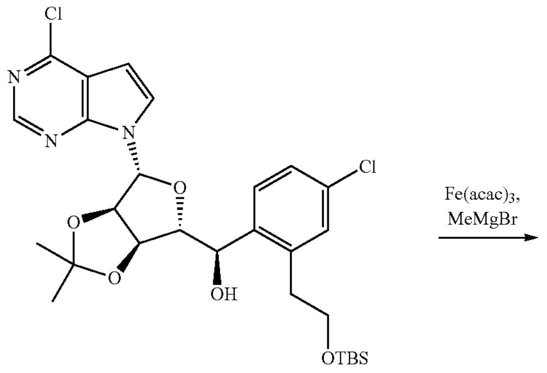

22d

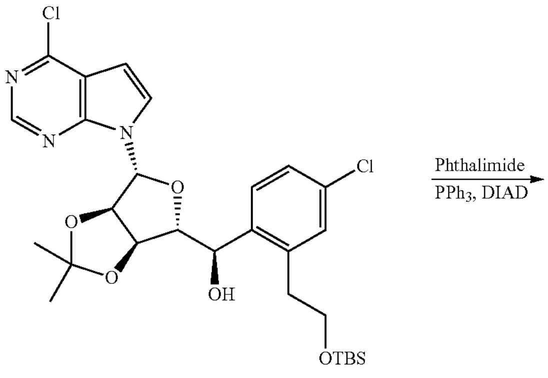

98a

-continued

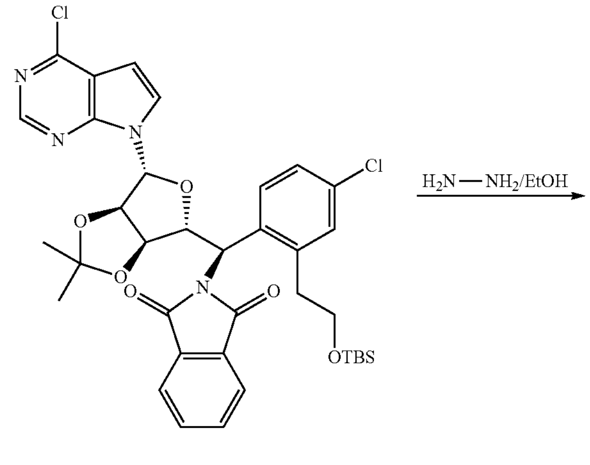

98b

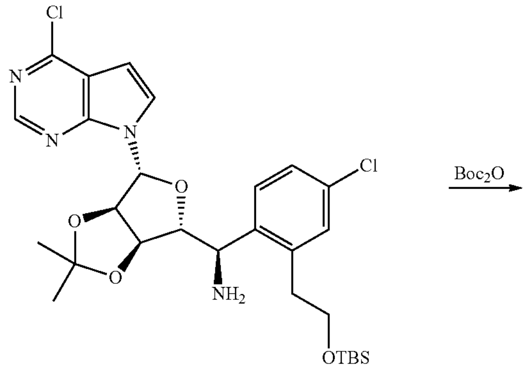

98c

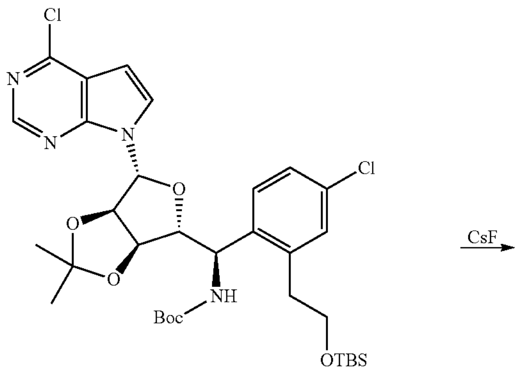

98d

-continued

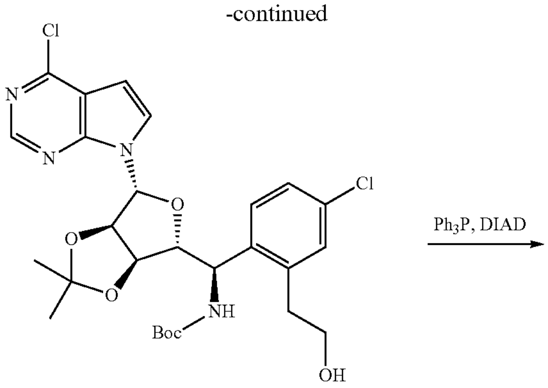

98e

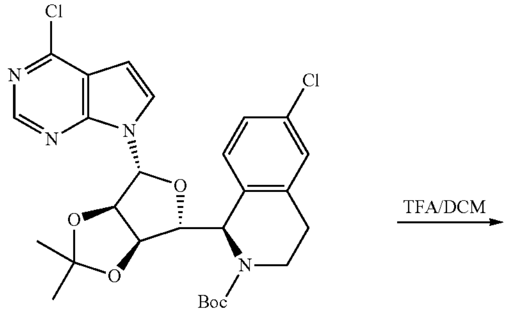

98f

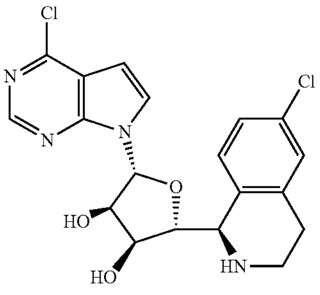

Ex. 98

Step 1. (S)-[2-[2-[tert-butyl(dimethyl)silyl]oxy-ethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (98a)

Methylmagnesium bromide, 3.2 M in MeTHF (0.09 mL, 0.30 mmol) was added dropwise into a suspension of (S)-[2-[2-[tert-butyl(dimethyl)silyl]oxyethyl]-4-chloro-phenyl]-[(3aR,4R,6R,6aR)-4-(4-chloropyrrolo[2,3-d]pyrimidin-7-yl)-2,2-dimethyl-3a,4,6,6a tetrahydrofuro[3,4-d][1,3]dioxol-6-yl]methanol (22d, 80 mg, 0.13 mmol) and iron(III) acetylacetonate (5 mg, 0.01 mmol) in THF (0.50 mL) at 0° C. The reaction mixture was stirred at 0° C. for 40 min, then at rt overnight. The reaction was quenched with EtOAc, followed by saturated aqueous $NH_4Cl$ and the mixture was diluted with EtOAc. The organic layer was separated, washed with brine, dried over $Na_2SO_4$ and concentrated. The crude product was purified by flash column chromatography (0-100% EtOAc/hexane) to yield (S)-[2-[2-[tert butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (98a, 35 mg, 0.049 mmol, 36% yield) as a yellow oil. LCMS [M+H]: 574.16.

Step 2. 2-[(R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]isoindoline-1,3-dione (98b)

Diisopropyl azodicarboxylate (0.02 mL, 0.12 mmol) was added dropwise into a solution of (S)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (98a, 35 mg, 0.06 mmol), triphenylphosphine (24 mg, 0.09 mmol), and phthalimide (13.45 mg, 0.09 mmol) in THF (0.50 mL). In 30 min, TLC (2:1 Hexane/EA) showed the reaction was complete. The reaction mixture was concentrated and the crude product was purified by flash column chromatography (0-100% EtOAc/hexane) to give 2-[(R)-[2-[2-[tert butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]isoindoline-1,3-dione (98b, 37 mg, 0.042 mmol, 69% yield) as a yellow foamy solid. LCMS [M+H]: 703.2/705.2.

Step 3. (R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanamine (98c)

Hydrazine monohydrate (2.7 mg, 0.08 mmol) was added to a suspension of 2-[(R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]isoindoline-1,3-dione (98b, 37 mg, 0.04 mmol) in EtOH (0.50 mL). The resulting mixture was stirred at rt overnight, then at 80° C. for 6 hr. The reaction mixture was concentrated to give the crude product, (R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a tetrahydrofuro[3,4-d][1,3]dioxol-6-yl]methanamine (98c, 40 mg, 0.042 mmol, 99.5% yield) which was carried on to the next step without purification. LCMS [M+H]: 574.2/576.1.

Step 4. tert-butyl N—[(R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a tetrahydrofuro[3,4-d][1,3]dioxol-6-yl]methyl]carbamate (98d)

Triethylamine (0.01 mL, 0.08 mmol) was added dropwise to a suspension of (R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanamine (98c, 40 mg, 0.04 mmol) and di-tert butyl dicarbonate (18 mg, 0.08 mmol) in dry DCM (0.50 mL) at rt and the resulting mixture was stirred at rt for 2 h. The reaction was concentrated and the residue was purified by flash column chromatography (0-8% MeOH/DCM) to give tert-butyl N—[(R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]carbamate (98d, 30 mg, 0.036 mmol, 85% yield) LCMS [M+H]: 673.1/675.3. $^1$H NMR (500 MHz, Methanol-d4) δ 8.71 (s, 1H), 7.50 (d, J=3.7 Hz, 1H), 7.36 (d, J=8.4 Hz, 1H), 7.19-7.01 (m, 2H), 6.73 (d, J=3.7 Hz, 1H), 6.19 (d, J=2.5 Hz, 1H), 5.33 (dd, J=2.4, 6.6 Hz, 1H), 5.24 (dd, J=4.4, 6.6 Hz, 1H), 5.16 (d, J=8.9 Hz, 1H), 4.32 (dd, J=4.4, 8.8 Hz, 1H), 3.62-3.52 (m, 1H), 3.46 (dt, J=5.6, 10.6 Hz, 1H), 2.72 (s, 3H), 2.50 (t, J=12.1 Hz, 2H), 1.63 (s, 2H), 1.60 (s, 3H), 1.45 (d, J=10.3 Hz, 9H), 1.36 (s, 3H), 0.77 (s, 9H), −0.25 (d, J=15.6 Hz, 6H).

Step 5. tert-butyl N—[(R)-[4-chloro-2-(2-hydroxyethyl)phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]carbamate (98e)

A suspension of tert-butyl N—[(R)-[2-[2-[tert-butyl(dimethyl)silyl]oxyethyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]carbamate (98d, 20 mg, 0.02 mmol), cesium fluoride (5.5 mg, 0.04 mmol) in DMSO (0.40 mL) was stirred at rt for 2 h. The reaction mixture was filtered and purified directly by reverse phase chromatography (10%-100% MeCN/water) to give tert-butyl N—[(R)-[4-chloro-2-(2-hydroxyethyl)phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]carbamate (98e, 10 mg, 0.018 mmol, 75% yield). LCMS [M+H]: 559.2/561.1.

Step 6. tert-butyl (1R)-6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-3,4-dihydro-1H-isoquinoline-2-carboxylate (98f)

Diisopropyl azodicarboxylate (0.01 mL, 0.04 mmol) was added a to a solution of triphenylphosphine (9.38 mg, 0.04 mmol) and tert-butyl N—[(S)-[4-chloro-2-(2-hydroxyethyl)phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]carbamate (98e, 10 mg, 0.02 mmol) in dry THF (0.50 mL). The reaction mixture was stirred at rt for 1 h. Diisopropyl azodicarboxylate (0.01 mL, 0.04 mmol) and triphenylphosphine (9.38 mg, 0.04 mmol) were added and the reaction was stirred for an additional 1 h. The reaction mixture was concentrate and purified by flash column chromatography (0-12% MeOH in DCM) to give tert-butyl (1R)-6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-3,4-dihydro-1H-isoquinoline-2-carboxylate (98f, 10 mg, 0.009 mmol, 52% yield). LCMS [M+H]: 541.1/543.3.

Step 7. (2R,3S,4R,5R)-2-[(1R)-6-chloro-1,2,3,4-tetrahydroisoquinolin-1-yl]-5-(4-methylpyrrolo[2,3-d]pyrimidin-7-yl)tetrahydrofuran-3,4-diol; 2,2,2-trifluoroacetic Acid (Ex. 98)

A mixture of tert-butyl (1R)-6-chloro-1-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-3,4-dihydro-1H-isoquinoline-2-carboxylate (98f, 10 mg, 0.02 mmol), HCl (0.67 mg, 0.02 mmol) and methanol (0.50 mL) was stirred at rt overnight. LCMS showed the acetonide was cleaved but not the Boc. The reaction mixture was concentrated and lyophilized to a white solid which was dissolved in DCM (0.50 mL) and TFA (0.26 mL, 2.89 mmol) and stirred at rt for 1h. The reaction mixture was concentrated and the residue was purified by reverse phase chromatography (0-70% MeCN/water/0.1% TFA) to give (2R,3S,4R,5R)-2-[(1R)-6-chloro-1,2,3,4-tetrahydroisoquinolin-1-yl]-5-(4-methylpyrrolo[2,3-d]pyrimidin-7-yl)tetrahydrofuran-3,4-diol; 2,2,2-trifluoroacetic acid (Ex. 98.3 mg, 0.006 mmol, 30% yield) as a white solid. LCMS [M+H]: 401.1. $^1$H NMR (500 MHz, DMSO-$d_6$) δ 8.74 (s, 1H), 7.37-7.15 (m, 3H), 7.00 (d, J=3.8 Hz, 1H), 6.75 (d, J=3.8 Hz, 1H), 6.08 (d, J=4.0 Hz, 1H), 4.83 (d, J=3.2 Hz, 1H), 4.50 (dd, J=3.3, 5.5 Hz, 1H), 4.39-4.26 (m, 2H), 3.49 (dd, J=6.8, 13.3 Hz, 1H), 3.33 (dt, J=6.0, 12.3 Hz, 1H), 3.00-2.82 (m, 2H), 2.69 (s, 3H).

Example 102. Synthesis of (2R,3R,4S,5S)-2-(4-aminopyrrolo[2,3-d]pyrimidin-7-yl)-5-[(1R)-7-chloro-1,3,4,5-tetrahydro-2-benzoxepin-1-yl]tetrahydrofuran-3,4-diol; Hydrochloride (Ex. 102)

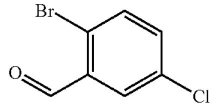

+

46a

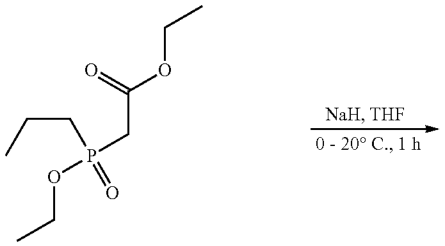

102a

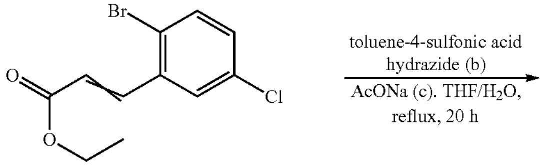

102b

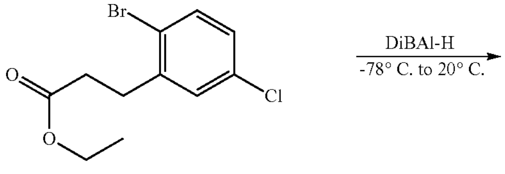

102c

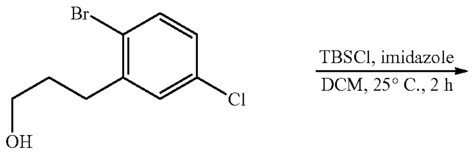

102d

-continued

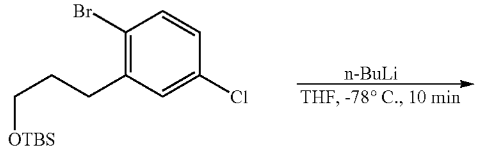

102f

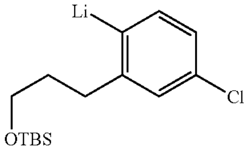

+

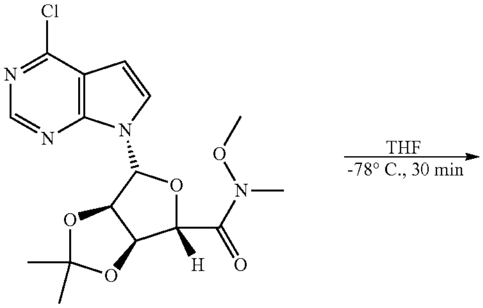

1Ad

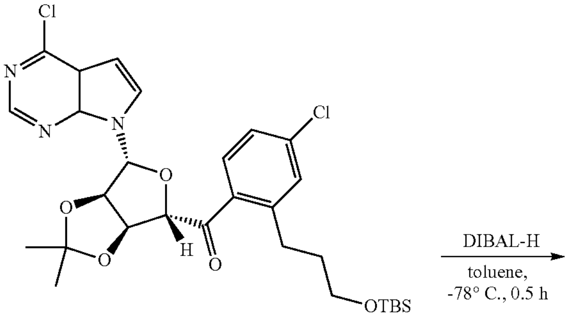

102g

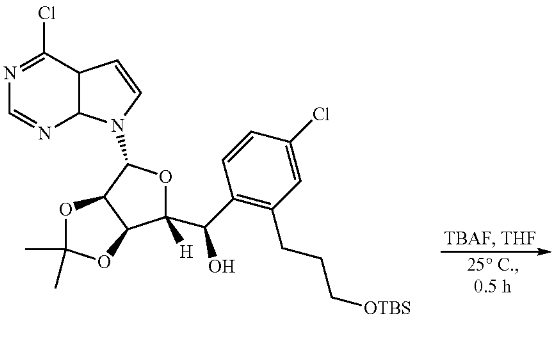

102h

-continued

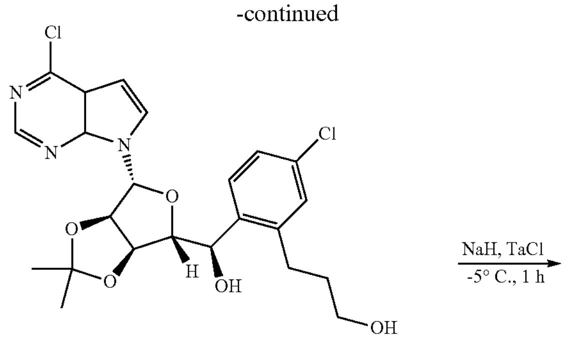

102i

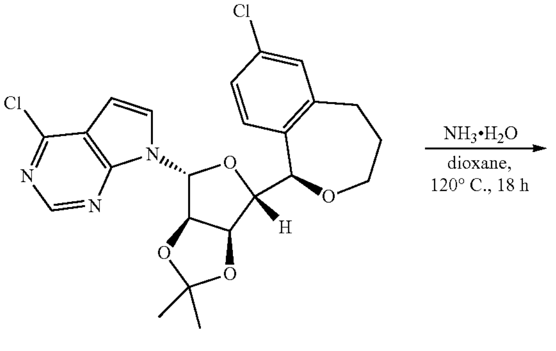

102j

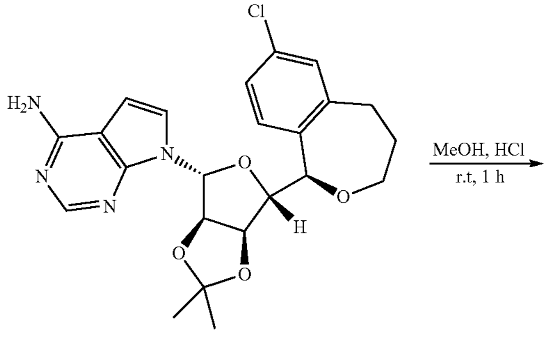

102k

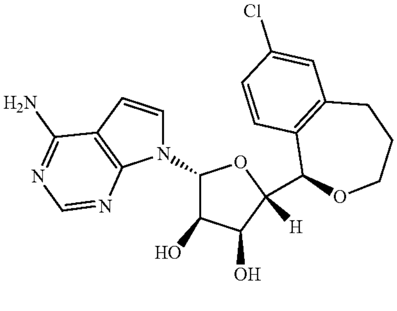

Ex. 102

Step 1. Synthesis of ethyl 3-(2-bromo-5-chloro-phenyl)prop-2-enoate (102b)

To a solution of NaH (0.01 mL, 54.68 mmol) in dry THF (50 mL) was slowly added ethyl 2-(diethoxyphosphoryl) acetate (102a, 12.258 g, 54.68 mmol) at 0° C. and stirred for 10 min. 2-bromo-5-chloro-benzaldehyde (46a, 10 g, 45.57 mmol) was added to the reaction mixture and stirred at rt for 1 h. TLC (petroleum ether, $R_f$=0.2) and LCMS showed the reaction was complete. The reaction mixture was poured into ice-water (100 mL), extracted with ethyl acetate (200 mL) and washed with water (50 mL) and brine (50 mL). The organic layer was dried over anhydrous $Na_2SO_4$, filtered, and concentrated in vacuum to give the crude product which was purified by silica gel column chromatography (petroleum ether:ethyl acetate=100:1 to 50:1) to give ethyl 3-(2-bromo-5-chloro-phenyl)prop-2-enoate (102b, 11.6 g, 36.58 mmol, 80% yield) as an off-white oil. LCMS [M+H]: 291.0. $^1$H NMR (400 MHz, $CDCl_3$) δ 7.92-7.97 (m, 1H), 7.53-7.57 (m, 2H), 7.19-7.21 (m, 1H), 6.37-6.40 (m, 1H), 4.26-4.31 (m, 2H), 1.33-1.37 (m, 3H).

Step 2. Synthesis of ethyl 3-(2-bromo-5-chloro-phenyl)propanoate (102c)

A mixture of ethyl 3-(2-bromo-5-chloro-phenyl)prop-2-enoate (102b, 5.0 g, 17.27 mmol), p-toluenesulfonyl hydrazide (32.15 g, 172.68 mmol) and sodium acetate trihydrate (35.24 g, 259.02 mmol) in THF (58 mL)/water (58 mL) was stirred and refluxed for 20 h. Water (50 mL) was added, then extracted with ethyl acetate (100 mL), washed with water (2×300 mL), and brine (100 mL). The organic layer was dried over anhydrous $Na_2SO_4$, filtered, and concentrated in vacuum to give the crude product which was purified by silica gel column chromatography (petroleum ether:ethyl acetate=100:1 to 20:1) to give ethyl 3-(2-bromo-5-chloro-phenyl)propanoate (102c, 4.6 g, 13.8 mmol, 80% yield) as an off-white oil. LCMS [M+H]: 293.0. $^1$H NMR (400 MHz, $CDCl_3$) δ 7.44-7.46 (m, 1H), 7.25-7.26 (m, 1H), 7.05-7.08 (m, 1H), 4.12-4.18 (m, H), 3.01-3.05 (m, 2H), 2.61-2.65 (m, 2H).

Step 3. Synthesis of 3-(2-bromo-5-chloro-phenyl) propan-1-ol (102d)

To a solution of ethyl 3-(2-bromo-5-chloro-phenyl)propanoate (102c, 4.6 g, 15.78 mmol) in toluene (50 mL) was added diisobutylaluminum hydride (31.55 mL, 47.33 mmol) at −78° C. under $N_2$ and the reaction mixture was stirred for 60 min at −78° C. TLC (petroleum ether:ethyl acetate=40:1, $R_f$=0.1, petroleum ether:ethyl acetate=10:1, $R_f$=0.3) showed the reaction was complete. Saturated $NH_4Cl$ solution (100 mL) was added to the mixture, and the mixture was extracted with ethyl acetate (100 mL) and washed with brine (50 mL). The organic layer was dried over anhydrous $Na_2SO_4$ and the solvent was removed in vacuum to give the crude 3-(2-bromo-5-chloro-phenyl)propan-1-ol (102d) which was used without further purification in the next step.

Step 4. Synthesis of 3-(2-bromo-5-chloro-phenyl)-propoxy-tert-butyl-dimethyl-silane (102e)

To a solution of 3-(2-bromo-5-chloro-phenyl)propan-1-ol (102d, 5.1 g, 20.44 mmol) and imidazole (2.78 g, 40.88 mmol) in DCM (20 mL) was slowly added t butylchlorodiphenylsilane (3.7 g, 24.53 mmol). The reaction mixture was stirred for 2 h at rt. TLC (petroleum ether, $R_f$=0.7) showed the reaction was complete. The solvent was removed in vacuum to yield the crude product which was purified by silica gel column chromatography (petroleum ether) to give 3-(2-bromo-5-chloro-phenyl)-propoxy-tert-butyl-dimethyl-silane (102e, 1.7 g, 4.67 mmol, 23% yield) as an off-white oil. $^1$H NMR (400 MHz, DMSO-d6) δ7.56 (d, 0.83 (s, J 7.6

Hz, 1H), 7.37 (d, J 2.8 Hz, 1H), 7.20 (d, J 2.8 Hz, 1H), 3.56-3.59 (m, 2H), 2.68-2.71 (m, 2H), 1.69-1.72 (m, 2H), 0.83 (s, 9H), 0.00 (s, 6H).

Step 5. Synthesis of [2-[3-[tert-butyl(dimethyl)silyl]oxypropyl]-4-chloro-phenyl]-[4-(4-chloropyrrolo[2,3-d]pyrimidin-7-yl)-2,2-dimethyl-3a,4,6,6a-tetrahydrofuro[3,4-d][1,3]dioxol-6-yl]methanone (102f)

To a solution of 3-(2-bromo-5-chloro-phenyl)propoxy-tert-butyl-dimethyl-silane (102e, 1130.9 mg, 3.11 mmol) in THF (15 mL) was added n-butyllithium (175.71 mg, 2.74 mmol) at −78° C. The reaction mixture was stirred at −78° C. for 10 min. 4-(4-chloropyrrolo[2,3-d]pyrimidin-7-yl)-N-methoxy-N,2,2-trimethyl-3a,4,6,6a-tetrahydrofuro[3,4-d][1,3]dioxole-6-carboxamide (1Ad, 700 mg, 1.83 mmol) was added and the reaction was stirred for 1 h at −78° C. The reaction mixture was poured into water (20 mL), extracted with ethyl acetate (30 mL). The organic layer was dried over anhydrous $Na_2SO_4$, filtered, and concentrated in vacuum to give the crude product which was purified by silica gel column chromatography (petroleum ether:ethyl acetate=1:7) to give [2-[3-[tert-butyl(dimethyl)silyl]oxypropyl]-4-chloro-phenyl]-[4-(4-chloropyrrolo[2,3-d]pyrimidin-7-yl)-2,2-dimethyl-3a,4,6,6a-tetrahydrofuro[3,4-d][1,3]dioxol-6-yl]methanone (102f, 600 mg, 0.99 mmol, 54% yield), as a yellow oil. LCMS [M+H]: 606.2.

Step 6. Synthesis of (R)-[2-[3-[tert-butyl(dimethyl)silyl]oxypropyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (102g)

To a mixture of [2-[3-[tert-butyl(dimethyl)silyl]oxypropyl]-4-chloro-phenyl]-[(3aR,4R,6S,6aS)-2,2-dimethyl-4-(4-methylpyrrolo[2,3-d]pyrimidin-7-yl)-3a,4,6,6a-tetrahydrofuro[3,4-d][1,3]dioxol-6-yl]methanone (102f, 600 mg, 1.02 mmol) in toluene (3 mL), DIBAL-H (0.24 mL, 2.05 mmol) was added at −78° C. The mixture was stirred at −78° C. for 30 min. The reaction mixture was poured into ethyl acetate (50 mL), concentrated in vacuum to give the crude product which was purified by silica gel column chromatography (petroleum ether:ethyl acetate=8:1) to give (R)-[2-[3-[tert-butyl(dimethyl)silyl]oxypropyl]-4-chloro-phenyl]-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methanol (102g, 320 mg, 0.54 mmol, 53% yield) as a yellow oil. LCMS [M+H]: 608.2.

Step 7. Synthesis of 3-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]propan-1-ol (102h)

To a mixture of (S)-[2-[3-[tert-butyl(dimethyl)silyl]oxypropyl]-4-chloro-phenyl]-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methanol (102g, 550 mg, 0.90 mmol) in THF (3 mL) was added tetrabutylammonium fluoride (0.03 mL, 1.08 mmol) at 25° C. The mixture was stirred at 25° C. for 30 min. The reaction mixture was poured into water (10 mL), extracted with ethyl acetate (20 mL). The organic layer was dried over anhydrous $Na_2SO_4$, filtered and concentrated in vacuum to give the crude product which was purified by silica gel column chromatography (ethyl acetate) to give 3-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]propan-1-ol (102h, 410 mg, 0.83 mmol, 91.8% yield) as a yellow oil. LCMS [M+H]: 494.2.

Step 8. Synthesis of 4-chloro-7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidine (102i)

To a mixture of 3-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]propan-1-ol (102h, 100 mg, 0.20 mmol) in THF (4 mL) was added sodium hydride (0.06 mL, 0.40 mmol) at −5° C. The reaction was stirred at −5° C. for 10 min. Tosyl chloride (38.56 mg, 0.20 mmol) was added at −5° C., then stirred at −5° C. for 30 min. The reaction mixture was poured into water (10 mL) and extracted with ethyl acetate (20 mL). The organic layer was dried over anhydrous $Na_2SO_4$, filtered, and concentrated in vacuum to give the crude 102i which was used without further purification in the next step. LCMS [M+H]: 476.3.

Step 9. Synthesis of 7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidin-4-amine (102j)

To a mixture of 4-chloro-7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidine (102i, 84 mg, 0.18 mmol) in 1,4-dioxane (3 mL) was added ammonium hydroxide (61.81 mg, 1.76 mmol). The mixture was stirred at 110° C. for 16 h. LCMS showed 10% of product was detected. The reaction was poured into water (10 mL) and extracted with ethyl acetate (20 mL). The organic layer was dried over anhydrous $Na_2SO_4$, filtered, and concentrated in vacuum to give crude product which was purified by prep-HPLC, eluted with MeCN in water (0.1% $NH_3$. water) from 10% to 95% to give 7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidin-4-amine (102j, 10 mg, 0.022 mmol, 12% yield). LCMS [M+H]: 457.3.

Step 10. Synthesis of (2R,3R,4S,5S)-2-(4-aminopyrrolo[2,3-d]pyrimidin-7-yl)-5-[(1R)-7-chloro-1,3,4,5-tetrahydro-2-benzoxepin-1-yl]tetrahydrofuran-3,4-diol; Hydrochloride (Ex. 102)

To a mixture of 7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidin-4-amine (102j, 10 mg, 0.02 mmol) in methanol (2 mL) was added HCl (1.6 mg, 0.04 mmol). The mixture was stirred at 25° C. for 1 h. The mixture was purified by prep-HPLC, eluting with MeCN in water:$CH_3CN$ (0.1% HCl) from 10% to 95% to give (2R,3R,4S,5S)-2-(4-aminopyrrolo[2,3-d]pyrimidin-7-yl)-5-[(1R)-7-chloro-1,3,4,5-tetrahydro-2-benzoxepin-1-yl]tetrahydrofuran-3,4-diol; hydrochloride (Ex. 102, 1.46 mg, 0.0031 mmol, 14% yield) as a white solid. LCMS [M+H]: 417.3. $^1H$ NMR (400 MHz, DMSO-d6) δ: 8.44-8.45 (m, 1H), 8.20 (d, J=5.6 Hz, 1H), 7.08-7.10 (m, 3H), 6.82 (d, J=4 Hz, 1H), 6.66-6.69 (m, 1H), 6.22 (d, J=3.6 Hz, 1H), 5.69 (m, 2H), 5.26 (d, J=2 Hz 1H), 5.16 (d, J=4 Hz 2H), 3.94-3.97 (m, 1H), 3.45-3.59 (m, 1H), 2.73-2.77 (m, 2H), 1.96-2.03 (m, 2H), 1.58-1.62 (m, 2H). $^1$H NMR (400 MHz, DMSO-d6+D2O) δ: 8.42-8.43 (m, 1H), 8.20-8.22 (m, 1H), 7.07-7.11 (m, 3H), 6.83 (d, J=4 Hz, 1H), 6.24 (d, J=3.6 Hz, 1H), 5.67-5.71 (m, 2H), 4.84-4.87 (m, 1H), 3.95-3.98 (m, 1H), 2.74-2.77 (m, 2H), 1.98-2.01 (m, 2H), 1.54-1.60 (m, 2H).

Example 101. Synthesis of (2R,3R,4S,5S)-2-(4-methylpyrrolo[2,3-d]pyrimidin-7-yl)-5-[(1R)-7-chloro-1,3,4,5-tetrahydro-2-benzoxepin-1-yl]tetrahydrofuran-3,4-diol (Ex. 101)

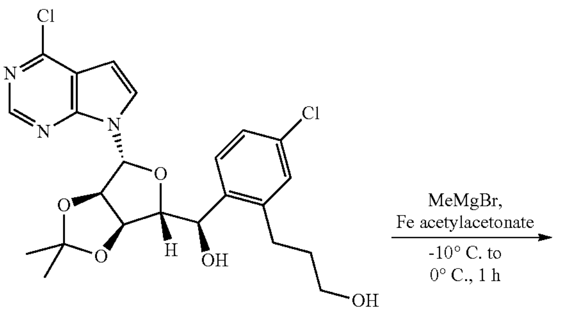

102i

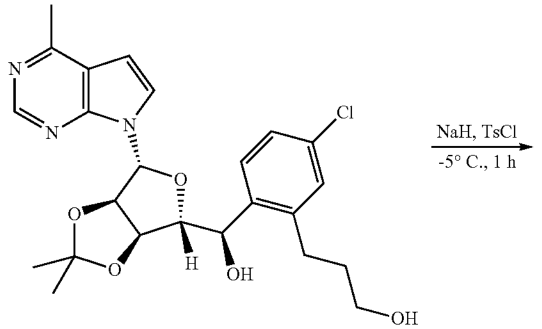

101a

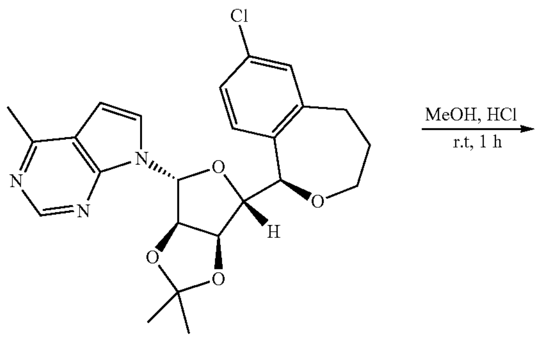

101b

-continued

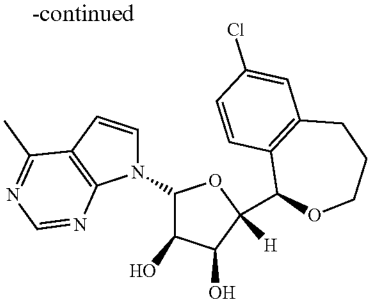

Ex. 101

Step 1. Synthesis of 3-[5-chloro-2-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]phenyl]propan-1-ol (101a)

To a mixture of 3-[5-chloro-2-[(R)-hydroxy-[(3aR,4R,6R,6aR)-4-(4-chloropyrrolo[2,3-d]-pyrimidin-7-yl)-2,2-dimethyl-3a,4,6,6a-tetrahydrofuro[3,4-d][1,3]dioxol-6-yl]methyl]phenyl]propan-1-ol (102i, 20 mg, 0.04 mmol) and ferric acetylacetonate (7.14 mg, 0.02 mmol) in THF (2 mL) was added methylmagnesium bromide (48.24 mg, 0.40 mmol) at −10° C. The mixture was warmed to 0° C. and stirred for 1h. TLC (petroleum ether:ethyl acetate=5:1, $R_f$=0.7) showed the reaction was complete. The reaction mixture was poured into water (5 mL), extracted with DCM (3×5 mL). The organic layer was dried over anhydrous $Na_2SO_4$, filtered, and concentrated in vacuum. The crude product was purified by silica gel column chromatography (petroleum ether:ethyl acetate=7:1) to give 3-[5-chloro-2-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]phenyl]propan-1-ol (101a, 10 mg, 0.0211 mmol, 52% yield) as a yellow oil. LCMS [M+H]: 474.2.

Step 2. Synthesis of 4-methyl-7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidine (101b)

To a mixture of 3-[5-chloro-2-[(R)-hydroxy-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]methyl]phenyl]propan-1-ol (101a, 20 mg, 0.04 mmol) in THF (2 mL) sodium hydride (0.06 mL, 0.08 mmol) was added at −5° C. and the reaction was stirred 10 min at −5° C. Tosyl chloride (8.05 mg, 0.04 mmol) was added and the mixture was stirred at −5° C. for 30 min. LCMS showed the reaction was complete. The reaction mixture was poured into $NH_4Cl$ (10 mL) and extracted with ethyl acetate (10 mL). The organic layer was dried over anhydrous $Na_2SO_4$, filtered and concentrated in vacuum. The crude product was purified by silica gel column chromatography chromatography (petroleum ether:ethyl acetate=7:1) to give 4-methyl-7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidine (101b, 4 mg, 0.0088 mmol, 21% yield), as a white solid. LCMS [M+H]: 456.3.

Step 3. Synthesis of (2R,3R,4S,5S)-2-(4-methylpyrrolo[2,3-d]pyrimidin-7-yl)-5-[(1R)-7-chloro-1,3,4,5-tetrahydro-2-benzoxepin-1-yl]tetrahydrofuran-3,4-diol (Ex. 101)

To a mixture of 4-methyl-7-[(3aR,4R,6R,6aR)-2,2-dimethyl-6-[(1R)-7-chloro-1,3,4,5-tetrahydro-2-benzoxepin-1-yl]-3a,4,6,6a-tetrahydrofuro[3,4-d][1,3]dioxol-4-yl]pyrrolo[2,3-d]pyrimidine (101b, 4 mg, 0.01 mmol) in methanol (2 mL) was added HCl (0.64 mg, 0.02 mmol). The mixture was stirred at 25° C. for 1 h. The reaction mixture was purified by prep-HPLC, eluted with MeCN in water (0.1% TFA) from 10% to 95% to give (2R,3R,4S,5S)-2-(4-methylpyrrolo[2,3-d]pyrimidin-7-yl)-5-[(1R)-7-chloro-1,3,4,5-tetrahydro-2-benzoxepin-1-yl]tetrahydrofuran-3,4-diol (Ex. 101, 1 mg, 0.0024 mmol, 27% yield) as a white solid. LCMS [M+H]: 416.3. $^{1}$H NMR (400 MHz, DMSO-$d_6$) δ:8.66 (s, 1H), 8.44 (s, 2H), 7.62 (d, J=3.6 Hz, 1H), 7.30 (d, J=1.6 Hz, 1H), 7.18-7.25 (m, 2H), 6.77 (d, J=3.6 Hz, 1H), 6.29 (d, J=7.6 Hz, 1H), 5.44-5.53 (m, 1H), 4.78 (d, J=4.2 Hz, 1H), 4.61-4.64 (m, 1H), 4.39 (d, J=4.8 Hz, 1H), 4.25-4.30 (m, 2H), 3.10-3.16 (m, 1H), 2.89-2.94 (m, 1H), 2.65-2.67 (m, 3H), 1.68-1.77 (m, 2H). $^{1}$H NMR (400 MHz, DMSO-$d_6$+D2O) δ:8.67 (s, 1H), 8.43 (s, 4H), 7.62 (d, J=4 Hz, 1H), 7.30 (d, J=1.6 Hz, 1H), 7.18-7.25 (m, 2H), 6.78 (d, J=3.6 Hz, 1H), 6.29 (d, J=8 Hz, 1H), 4.78 (d, J=4.2 Hz, 1H), 4.62-4.65 (m, 1H), 4.39 (d, J=4.2 Hz, 1H), 4.25-4.30 (m, 2H), 3.10-3.12 (m, 1H), 2.89-2.94 (m, 1H), 2.65-2.69 (m, 3H), 1.68-1.81 (m, 2H).

TABLE 1

Examples prepared according to the above procedures.

| Ex. # | Structure | Prepared as in Ex. # | Spectral data |
|---|---|---|---|
| 4 | 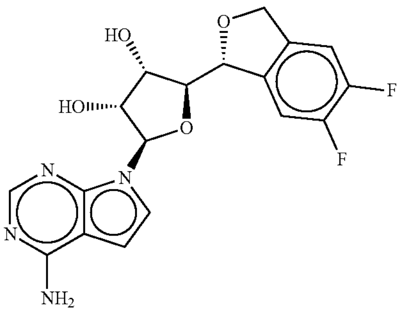 | 1A | HCl salt: $^{1}$H NMR (400 MHz, DMSO-d6): δ 8.40 (s, 1 H), 7.72 (d, J = 3.2 Hz, 1 H), 7.45-7.49 (m, 1 H), 7.32-7.36 (m, 1 H), 7.06 (s, 1 H), 6.19 (d, J = 7.2 Hz, 1 H), 5.36 (s, 1 H), 5.04-5.13 (m, 2 H), 4.48 (t, J = 6.0 Hz, 1 H), 4.21 (d, J = 4.4 Hz, 1 H), 3.89 (d, J = 4.4 Hz, 1 H). |
| 12 | 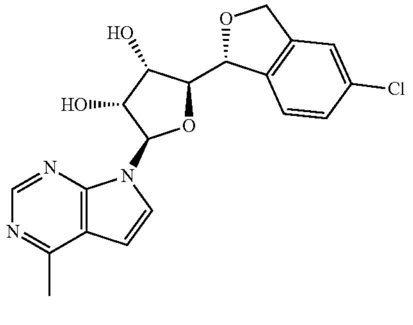 [SMILES: Cc1ncnc2c1ccn2[C@@H]1O[C@H]([C@@H]2OCc3cc(Cl)ccc32)[C@@H](O)[C@H]1O] | 15 | $^{1}$H NMR (400 MHz, DMSO-d6 + $D_2O$):δ8.66 (s, 1 H), 7.74 (d, J = 3.2 Hz, 1 H), 7.44 (s, 1 H), 7.32 (d, J = 8.4 Hz, 1 H), 7.25 (d, J = 8.0 Hz, 1 H), 6.84 (d, J = 3.2 Hz, 1 H), 6.29 (d, J = 7.2 Hz, 1 H), 5.38 (br, 1 H), 5.07-5.15 (m, 2 H), 4.56-4.59 (m, 1 H), 4.16 (d, J = 4.4 Hz, 1 H), 3.95 (d, J = 4.8 Hz, 1 H), 2.68 (s, 3 H). |
| 16 | 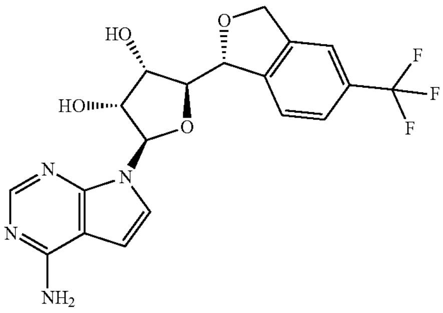 [SMILES: Nc1ncnc2c1ccn2[C@@H]1O[C@H]([C@@H]2OCc3cc(C(F)(F)F)ccc32)[C@@H](O)[C@H]1O] | 1A | $^{1}$HNMR (DMSO-d6 + $D_2O$, 400 MHz) δ 8.07 (s, 1 H), 7.74 (s, 1 H), 7.63-7.65 (d, J = 8.0 Hz, 1 H), 7.45-7.47 (d, J = 8.0 Hz, 1 H), 7.32-7.33 (d, J = 3.6 Hz, 1 H), 6.66 (d, J = 3.6 Hz, 1H), 6.15-6.17 (d, J = 7.6 Hz, 1H), 5.47 (m, 1 H), 5.16-5.18 (m, 2 H), 4.52-4.55 (m, 1 H), 4.13-4.14 (m, 1 H), 3.97-3.98 (m, 1 H). |

TABLE 1-continued

Examples prepared according to the above procedures.

| Ex. # | Structure | Prepared as in Ex. # | Spectral data |
|---|---|---|---|
| 17 | 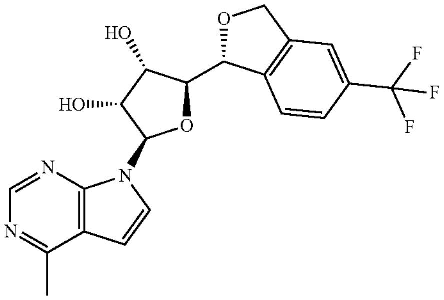 [SMILES: Cc1ncnc2c1ccn2[C@@H]1O[C@H]([C@@H]2OCc3cc(C(F)(F)F)ccc32)[C@@H](O)[C@H]1O] | 15 | $^1$HNMR (DMSO-d6 + $D_2O$, 400 MHz) δ 8.67 (s, 1 H), 7.74-7.76 (m, 2 H), 7.62-7.64 (d, J = 7.6 Hz, 1 H), 7.44-7.46 (d, J = 8.0 Hz, 1H), 6.82-6.83 (d, J = 3.6 Hz, 1 H), 6.28-6.30 (d, J = 7.6 Hz, 1 H), 5.49 (m, 1 H), 5.17-5.20 (m, 2 H), 4.59-4.62 (m, 1 H), 4.17-4.19 (m, 1 H), 3.98-3.99 (m, 1 H), 2.68 (s, 3 H) |
| 42 | 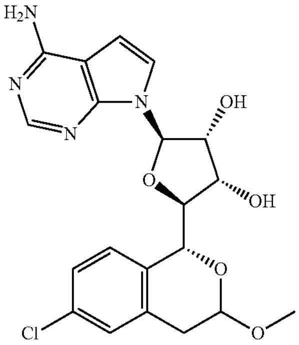 | 44, 1A | LCMS [M + H]: 433.1<br>$^1$H NMR (400 MHz, DMSO-d6) δ 8.39 (s, 1H), 7.71 (s, 1H), 7.23-7.32 (m, 3H) 7.05 (s, 1H), 6.22 (d, 1H), 5.27 (d, 1H), 4.82 (d, 1H), 4.48-4.51 (m, 2H), 3.87 (d, 1H), 3.07-3.12 (q, 2H), 2.78 (d, 1H).<br>$^1$H NMR (400 MHz, DMSO-d6 + D2O) δ 8.37 (d, 1H), 7.73 (s, 1H) 7.25-7.32 (m, 3H), 7.02 (s, 1H), 6.23 (d, 1H), 5.28 (s, 1H), 4.84 (s, 1H), 4.50-4.52 (m, 2H), 3.86 (d, 1H), 3.09 (d, 1H), 2.78 (d, 1H).<br>$CH_3$ peak is under the water peak. |
| 43 | 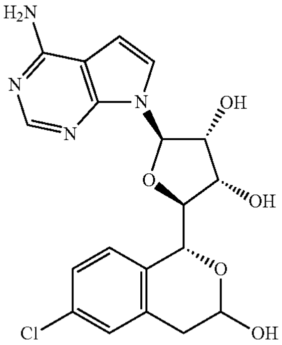 | 50, 1A | LCMS [M + H]: 419.0<br>$^1$H NMR (400 MHz, DMSO-d6) δ 8.05 (s, 1H), 7.58 (s, 1H), 7.06 (s, 1H) 7.22-7.41 (m, 3H), 7.10 (s, 2H), 6.61-6.64 (m, 2H), 6.16-6.23 (m, 1H), δ 5.56 (s, 1H), 5.15-5.18 (m, 1H), 4.95-5.06 (m, 3H) 4.38-4.52 (m, 3H), 3.85 (s, 1H), 3.72-3.74 (m, 1H), 2.76-2.90 (m, 1H), δ 2.49-2.51(m, 1H).<br>$^1$H NMR (400 MHz, DMSO-d6 + D2O) δ 8.06 (s, 1H), 7.61 (s, 1H), 7.22-7.34 (m, 3H), 6.65 (s, 1H), 6.16-6.23 (m, 1H), 5.56 (s, 1H), 4.95-5.02 (m, 2H), δ 4.39-4.53 (m, 2H), 3.71-3.85 (d, 1H), 2.90-3.00 (m, 1H), 2.67-2.80 (m, 1H). |
| 68 | 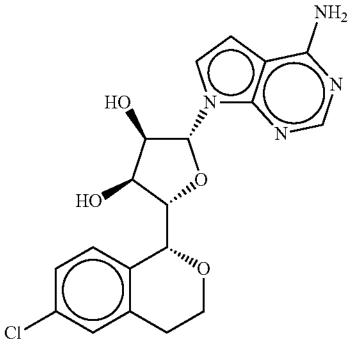 | 22, 1A | LCMS [M + H]: 403.2. 1H NMR (400 MHz DMSO-d6): δ 8.06 (s, 1 H), 7.37 (d, J = 3.6 Hz, 1 H), 7.28-7.31 (m, 2 H), 7.21-7.24 (m, 1 H), 7.01 (s, 2 H), 6.64 (d, J = 4.0 Hz, 1 H), 6.17 (d, J = 7.6 Hz, 1 H), 5.13 (br, 2 H), 4.86-4.88 (m, 1 H), 4.43-4.47 (m, 1 H), 4.35-4.36 (m, 1 H), 4.21-4.24 (m, 1 H), 3.83-3.85 (m, 1 H), 3.64-3.71 (m, 1 H), 2.89-2.94 (m, 1 H), 2.69-2.74 (m, 1 H).<br>1H NMR (400 MHz, DMSO-d6 + D2O): δ 8.07 (s, 1 H), 7.38 (d, J = 4.0 Hz, 1 H), 7.27-7.29 (m, 2 H), 7.22-7.25 (m, 1 H), 6.66 (d, J = 3.6 Hz, 1 H), 6.18 (d, J = 7.6 Hz, 1 H), 4.87-4.88 (m, 1 H), 4.44-4.48 (m, 1 H), 4.37-4.39 (m, 1 H), 4.21-4.25 (m, 1 H), 3.83-3.85 (m, 1 H), 3.64-3.70 (m, 1 H), 2.91-2.99 (m, 1 H), 2.70-2.74 (m, 1 H). |

TABLE 1-continued

| Examples prepared according to the above procedures. | | | |
|---|---|---|---|
| Ex. # | Structure | Prepared as in Ex. # | Spectral data |
| 70 | 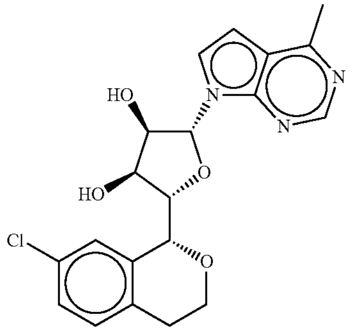 | 22 | LCMS [M + H]: 402.2. 1H NMR (400 MHz, DMSO-d6 + D2O) δ8.95 (s, 1 H), 8.07 (d, J = 2.1 Hz, 1 H), 7.29-7.15 (m,4H), 6.34 (d, J = 7.5 Hz, 1 H), 4.90 (brs, 1 H), 4.55-4.49 (m, 2 H), 4.28-4.24(m,1H), 3.83-3.82 (m, 1 H), 3.66-3.61 (m, 1 H), 2.93-2.86(m,4H), 2.69-2.65 (m, 1 H). |
| 71 | 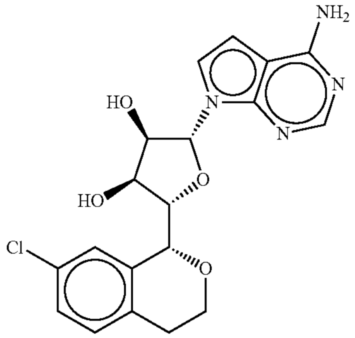 | 22, 1A | LCMS [M + H]: 403.3. 1H NMR (400 MHz, DMSO-d6 + D2O) δ8.32 (s, 1 H), 7.71 (d, J = 3.1 Hz, 1 H), 7.26-7.21 (m,3H), 6.98 (s, 1H), 6.18 (d, J = 7.4 Hz, 1 H), 4.86 (brs, 1 H), 4.49-4.44 (m, 2 H), 4.23-4.21(m,1H), 3.81-3.80 (m, 1 H), 3.64-3.59 (m, 1 H), 2.90-2.85(m,1H), 2.68-2.63 (m, 1 H). |
| 72 | 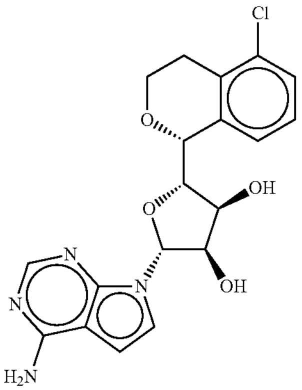 | 22, 1A | LCMS [M + H]: 403.2. 1H NMR (400 MHz, DMSO-d6) δ8.06 (s, 1 H), 7.37 (d, J = 4 Hz, 2 H), 7.29 (d, J = 7.6 Hz, 1 H), 7.24-7.20 (t, J = 7.6 Hz, 1 H), 7.01 (s, 2 H), 6.64 (d, J = 3.6 Hz, 1 H), 6.17 (d, J = 7.6 Hz, 1 H), 5.17 (d, J = 7.2 Hz, 1 H), 5.04 (d, J = 4 Hz, 1 H), 4.90 (br,1H), 4.47-4.40 (m, 2 H), 4.33-4.28 (m, 1 H), 3.83 (t, J = 7.6 Hz, 1 H), 3.76-3.69 (m, 1 H), 2.87-2.76 (m, 2 H). 1H NMR (400 MHz, DMSO-d6 + D2O) δ8.08 (s, 1 H), 7.40-7.37 (m, 2 H), 7.29-7.22 (m, 2 H), 6.67 (d, J = 3.6 Hz, 1 H), 6.18 (d, J = 7.6 Hz, 1 H), 4.91 (br, 1H), 4.48-4.42 (m, 2 H), 4.33-4.30 (m, 1 H), 3.83-3.78 (m, 2 H), 2.81 (br, 2 H). |
| 73 | 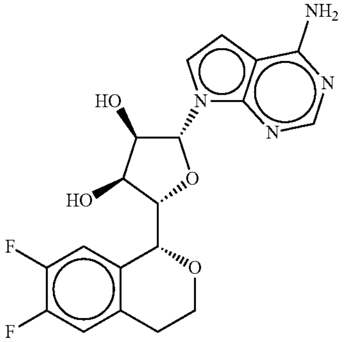 | 22, 1A | LCMS [M + H]: 405.3. 1H NMR (400 MHz, DMSO-d6 + D2O): δ 8.08 (s, 1H), 7.35-7.31(m, 3H), 7.01-7.04 (m, 2H), 6.63-6.65 (m, 1H), 6.17 (d, J = 8.0, 1H) 5.17-5.19 (d, J = 8.8 Hz, 1H), 5.07 (d, J = 4.0 Hz, 1H), 4.83 (d, J = 3.6 Hz, 1H), 4.44-4.49 (m, 1H), 4.35-4.38 (m, 1H), 4.20-4.24 (m, 1H), 3.84-3.87 (m, 1H), 3.64-3.72 (m, 1H), 2.85-2.93 (m, 1H), 2.76-2.71 (m, 1H). |

TABLE 1-continued

| Examples prepared according to the above procedures. | | | |
|---|---|---|---|
| Ex. # | Structure | Prepared as in Ex. # | Spectral data |
| 74 | 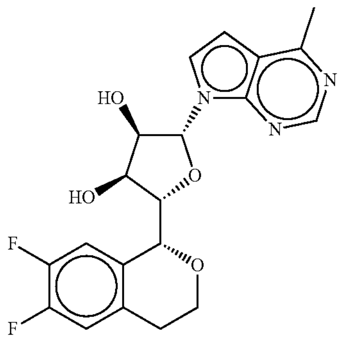 | 22 | LCMS [M + H]: 404.4. 1H NMR(400 MHz, DMSO-d6 + D2O): δ 8.87 (s, 1H), 7.95 (d, J = 3.6 Hz, 1H), 7.28-7.41(m, 2H), 7.02 (d, J = 3.6 Hz, 1H), 6.3 (d, J = 8.0 Hz, 1H), 4.88 (s, 1H), 4.47-4.54 (m, 2H), 4.24-4.28 (m, 1H), 3.85 (m, 1H), 3.48-3.72 (m, 1H), 2.88 (m, 1H), 2.79 (s, 3H), 2.68-2.72 (m, 1H). |
| 75 | 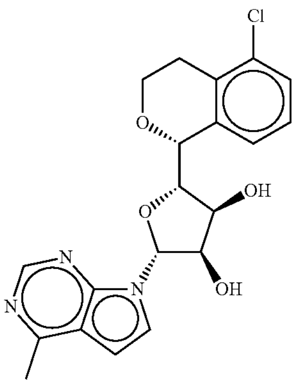 | 22 | LCMS [M + H]: 402.2. 1H NMR (400 MHz, DMSO-d6) δ 8.67 (s, 1 H), 7.77 (d, J = 3.6 Hz, 1 H), 7.37 (d, J = 8 Hz, 1 H), 7.37 (d, J = 7.6 Hz, 1 H), 7.22 (t, J = 7.6 Hz, 1 H), 6.81 (d, J = 3.6 Hz, 1 H), 6.30 (d, J = 7.6 Hz, 1 H), 5.26 (d, J = 7.2 Hz, 1 H), 5.5.13 (d, J = 4 Hz, 1 H), 4.92(br,1H), 4.53-4.46 (m, 2 H), 4.34-4.30 (m, 1 H), 3.84 (t, J = 4.4 Hz, 1 H), 3.77-3.70 (m, 1 H), 2.87-2.76 (m, 2 H), 2.67 (s, 3 H).<br>1H NMR (400 MHz, DMSO-d6 + D2O) δ 8.67 (s, 1 H), 7.77 (d, J = 4 Hz, 1 H), 7.40-7.36 (m, 1 H), 7.30-7.23 (m, 2 H), 6.84 (d, J = 4 Hz, 1 H), 6.31 (d, J = 7.6 Hz, 1 H), 4.93 (br,1H), 4.54-4.48 (m, 2 H), 4.36-4.32 (m, 1 H), 3.82 (d, J = 5.6 Hz, 1 H), 3.79 (s, 1 H), 2.84-2.81 (br, 2 H), 2.68 (s, 3H). |
| 77 | 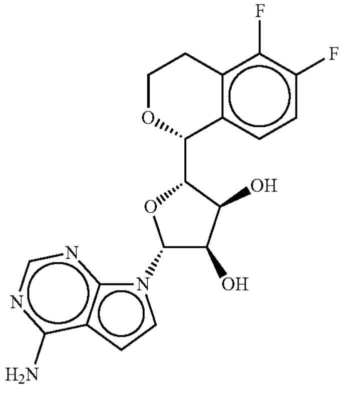 | 22, 1A | LCMS [M + H]: 405.2. 1H NMR (400 MHz, DMSO-d6) δ 8.06 (s, 1 H), 7.38-7.37 (d, J = 4 Hz, 1 H), 7.27-7.22 (m, 1 H), 7.17-7.13 (m, 1 H), 7.02 (s, 2 H), 6.65-6.64 (d, J = 4 Hz, 1 H), 6.18-6.17 (d, J = 4 Hz, 1 H), 5.21-5.20 (d, J = 4 Hz, 1H), 5.08-5.07 (d, J = 4 Hz, 1 H), 4.87-4.86 (d, J = 4 Hz, 1 H), 4.46-4.45 (m, 1 H), 4.39-4.38(d, J = 4 Hz, 1 H), 4.29-4.25 (m, 1 H), 3.89-3.88 (m, 1 H), 3.75-3.67 (m, 1 H), 2.84-2.80 (m, 2 H).<br>1H NMR (400 MHz, DMSO-d6 + D2O) δ 8.07 (s, 1 H), 7.38-7.37 (d, J = 4 Hz, 1 H), 7.26-7.24(m, 1 H), 7.17-7.14 (m, 1 H), 6.65-6.64 (d, J = 4 Hz, 1 H), 6.18-6.17 (d, J = 4 Hz, 1 H), 4.87-4.86 (d, J = 4 Hz, 1 H), 4.46-4.45 (m, 1 H), 4.39-4.38(d, J = 4 Hz, 1 H), 4.29-4.25 (m, 1 H), 3.89-3.88 (m, 1 H), 3.75-3.67 (m, 1 H), 2.81 (s, 2 H). |

TABLE 1-continued

Examples prepared according to the above procedures.

| Ex. # | Structure | Prepared as in Ex. # | Spectral data |
|---|---|---|---|
| 78 | 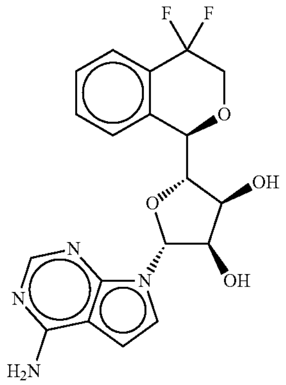 | 76, 1A | LCMS [M + H]: 405.1. 1H NMR (400 MHz, DMSO-d6) δ 8.08 (s, 1 H), 7.73 (d, J = 8 Hz, 1 H), 7.57-7.48 (m, 3 H), 7.34 (d, J = 3.6 Hz, 1 H), 7.05 (s, 2 H), 6.66 (d, J = 3.6 Hz, 1 H), 6.20 (d, J = 7.6 Hz, 1 H), 5.26 (d, J = 7.2 Hz, 1 H), 5.11 (d, J = 4.4 Hz, 1 H), 5.06 (m, 1 H), 4.56-4.40 (m, 3 H), 4.15-4.05 (m, 1H), 3.80 (t, J = 4.2 Hz, 1H). 1H NMR (400 MHz, DMSO-d6, + D2O) δ 8.08 (s, 1 H), 7.74 (d, J = 7.6 Hz, 1 H), 7.57-7.47 (m, 3 H), 7.34 (d, J = 3.6 Hz, 1 H), 6.67 (d, J = 3.6 Hz, 1 H), 6.20 (d, J = 8 Hz, 1 H), 5.07 (m, 1 H), 4.56-4.41 (m, 3 H), 4.13-4.04 (m, 1 H), 3.81-3.796 (m, 1 H). |
| 79 | 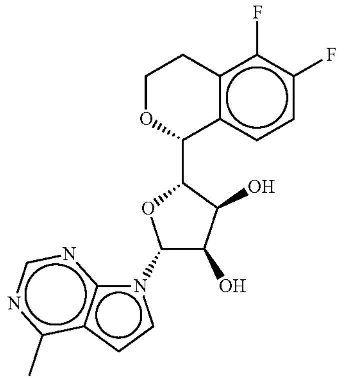 | 22 | LCMS [M + H]: 404.2. 1H NMR (400 MHz, DMSO-d6): δ 8.67 (s, 1 H), 7.77-7.76 (d, J = 4 Hz, 1 H), 7.27-7.25 (m, 1 H), 7.17-7.14 (m, 1 H), 6.81-6.80 (d, J = 4 Hz, 1 H), 6.31-6.29 (d, J = 8 Hz, 1 H), 5.29-5.28 (d, J = 4 Hz, 1 H), 5.15-5.14 (d, J = 4 Hz, 1 H), 4.90-4.89 (d, J = 4 Hz, 1 H), 4.53-4.51 (m, 1 H), 4.45-4.44 (m, 1 H), 4.32-4.29 (m, 1 H), 3.90-3.88 (m, 1 H), 3.73-3.70 (m, 1 H), 2.84-2.82 (m, 2 H), 2.67 (s, 3H). 1H NMR (400 MHz, DMSO-d6 + D2O): δ 8.66 (s, 1 H), 7.79-7.78 (d, J = 4 Hz, 1 H), 7.25-7.20 (m, 1 H), 7.14-7.11 (m, 1 H), 6.88-6.87 (d, J = 4 Hz, 1 H), 6.33-6.31 (d, J = 8 Hz, 1 H), 4.90 (s, 1 H), 4.59-4.57 (m, 1 H), 4.55-4.50 (m, 1 H), 4.35-4.31 (m, 1 H), 3.90-3.89 (m, 1 H), 3.70-3.68(m, 1 H), 2.87-2.85 (m, 2 H), 2.70 (s, 3H). |
| 80 | 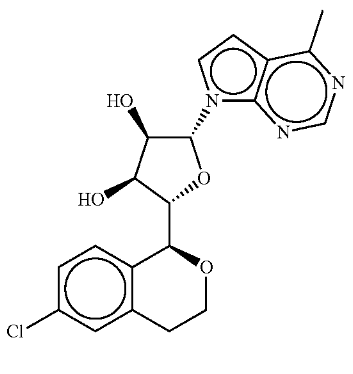 | 22, 1B | LCMS [M + H]: 402.2. 1H NMR (400 MHz, DMSO-d6 + D2O): δ 8.62 (s, 1 H), 7.66 (d, J = 3.6 Hz, 1H), 7.27 (d, J = 8.4 Hz, 1H), 7.21-7.15 (m, 2 H), 6.76 (d, J = 4 Hz, 1 H), 6.20 (d, J = 6.4 Hz, 1 H), 4.93 (s, 1 H), 4.49 (s, 1 H), 4.46-4.44 (m, 1 H), 4.36-4.33 (m, 1 H), 4.26-4.22 (m, 1 H), 3.76-3.69 (m, 1 H), 2.87-2.78 (m, 1 H), 2.68-2.63 (m, 4 H). |

TABLE 1-continued

Examples prepared according to the above procedures.

| Ex. # | Structure | Prepared as in Ex. # | Spectral data |
|---|---|---|---|
| 84 | 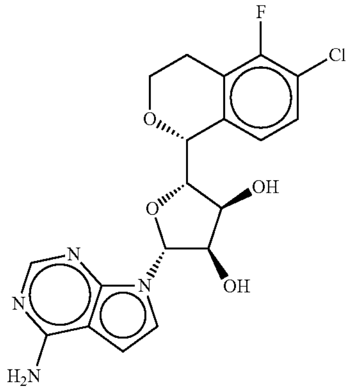 | 83, 1A | LCMS [M + H]: 421.1 $^1$H NMR (400 MHz, DMSO-$d_6$)8.06 (s, 1 H), 7.39 (d, J = 3.6 Hz,1H),7.32-7.27 (m,2H), 7.03 (s, 2 H), 6.65(d, J = 3.6 Hz, 1 H),6.18 (d, J = 7.6 Hz, 1 H), 5.23 (d, J = 7.2 Hz, 1 H), 5.13(d, J = 4.4 Hz, 1 H), 4.88(d, J = 3.6 Hz, 1H), 4.62(dd, J = 6.8 Hz, 1H), 4.40(d, J = 3.2 Hz,1H),4.27(s, 1 H),3.87(t, J = 4 Hz, 1 H),3.69(s, 1 H),2.76(s, 2H). $^1$H NMR (400 MHz, DMSO-$d_6$ + $D_2O$)8.07 (s, 1 H), 7.40(d, J = 3.2 Hz,1H),7.30-7.24 (m,2H), 6.67(d, J = 4 Hz, 1 H),6.18 (d, J = 8 Hz, 1 H), 4.89(d, J = 3.6 Hz, 1H), 4.78(dd, J = 6.8 Hz, 1H), 4.39(d, J = 3.2 Hz,1H), 4.26(s, 1 H),3.88(d, J = 5.2 Hz, 1 H),3.70(s, 1 H),2.76(s, 2H). |
| 85 | 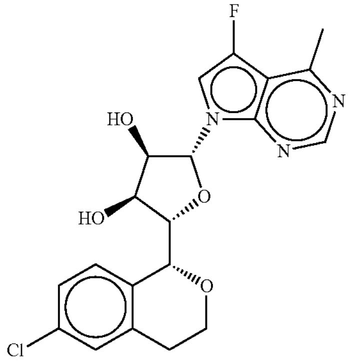 | 87, 15 | LCMS [M + H]: 420.1 $^1$H NMR (400 MHz, DMSO-$d_6$) δ 8.71 (s, 1 H), 7.69 (s, 1 H), 7.23-7.31(m, 3 H), 6.36 (m, 1 H), 5.18-5.30 (m, 2 H), 4.89 (s, 1 H), 4.41-4.45 (m, 2 H), 4.26-4.29 (m, 1 H), 3.81-3.83 (m, 1 H), 3.66-3.72 (m, 1 H), 2.90-2.97 (m, 1 H), 2.70-2.74 (m, 4 H). $^1$H NMR (400 MHz, DMSO-$d_6$ + $D_2O$) δ 8.71 (s, 1 H), 7.69 (s, 1 H), 7.23-7.31(m, 3 H), 6.36 (m, 1 H), 4.89 (s, 1 H), 4.41-4.45 (m, 2 H), 4.26-4.29 (m, 1 H), 3.81-3.83 (m, 1 H), 3.66-3.72 (m, 1 H), 2.90-2.97 (m, 1 H), 2.70-2.74 (m, 4 H). |
| 87 | 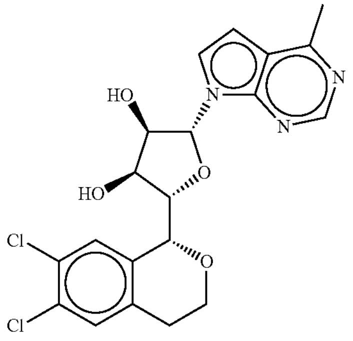 | 89, 22 | LCMS [M + H]: 436.1 $^1$H NMR (400 MHz, DMSO-$d_6$) δ 8.80 (s, 1 H), 7.88(s, 1 H), 7.59 (s, 1 H), 7.52 (s, 1 H), 6.94 (s, 1 H), 6.33-6.31 (d, J = 8 Hz, 1 H), 5.43-5.11 (m, 2 H), 4.91-4.90 (d, J = 4 Hz, 1 H),4.52-4.51 (m, 1 H), 4.46-4.45 (m, 1 H), 3.87-3.86 (d, J = 4 Hz, 1 H), 3.69-3.65(m, 1 H), 3.30-2.96(m, 1 H), 2.92-2.90 (m, 1 H), 2.74 (s, 3 H), 2.71 (s, 1 H). $^1$H NMR (400 MHz, DMSO-$d_6$ + $D_2O$) δ8.84 (s, 1 H), 7.93-7.92(d, J = 4 Hz, 1 H), 7.56 (s, 1 H), 7.52 (s, 1 H), 7.01-7.00 (d, J = 4 Hz, 1 H), 6.34-6.32 (d, J = 8 Hz, 1 H), 4.91 (s, 1 H), 4.55-4.52 (m, 1 H), 4.48-4.47 (d, J = 4 Hz, 1 H), 4.28-4.24 (m, 1 H), 3.88-3.87 (d, J = 4 Hz, 1 H), 2.93-2.90 (m, 1 H), 2.77 (s, 3 H), 2.76 (s, 1 H). |
| 99 | 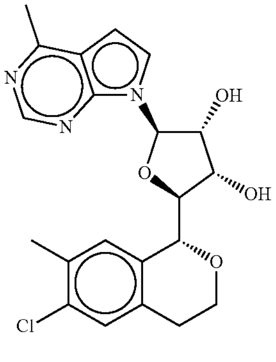 | 100, 22 | LCMS [M + H]: 416.2 $^1$H NMR (400 MHz, DMSO-$d_6$ + $D_2O$) δ9.02 (s, 1 H), 8.08-8.10 (m, 1 H), 7.26-7.28 (m, 2 H), 7.20-7.21 (d, J = 4 Hz, 1 H), 6.37-6.41 (m, 1 H), 4.91 (s, 1 H), 4.53-4.55 (m, 2 H), 4.27-4.31 (m, 1 H), 3.78-3.83 (m, 1 H), 3.63-3.68 (m, 1 H), 2.90-2.93 (m, 4 H), 2.67-2.71 (d, J = 16 Hz, 1 H), 2.25 (s, 3 H). |

TABLE 1-continued

Examples prepared according to the above procedures.

| Ex. # | Structure | Prepared as in Ex. # | Spectral data |
|---|---|---|---|
| 100 | 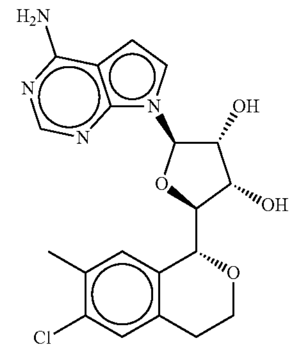 | 88, using 2-Br-6-Cl-4-methyl benzaldehyde | LCMS [M + H]: 417.2 $^1$H NMR (400 MHz, DMSO-$d_6$ + $D_2O$) δ8.40 (s, 1 H), 7.72-7.73(d, J = 3.6 Hz, 1H), 7.27-7.28 (m, 2 H), 7.04-7.05 (d, J = 4 Hz, 1 H), 6.20-6.22 (d, J = 7.6 Hz, 1 H), 4.87 (s, 1 H), 4.44-4.51 (m, 2 H), 4.25-4.27 (m, 1 H), 3.77-3.78 (d, J = 4.8 Hz, 1 H),3.61-3.68 (m, 1 H), 2.66-2.91 (m, 2 H), 2.28(s, 3 H). |
| 103 | 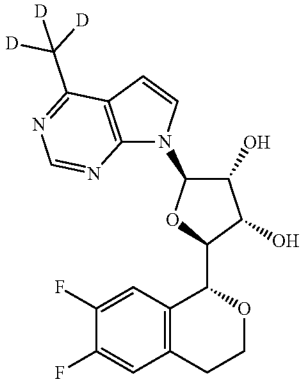 [SMILES: [2H]C([2H])([2H])c1ncnc2c1ccn2[C@@H]1O[C@H]([C@@H]2OCCc3cc(F)c(F)cc32)[C@@H](O)[C@H]1O] | 22, using $CD_3MgI$ | LCMS (ESI): m/z calcd for $C_{20}H_{17}D_3F_2N_3O_4$ $[M + H]^+$: 407.15; observed: 406.99. $^1$H NMR (600 MHz, DMSO-d6) δ 8.69 (s, 1H), 7.79 (d, J = 3.8 Hz, 1H), 7.42-7.34 (m. 1H), 7.34-7.25 (m, 1H), 6.82 (d, J = 3.7 Hz, 1H), 6.32 (d, J = 7.7 Hz, 1H), 5.26 (d, J = 6.7 Hz, 1H), 5.15 (s, 1H), 4.88 (d, J = 3.5 Hz, 1H), 4.52 (d, J = 5.8 Hz, 1H), 4.44 (d, J = 3.2 Hz, 1 H), 4.30-4.19 (m, 1H), 3.88 (d, J = 4.9 Hz, 1H), 3.70 (td, J = 11.0, 3.2 Hz, 1H), 2.97-2.85 (m, 1H), 2.70 (d, J = 16.4 Hz, 1H). |

Biochemical Assay Protocol

Compounds were solubilized and 3-fold diluted in 100% DMSO. These diluted compounds were further diluted in the assay buffer (20 mM Tris-HCl, pH 8.0, 50 mM NaCl, 0.002% Tween20, 1 mM TCEP, 100 DMSO) for 10-dose $IC_{50}$ mode at a concentration 10-fold greater than the desired assay concentration. Standard reactions were performed in a total volume of 30 µl in assay buffer, with 300 nM histone H4 based AcH4-23 (Anaspec: AS-65002) as substrate. To this was added the PRMT5/MEP50 complex diluted to provide a final assay concentration of 2.5 nM and the compounds were allowed to preincubate for 20 minutes at 37° C. The reaction was initiated by adding S-[3H-methyl]-adenosyl-L-methionine (PerkinElmer: NET155001 MC) to final concentration of 1 µM. Following a 30 minutes incubation at 37° C., the reaction was stopped by adding 25 µL of 8 M Guanidine HCl. Prepare streptavidin YSI SPA beads (Perkinelmer: RPNQ0012) at 0.3 mg/mL in assay buffer. To each reaction, add 150 µL of SPA beads suspension, and incubated while shaking at room temperature for 30 minutes. The plate was centrifuged at 100×g for 30 second before reading in a scintillation counter. $IC_{50}$ values were determined by fitting the data to the standard 4 parameters with Hill Slope using GraphPad Prism software. See Table 2, below (PRMT5 $IC_{50}$).

Cellular Assay Protocol

Cell Treatment and Western Blotting for Detecting Symmetric Di-Methyl Arginine (sDMA) Marks Compound titration and cell culture: Compounds were dissolved in DMSO to make 10 mM stock and 3-fold series dilutions were further conducted to make working stocks top at 1 mM. Granta-519 cells were maintained in PRMI 1640 (Corning Cellgro, Catalog #: 10-040-CV) supplemented with 10% v/v FBS (GE Healthcare, Catalog #: SH30910.03) and U-87 MG cells were maintained in DMEM (Corning Cellgro, Catalog #: 10-013-CV) with 10% FBS and 2 mM Glutamin (Corning Cellgro, Catalog #25005CV).

To determine enzyme inhibition $IC_{50}$ values in Granta-519 and U-87 MG cells using Western Blot analysis. One day before experiment, Granta-519 cells were passaged to a density of $0.5\times10^6$ cells/ml. U-87 MG cells were trypsinized and $4\times10^5$ cells were seeded into 6-well plates and allow to grow overnight. The next day, Granta-519 cells were spun down at 1,500 rpm for 4 min, resuspend in fresh medium at $0.5\times10^6$ cells/ml and 3 mL of culture ($1.5\times10^6$ cells) were seeded into 6 well plate. Eight-point, 3-fold serial dilutions of compound working stocks were added to cells (3 ul, 1:1,000 dilution, DMSO concentration was 0.1%; final top concentration at 1 uM) and incubated for 3 days. Cells incubated with DMSO was used as a vehicle control.

Cells were harvested 3 days later, resuspended in 15 uL PBS, lysed in 4% SDS, and homogenized by passing through homogenizer column (Omega Biotek, Catalog #: HCR003). Total protein concentrations were determined by BCA assay (ThermoFisher Scientific, Catalog #: 23225). Lysates were mixed with 5× Laemmli buffer and boiled for 5 min. Forty ug of total protein was separated on SDS-PAGE gels (Bio-Rad, catalog #: 4568083, 4568043), transferred to PVDF membrane, blocked with 5% dry milk (Bio-Rad, Catalog #: 1706404) in TBS with 0.1% v/v Tween 20

(TBST) for 1 hour at room temperature (RT), and incubated with primary antibodies (sDMA: Cell signaling, Catalog #: 13222, 1:3,000; β-Actin: sigma, Catalog #: 1:5,000) in 5% dry milk in TBST at 4® C. overnight. The next day, membranes were washed with TBST, 5×5 min, and incubated with HRP conjugated seconded antibody (GE Healthcare; Catalog #: NA934-1 ML, NA931-1 ML; 1:5,000) for 2 hours at RT, followed by 5×5 min washes with TBST, and incubation with ECL substrates (Bio-Rad, Catalog #: 1705061, 1705062). Chemiluminescent signal was captured with Fluochem HD2 imager (Proteinsimple). SmD3me2s bands were quantified by ImageJ. Signals were normalized to β-Actin and DMSO control. $IC_{50}$ values were calculated using Graphpad Prism ([Inhibitor] vs. normalized response—Variable slope). See Table 2, below (sDMA $IC_{50}$).

Cell Proliferation Assay to Determine $IC_{50}$ in Granta-519 and U-87 MG Cells

One day before experiment, Granta-519 cells were passaged to a density of $0.5\times10^6$ cells/ml. U-87 MG cells were trypsinized and 2,000 cells were seeded into 96-well plates and allow to grow overnight. On the day of experiment (day 0), Granta-519 Cells were spun down at 1,500 rpm for 4 min, resuspended in fresh medium to $0.5\times10^6$ cells/ml and 190 ul of cells were added to 96 well plates. For U-87 MG cells, old medium was removed and replaced with 190 uL fresh medium. Compound working stocks were first diluted at 1:50 with fresh medium in 96 well plate and 10 μL of diluted drugs were added to 96 well plates containing cells and incubated for 3 days. DMSO was used a vehicle control.

One day 3, 50 uL of Granta-519 cells were transferred to a new 96-well plate and 140 uL fresh medium was added. For U-87 MG cells, old medium was removed and replaced with 190 uL fresh medium. Compound working stocks were freshly diluted at 1:50 with medium and 10 μL of diluted drugs were added to cells and grow for 3 additional days. The same process was repeated on day 6. Cells were allowed to grow for additional 4 days.

On day 10, 100 uL Granta-519 cells were transferred to a new 96 well plate and 10 μL of Cell Counting Kit-8 (CCK-8, Jojindo, CK04-13) solution was added. For U-87 MG cells, old medium was removed and replaced with 100 uL fresh medium and 10 uL CCK-8 solution was added. Plates were incubated in $CO_2$ incubator for 2 hours (Granta-519 cells) or 30 min (U-87 MG cells) and $OD_{450}$ values were measured with a microplate reader (iMark microplate reader, Bio-Rad). Percentage of viable cells, relative to DMSO vehicle control, were calculated and plotted in Graphpad Prism ([Inhibitor] vs. normalized response—Variable slope) to determine proliferation $IC_{50}$ values on day 10. See Table 2, below (Prolif. $IC_{50}$).

TABLE 2

Biochemical and cellular potency in U-87 MG cell line [Granta-519 cell line]

| Ex# | PRMT5 $IC_{50}$ μM | PRMT5 $IC_{50}$_N | sDMA $IC_{50}$ μM | sDMA $IC_{50}$_N | Prolif. $IC_{50}$ μM | Prolif. $IC_{50}$_N |
|---|---|---|---|---|---|---|
| 1A | 0.0038 | 1 | 0.12 [0.027] | 1[1] | 0.142 | 2 |
| 2A | 0.68 | 1 | | | | |
| 3A | 0.021 | 1 | [1.62] | [1] | | |
| 3B | 1.02 | 1 | | | | |
| 1B | 0.27 | 1 | | | | |
| 2B | 0.031 | 1 | 0.563 | 1 | >1 | 2 |
| 4 | 0.0015 | 1 | 0.031 | 1 | 0.095 | 2 |
| 5 | 0.001 | 1 | 0.025 | 1 | | |
| 15 | 0.001 | 1 | | | | |
| 22 | 0.0048 | 2 | 0.0176 | 2 | 0.054 | 3 |
| 42 | 0.428 | | | | | |
| 43 | 0.019 | | | | | |
| 44 | 0.606 | | | | | |
| 50 | 0.059 | | | | | |
| 55 | 0.0117 | 1 | 4.58 | 2 | 10 | 2 |
| 68 | 0.0012 | 2 | 0.00258 | 3 | 0.0091 | 2 |
| 69 | 0.0149 | 2 | 0.109 | 1 | 0.181 | 2 |
| 70 | 0.303 | 1 | 0.382 | 1 | 0.458 | 1 |
| 71 | 0.0062 | 1 | 0.0297 | 1 | 0.073 | 2 |
| 72 | 0.00298 | 1 | | | 0.078 | 2 |
| 73 | 0.00145 | 1 | | | 0.0091 | 2 |
| 74 | 0.00728 | 1 | | | 0.066 | 1 |
| 75 | 0.0151 | 1 | | | 0.339 | 1 |
| 76 | 0.081 | 1 | | | | |
| 77 | 0.00282 | 1 | | | | |
| 78 | 0.0067 | 1 | | | | |
| 79 | 0.0084 | 1 | | | | |
| 80 | 1.01 | 1 | | | | |
| 81 | 0.0415 | 1 | | | | |
| 82 | 0.585 | 1 | | | | |
| 83 | 0.0132 | 1 | 0.199 | 2 | 0.377 | 2 |
| 84 | 0.0044 | 1 | 0.0276 | 2 | 0.094 | 2 |
| 85 | 0.0147 | 2 | 0.173 | 1 | 0.304 | 1 |
| 86 | 0.002 | 2 | 0.0054 | 2 | 0.013 | 1 |
| 87 | 0.0077 | 1 | 0.12 | 2 | 0.509 | 1 |
| 88 | 0.0016 | 2 | 0.0185 | 2 | 0.06 | 2 |
| 89 | 0.0157 | 1 | 0.0844 | 2 | 0.179 | 2 |
| 90 | 0.0022 | 1 | 0.0114 | 2 | 0.0333 | 2 |
| 91 | 0.554 | 1 | | | | |
| 92 | 0.02 | 1 | | | | |
| 93 | 0.014 | 1 | | | | |
| 94 | 0.0032 | 1 | | | | |

TABLE 2-continued

| Biochemical and cellular potency in U-87 MG cell line [Granta-519 cell line] | | | | | | |
|---|---|---|---|---|---|---|
| Ex# | PRMT5 $IC_{50}$ μM | PRMT5 $IC_{50}$_N | sDMA $IC_{50}$ μM | sDMA $IC_{50}$_N | Prolif. $IC_{50}$ μM | Prolif. $IC_{50}$_N |
| 95 | 0.0016 | 3 | 0.0111 | 1 | 0.0185 | 1 |
| 97 | 0.0047 | 2 | 0.0517 | 2 | 0.117 | 2 |
| 98 | 0.0119 | 2 | 0.579 | 1 | 0.662 | 1 |
| 99 | 0.0396 | 1 | | | | |
| 100 | 0.0056 | 1 | | | | |
| 101 | 1.58 | 1 | | | | |
| 102 | 6.28 | 1 | | | | |

Additional Data

Cell Culture and Compound Treatment

Compounds were dissolved in DMSO to make 10 mM stock solutions, and further diluted to make 1 mM and 0.1 mM stocks.

K562 cells were purchased from ATCC and maintained in Iscove's DMVEM (Corning Cellgro, Catalog #15-016-CVR) supplemented with 10% v/v FBS (GE Healthcare, Catalog #: SH30910.03) in a $CO_2$ incubator (5% $CO_2$) at 37° C. Cells were plated at a density of $5\times10^5$ cells/ml and treated with compound at final concentrations of 0.1 and 1 μM. Media and compound were renewed after 3 days in culture and cells were collected for RNA isolation after 6 days of treatment.

Human erythroid progenitor cells were generated from purified $CD_{34}$+ cells from mobilized peripheral blood purchased from AllCells. CD34+ cells were cultured in StemSpan SFEM II (StemCell Technologies, Catalog #09605) supplemented with 100 ng/ml FLT3 ligand (R & D systems, Catalog #308-FK), 100 ng/ml SCF (R & D systems, Catalog #255-SC), 20 ng/ml IL-3 (R & D systems, Catalog #203-IL), 20 ng/ml IL-6 (R & D systems, Catalog #206-IL) for 6 days, then reseeded into the same medium supplemented with 20 ng/ml SCF, 5 ng/ml IL-3, 1 U/ml EPO (R & D systems, Catalog #287-TC), 2 μM dexamethasone (Sigma-Aldrich, Catalog #D4902), 1 μM β-estradiol (Sigma-Aldrich, Catalog #E2758). Cells were treated with 0.1 and 1 μM compound from Day 8 of differentiation. Media and compound were renewed every 3 days and cells were collected for RNA isolation after 9 days of treatment.

Assessment of γ-Globin Induction by Quantitative PCR

RNA was isolated using Quick-RNA Microprep kit (Zymo Research, Catalog #Z1050), cDNA was synthesized using qScript cDNA SuperMix (Quantabio, Catalog #95048). Quantitative PCR for γ-globin was performed using PerfeCTa SYBR Green FastMix (Quantabio, Catalog #95071) on Bio-Rad CFX Connect Real-Time PCR Detection System. Gene expression analysis was performed using CFX Manager software.

Treatment of K562 cells with 0.1 and 1 μM of Example 5 resulted in dose-dependent increase in expression of γ-globin (3 and 8-fold respectively, N=1).

Treatment of erythroid progenitors with 0.1 and 1 μM of Example 5 resulted in dose-dependent increase in expression of γ-globin (1.5-fold and 2-fold respectively, N=1).

Assessment of % F Cells by Flow Cytometry

Human erythroid cells were collected on Day 7 of treatment with compound. Cells were fixed in 0.05% glutaraldehyde (Electron Microscopy Sciences, Catalog #16019), permeabilized with 0.1% Triton-X and stained with FITC-conjugated antibody directed to fetal hemoglobin (ThermoFisher, Catalog #MHFH01). Analysis of fetal hemoglobin expressing erythroid cells (% F cells) was performed on an Attune Nxt flow cytometer (ThermoFisher).

Treatment of erythroid progenitors with 0.1 and 1 μM of Example 5 resulted in dose-dependent increase in % F cells compared to DMSO treated control (1.3-fold and 3-fold respectively, N=1).

Assessment of γ-Globin Induction by Quantitative PCR in K562 Cells

Compounds were dissolved in DMSO to make 10 mM stock solutions, and further diluted to make 1 mM and 0.1 mM stocks. K562 cells were purchased from ATCC and maintained in Iscove's DMEM (Corning Cellgro, Catalog #15-016-CVR) supplemented with 10% v/v FBS (GE Healthcare, Catalog #: SH30910.03) in a $CO_2$ incubator (5% $CO_2$) at 37° C. Cells were plated at a density of $5\times10^5$ cells/ml and treated with compound at final concentrations of 0.1 and 1 μM. Media and compound was renewed after 3 days in culture and cells were collected for RNA isolation after 6 days of treatment.

Treatment of K562 cells with 0.1 and 1 μM of Example 5 resulted in dose-dependent increase in expression of γ-globin (3 and 8-fold respectively, N=1)

Compound titration and cell culture: Compounds were dissolved in DMSO to make 10 mM stock solutions. Human peripheral blood mononuclear cells (PBMCs) from healthy donors were purchased from AllCells (Emeryville, CA), maintained in RPMI 1640 (Corning Cellgro, Catalog #: 10-040-CV) supplemented with 10% v/v heat-inactivated FBS (GE Healthcare, Catalog #: SH30910.03), 2 mM L-Glutamine (Corning Cellgro, Catalog #25005CV) and 1× Penicillin-Streptomycin (Sigma-Aldrich, Catalog #P4333) in a $CO_2$ incubator (5% $CO_2$) at 37° C.

To determine enzyme inhibition $IC_{50}$ values in human PBMCs: Freshly thawed cells were seeded at a density of $25\times10^5$ cells/ml in 2 ml of media in a 12 well plate. Cells were activated by addition of 5 g/ml PHA-L (Sigma-Aldrich, Catalog #L4144) for 3 days. A series of 8-point, 3-fold dilutions of compound were dispensed into wells from 1 mM stock solution using TECAN digital dispenser (D300e) and concentration of DMSO was normalized to 0.1%. Cells incubated with 0.1% DMSO only was used as a control.

Cells were harvested 3 days later, resuspended in 15 μL PBS, lysed in 4% SDS, and homogenized by passing through homogenizer column (Omega Biotek, Catalog #: HCR003). Total protein concentration were determined by BCA assay (ThermoFisher Scientific, Catalog #: 23225). Lysates were mixed with 5× Laemmli buffer and boiled for 5 minutes. 30 μg of total protein was separated on SDS-PAGE gels (Bio-Rad, catalog #: 4568083, 4568043), transferred to PVDF membrane, blocked with 5% dry milk (Bio-Rad, Catalog #: 1706404) in TBS with 0.1% v/v Tween 20 (TBST) for 1 hour at room temperature (RT), and incubated with primary antibodies (sDMA: Cell signaling, Catalog #: 13222, 1:2,000; β-Actin: sigma, Catalog #: 1:5,000) in 5% dry milk in TBST at 4° C. overnight. The following day, membranes were washed with TBST, 5×5 min, and incubated with HRP-conjugated secondary antibodies (GE Healthcare; Catalog #: NA934-1 ML, NA931-1 ML; 1:5,000) for 2 hours at RT, followed by 5×5 min washes with TBST, and incubation with ECL substrates (Bio-Rad, Catalog #: 1705061, 1705062). Chemiluminescent signal was captured with Fluochem HD2 imager (Proteinsimple). SmD3me2s bands were quantified by ImageJ. Signals were normalized to β-Actin and DMSO control. $IC_{50}$ values were calculated using Graphpad Prism ([Inhibitor] vs. normalized response—Variable slope). See Table 3, below.

TABLE 3

| Cellular potency in human PBMCs | | |
|---|---|---|
| Ex# | sDMA $IC_{50}$ μM | sDMA $IC_{50}$_N |
| 5 | 0.016 | 3 |

The disclosure is also directed to the following aspects:

Aspect 1. A compound of Formula I:

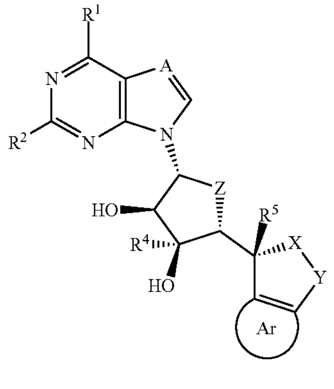

I or a pharmaceutically acceptable salt or solvate thereof; wherein

A is N or C—$R^3$;

$R^1$ is H, halo, —$C_1$-$C_6$ alkyl, —$C_1$-$C_6$ alkoxy, —$C_1$-$C_4$ haloalkyl, —$C_3$-$C_6$ cycloalkyl, —$C_3$-$C_6$halocycloalkyl, —$C_1$-$C_6$ alk-O—$C_1$-$C_6$ alkyl, —$C_1$-$C_6$ alk-S(O)—$C_1$-$C_6$ alkyl, —$C_1$-$C_6$ alk-S$(O)_2$—$C_1$-$C_6$ alkyl, —$CR^6R^{6'}$CN, —$NR^6R^{6'}$, —NHC$R^6R^{6'}$CN, —NHCON$R^6R^{6'}$, —NHC(O)O$R^7$, NHC(O)—$C_1$-$C_6$ alkyl, NHC(O)—$C_1$-$C_6$ haloalkyl, —NH—$C_1$-$C_6$ alk-C(O)—$C_1$-$C_6$ alkyl, —NHC(S)N$R^6R^{6'}$, —NH—O—$R^6$, or —NH—N$R^6R^{6'}$;

$R^2$ is H, halo, —$C_1$-$C_6$ alkyl, or $NH_2$;

$R^3$ is H, halo, —$C_1$-$C_6$ alkyl, —$C_1$-$C_6$ alkoxy, —$C_2$-$C_6$ alkenyl, or —$C_2$-$C_6$ alkynyl;

$R^4$ is H, —$C_1$-$C_6$ alkyl, —$C_1$-$C_6$ haloalkyl, —$C_2$-$C_6$ alkenyl, or —$C_2$-$C_6$ alkynyl;

$R^5$ is H or —$C_1$-$C_6$ alkyl;

$R^6$ and $R^{6'}$ are each independently H, $C_1$-$C_6$ alkyl, or —$C_1$-$C_6$ alk-O$C_1$-$C_6$ alkyl;

or $R^6$ and $R^{6'}$, together with the atom to which they are attached, form a $C_2$-$C_6$ heterocycloalkyl ring or a $C_3$-$C_6$ cycloalkyl ring;

$R^7$ is —$C_1$-$C_6$ alkyl or —$C_0$-$C_6$ alk-$C_3$-$C_6$ cycloalkyl;

X is O, S, $SO_2$, NH, or N($C_1$-$C_6$ alkyl);

Y is $CH_2$, —$CH_2CH_2$—, $C(CH_3)_2$, $CF_2$, C(═O), or CH—$C_1$-$C_4$ alk-$NH_2$;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Aspect 2. The compound of aspect 1 wherein $R^1$ is halo, —$NR^6R^{6'}$, —$C_1$-$C_6$ alkyl, —$C_1$-$C_6$ alkoxy, or —$C_1$-$C_6$ alk-O—$C_1$-$C_6$ alkyl.

Aspect 3. The compound of aspect 2, wherein $R^1$ is halo, preferably —F, or —Cl.

Aspect 4. The compound of aspect 2, wherein $R^1$ is —$NR^6R^{6'}$, preferably —$NH_2$.

Aspect 5. The compound of aspect 2, wherein $R^1$ is —$C_1$-$C_6$ alkyl, preferably —$CH_3$.

Aspect 6. The compound of aspect 2, wherein $R^1$ is —$C_1$-$C_6$ alk-O—$C_1$-$C_6$ alkyl, preferably —$CH_2$—O—$CH_2CH_3$.

Aspect 7. The compound of any one of aspects 1 to 6, wherein $R^2$ is H.

Aspect 8. The compound of any one of aspects 1 to 7, wherein $R^4$ is H or —$C_1$-$C_6$ alkyl.

Aspect 9. The compound of aspect 8, wherein $R^4$ is H.

Aspect 10. The compound of aspect 8, wherein $R^4$ is —$C_1$-$C_6$ alkyl, preferably methyl.

Aspect 11. The compound of any one of aspects 1 to 10, wherein $R^5$ is H.

Aspect 12. The compound of any one of aspects 1 to 10, wherein $R^5$ is —$C_1$-$C_6$ alkyl, preferably —$CH_3$.

Aspect 13. The compound of any one of aspects 1 to 12, wherein Ar is an optionally substituted 6-membered aryl ring.

Aspect 14. The compound of aspect 13, wherein the 6-membered aryl ring is substituted with one or more halogen atoms, preferably —F, or —Cl.

Aspect 15. The compound of aspect 13 or 14, wherein the 6-membered aryl ring is substituted with one or more —$CH_3$, $CF_3$, or —$OCF_3$ groups.

Aspect 16. The compound of any one of aspects 1 to 12, wherein Ar is an optionally substituted 6-membered heteroaryl ring.

Aspect 17. The compound of aspect 16, wherein the 6-membered heteroaryl ring is substituted with one or more halogen atoms, preferably —F, or —Cl.

Aspect 18. The compound of aspect 16 or 17, wherein the 6-membered heteroaryl ring is substituted with one or more —$CH_3$, $CF_3$, or —$OCF_3$ groups.

Aspect 19. The compound of any one of aspects 1 to 12, wherein Ar is an optionally substituted 5-membered heteroaryl ring.

Aspect 20. The compound of aspect 19, wherein the 5-membered heteroaryl ring is substituted with one or more halogen atoms, preferably —F, or —Cl.

Aspect 21. The compound of aspect 19 or 20, wherein the 5-membered heteroaryl ring is substituted with one or more —$CH_3$, $CF_3$, or —$OCF_3$ groups.

Aspect 22. The compound of any one of aspects 1 to 21, wherein X is O.

Aspect 23. The compound of any one of aspects 1 to 21, wherein X is S.

Aspect 24. The compound of any one of aspects 1 to 21, wherein X is $SO_2$.

Aspect 25. The compound of any one of aspects 1 to 21, wherein X is NH.

Aspect 26. The compound of any one of aspects 1 to 21, wherein X is N($C_1$-$C_6$ alkyl), preferably N($CH_3$).

Aspect 27. The compound of any one of aspects 1 to 26, wherein Y is $CH_2$.

Aspect 28. The compound of any one of aspects 1 to 26, wherein Y is $—CH_2CH_2—$.

Aspect 29. The compound of any one of aspects 1 to 26, wherein Y is $C(CH_3)_2$.

Aspect 30. The compound of any one of aspects 1 to 26, wherein Y is or $CF_2$.

Aspect 31. The compound of any one of aspects 1 to 26, wherein Y is C(═O).

Aspect 32. The compound of any one of aspects 1 to 26, wherein Y is CH—$C_1$-$C_4$ alk-$NH_2$.

Aspect 33. The compound of any one of aspects 1 to 32, wherein Z is O.

Aspect 34. The compound of any one of aspects 1 to 32, wherein Z is $CH_2$.

Aspect 35. The compound of any one of aspects 1 to 32, wherein Z is $CF_2$.

Aspect 36. The compound of any one of aspects 1 to 35, wherein A is N.

Aspect 37. The compound of any one of aspects 1 to 35, wherein A is C—$R^3$.

Aspect 38. The compound of aspect 37, wherein $R^3$ is H.

Aspect 39. The compound of aspect 37, wherein $R^3$ is halo, preferably —F.

Aspect 40. A pharmaceutical composition comprising a compound according to any one of aspects 1 to 39 and a pharmaceutically acceptable excipient.

Aspect 41. A method of inhibiting a protein arginine methyltransferase 5 (PRMT5) enzyme, comprising: contacting the PRMT5 enzyme with an effective amount of a compound of any one of any one of aspects 1 to 39.

Aspect 42. A method of treating a disease or disorder associated with aberrant PRMT5 activity in a subject comprising administering to the subject, a compound of any one of aspects 1 to 39.

Aspect 43. The method of aspect 42, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; glioblastoma, NSCLC, head and neck cancer, bladder cancer, or hepatocellular carcinoma.

Aspect 44. A compound of Formula I:

I

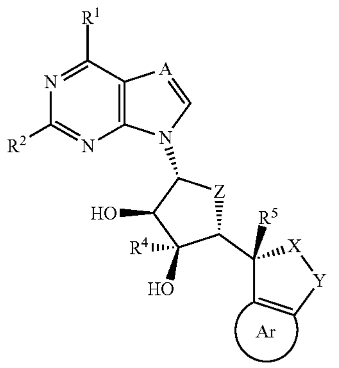

or a pharmaceutically acceptable salt or solvate thereof; wherein

A is N or C—$R^3$;

$R^1$ is H, halo, —$C_1$-$C_6$ alkyl, —$C_1$-$C_6$ alkoxy, —$C_1$-$C_4$ haloalkyl, —$C_3$-$C_6$ cycloalkyl, —$C_3$-$C_6$halocycloalkyl, —$C_1$-$C_6$ alk-O—$C_1$-$C_6$ alkyl, —$C_1$-$C_6$ alk-S(O)—$C_1$-$C_6$ alkyl, —$C_1$-$C_6$ alk-$S(O)_2$—$C_1$-$C_6$ alkyl, —$CR^6R^{6'}$CN, —$NR^6R^{6'}$, —$NHCR^6R^{6'}$CN, —$NHCONR^6R^{6'}$, —NHC(O)$OR^7$, NHC(O)—$C_1$-$C_6$ alkyl, NHC(O)—$C_1$-$C_6$ haloalkyl, —NH—$C_1$-$C_6$ alk-C(O)—$C_1$-$C_6$ alkyl, —NHC(S)$NR^6R^{6'}$, —NH—O—$R^6$, or —NH—$NR^6R^{6'}$;

$R^2$ is H, halo, —$C_1$-$C_6$ alkyl, or $NH_2$;

$R^3$ is H, halo, —$C_1$-$C_6$ alkyl, —$C_1$-$C_6$ alkoxy, —$C_2$-$C_6$ alkenyl, or —$C_2$-$C_6$ alkynyl;

$R^4$ is H, —$C_1$-$C_6$ alkyl, —$C_1$-$C_6$ haloalkyl, —$C_2$-$C_6$ alkenyl, or —$C_2$-$C_6$ alkynyl;

$R^5$ is H or —$C_1$-$C_6$ alkyl;

$R^6$ and $R^{6'}$ are each independently H, $C_1$-$C_6$ alkyl, or —$C_1$-$C_6$ alk-$OC_1$-$C_6$ alkyl;

or $R^6$ and $R^{6'}$, together with the atom to which they are attached, form a $C_2$-$C_6$ heterocycloalkyl ring or a $C_3$-$C_6$ cycloalkyl ring;

$R^7$ is —$C_1$-$C_6$ alkyl or —$C_0$-$C_6$ alk-$C_3$-$C_6$ cycloalkyl;

X is O, S, NH, or N($C_1$-$C_6$ alkyl), and Y is —$(CR^9R^{9'})_n$—, —$CR^9$═$CR^{9'}$—, C(═O), —C(═O)—$(CR^9R^{9'})_n$—, —C(═O)—O—$(CR^9R^{9'})_n$—, —$CR^9R^{9'}$—O—, —$(CR^9R^{9'})_n$—O—$(CR^9R^{9'})_m$—, —$(CR^9R^{9'})_n$—$NR^{10}$, C(═O)$NR^{10}$, or CH—$C_1$-$C_4$ alk-$NH_2$; or X is —$SO_2$— and Y is —$(CR^9R^{9'})_n$—, —$CR^9$═$CR^{9'}$—, —$CR^9R^{9'}$—O—, —$(CR^9R^{9'})_n$—O—$(CR^9R^{9'})_m$—, —$(CR^9R^{9'})_n$—$NR^{10}$, or CH—$C_1$-$C_4$ alk-$NH_2$;

wherein n=1 or 2; m=1 or 2;

each instance of $R^9$ or $R^{9'}$ is independently H, D, $C_1$-$C_6$ alkyl, $C_1$-$C_6$ haloalkyl, halo, —$C_1$-$C_6$ alkoxy, or hydroxy;

$R^{10}$ is H or $C_1$-$C_6$ alkyl;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

Aspect 45. The compound of aspect 44 wherein $R^1$ is halo, —$NR^6R^{6'}$, —$C_1$-$C_6$ alkyl, —$C_1$-$C_6$ alkoxy, or —$C_1$-$C_6$ alk-O—$C_1$-$C_6$ alkyl.

Aspect 46. The compound of aspect 45, wherein $R^1$ is halo, preferably —F, or —Cl.

Aspect 47. The compound of aspect 45, wherein $R^1$ is —$NR^6R^{6'}$, preferably —$NH_2$.

Aspect 48. The compound of aspect 45, wherein $R^1$ is —$C_1$-$C_6$ alkyl, preferably —$CH_3$.

Aspect 49. The compound of aspect 45, wherein $R^1$ is —$C_1$-$C_6$ alk-O—$C_1$-$C_6$ alkyl, preferably —$CH_2$—O—$CH_2CH_3$.

Aspect 50. The compound of any one of aspects 44 to 49, wherein $R^2$ is H.

Aspect 51. The compound of any one of aspects 44 to 50, wherein $R^4$ is H or —$C_1$-$C_6$ alkyl.

Aspect 52. The compound of aspect 51, wherein $R^4$ is H.

Aspect 53. The compound of aspect 51, wherein $R^4$ is —$C_1$-$C_6$ alkyl, preferably methyl.

Aspect 54. The compound of any one of aspects 44 to 53, wherein $R^5$ is H.

Aspect 55. The compound of any one of aspects 44 to 53, wherein $R^5$ is —$C_1$-$C_6$ alkyl, preferably —$CH_3$.

Aspect 56. The compound of any one of aspects 44 to 55, wherein Ar is an optionally substituted 6-membered aryl ring.

Aspect 57. The compound of aspect 56, wherein the 6-membered aryl ring is substituted with one or more halogen atoms, preferably —F, or —Cl.

Aspect 58. The compound of aspect 56 or 57, wherein the 6-membered aryl ring is substituted with one or more —$CH_3$, $CF_3$, or —$OCF_3$ groups.

Aspect 59. The compound of any one of aspects 44 to 55, wherein Ar is an optionally substituted 6-membered heteroaryl ring.

Aspect 60. The compound of aspect 59, wherein the 6-membered heteroaryl ring is substituted with one or more halogen atoms, preferably —F, or —Cl.

Aspect 61. The compound of aspect 59 or 60, wherein the 6-membered heteroaryl ring is substituted with one or more —$CH_3$, $CF_3$, or —$OCF_3$ groups.

Aspect 62. The compound of any one of aspects 44 to 55, wherein Ar is an optionally substituted 5-membered heteroaryl ring.

Aspect 63. The compound of aspect 62, wherein the 5-membered heteroaryl ring is substituted with one or more halogen atoms, preferably —F, or —Cl.

Aspect 64. The compound of aspect 62 or 63, wherein the 5-membered heteroaryl ring is substituted with one or more —$CH_3$, $CF_3$, or —$OCF_3$ groups.

Aspect 65. The compound of any one of aspects 44 to 64, wherein X is O.

Aspect 66. The compound of any one of aspects 44 to 64, wherein X is S.

Aspect 67. The compound of any one of aspects 44 to 64, wherein X is $SO_2$.

Aspect 68. The compound of any one of aspects 44 to 64, wherein X is NH.

Aspect 69. The compound of any one of aspects 44 to 64, wherein X is N($C_1$-$C_6$ alkyl), preferably N($CH_3$).

Aspect 70. The compound of any one of aspects 44 to 69, wherein Y is —$(CR^9R^{9'})_n$ Aspect 71. The compound of aspect 70, wherein —$(CR^9R^{9'})_n$ is —$CH_2$—, —$CH_2CH_2$—, —$C(CH_3)_2$—, or —$CF_2$—

Aspect 72. The compound of any one of aspects 44 to 69, wherein Y is —$CR^9$=$CR^{9'}$—.

Aspect 73. The compound of any one of aspects 44 to 66, and 68 to 69, wherein Y is —C(=O)—$(CR^9R^{9'})_n$—.

Aspect 74. The compound of any one of aspects 44 to 66, and 68 to 69, wherein Y is —C(=O)—O—$(CR^9R^{9'})_n$—.

Aspect 75. The compound of any one of aspects 44 to 69, wherein Y is —$CR^9R^{9'}$—O.

Aspect 76. The compound of any one of aspects 44 to 69, wherein Y is —$(CR^9R^{9'})_n$—O—$(CR^9R^{9'})_m$-Aspect 77. The compound of any one of aspects 44 to 66, and 68 to 69, wherein Y is C(=O).

Aspect 78. The compound of any one of aspects 44 to 69, wherein Y is CH—$C_1$-$C_4$ alk-$NH_2$.

Aspect 79. The compound of any one of aspects 44 to 69 wherein Y is —$(CR^9R^{9'})_n$—$NR^{10}$.

Aspect 80. The compound of any one of aspects 44 to 66, and 68 to 69 wherein Y is —C(=O)$NR^{10}$.

Aspect 81. The compound of any one aspects 70, 72-76, or 79, wherein each $R^9$ and each $R^{9'}$ is independently H, D, —$CH_3$, OH, —$OCH_3$, F, or $CF_3$.

Aspect 82. The compound of any one of aspects 70, 73, 74, 76, 79, or 81 wherein n=1.

Aspect 83. The compound of any one of aspects 70, 73, 74, 76, 79, or 81 wherein n=2.

Aspect 84. The compound of aspect 76 wherein m=1.

Aspect 85. The compound of aspect 76 wherein m=2.

Aspect 86. The compound of any one of aspects 44 to 85, wherein Z is O.

Aspect 87. The compound of any one of aspects 44 to 85, wherein Z is $CH_2$.

Aspect 88. The compound of any one of aspects 44 to 85, wherein Z is $CF_2$.

Aspect 89. The compound of any one of aspects 44 to 88, wherein A is N.

Aspect 90. The compound of any one of aspects 44 to 88, wherein A is C—$R^3$.

Aspect 91. The compound of aspect 90, wherein $R^3$ is H.

Aspect 92. The compound of aspect 90, wherein $R^3$ is halo, preferably —F.

Aspect 93. A pharmaceutical composition comprising a compound according to any one of aspects 44 to 92 and a pharmaceutically acceptable excipient.

Aspect 94. A method of inhibiting a protein arginine methyltransferase 5 (PRMT5) enzyme, comprising: contacting the PRMT5 enzyme with an effective amount of a compound of any one of any one of aspects 44 to 92.

Aspect 95. A method of treating a disease or disorder associated with aberrant PRMT5 activity in a subject comprising administering to the subject, a compound of any one of aspects 44 to 92.

Aspect 96. The method of aspect 95, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; glioblastoma, NSCLC, head and neck cancer, bladder cancer, or hepatocellular carcinoma.

What is claimed:

1. A compound of Formula I:

I

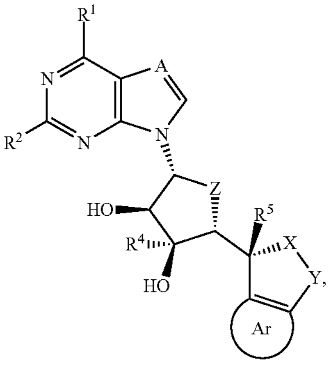

or a pharmaceutically acceptable salt or solvate thereof; wherein:

A is N or C—$R^3$;

$R^1$ is H, halo, —$C_1$-$C_6$alkyl, —$C_1$-$C_6$alkoxy, —$C_1$-$C_4$ haloalkyl, —$C_3$-$C_6$ cycloalkyl, —$C_3$-$C_6$ halocycloalkyl, —$C_1$-$C_6$alk-O—$C_1$-$C_6$alkyl, —$C_1$-$C_6$alk-S(O)—$C_1$-$C_6$alkyl, —$C_1$-$C_6$alk-S$(O)_2$—$C_1$-$C_6$alkyl, —$CR^6R^{6'}$CN, —$NR^6R^{6'}$, —NHC$R^6R^{6'}$CN, —NHCON$R^6R^{6'}$, —NHC(O)O$R^7$, NHC(O)—$C_1$-$C_6$alkyl, NHC(O)—$C_1$-$C_6$ haloalkyl, —NH—$C_1$-$C_6$alk-C(O)—$C_1$-$C_6$alkyl, —NHC(S) N$R^6R^{6'}$, —NH—O—$R^6$, or —NH—N$R^6R^{6'}$;

$R^2$ is H, halo, —$C_1$-$C_6$alkyl, or $NH_2$;

$R^3$ is H, halo, —$C_1$-$C_6$alkyl, —$C_1$-$C_6$alkoxy, —$C_2$-$C_6$alkenyl, or —$C_2$-$C_6$alkynyl;

$R^4$ is H, —$C_1$-$C_6$alkyl, —$C_1$-$C_6$ haloalkyl, —$C_2$-$C_6$alkenyl, or —$C_2$-$C_6$alkynyl;

$R^5$ is H or —$C_1$-$C_6$alkyl;

$R^6$ and $R^{6'}$ are each independently H, $C_1$-$C_6$alkyl, or —$C_1$-$C_6$alk-O$C_1$-$C_6$alkyl;

or $R^6$ and $R^{6'}$, together with the atom to which they are attached, form a $C_2$-$C_6$ heterocycloalkyl ring or a $C_3$-$C_6$ cycloalkyl ring;

$R^7$ is —$C_1$-$C_6$alkyl or —$C_0$-$C_6$alk-$C_3$-$C_6$ cycloalkyl;

X is O, S, NH, or N ($C_1$-$C_6$alkyl), and Y is —$(CR^9R^{9'})_n$—, —$CR^9$=$CR^{9'}$—, C(=O), —C(=O)—$(CR^9R^{9'})_n$—, —C(=O)—O—$(CR^9R^{9'})_n$—, —$CR^9R^{9'}$—O—, —$(CR^9R^{9'})_n$—O—$(CR^9R^{9'})_m$—, —$(CR^9R^{9'})_n$—$NR^{10}$, C(=O) $NR^{10}$, or CH—$C_1$-$C_4$alk-$NH_2$; or X is —$SO_2$— and Y is —$(CR^9R^{9'})_n$—, —$CR^9$=$CR^{9'}$—, —$CR^9R^{9'}$—O—, —$(CR^9R^{9'})_n$—O—$(CR^9R^{9'})_m$—, -$(CR^9R^{9'})_n$—$NR^{10}$, or CH—$C_1$-$C_4$alk-$NH_2$;

wherein n=1 or 2; m=1 or 2;

each instance of $R^9$ or $R^{9'}$ is independently H, D, $C_1$-$C_6$alkyl, $C_1$-$C_6$ haloalkyl, halo, —$C_1$-$C_6$alkoxy, or hydroxy;

$R^{10}$ is H or $C_1$-$C_6$alkyl;

Z is O, $CH_2$, or $CF_2$; and

Ar is an optionally substituted 6-membered aryl ring, an optionally substituted 6-membered heteroaryl ring, or an optionally substituted 5-membered heteroaryl ring.

2. The compound of claim 1 wherein $R^1$ is halo, —$NR^6R^{6'}$, —$C_1$-$C_6$alkyl, —$C_1$-$C_6$ alkoxy, or —$C_1$-$C_6$ alk-O—$C_1$-$C_6$ alkyl.

3. The compound of claim 1, wherein $R^2$ is H.

4. The compound of claim 1, wherein $R^4$ is H or —$C_1$-$C_6$ alkyl.

5. The compound of claim 1, wherein $R^5$ is H.

6. The compound of claim 1, wherein $R^5$ is —$C_1$-$C_6$ alkyl.

7. The compound of claim 1, wherein Ar is an optionally substituted 6-membered aryl ring.

8. The compound of claim 1, wherein Ar is an optionally substituted 6-membered heteroaryl ring.

9. The compound of claim 1, wherein Ar is an optionally substituted 5-membered heteroaryl ring.

10. The compound of claim 1, wherein X is O.

11. The compound of claim 1, wherein Y is —$(CR^9R^{9'})_n$.

12. The compound of claim 1, wherein each $R^9$ and each $R^{9'}$ is independently H, D, —$CH_3$, OH, —$OCH_3$, F, or $CF_3$.

13. The compound of claim 1 wherein n=1.

14. The compound of claim 1 wherein n=2.

15. The compound of claim 1 wherein m=1.

16. The compound of claim 1 wherein m=2.

17. The compound of claim 1, wherein Z is O.

18. A pharmaceutical composition comprising a compound according to claim 1 and a pharmaceutically acceptable excipient.

19. A method of treating a disease or disorder associated with aberrant PRMT5 activity in a subject comprising administering to the subject, a compound of claim 1.

20. The method of claim 19, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; glioblastoma, NSCLC, head and neck cancer, bladder cancer, or hepatocellular carcinoma.

* * * * *